US012708363B2

(12) United States Patent
Wenchell, Jr. et al.

(10) Patent No.: US 12,708,363 B2
(45) Date of Patent: Aug. 18, 2026

(54) POWER PACK FOR ACTIVATING SURGICAL INSTRUMENTS AND PROVIDING USER FEEDBACK

(71) Applicant: RevMedica, Inc., Middletown, CT (US)

(72) Inventors: Thomas G. Wenchell, Jr., Durham, CT (US); C. Robert Satti, III, Westbrook, CT (US); Dawson Hettrick, Branford, CT (US); Stephen Pang, Avon, CT (US)

(73) Assignee: RevMedica, Inc., Middletown, CT (US)

( * ) Notice: Subject to any disclaimer, the term of this patent is extended or adjusted under 35 U.S.C. 154(b) by 0 days.

(21) Appl. No.: 19/177,766

(22) Filed: Apr. 14, 2025

(65) Prior Publication Data

US 2025/0331852 A1 Oct. 30, 2025

Related U.S. Application Data

(63) Continuation of application No. 18/387,875, filed on Nov. 8, 2023, now Pat. No. 12,279,770, which is a (Continued)

(51) Int. Cl.
*A61B 17/072* (2006.01)
*A61B 17/068* (2006.01)
(Continued)

(52) U.S. Cl.
CPC .......... *A61B 17/072* (2013.01); *A61B 17/068* (2013.01); *A61B 34/20* (2016.02); (Continued)

(58) Field of Classification Search
CPC ...... A61B 17/072; A61B 17/068; A61B 34/20
See application file for complete search history.

(56) References Cited

U.S. PATENT DOCUMENTS 5,129,570 A 7/1992 Schulze et al.
5,383,880 A 1/1995 Hooven
(Continued)

FOREIGN PATENT DOCUMENTS

WO WO 2021/016006 1/2021
WO WO 2024/201198 10/2024

OTHER PUBLICATIONS

EP 22 76 3759 European Search Report & Written Opinion dated: Jan. 2, 2025.

*Primary Examiner* — Nathaniel C Chukwurah
(74) *Attorney, Agent, or Firm* — Neil D. Gershon

(57) ABSTRACT

A power pack removably loadable into a compartment of an instrument. The power pack has a first motor and a first engagement member removably engageable with a firing mechanism to effect firing of fasteners and a second motor and second engagement member removably engageable with an articulation mechanism when the power pack is loaded into the compartment to effect movement of the articulation mechanism from a first position to a second position. A display screen indicates one or more of the following a) a specific direction and angle of the first and second jaws with respect to the longitudinal axis; b) a tissue force during firing of fasteners; c) a clamping force by the instrument jaws on tissue prior to firing; and/or d) change in clamping force over time. The display screen can alternatively be on the instrument.

19 Claims, 89 Drawing Sheets

Related U.S. Application Data continuation-in-part of application No. 18/222,548, filed on Jul. 17, 2023, now Pat. No. 12,213,669, which is a continuation of application No. 18/078,308, filed on Dec. 9, 2022, now Pat. No. 12,167,850, which is a continuation of application No. 17/269,907, filed as application No. PCT/US2020/042033 on Jul. 15, 2020, now Pat. No. 11,564,685, said application No. 18/387,875 is a continuation-in-part of application No. 18/273,048, filed as application No. PCT/US2023/021289 on May 8, 2023, now Pat. No. 12,357,307.

(60) Provisional application No. 62/876,586, filed on Jul. 19, 2019, provisional application No. 62/962,388, filed on Jan. 17, 2020, provisional application No. 63/341,448, filed on May 13, 2022.

(51) Int. Cl.

| | |
|---|---|
| ***A61B 34/20*** | (2016.01) |
| ***A61B 34/30*** | (2016.01) |
| *A61B 17/00* | (2006.01) |
| *A61B 17/115* | (2006.01) |
| *A61B 17/29* | (2006.01) |
| *A61B 17/32* | (2006.01) |
| *A61B 90/00* | (2016.01) |

(52) U.S. Cl.

CPC ............... *A61B 2017/00022* (2013.01); *A61B 2017/00398* (2013.01); *A61B 2017/00473* (2013.01); *A61B 2017/00734* (2013.01); *A61B 17/07207* (2013.01); *A61B 2017/07214* (2013.01); *A61B 2017/07257* (2013.01); *A61B 2017/07271* (2013.01); *A61B 17/1155* (2013.01); *A61B 2017/2927* (2013.01); *A61B 2017/320052* (2013.01); *A61B 2034/2059* (2016.02); *A61B 34/30* (2016.02); *A61B 2090/0807* (2016.02); *A61B 2090/0811* (2016.02)

(56) References Cited

U.S. PATENT DOCUMENTS

| | | | | |
|---|---|---|---|---|
| 5,878,938 | A | 3/1999 | Bittner et al. | |
| 8,011,555 | B2 | 9/2011 | Tarinelli et al. | |
| 9,078,653 | B2 | 7/2015 | Leimbach et al. | |
| 9,265,501 | B2 | 2/2016 | Tiwari | |
| 9,717,498 | B2 | 8/2017 | Aranyi et al. | |
| 10,154,841 | B2 | 12/2018 | Weaner et al. | |
| 10,278,702 | B2 | 5/2019 | Shelton, IV et al. | |
| 10,456,140 | B2 | 10/2019 | Shelton, IV et al. | |
| 10,478,190 | B2 | 11/2019 | Miller et al. | |
| 10,492,785 | B2 | 12/2019 | Overmyer et al. | |
| 10,639,034 | B2 | 5/2020 | Harris et al. | |
| 10,835,247 | B2 | 11/2020 | Shelton, IV et al. | |
| 10,881,401 | B2 | 1/2021 | Baber et al. | |
| 10,980,536 | B2 | 4/2021 | Weaner et al. | |
| 11,096,689 | B2 | 8/2021 | Overmyer et al. | |
| 11,166,716 | B2 | 11/2021 | Shelton, IV et al. | |
| 11,191,543 | B2 | 12/2021 | Overmyer et al. | |
| 11,197,668 | B2 | 12/2021 | Shelton, IV et al. | |
| 11,229,433 | B2 | 1/2022 | Schings et al. | |
| 11,234,698 | B2 | 2/2022 | Shelton, IV et al. | |
| 11,311,293 | B2 | 4/2022 | Roberts et al. | |
| 11,389,143 | B2 | 7/2022 | Ranucci et al. | |
| 11,406,382 | B2 | 8/2022 | Shelton, IV et al. | |
| 11,439,390 | B2 | 9/2022 | Patel et al. | |
| 11,452,524 | B2 | 9/2022 | Chavan et al. | |
| 11,517,312 | B2 | 12/2022 | Wixey | |
| 11,523,825 | B2 | 12/2022 | Becerra et al. | |
| 11,666,330 | B2 | 6/2023 | Whitfield et al. | |
| 11,751,871 | B2 | 9/2023 | Roberts et al. | |
| 11,896,223 | B2 | 2/2024 | Baxter, III et al. | |
| 11,903,601 | B2 | 2/2024 | Shelton, IV et al. | |
| 11,937,812 | B2 | 3/2024 | Schings et al. | |
| 11,998,201 | B2 | 6/2024 | Huang et al. | |
| 12,004,745 | B2 | 6/2024 | Shelton, IV et al. | |
| 12,035,909 | B2 | 7/2024 | Fernandes et al. | |
| 12,478,535 | B2 | 11/2025 | Olsen et al. | |
| 2005/0131390 | A1 | 6/2005 | Heinrich | |
| 2007/0175950 | A1 | 8/2007 | Shelton et al. | |
| 2008/0255413 | A1 | 10/2008 | Zemlok et al. | |
| 2010/0057107 | A1 | 3/2010 | Sorrentino | |
| 2012/0223122 | A1 | 9/2012 | Roy | |
| 2014/0249557 | A1 | 9/2014 | Koch, Jr. et al. | |
| 2016/0310134 | A1 | 10/2016 | Contini | |
| 2017/0296173 | A1 | 10/2017 | Shelton et al. | |
| 2018/0168608 | A1 | 6/2018 | Shelton, IV et al. | |
| 2019/0069887 | A1* | 3/2019 | Satti, III | A61B 17/0682 |
| 2019/0069895 | A1* | 3/2019 | Satti, III | A61B 17/07207 |
| 2020/0315726 | A1 | 10/2020 | Zemlok et al. | |
| 2020/0405406 | A1 | 12/2020 | Harris et al. | |
| 2022/0054130 | A1 | 2/2022 | Overmyer et al. | |
| 2023/0149016 | A1 | 5/2023 | Williams et al. | |
| 2023/0255626 | A1 | 8/2023 | Marecki et al. | |
| 2023/0338021 | A1 | 10/2023 | Zhang | |
| 2023/0338027 | A1 | 10/2023 | Schings et al. | |
| 2024/0074749 | A1 | 3/2024 | Schings et al. | |
| 2024/0148376 | A1 | 5/2024 | Williams | |
| 2024/0350140 | A1 | 10/2024 | Leimbach et al. | |

* cited by examiner

AY
AY
18
19
27a
27b
27c
27d
30
32
33
34
36
38
39a
39b
40
42
43
43a
43b
44
46

4
19A
19
28
28
22
18
22
19B
6
8a 19a
18
AT
19c
28
19b
AT 40
36
19
32
34
30
38

Motor
Drive Rod in Housing-Linear Movement
Drive Rod in Stapler-Linear Movement
Articulation
Staple Firing
Clamping Motor
Drive Rod in Housing-Linear Movement
Block in Stapler-Linear Movement
Male Lead Screw-Rotational Movement
Articulation
Staple Firing
Clamping 4
42
40
36
44
49
46
38
14a 18
4
22
22a
12
6
4
A
6
8a
A
42
AR
44
46
14a
18
14b
22
6
14

91
92
98
93
95
99a
96
94

90
92
98
93
96
95
79
78

95
96
98
93
92
91

95
94
99b
96
93
98
91
92

704
706
700
702

716
710
715
742
718a
718b
723
724
722
720

A
H
704
700

A
H
704
700
C
710

B

X
846
852

856
850
858
846
854
848
852

Y
Y
W
W
844
840

Z
848
850

846
848
850

POWER PACK FOR ACTIVATING SURGICAL INSTRUMENTS AND PROVIDING USER FEEDBACK

This application is a continuation of application Ser. No. 18/387,875, filed Nov. 8, 2023 now U.S. Pat. No. 12,279,770, which is a continuation in part of application Ser. No. 18/222,548, filed Jul. 17, 2023, now U.S. Pat. No. 12,213,669, which is a continuation of application Ser. No. 18/078,308, filed Dec. 9, 2022, now U.S. Pat. No. 12,167,850, which is a continuation of application Ser. No. 17/269,907, filed Feb. 19, 2021, now U.S. Pat. No. 11,564,685, which is a 371 of PCT/US2020/042033, filed Jul. 15, 2020, which claims the benefit of U.S. Provisional Application Nos. 62/876,586, filed Jul. 19, 2019 and 62/962,388, filed Jan. 17, 2020, and application Ser. No. 18/387,875, filed Nov. 8, 2023 is a continuation in part of application Ser. No. 18/273,048, filed Jul. 19, 2023, which is a 371 of PCT/US2023/021289, filed May 8, 2023 which claims the benefit of U.S. Provisional Application No. 63/341,448, filed May 13, 2022. The entire contents of each of these applications are incorporated herein by reference.

BACKGROUND OF THE INVENTION

1. Field of the Invention

This application relates to surgical instruments and power packs loadable into the surgical instruments to effect functions of the instruments and provide user feedback.

2. Background

Surgical staplers are used in various medical applications where a device is needed to join and dissect anatomical tissue. However, there are drawbacks and costs associated with use of surgical staplers. Currently staplers are either fully disposable, reusable or partially reusable. Due to contamination during the surgical procedure, e.g., exposure to the patient's body fluids, the staplers are required to be sterilized after use, a time consuming and expensive process, with possible risks of infection if not properly sterilized as contaminants adhered to the surgical stapler from a previous use could be transferred to another patient. To avoid the risks of resterilization, some surgical staplers are disposed after use in the surgical procedure. These staplers can be reloaded to fire multiple cartridges of staples, but after the procedure, the staplers are discarded. However, the practice of using single use disposable surgical staplers is costly.

In certain procedures, high forces are required to fire the staples through tissue into contact with the anvil for formation. This is compounded when multiple rows of staples are fired either simultaneously or sequentially from the stapler. Therefore, powered staplers have been introduced to reduce the force requirements of the user. Such powered staplers have motor driven mechanisms (assemblies) to advance components within the stapler to fire the staples from the cartridge through tissue. Such powered staplers, if reusable, are subject to the same aforementioned costs and risk of resterilization. However, they suffer from additional drawbacks since the sterilization process and/or heat or chemicals used in the sterilization process can damage the electronic components of the drive assemblies, which may shorten the lifespan of the surgical stapler or adversely affect its function if resterilization compromises the function of the motor or drive assembly. If the stapler is disposable, the stapler becomes more costly since the electronic components, which add to the cost of the stapler, are also discarded with the stapler.

It would be advantageous to provide a cost effective, efficient, simple to use and advanced assemblies for powering surgical instruments which overcome the drawbacks of manual actuation without suffering from the disadvantages of current power driven staplers.

Further, it would be advantageous to provide such surgical instruments which include systems to evaluate various parameters and functionalities to improve operation of the instruments and improve the surgical procedures and outcomes. These would advantageously include user feedback both during and post procedure.

SUMMARY

The present invention overcomes the deficiencies and disadvantages of the prior art. The present invention advantageously provides surgical staplers that overcome the drawbacks discussed above by having a fully enclosed and removable power pack. The surgical staplers according to the present invention may be used multiple times without the need to sterilize the power pack between uses because the power pack is fully enclosed and sealed by the surgical stapler handle assembly or housing, thereby preventing contact between the power pack and the patient and/or patient's bodily fluids or the like. Thus, the surgical staplers of the present invention advantageously reduce the time, resources and/or costs for preparing the surgical stapler for its next use. The present invention also provides power packs that are cost effective, efficient and easily loadable into surgical staplers where they engage structure in the housing to effect varied functions of the stapler.

The present invention also provides power packs and surgical instruments, such as surgical staplers, that can be used in robotic controlled surgical procedures. That is, the present invention also provides robotic systems utilizing the control modules/power packs disclosed herein.

In accordance with one aspect of the present invention, a surgical fastener applier is provided comprising a housing, an elongated member extending distally from the housing and having a longitudinal axis, and a first jaw and a second jaw at a distal portion of the elongated member, at least the first jaw movable with respect to the second jaw to clamp tissue between the first and second jaws. A motor powered firing mechanism is positioned within the housing, the firing mechanism movable between a first position and a second position, wherein movement to the second position effects firing of fasteners into the tissue clamped between the first and second jaws. A visual display indicates one of more of the following a) a force on tissue during fastener application correlated with the extent of fastener firing (firing stroke); b) an indication to a clinician whether proper fastener size has been selected; c) clamping force by the instrument jaws on tissue prior to firing; d) change of clamping pressure over time and/or e) specific direction and articulation angle of the first and second jaws with respect to the longitudinal axis.

In accordance with another aspect of the present invention, a power pack removably loadable into a compartment of an instrument is provided, the power pack having a first motor and a first engagement member removably engageable with a firing mechanism to effect firing of fasteners and a second motor and second engagement member removably engageable with an articulation mechanism when the power pack is loaded into the compartment to effect movement of the articulation mechanism from the first position to the second position. A display screen indicates one or more of the following a) the specific direction and articulation angle of the first and second jaws with respect to the longitudinal axis b) an indication whether proper fastener size has been selected; c) the tissue force during firing of fasteners (firing stroke); fasteners; d) change in clamping pressure over time; and/or e) clamping force by the instrument jaws on tissue prior to firing.

The viewing/display screen can be on the power pack and viewable through the housing of the instrument. In other embodiments, the viewing screen can be on the instrument housing, particularly, but not exclusively, in embodiments which do not have a removable power pack.

Further features of the displays, and additional displays, as well as sensors for tissue and force measurement, clamping and firing stroke, etc. are described in detail below.

In accordance with another aspect of the present invention, a surgical fastener applier is provided comprising a housing, an elongated member extending distally of the housing and having a longitudinal axis and a first jaw and a second jaw at a distal portion of the elongated member, at least the first jaw movable with respect to the second jaw to a clamping position to clamp tissue between the first and second jaws. A manually actuated jaw clamping mechanism includes an elongated clamping member movable linearly from a distal position to a proximal position to move at least the first jaw toward the second jaw to clamp tissue. The instrument includes one or both of a) a motor powered firing mechanism positioned within the housing, the firing mechanism movable between a first position and a second position, wherein movement to the second position effects firing of fasteners into the tissue clamped between the first and second jaws; and b) a motor powered articulation mechanism positioned within the housing, the articulation mechanism movable between a first position and second position to move the first and second jaws to a position angled with respect to the longitudinal axis, wherein the first and second jaws are articulable in a first direction with respect to the longitudinal axis and articulable in a second direction with respect to the longitudinal axis. The instrument includes a sensor for sensing clamping pressure of the first and second jaws on tissue, the sensor axially aligned with the elongated clamping member wherein proximal movement of the clamping member applies a force to the sensor.

In some embodiments, a transverse load pin is operatively connected to the elongated clamping member, the load pin applying a force to the sensor. In some embodiments, the jaw clamping mechanism further comprises an alignment member connected to the elongated clamping member, the alignment member movable to apply a force to the sensor.

In some embodiments, the motor powered firing mechanism cannot be actuated when the jaws are in the open position. In some embodiments, the motor powered articulation mechanism can be actuated only when the jaws are in the open position.

In some embodiments, the jaw mechanism includes a first slot and a pin movable within the slot to effect movement of the at least one jaw to the closed position when the elongated clamping member is moved proximally.

In some embodiments, the surgical fastener includes an I-beam movable distally to fire fasteners, the distal movement of the I-beam independent of the jaw clamping mechanism such that the I-beam does not effect clamping of tissue.

In some embodiments, the jaw clamping mechanism comprises a clamping handle pivotably mounted to the housing, and a switch is positioned on the clamping handle and an engagement surface is positioned on the firing trigger, wherein movement of the clamping handle changes a distance between the switch and engagement surface to enable activation of the switch to actuate the firing mechanism.

In some embodiments, the jaw clamping mechanism comprises a clamping handle pivotably mounted to the housing, and the applier further comprises an actuation button movable to activate the motor powered articulation, wherein a first contact on the articulation button is in alignment with a second contact (switch) in the housing to enable movement of the actuation button to activate the switch for activation of the motor powered articulation when the clamping handle is in an unclamped position and movement of the clamping handle from the unclamped position places the first contact out of alignment with the second contact.

In some embodiments, the jaw clamping mechanism includes a clamping handle pivotably mounted to the housing and a pivot plate, the pivot plate having a slot with a dwell portion, wherein further pulling of the clamping handle from a clamping position to release the clamping handle from the locked position does not further move the first jaw toward the second jaw.

In some embodiments, the elongated clamping member slides axially within the firing mechanism.

In some embodiments, the sensor is in wired electrical communication to a bus in the housing, and the firing mechanism and articulation mechanism are contained in a removable power pack removably loadable into the applier to electrically connect to the bus to receive data transmitted by the sensor. In some embodiments, the data transmitted by the sensor is processed by a microprocessor contained within the power pack and transmitted to a screen on the power pack to provide a visual display to the user.

In some embodiments, a dummy cartridge and/or a spent cartridge is utilized to measure clamping force and communicated to the user via a viewing screen in communication with a clamping force sensor.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIGS. 42A-43C illustrate alternate embodiments of the surgical instrument of the present invention having measurement devices to provide feedback, wherein:

FIG. 42A is a side view of the surgical instrument;

FIG. 43C is an enlarged view of the area of detail F of FIG. 43A;

FIGS. 45A-45F illustrate an alternate embodiment of the surgical instrument of the present invention having a feedback feature (measurement device) in the power pack, wherein:

FIG. 45A is a top view of the surgical instrument with the power pack loaded into the instrument;

FIG. 45B is a cross-sectional view taken along line J-J of FIG. 45A showing the power pack being loaded into the instrument;

FIG. 45C is an enlarged view of the area of detail K of FIG. 45B;

FIG. 45D is a top view of the surgical instrument, the view being the same as FIG. 45A but having section line L-L;

FIG. 45E is a cross-sectional view taken along line L-L of FIG. 45D showing the power pack in the instrument;

FIG. 45F is an enlarged view of the area of detail M of FIG. 45E;

FIG. 63 is a perspective of the articulation screw assembly of the power pack of FIG. 55;

FIG. 64 is a side view of the assembly of FIG. 63;

FIG. 65A is an enlarged view of the area of detail L of FIG. 64;

FIG. 65B is a cross-sectional view taken along line M-M of FIG. 65A;

FIG. 66A is an enlarged view of the area of detail N of FIG. 64;

FIG. 66B is a cross-sectional view taken along line O-O of FIG. 66A;

FIG. 67 is side view of the power pack in accordance with an alternate embodiment of the present invention having an encoder;

FIG. 68 is an exploded view of the deployment screw assembly and encoder of the power pack of FIG. 67;

FIG. 69A is a cross-sectional view taken along line P-P of FIG. 67;

FIG. 69B is an enlarged view of the area of detail Q of FIG. 69A;

FIG. 69C is a cross-sectional view taken along line R-R of FIG. 69A;

FIG. 69D is an enlarged view of the area of detail S of FIG. 69C;

Figure 67:
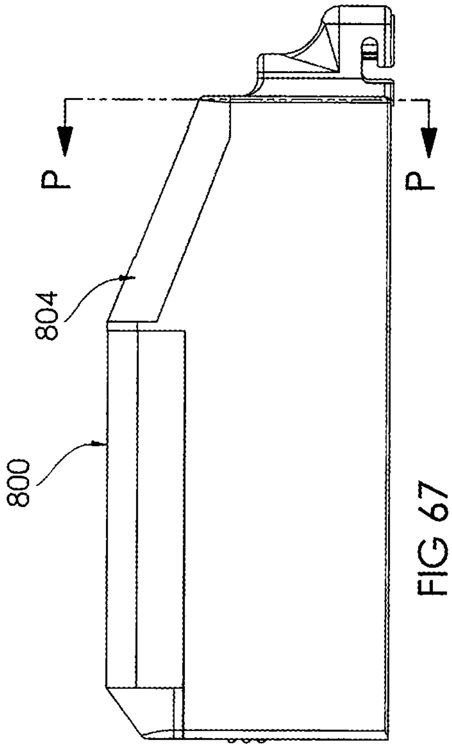
Figure 69A:
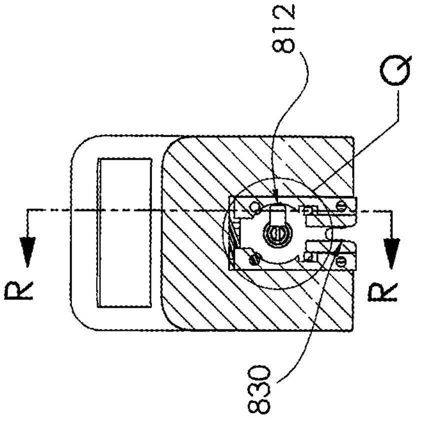
Figure 69C:
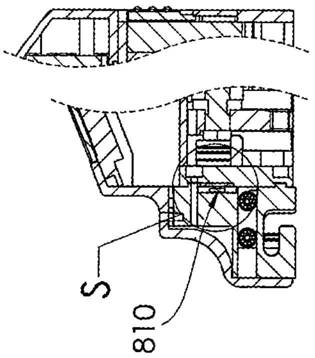
Figure 69B:
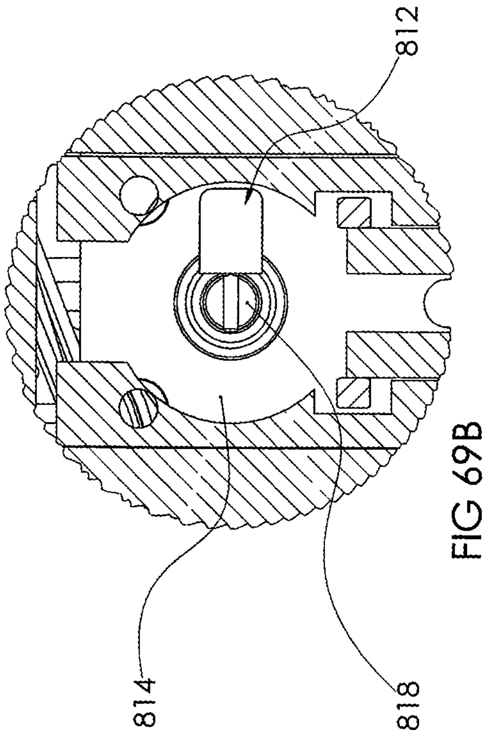
Figure 69D:
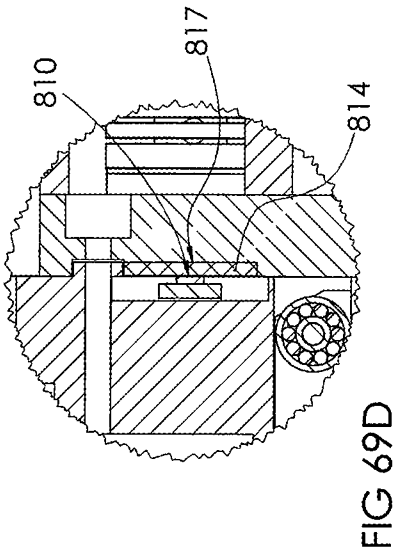
Figure 71:
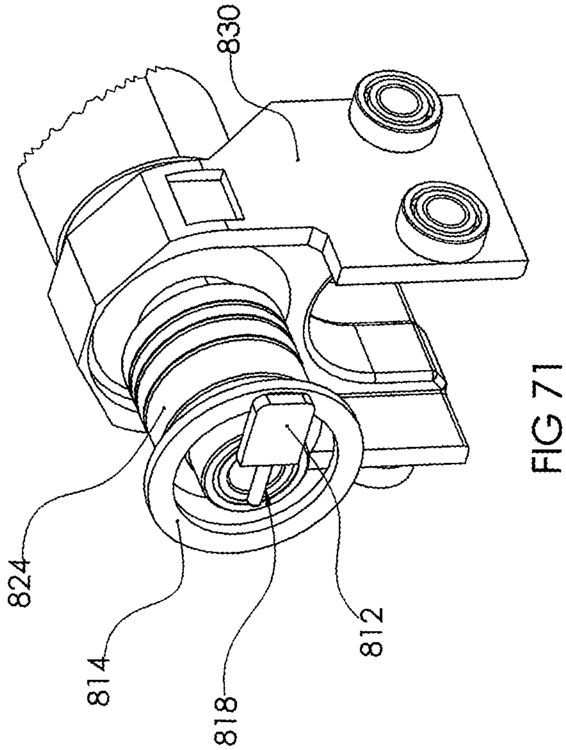
Figure 70:
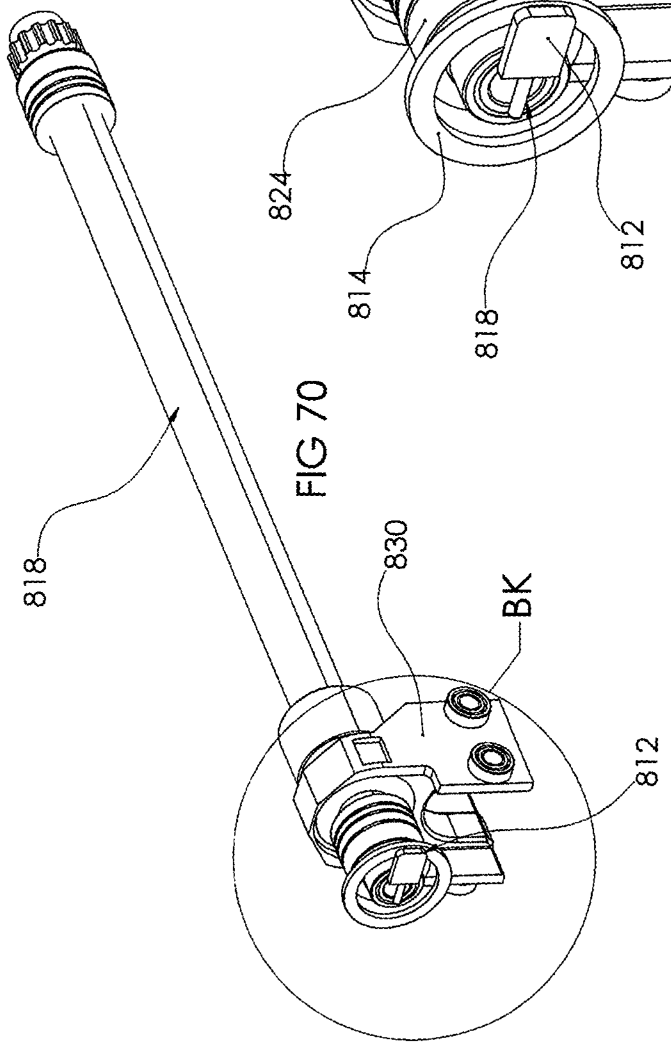
Figure 73A:
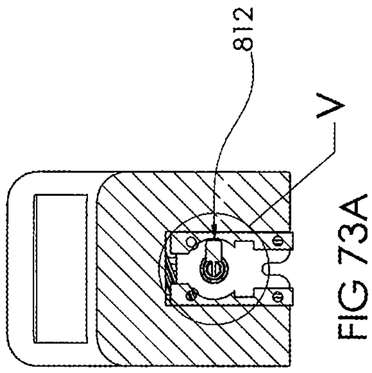
Figure 72:
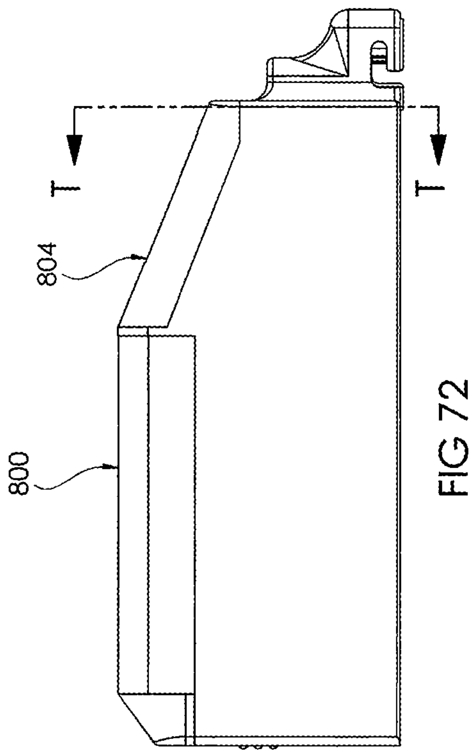
Figure 73B:
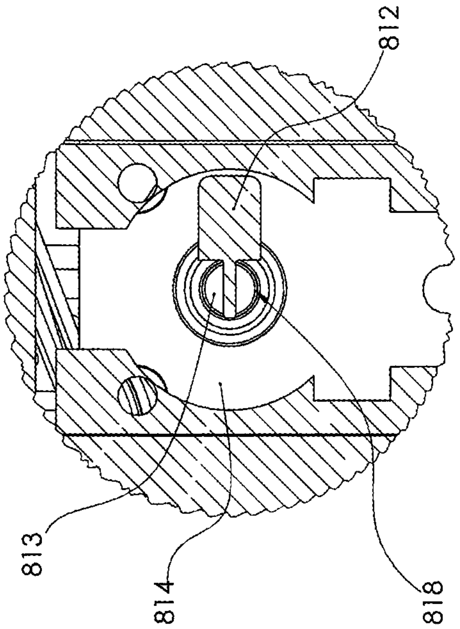
Figure 75:
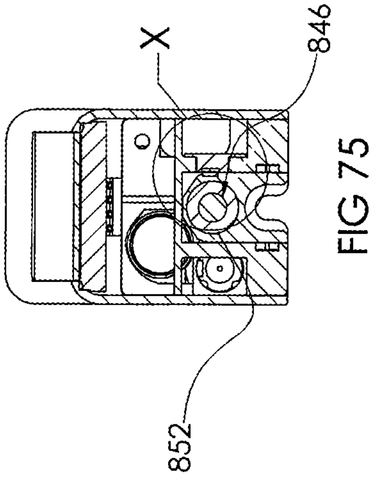
Figure 76B:
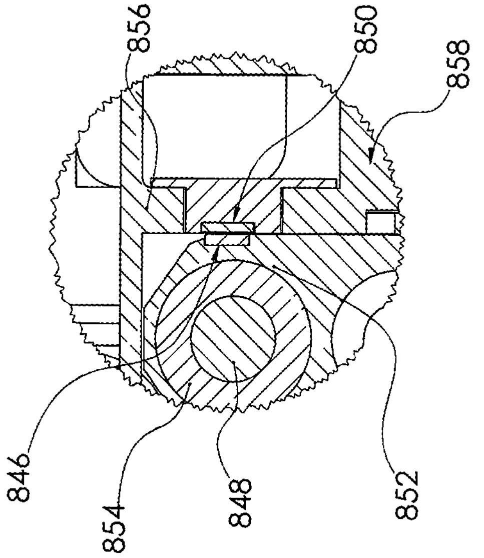
Figure 74:
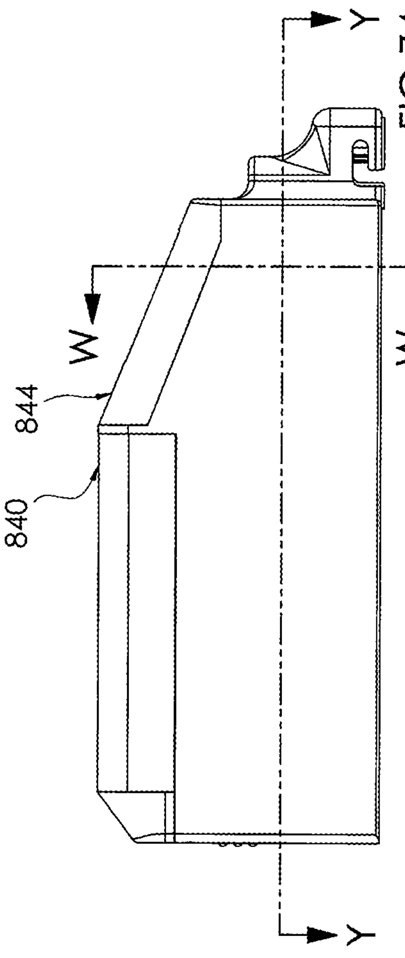
Figure 76A:
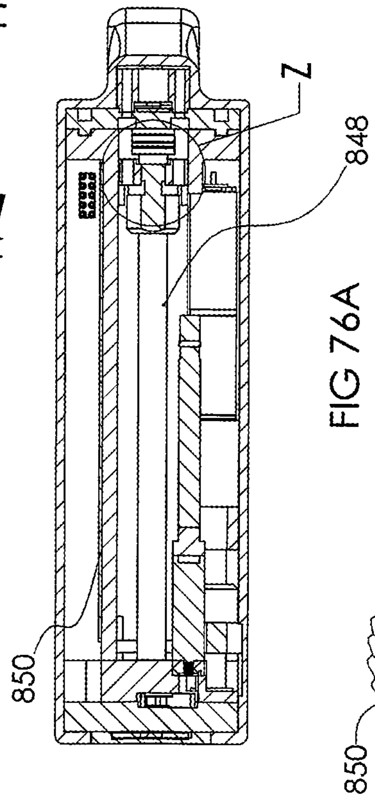
Figure 76C:
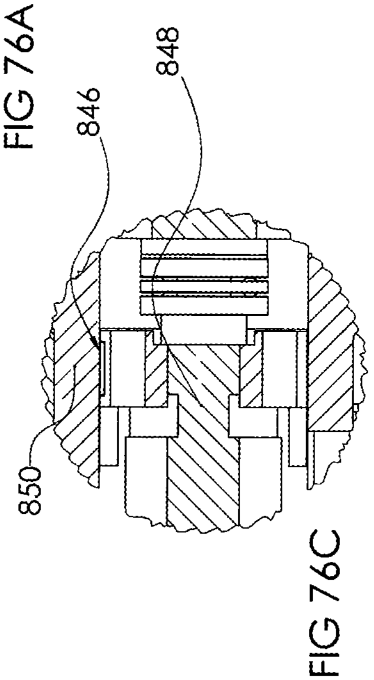
Figure 77:
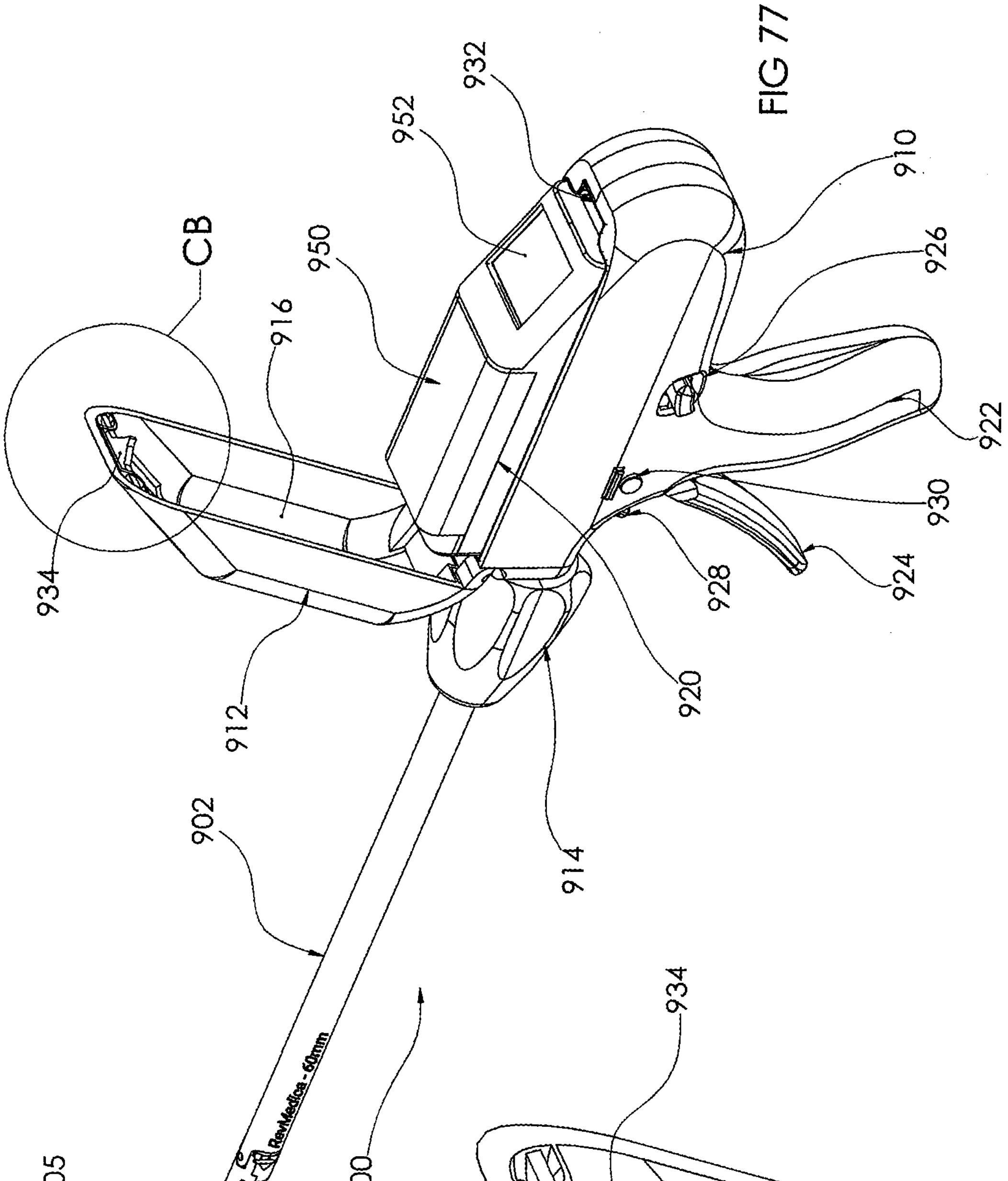
Figure 78:
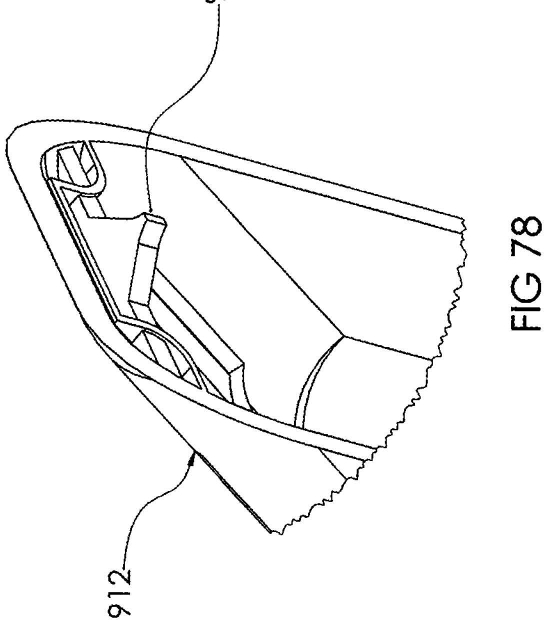
Figure 79A:
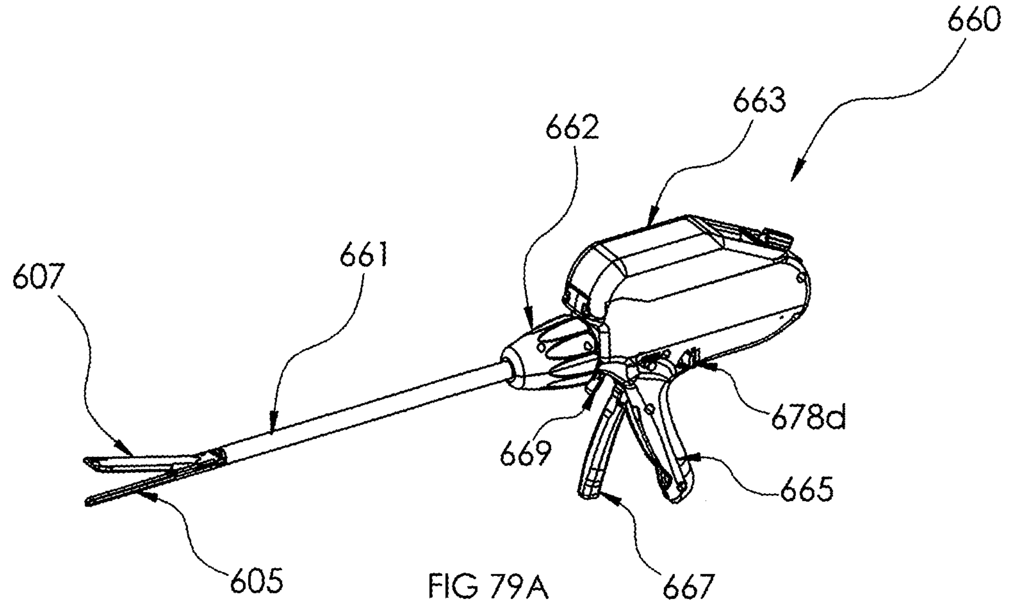
Figure 79B:
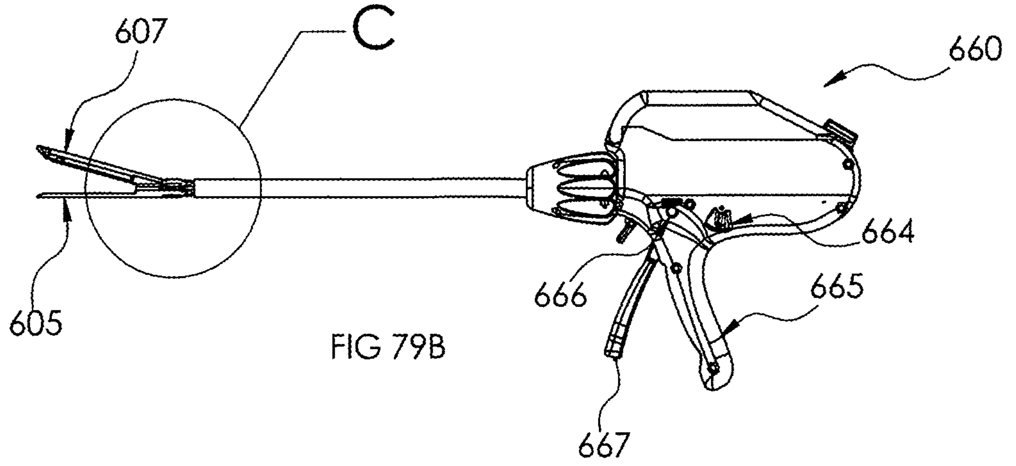
Figure 79C:
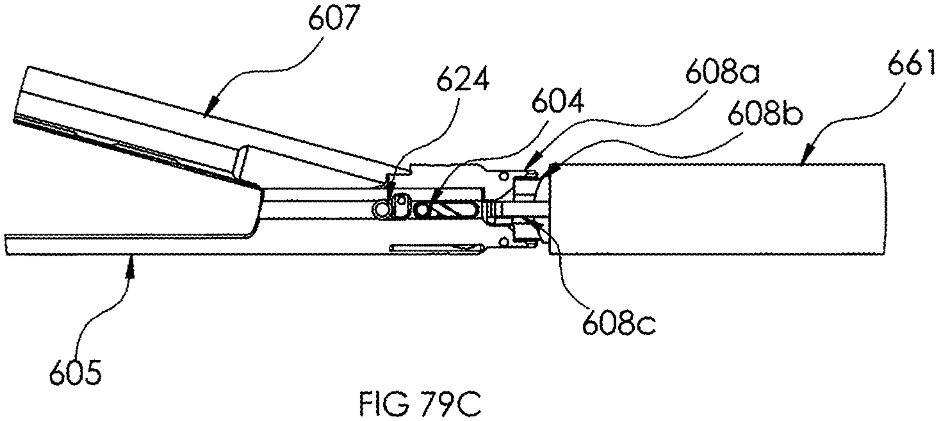
Figure 79D:
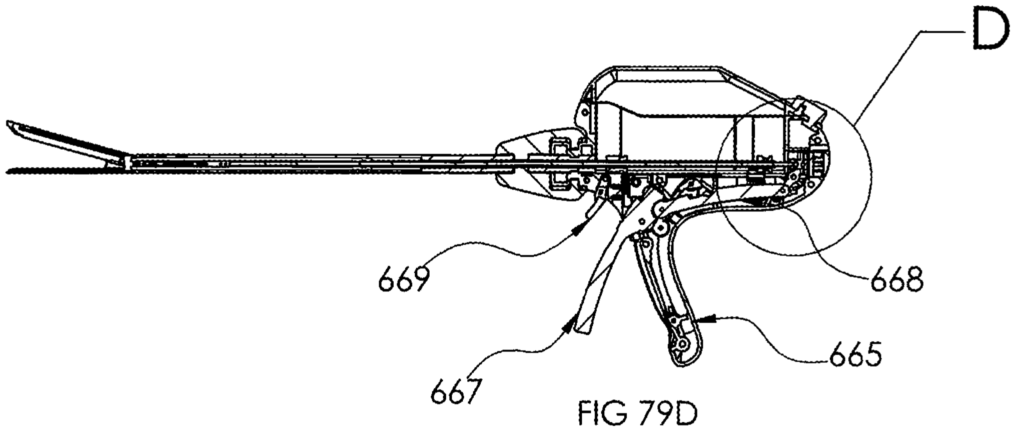
Figure 79E:
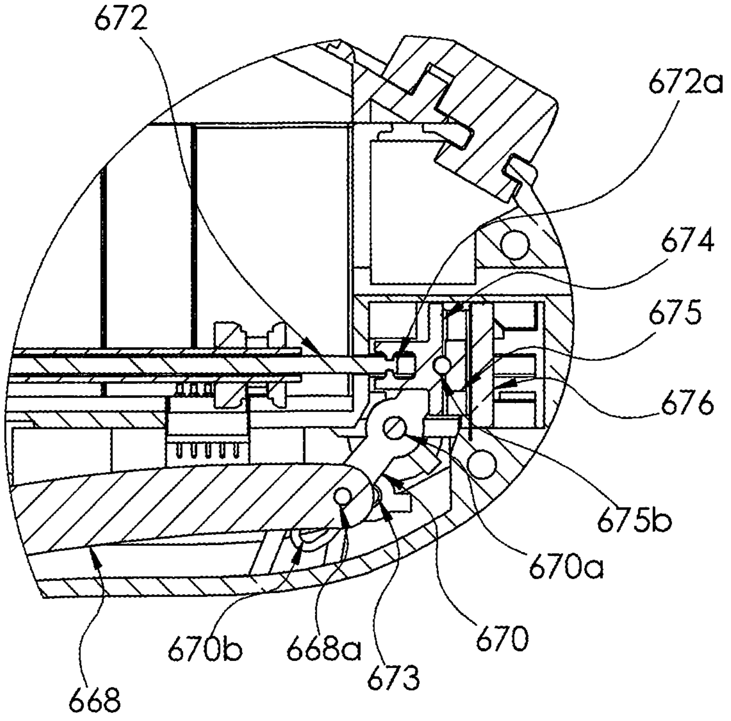
Figure 79F:
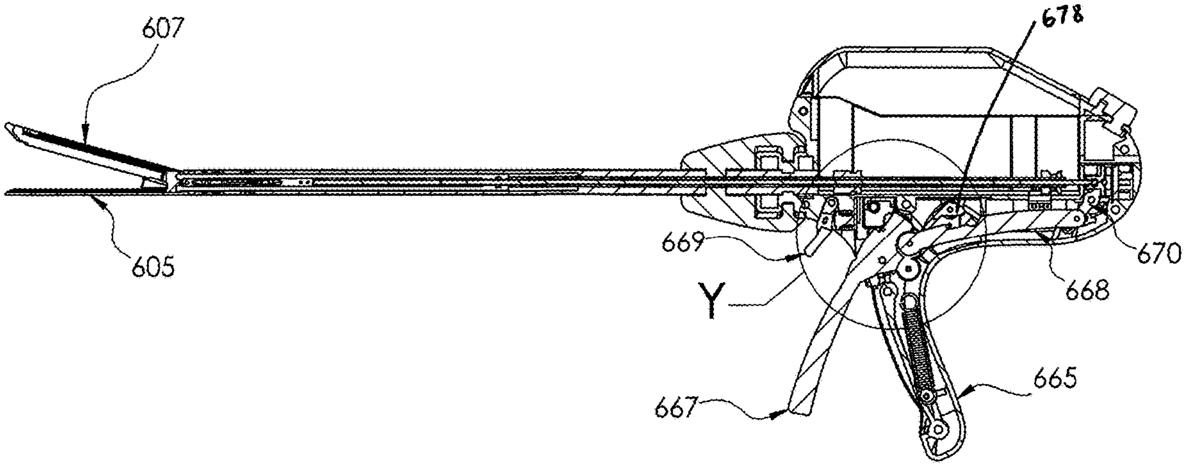
Figure 79G:
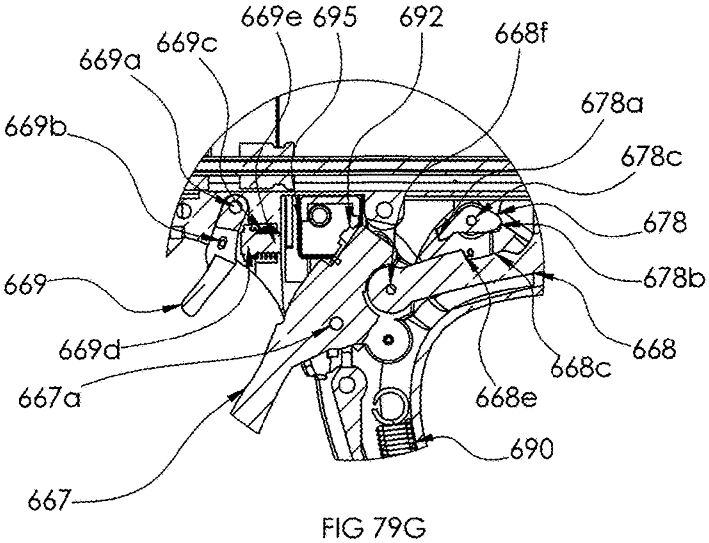
Figure 79H:
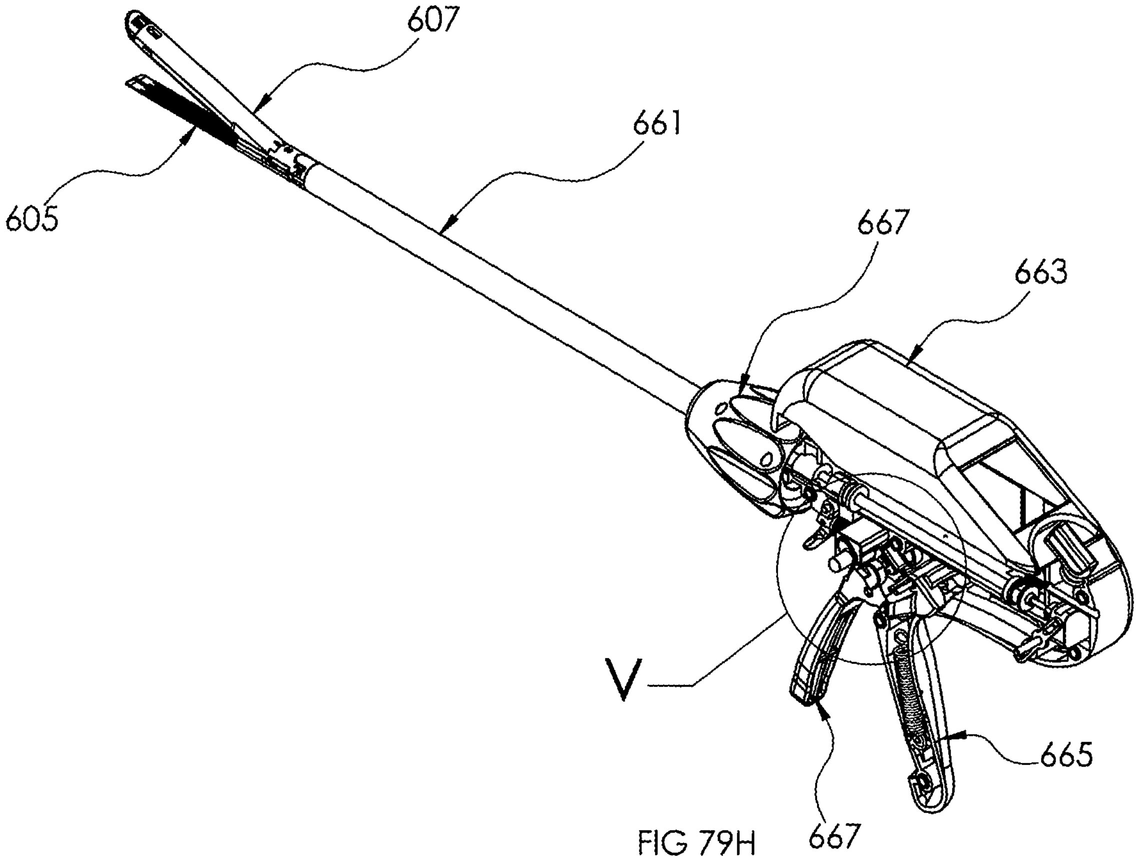
Figure 79I:
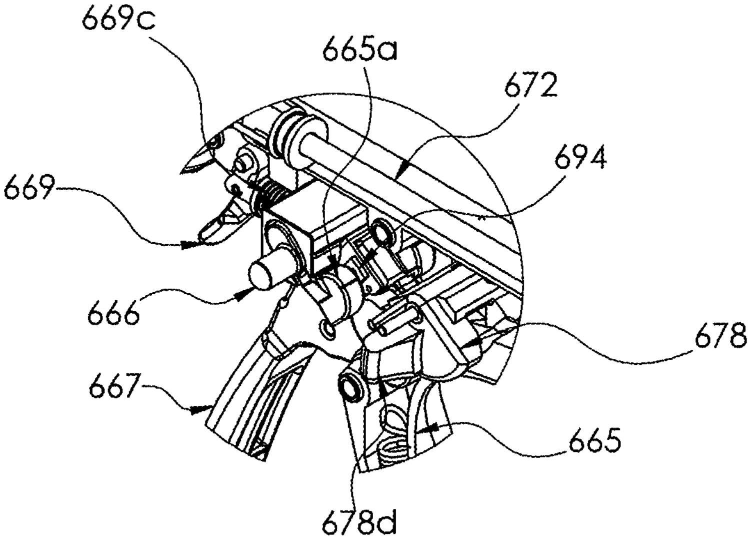
Figure 80A:
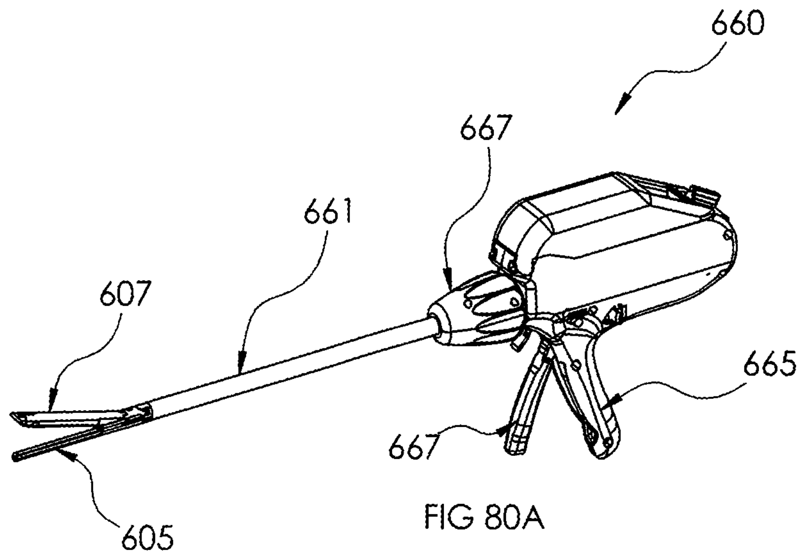
Figure 80B:
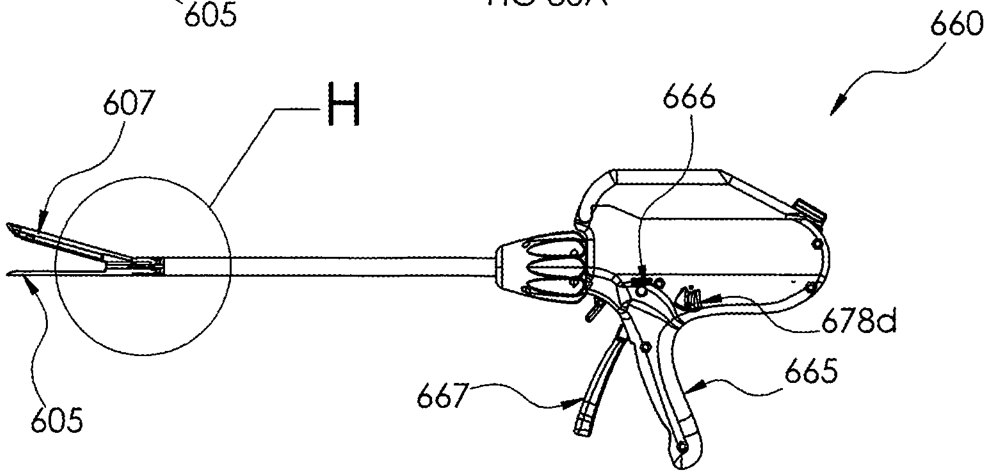
Figure 80C:
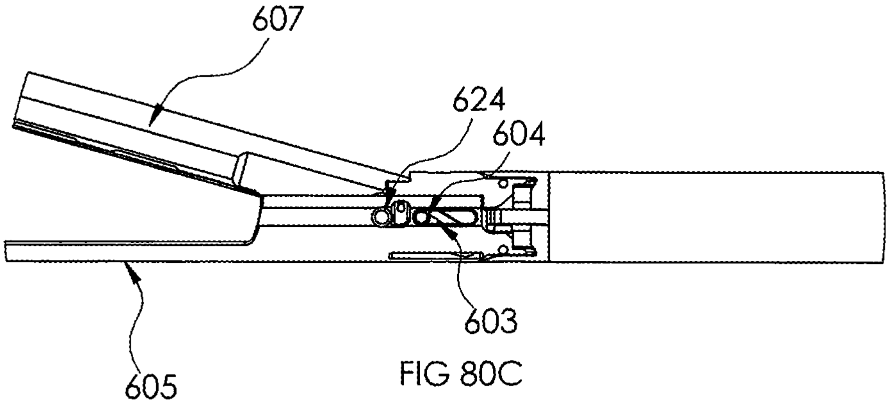
Figure 80D:
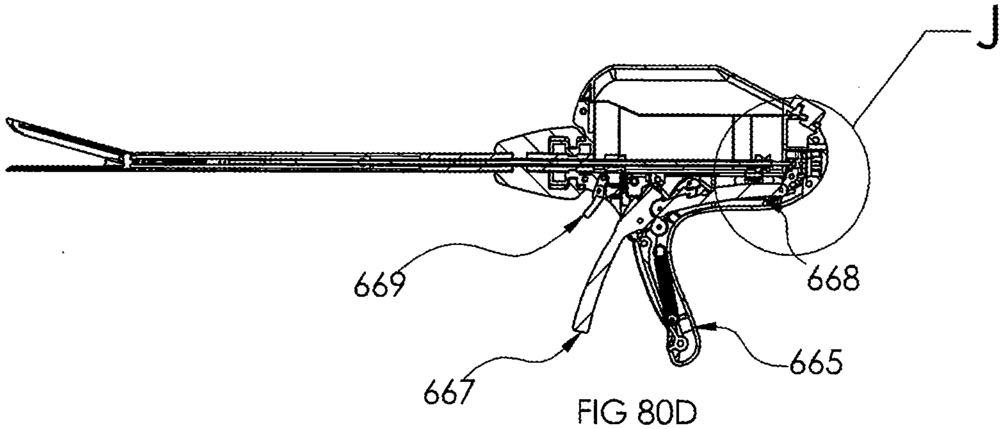
Figure 80E:
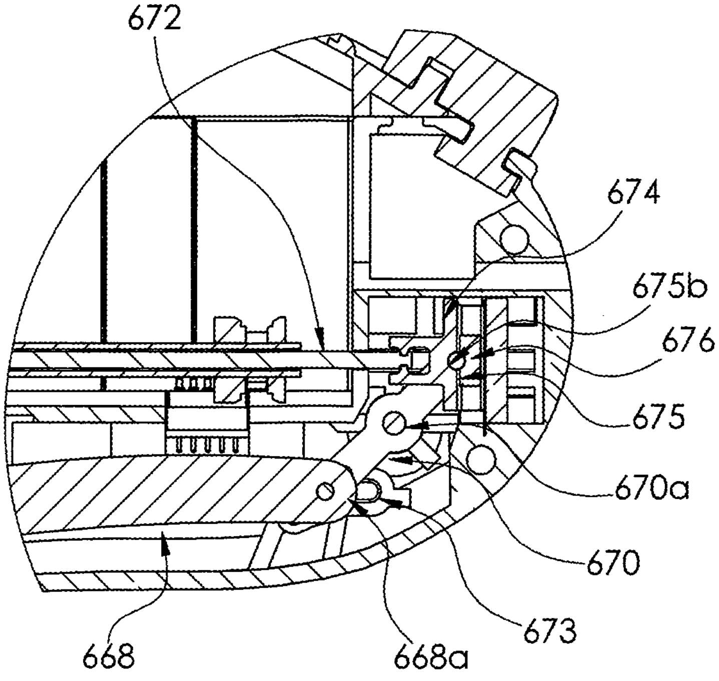
Figure 80F:
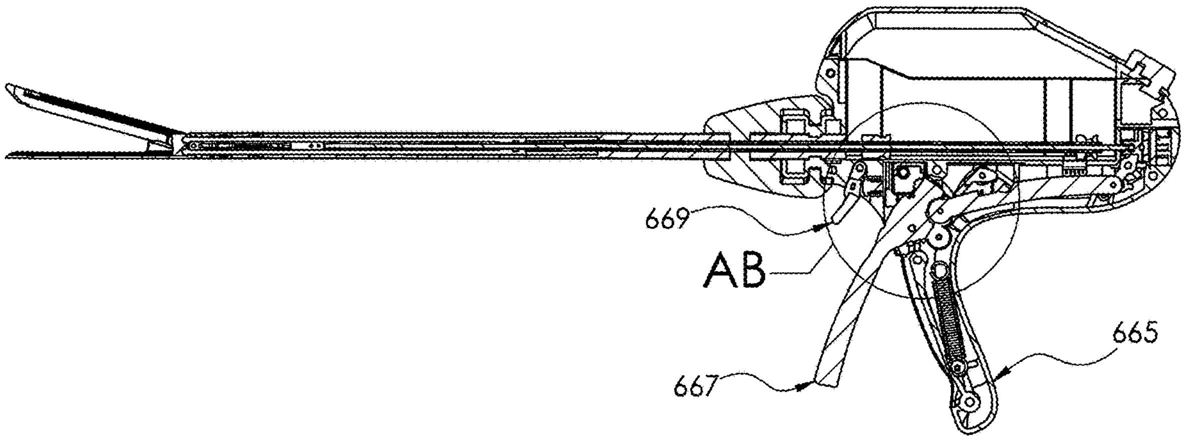
Figure 80G:
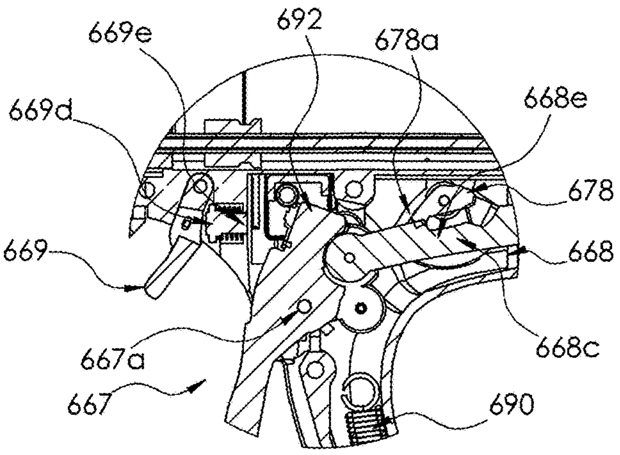
Figure 80H:
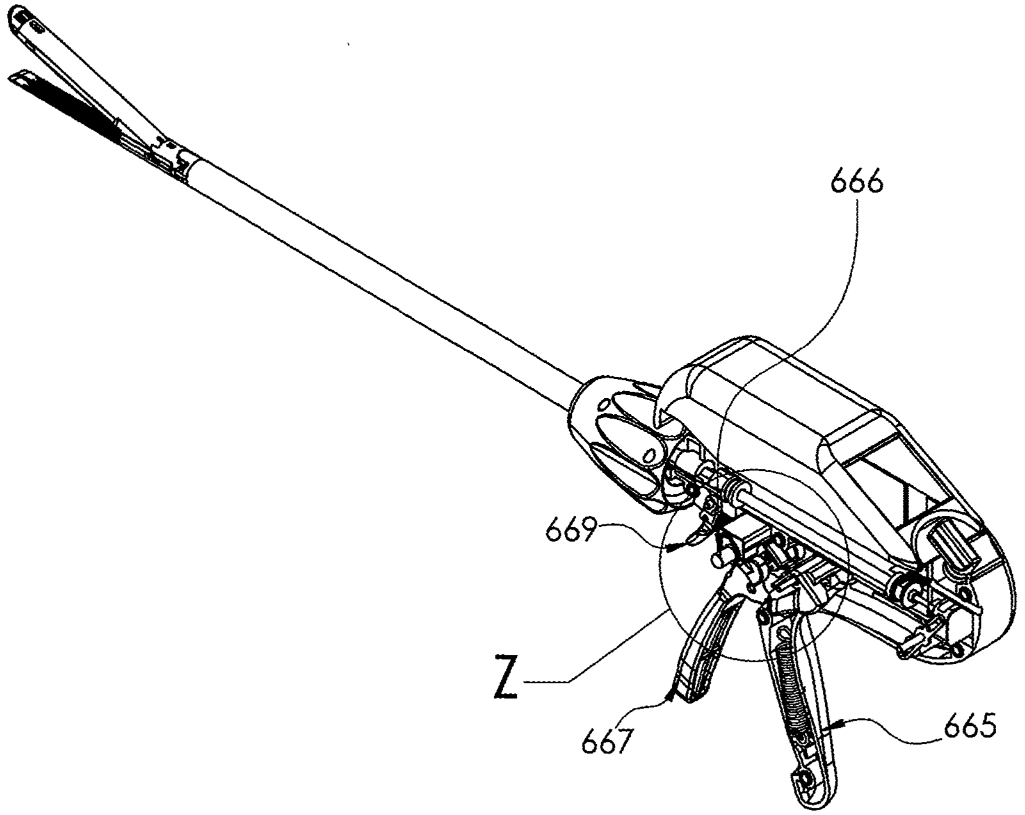
Figure 80I:
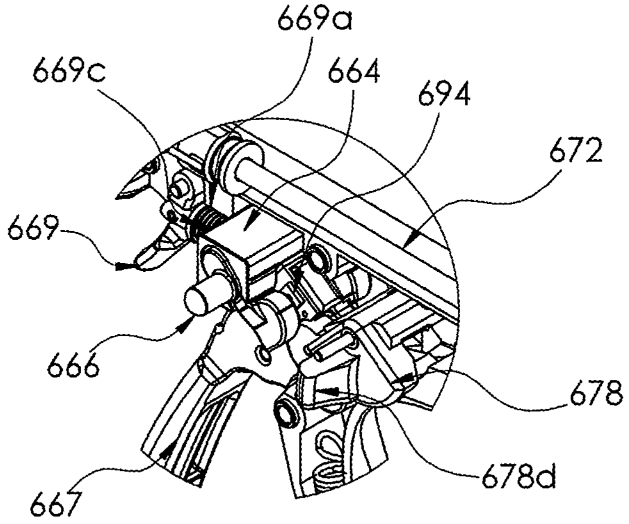
Figure 81A:
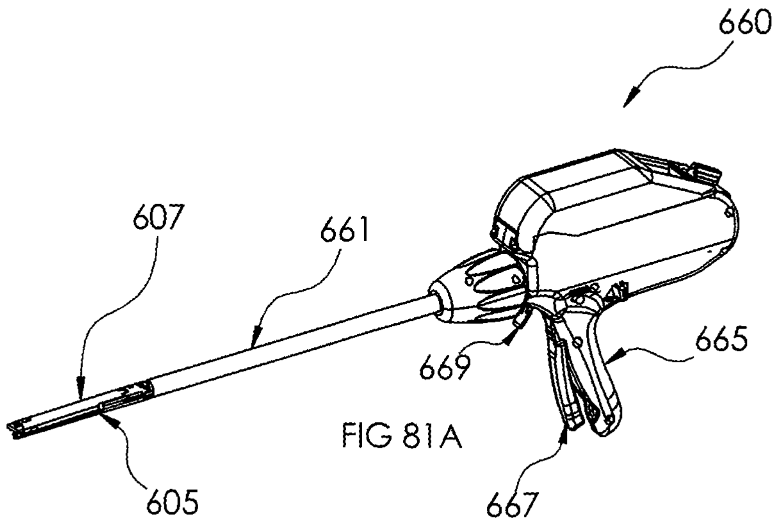
Figure 81B:
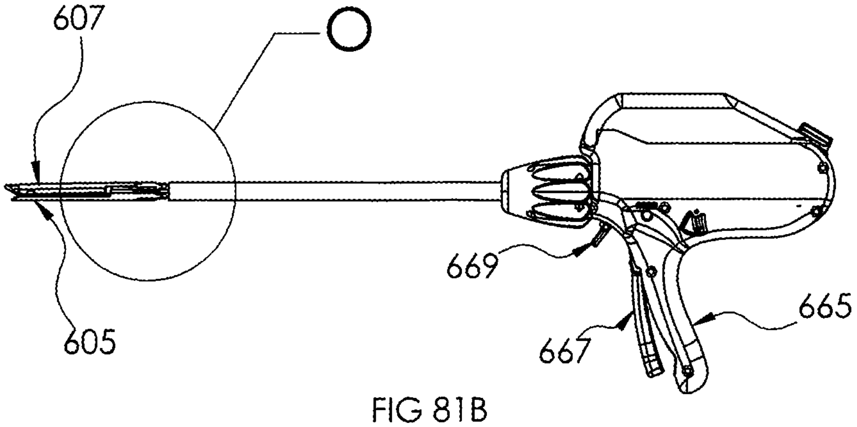
Figure 81C:
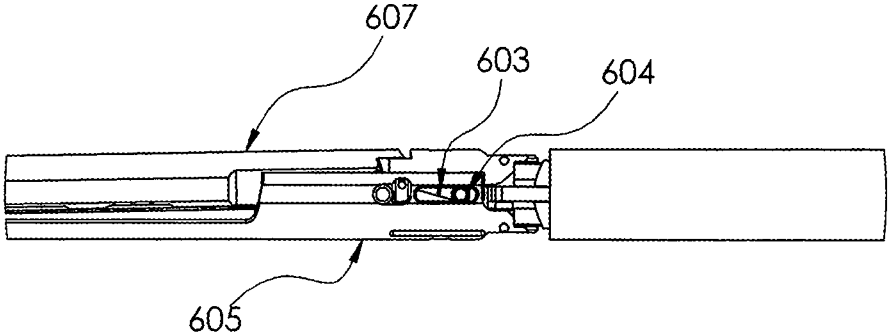
Figure 81D:
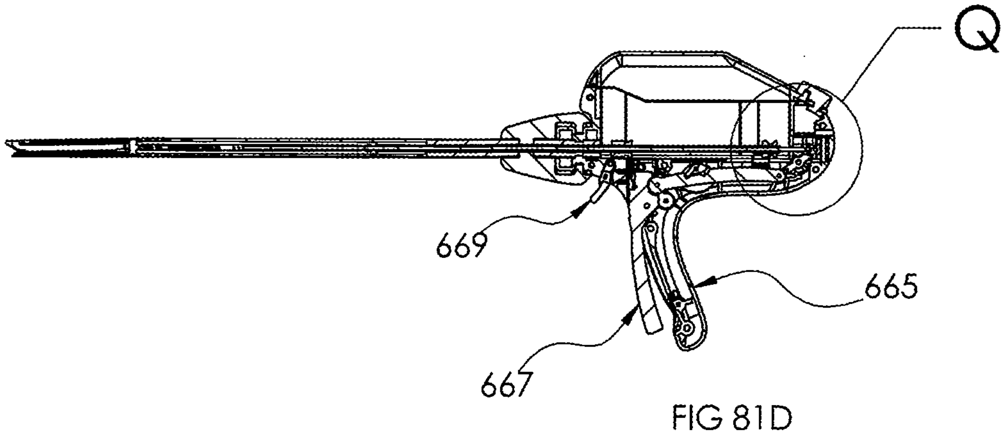
Figure 81E:
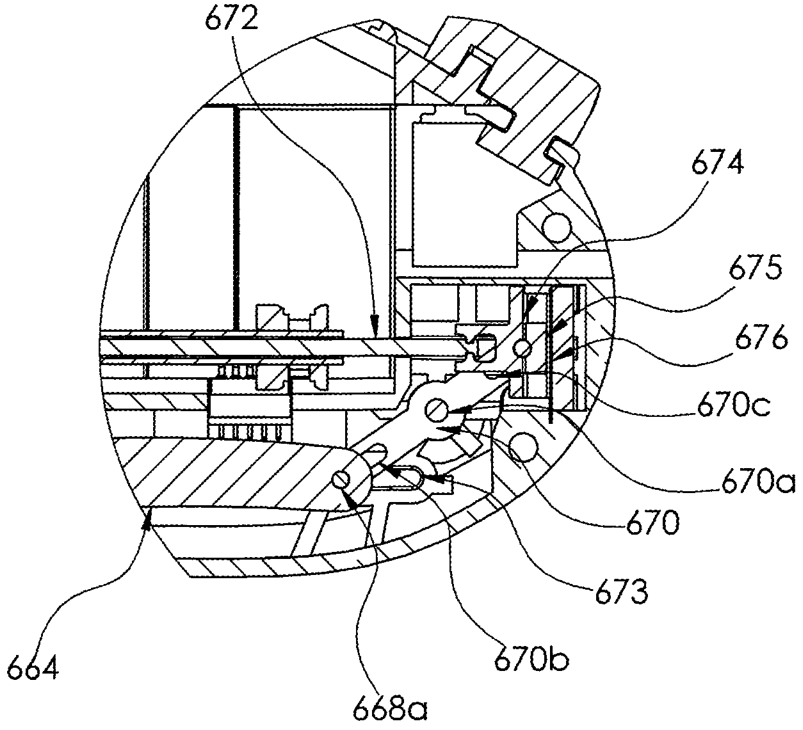
Figure 81F:
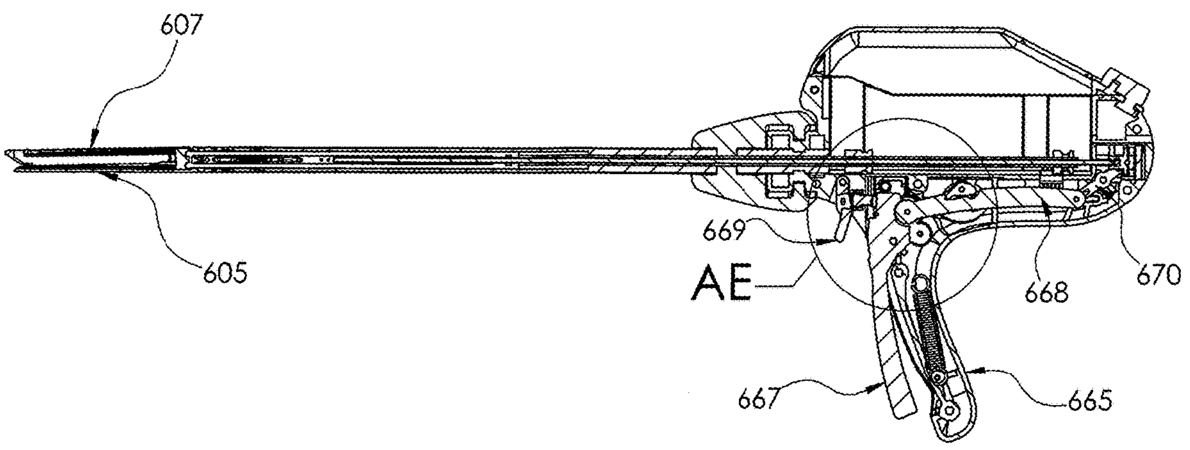
Figure 81G:
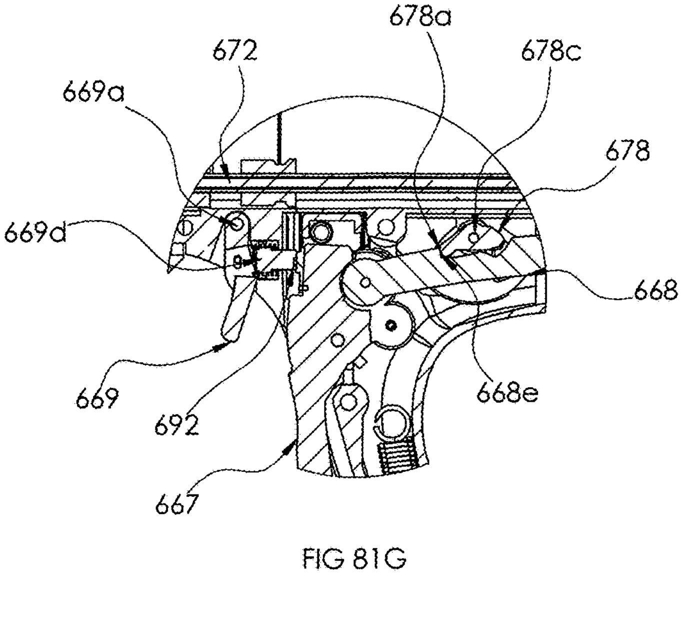
Figure 81H:
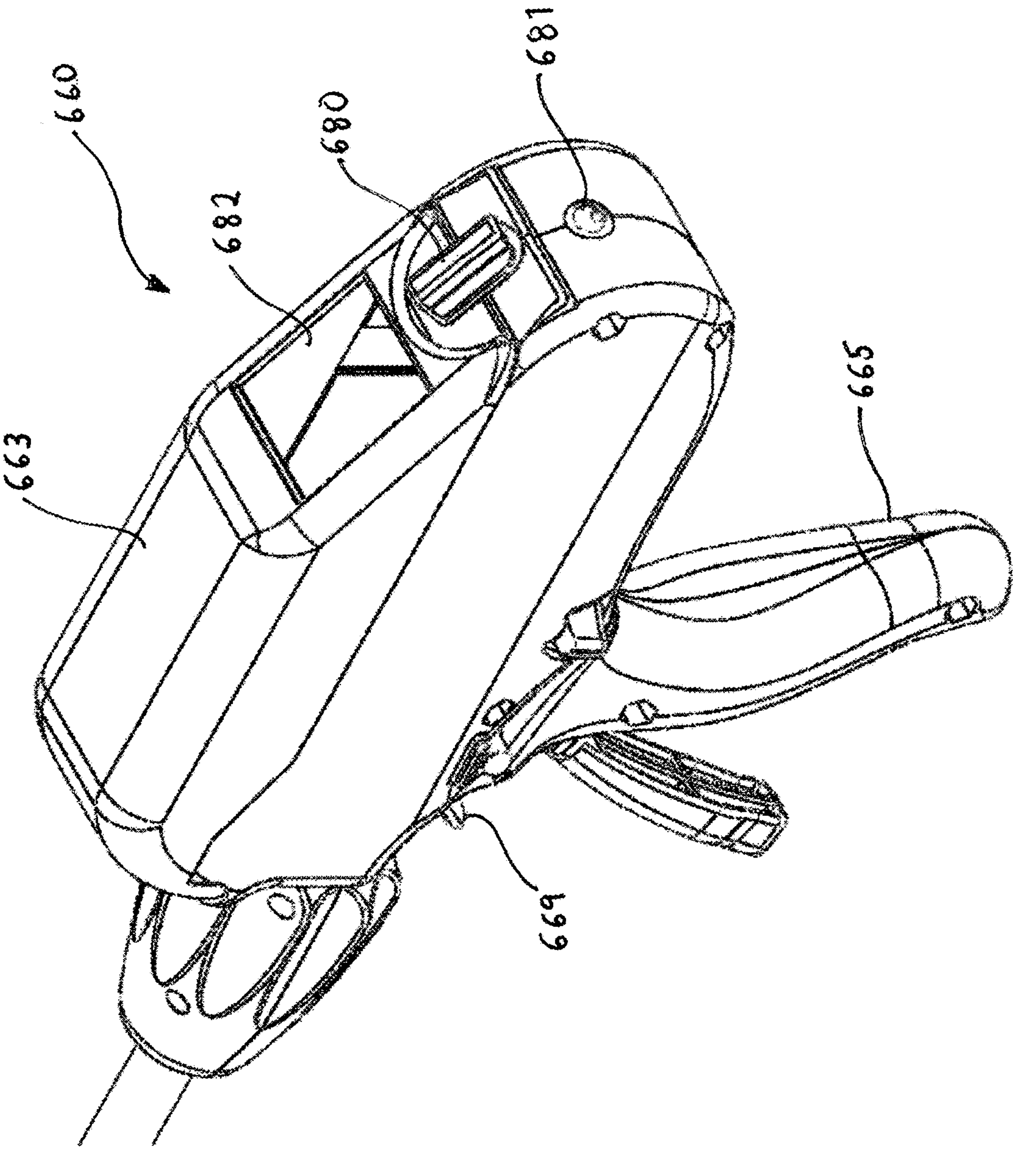
Figure 81I:
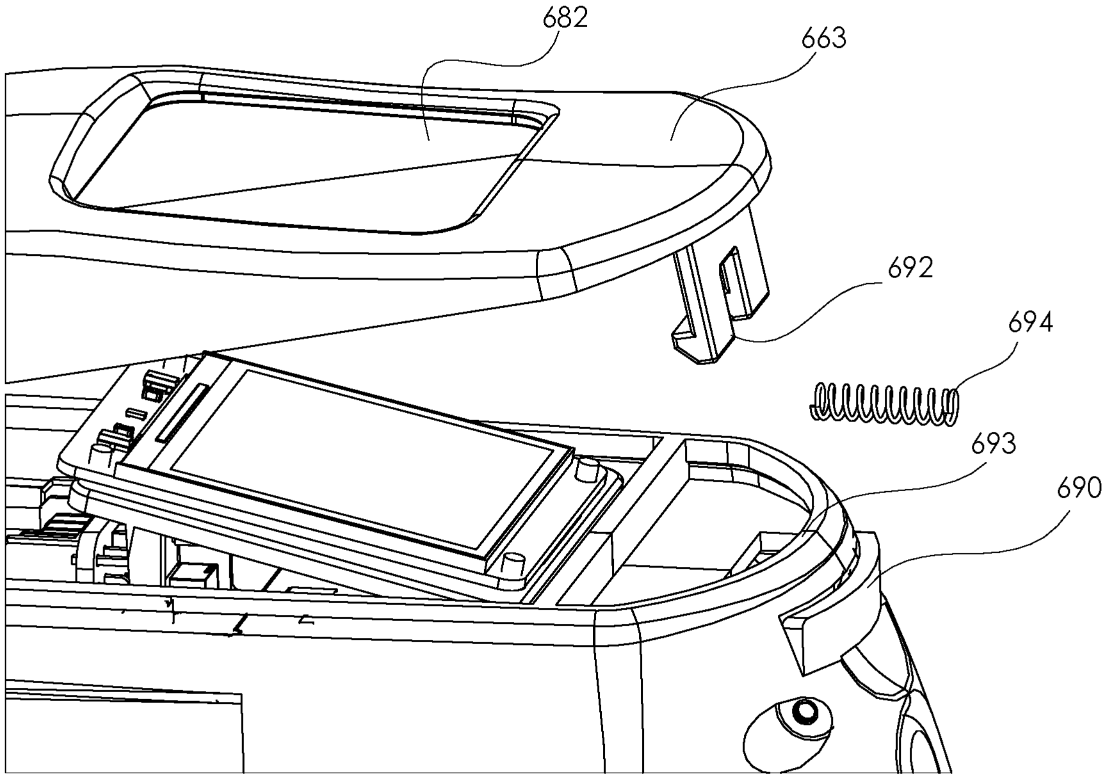
Figure 81J:
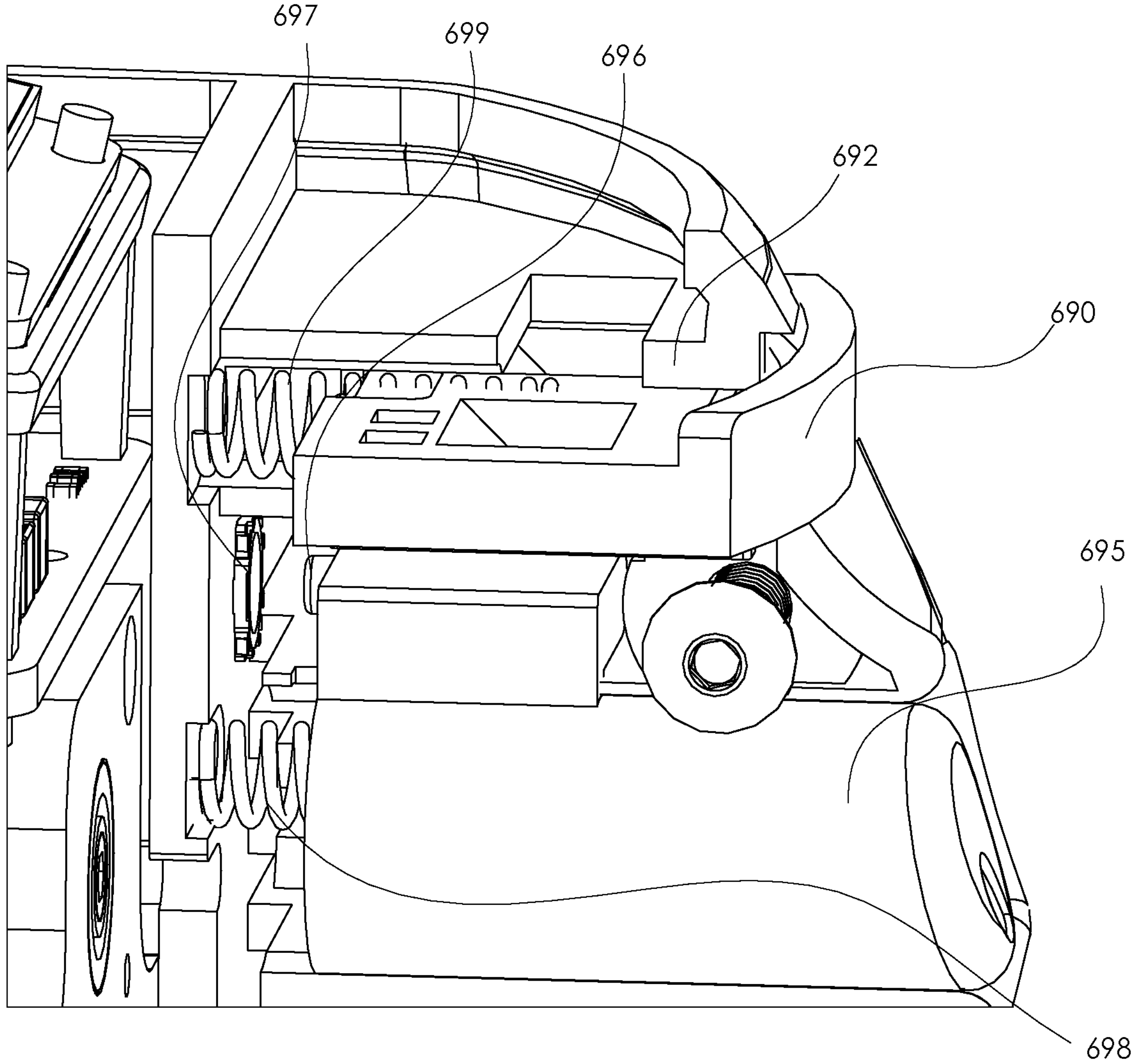
Figure 82:
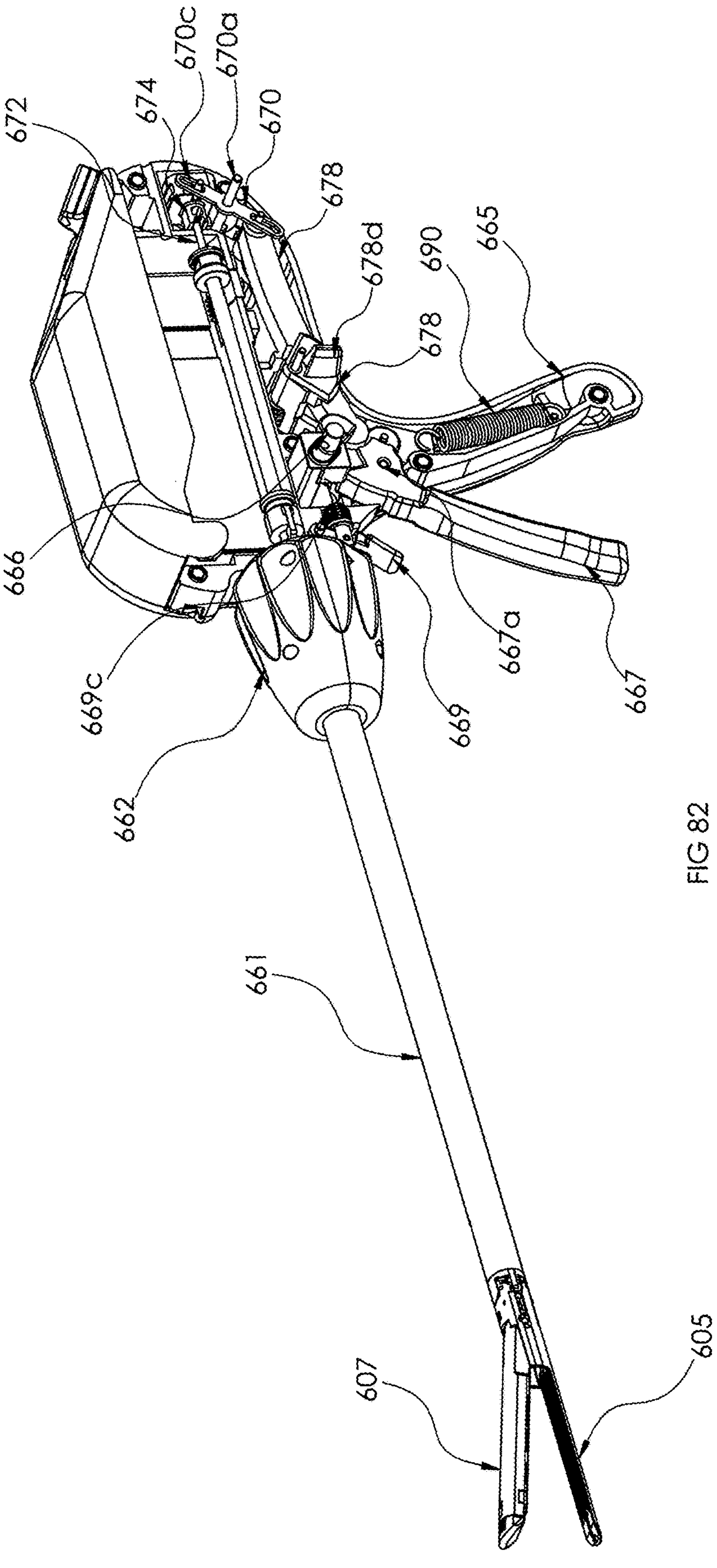
Figure 83A:
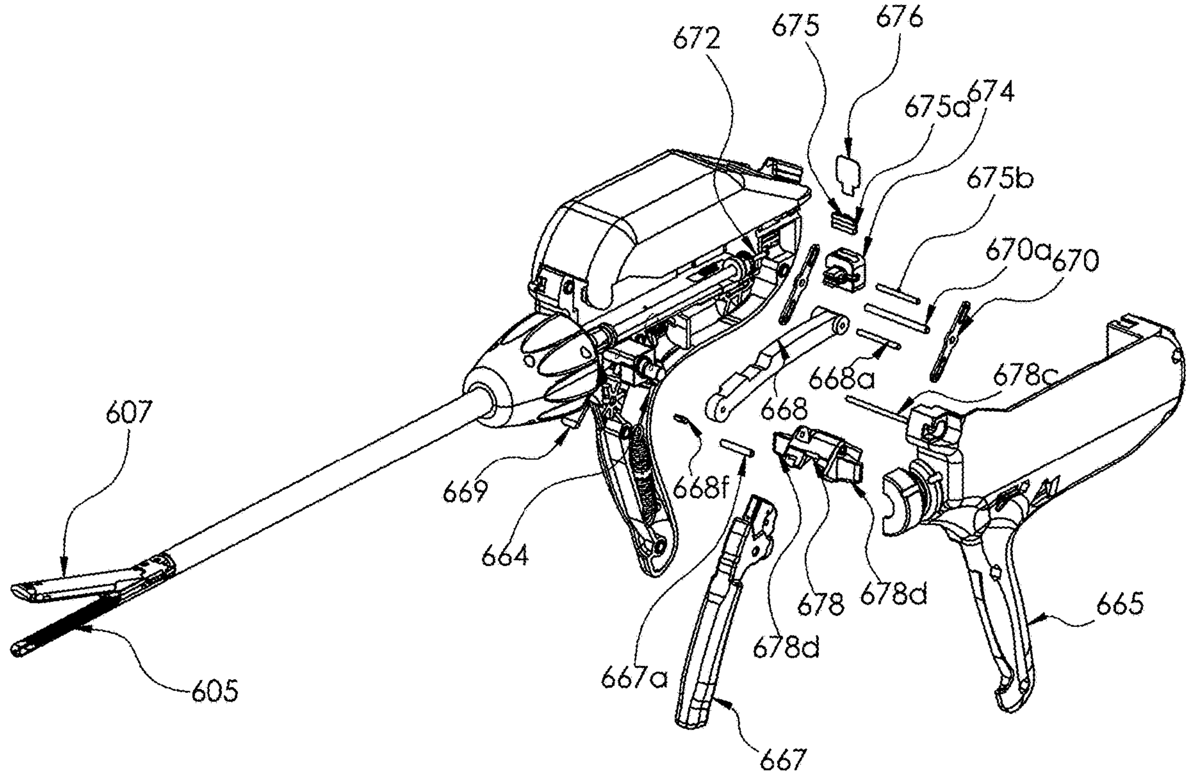
Figure 83B:
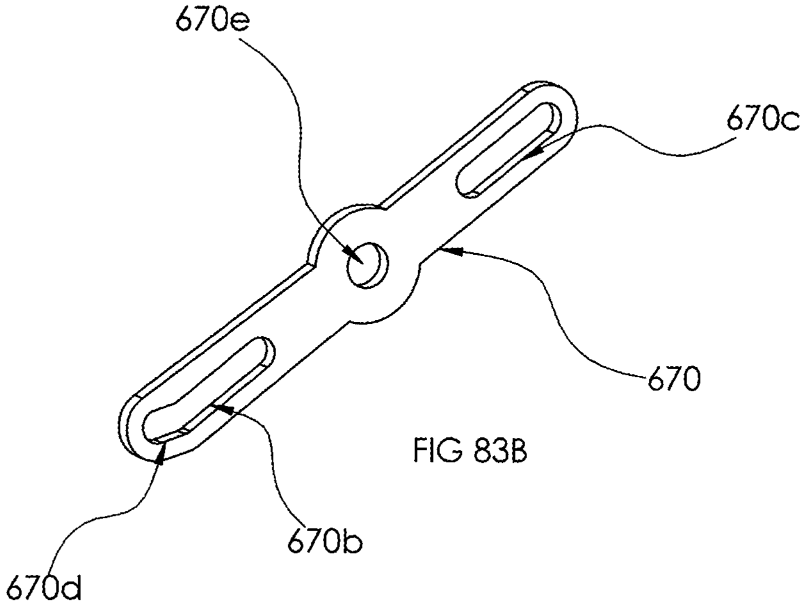
Figure 83C:
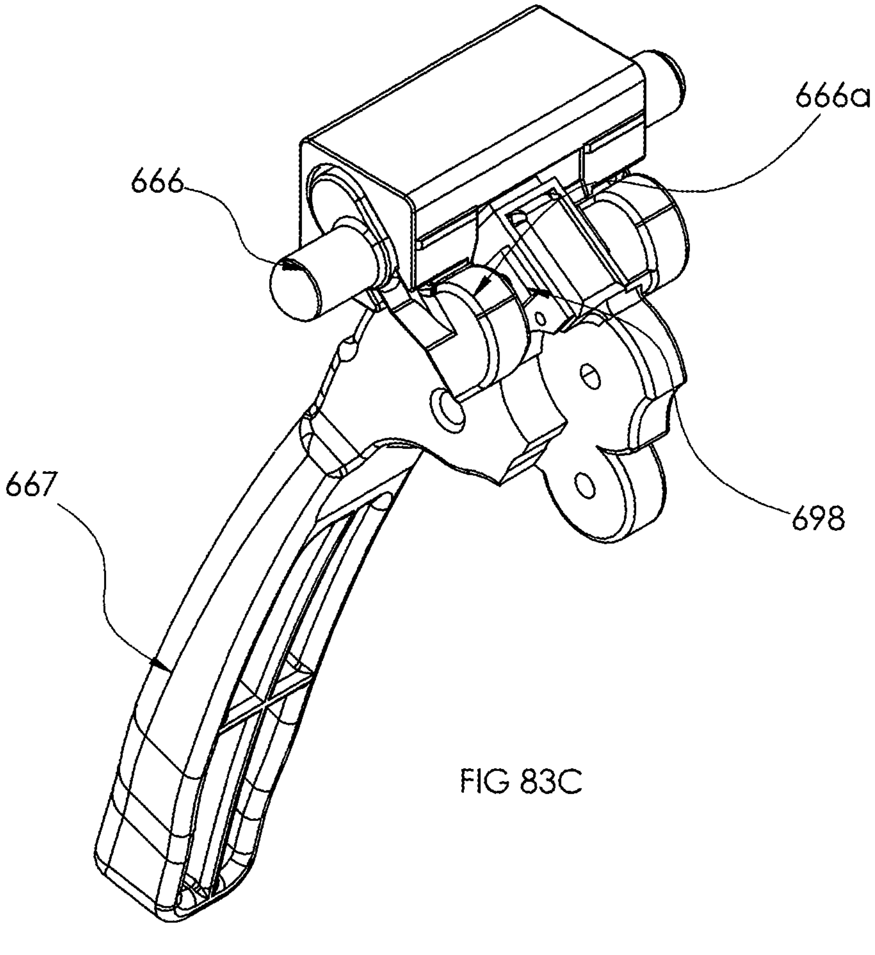
Figure 83D:
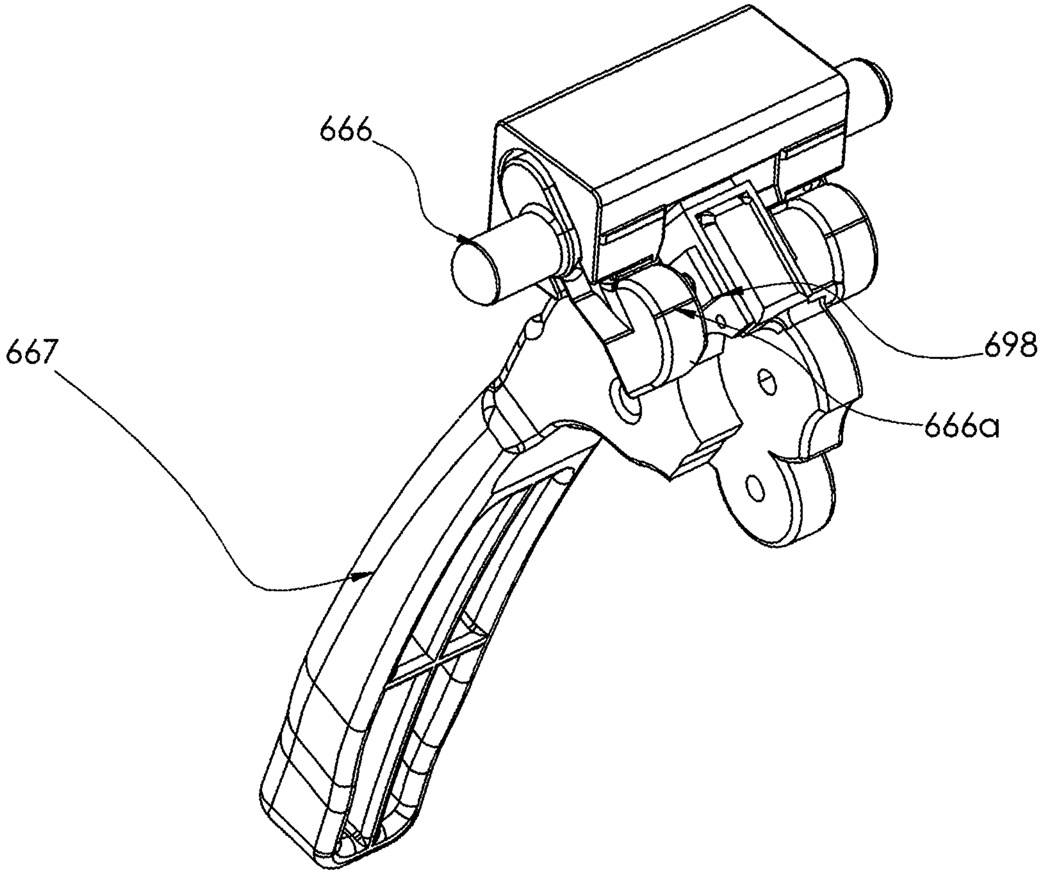
Figure 83E:
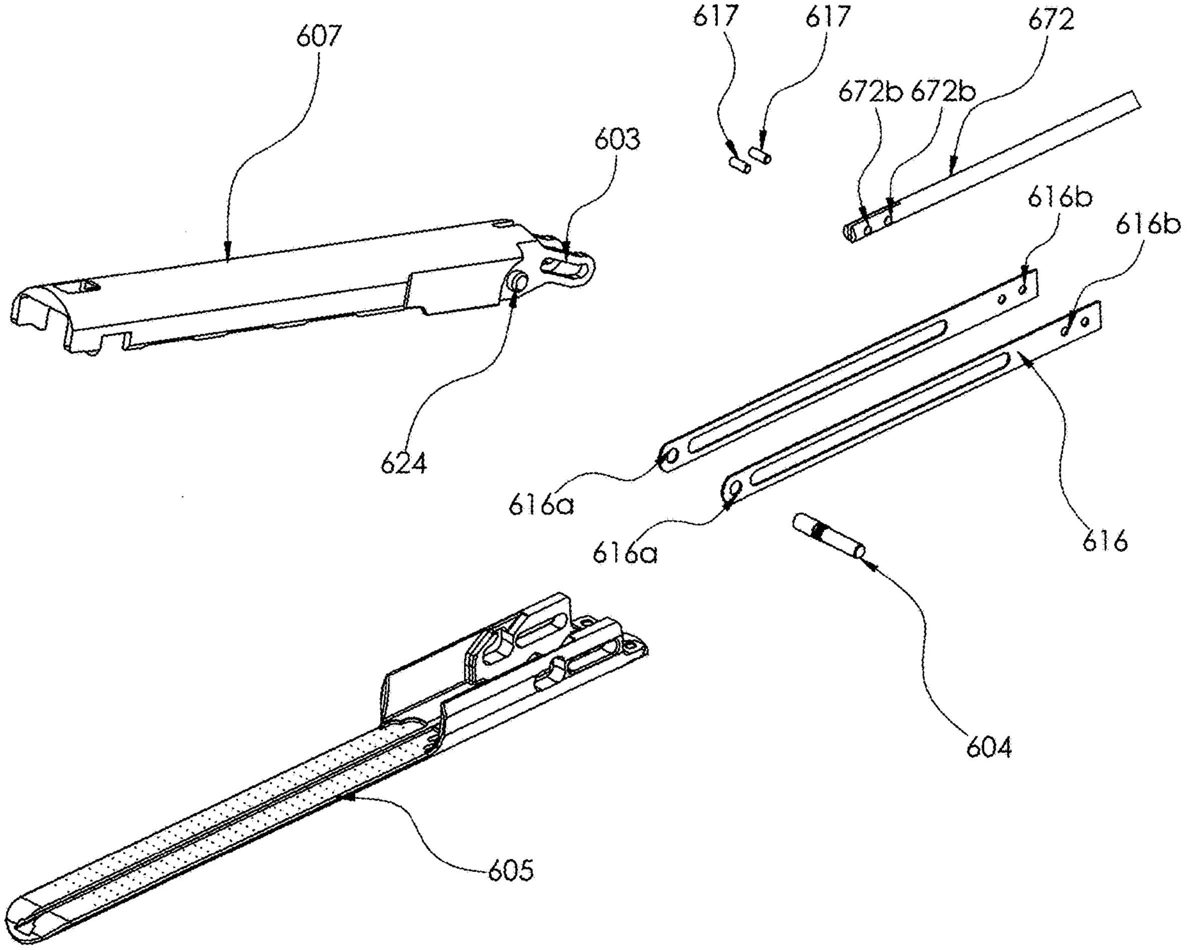
Figure 84A:
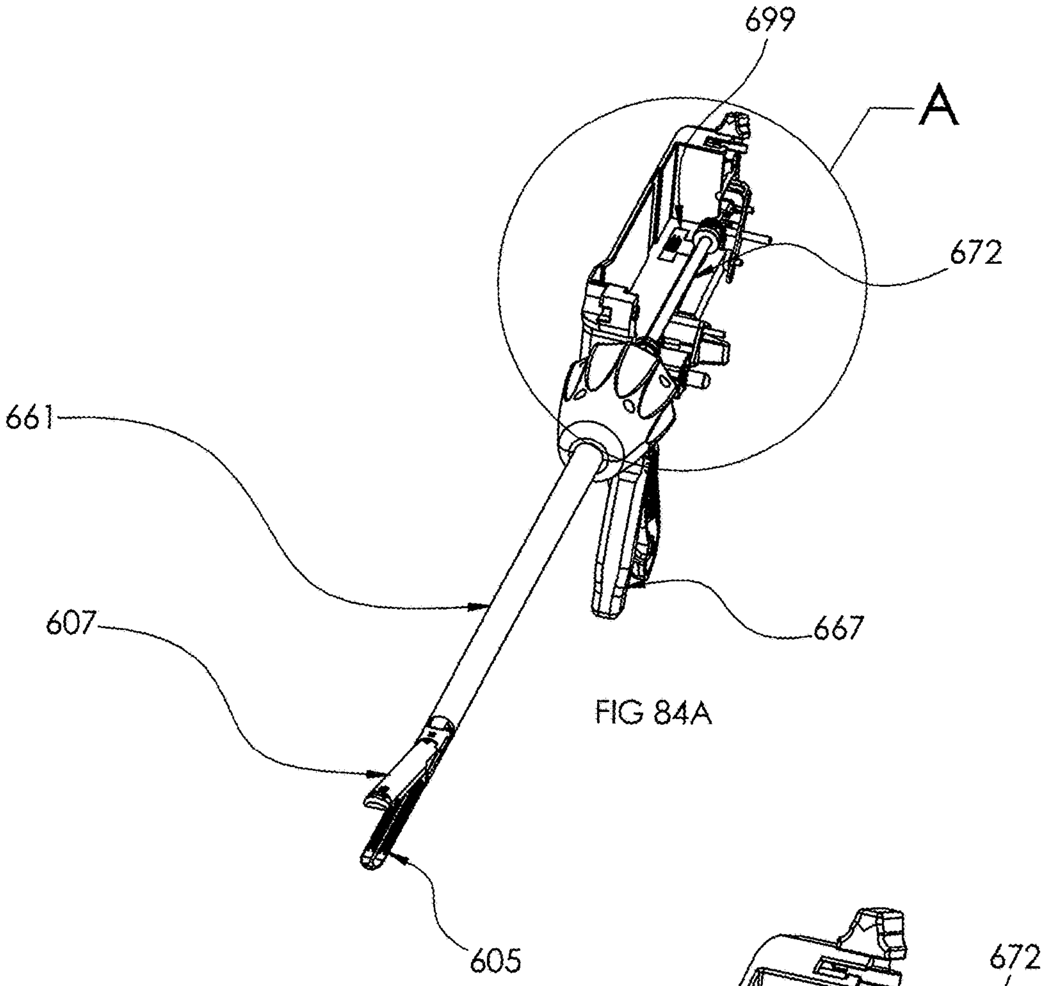
Figure 84B:
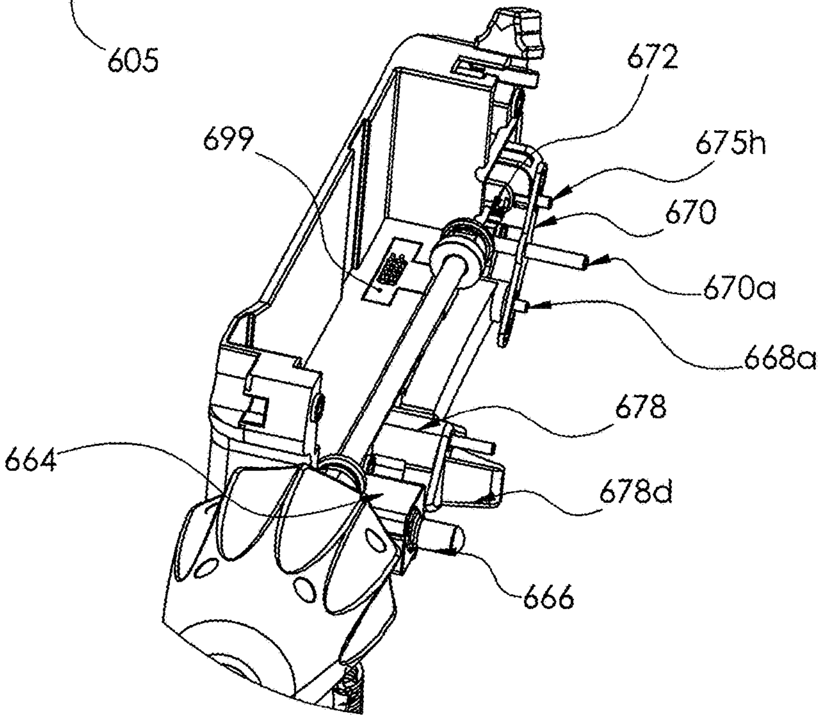
Figure 85:
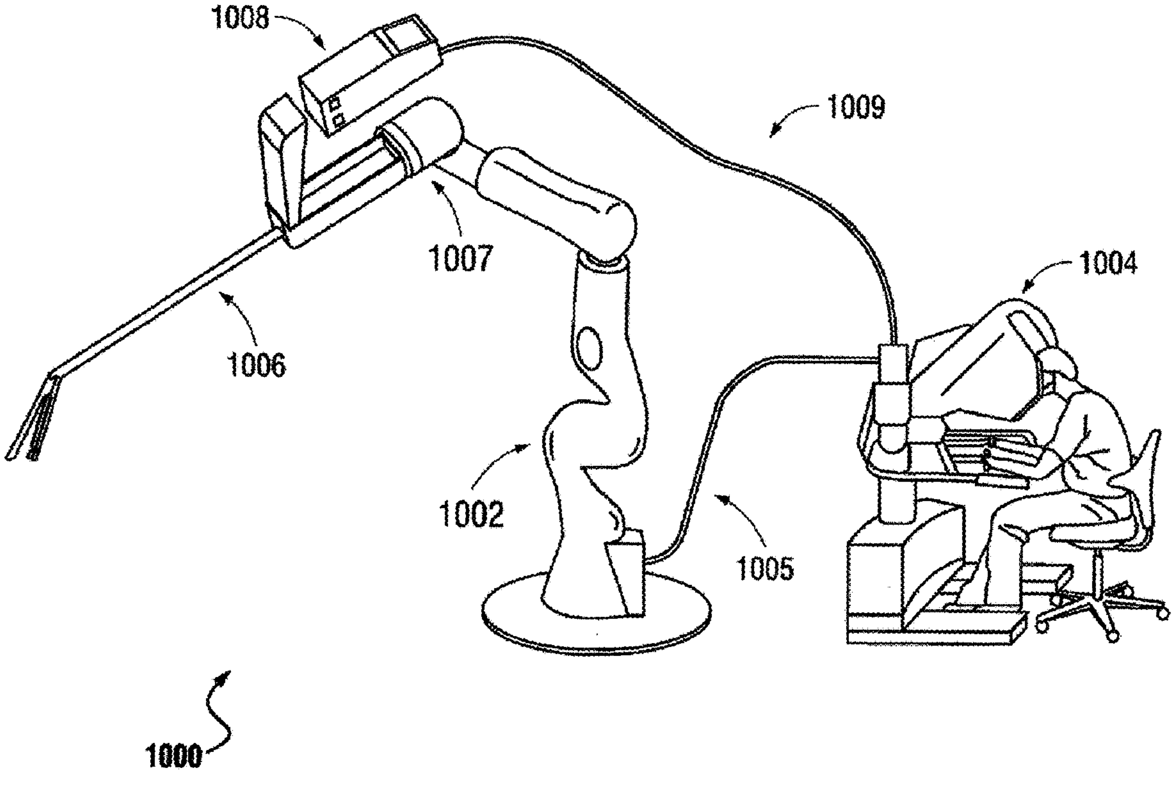
Figure 86:
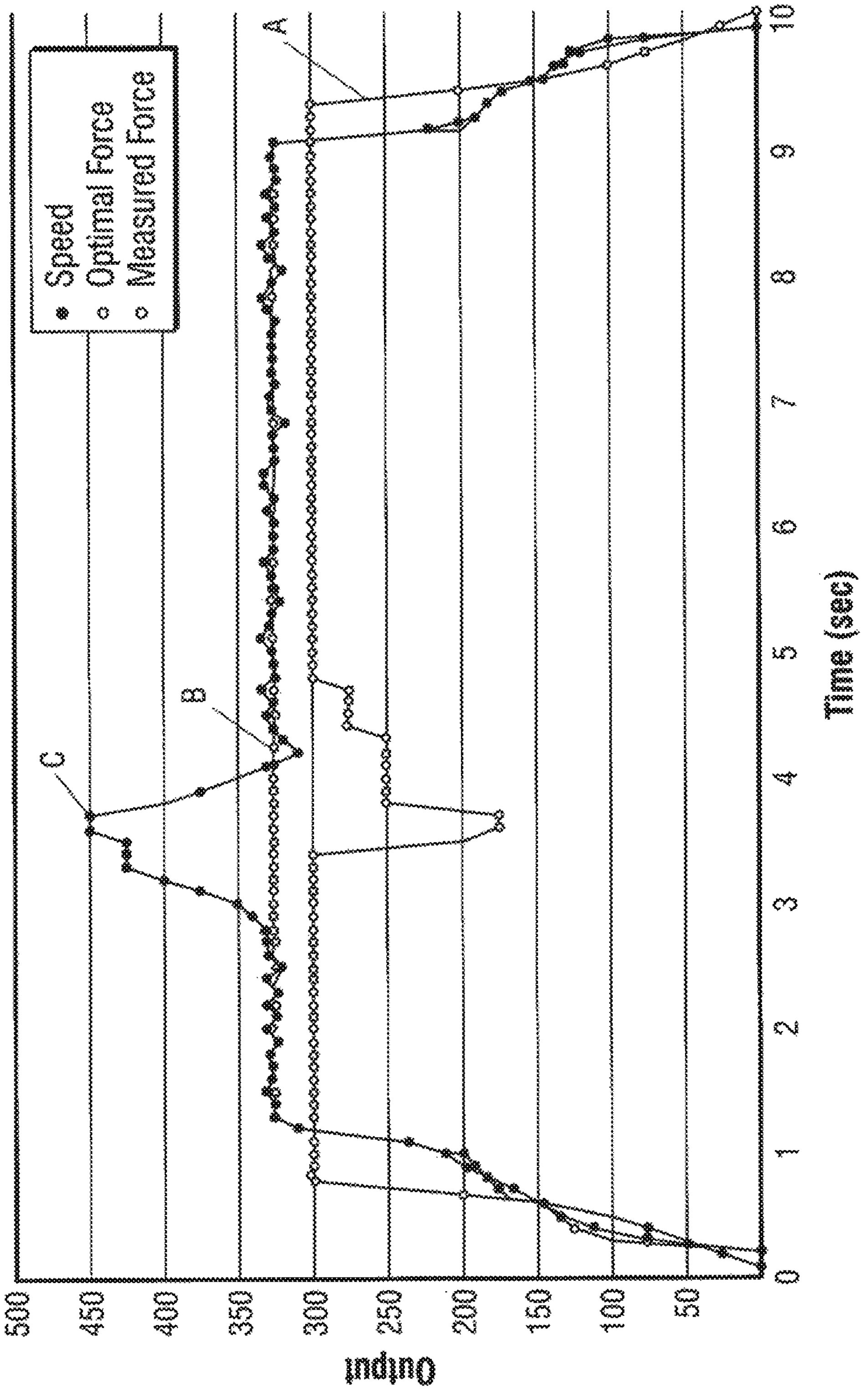
Figure 87A:
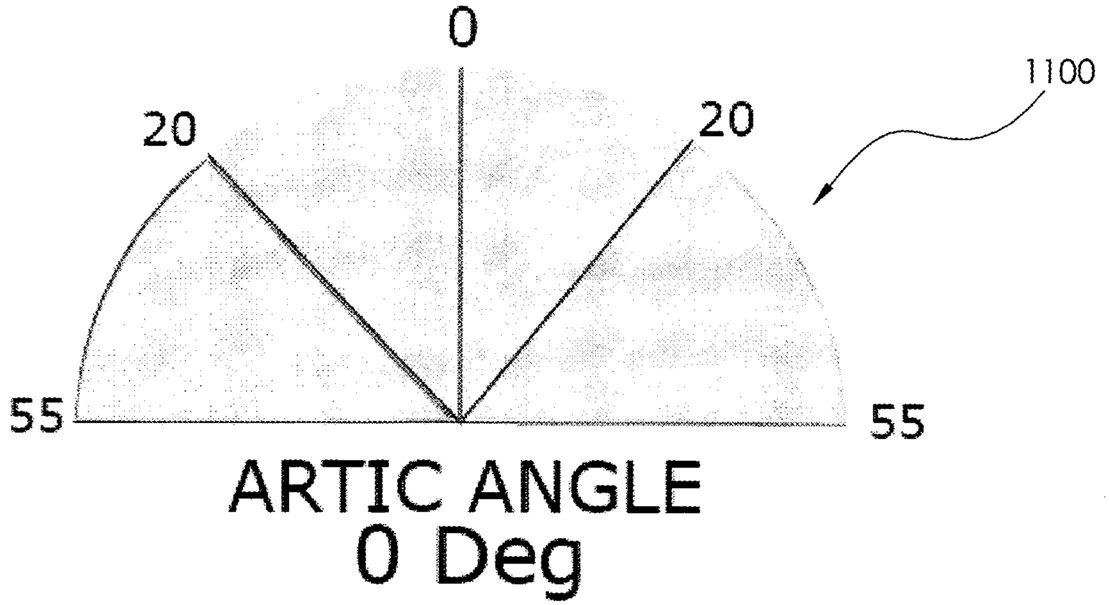
Figure 87B:
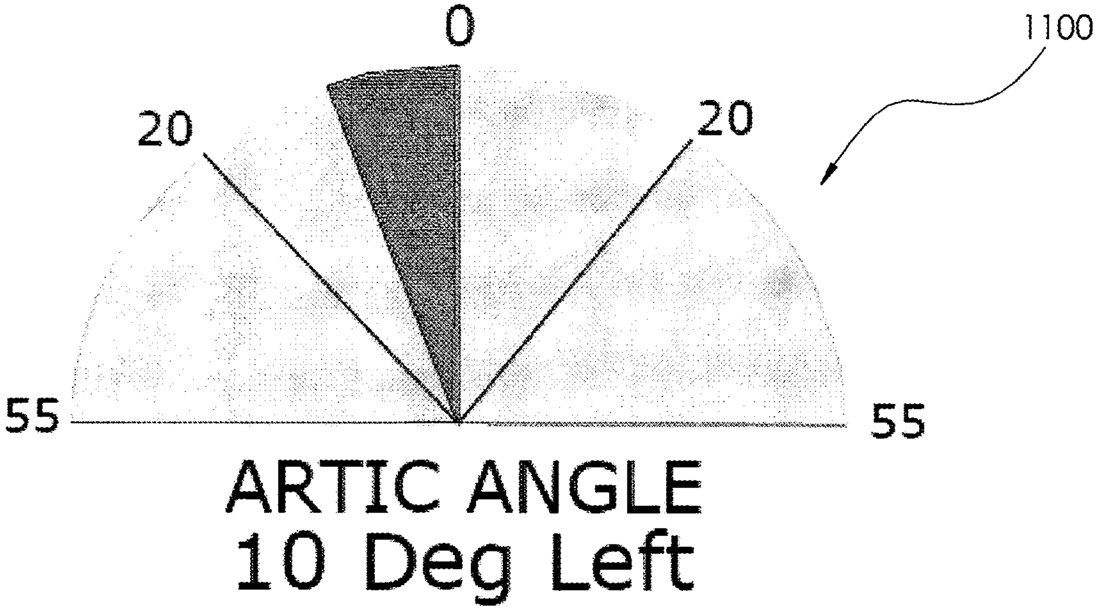
Figure 87C:
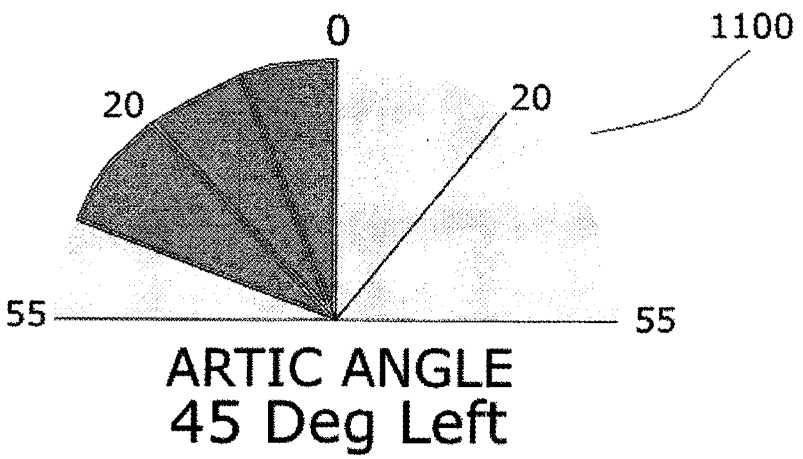
Figure 87D:
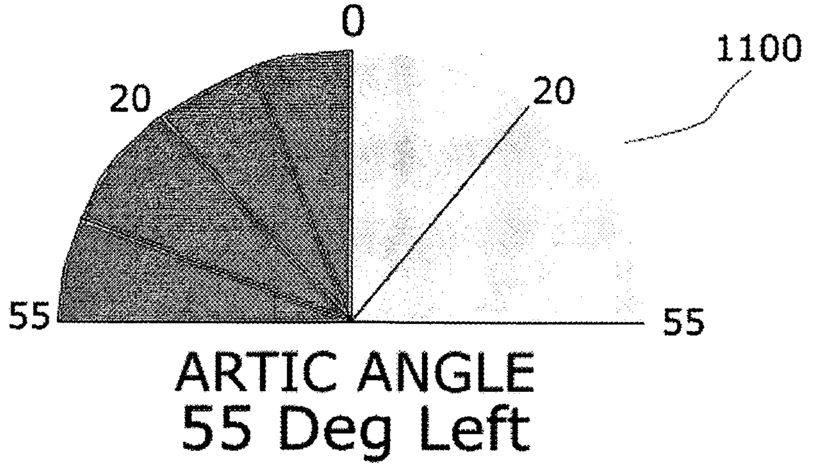
Figure 88A:
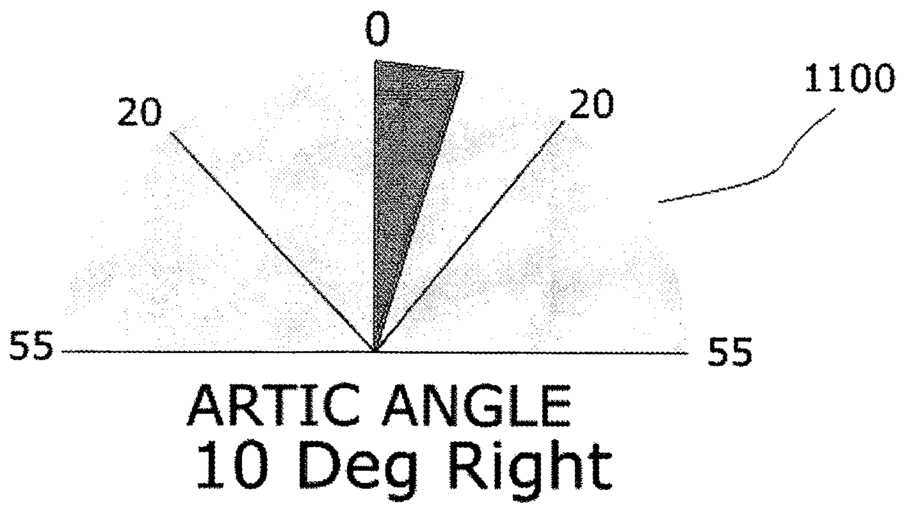
Figure 89A:
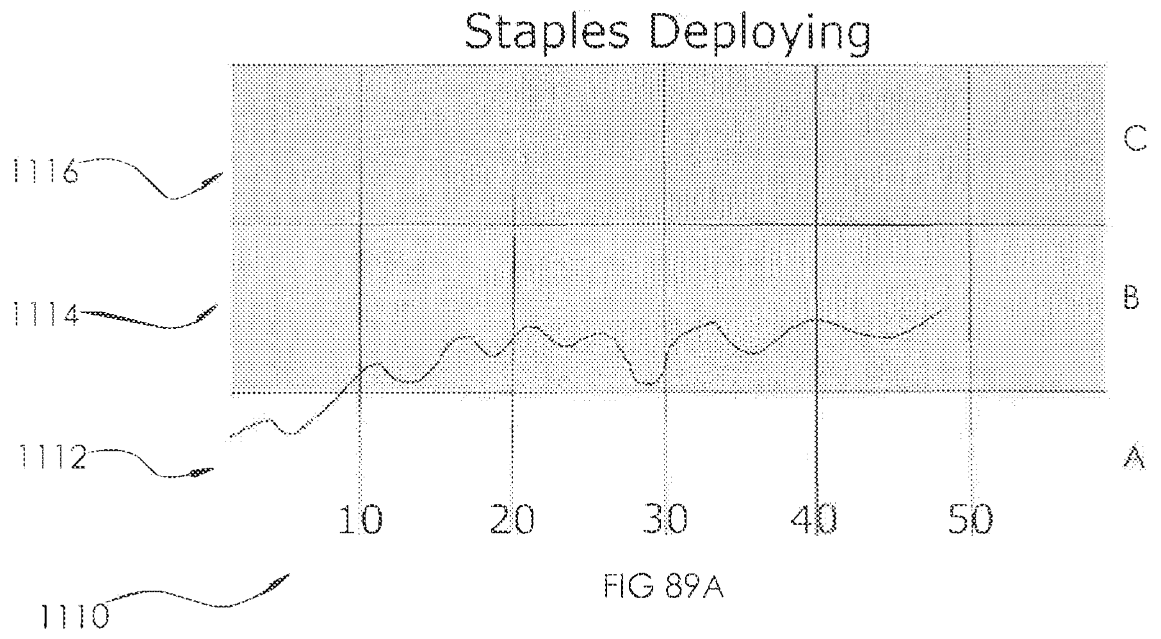
Figure 89B:
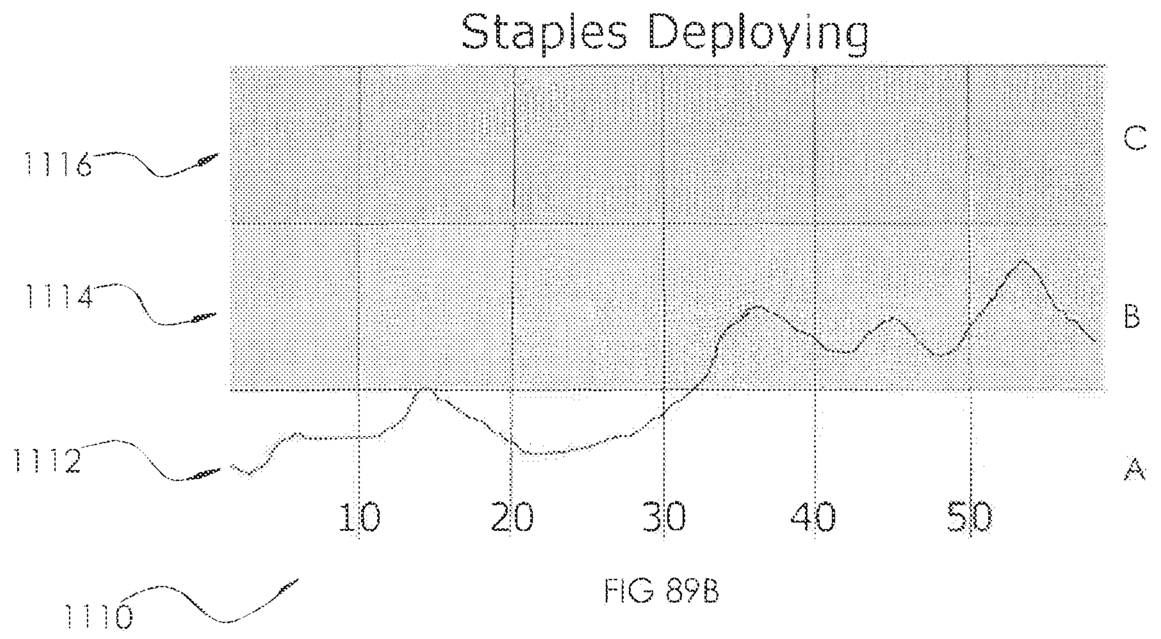
Figure 89C:
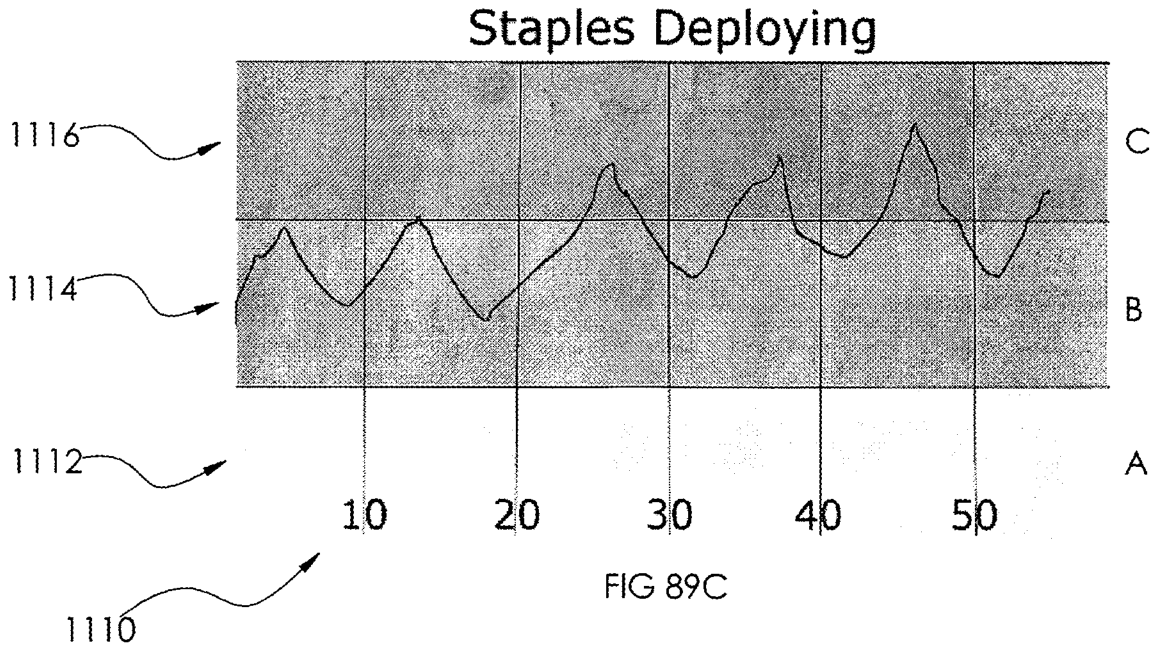
Figure 90A:
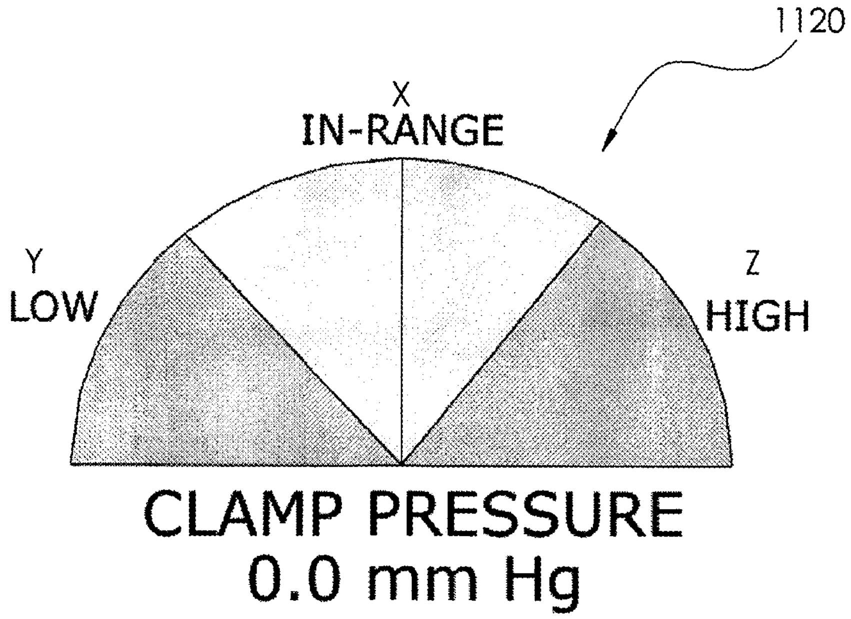
Figure 90B:
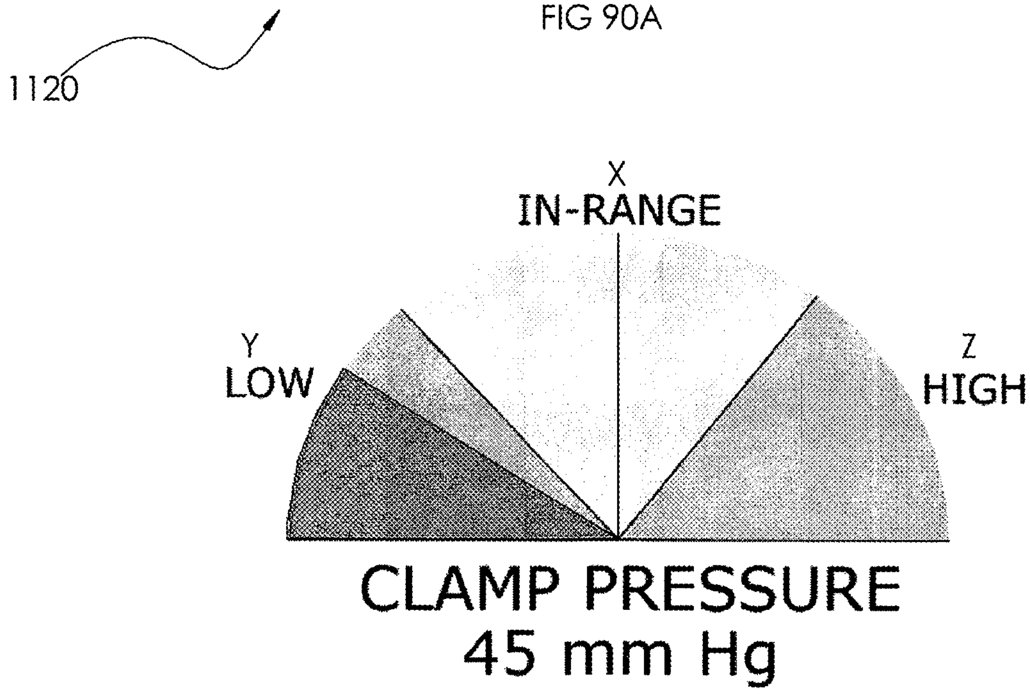
Figure 90C:
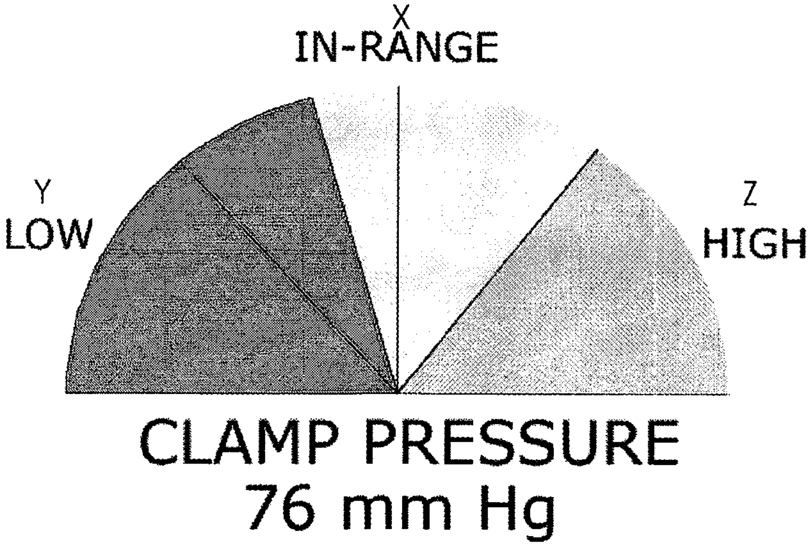
Figure 90D:
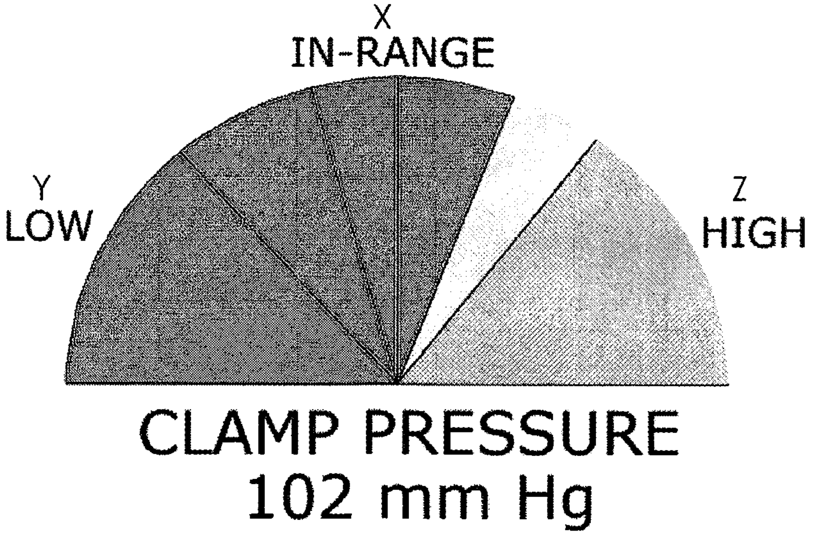
Figure 90E:
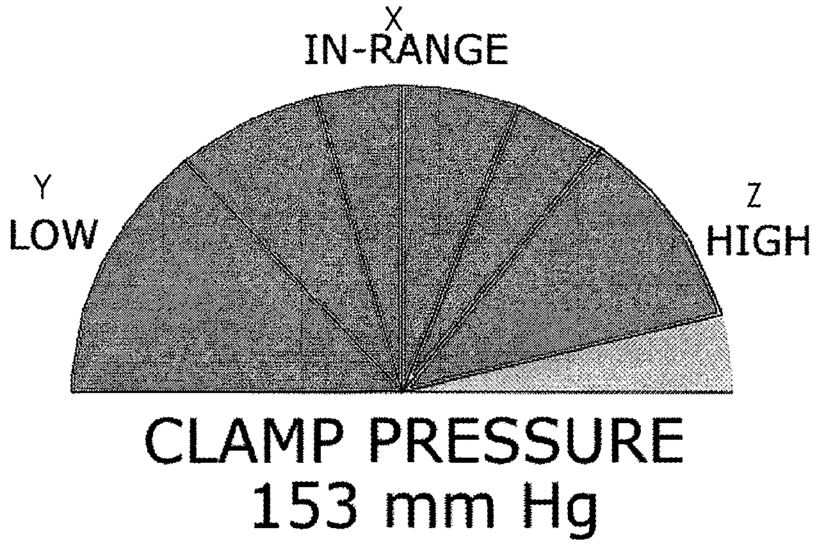
Figure 91:
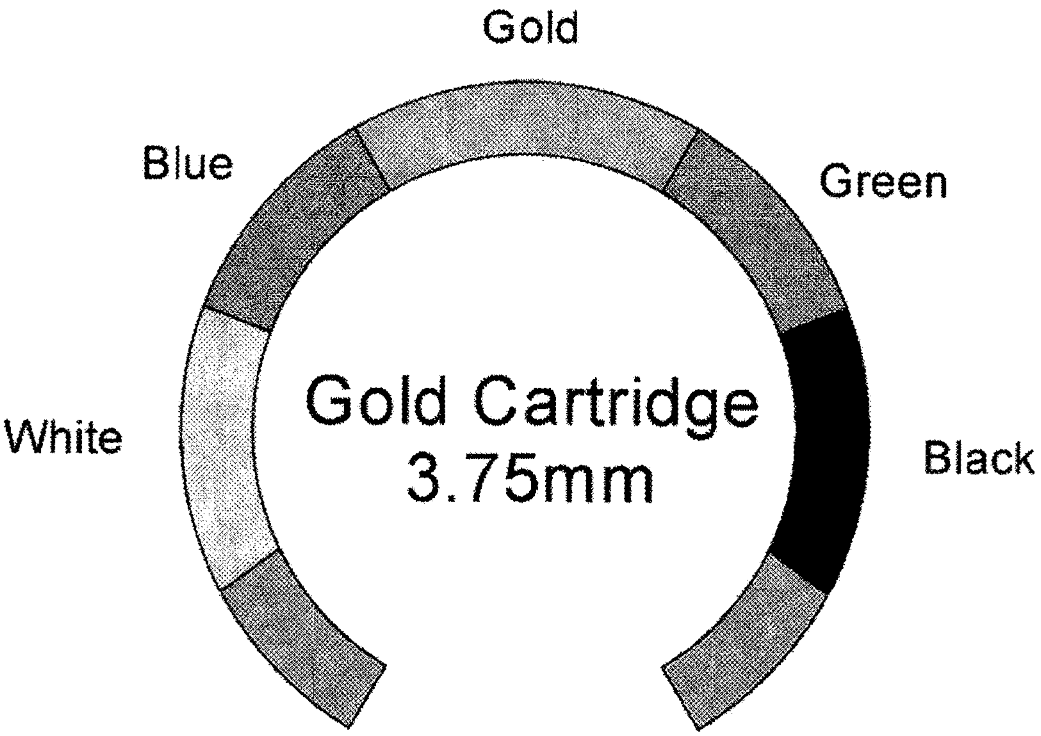

FIG. 70 is a perspective view of the deployment screw assembly and encoder of the power pack of FIG. 67;

FIG. 71 is an enlarged view of the area of detail BK of FIG. 70;

FIG. 72 is a side view of the power pack of FIG. 67 showing section line T-T;

FIG. 73A is a cross-sectional view taken along line T-T of FIG. 72;

FIG. 73B is an enlarged view of the area of detail V of FIG. 73A;

FIG. 74 is side view of the power pack of an alternate embodiment of the present invention having an encoder;

FIG. 75 is a cross-sectional view taken along line W-W of FIG. 74;

FIG. 76A is a cross-sectional view taken along line Y-Y of FIG. 74;

FIG. 76B is an enlarged view of the area of detail X of FIG. 75;

FIG. 76C is an enlarged view of the area of detail Z of FIG. 76A;

FIG. 77 is a perspective view of an alternate embodiment of the surgical instrument of the present invention having a cover to activate a switch of the power pack, the cover shown in an open position;

FIG. 78 is an enlarged view of the area of detail CB of FIG. 77;

FIG. 79A is a perspective of an alternate embodiment of the surgical instrument showing the clamp handle and jaws in the open position;

FIG. 79B is a side view of the surgical instrument of FIG. 79A;

FIG. 79C is an enlarged view of the area of detail C of FIG. 79B;

FIG. 79D is a cross-sectional view of the surgical instrument of FIG. 79A;

FIG. 79E is an enlarged view of the area of detail D of FIG. 79D;

FIG. 79F is across-sectional view of the surgical stapler of FIG. 79A, the view being the same as FIG. 79D but having identified area of detail Y;

FIG. 79G an enlarged view of the area of detail Y of FIG. 79F;

FIG. 79H is a perspective view of the instrument of FIG. 79A with part of the housing removed to show internal components;

FIG. 79I is an enlarged view of the area of detail V of FIG. 79I;

FIG. 80A is a perspective of the surgical instrument of FIG. 79A showing the clamp handle and jaws in the partially closed (partially clamped) position;

FIG. 80B is a side view of the surgical instrument of FIG. 80A;

FIG. 80C an enlarged view of the area of detail H of FIG. 80B;

FIG. 80D is a cross-sectional view of the surgical instrument of FIG. 80A;

FIG. 80E an enlarged view of the area of detail J of FIG. 80D;

FIG. 80F is a cross-sectional of the surgical instrument of FIG. 80A, the view being the same as FIG. 80D but having identified area of detail AB;

FIG. 80G is an enlarged view of the area of detail AB of FIG. 80F;

FIG. 80H is a perspective view of the instrument of FIG. 80A with part of the housing removed to show internal components;

FIG. 80I is an enlarged view of the area of detail Z of FIG. 80H;

FIG. 81A is a perspective of the surgical instrument of FIG. 79A showing the clamp handle and jaws in the fully closed (fully clamped) position;

FIG. 81B is a side view of the surgical instrument of FIG. 81A;

FIG. 81C an enlarged view of the area of detail O of FIG. 81B;

FIG. 81D is a cross-sectional view of the surgical instrument of FIG. 81A;

FIG. 81E an enlarged view of the area of detail Q of FIG. 81D;

FIG. 81F is a side view of the surgical stapler of FIG. 81A, the view being the same as FIG. 81D but having identified area of detail AE;

FIG. 81G is an enlarged view of the area of detail AE of FIG. 81F;

FIG. 81H is a perspective view of an embodiment of the instrument having a button for toggling the viewing screen to the selected cartridge size and for reversal of the firing motor to retract the firing mechanism;

FIG. 81I is a perspective view of an alternate embodiment of the instrument having a press button latch release for the compartment cover;

FIG. 81J is a cross sectional view showing the latch release of FIG. 81H;

FIG. 82 is a perspective view of the surgical instrument of FIG. 79A with a housing half removed to show internal components;

FIG. 83A is an exploded view of the clamping mechanism of the instrument of FIG. 79A;

FIG. 83B is an enlarged view of the pivot plate of FIG. 83A;

FIG. 83C is an enlarged view of the clamp handle and articulation button of FIG. 83A showing alignment of the articulation button contact with the articulation electrical switch;

FIG. 83D is an enlarged view similar to FIG. 83C except showing the articulation button contact non-aligned with the articulation switch, corresponding to a partially clamped position such as shown in FIG. 80A;

FIG. 83E is an exploded view of the jaw region of the instrument of FIG. 79A;

FIG. 84A is a top view of the surgical instrument of FIG. 79A with the top cover and some internal components removed to show the electrical connector within the housing;

FIG. 84B is an enlarged view of the area of detail A of FIG. 84A;

FIG. 85 illustrates a robotically assisted system showing the instrument (end effector), the control module (power pack) being loaded into the instrument, the robot arm for controlling instrument positioning and the surgeon console (with central processor) in accordance with an embodiment of the present invention;

FIG. 86 illustrates a firing profile graph with line A representing motor speed, line C representing the measured force and line B representing the optimal force;

FIGS. 87A, 87B, 87C, 87D, 88A and 88B show the screen of the power pack displaying the articulation position of the jaws wherein FIG. 87A corresponds to the unarticulated position of the jaws, FIG. 87B indicates jaw articulation to a 10 degree angle to the left, FIG. 87C indicates jaw articulation to a 45 degree angle to the left, FIG. 87D indicates jaw articulation to a 55 degree angle to the left; FIG. 88A indicates jaw articulation to a 10 degree angle to the right and FIG. 88B indicates jaw articulation to a 55 degree angle to the right;

FIGS. 89A-89C show the screen of the power pack displaying force on the system simultaneously with stroke distance during a staple firing wherein FIG. 89A provides an example wherein the force is in the intended range; FIG. 89B provides an example wherein the force is below the intended range for a portion of the firing stroke and FIG. 89C provides an example wherein the force ranges between the intended range and above the intended range during the firing stroke; and FIGS. 90A-90E show the screen of the power pack displaying pre-firing clamping pressure on tissue wherein FIG. 90A shows clamping pressure at 0 before initiation of the clamping stroke; FIG. 90B provides an example wherein the clamping force is in the low range; FIG. 90C provides an example wherein the clamping force is in the low end of the intended range; FIG. 90D provides an example wherein the clamping force is within the intended range; and FIG. 90E provides an example wherein the clamping force is above the intended range and in the high range; and FIG. 91 shows a screen of the power pack showing force ranges for cartridge size selection.

DETAILED DESCRIPTION OF PREFERRED EMBODIMENTS

The present disclosure provides power packs, containing a battery and power train, which are loadable into a surgical stapler to power various functions of the surgical stapler to reduce the forces exerted by the clinician otherwise required if manual force was utilized. The present disclosure also provides surgical staplers designed to receive the power pack and to interact with the power pack to effect firing of the staples from the stapler. In some embodiments, the power pack can be used to effect articulation of the jaw assembly of the stapler to pivot the jaw assembly with respect to the longitudinal axis of the stapler. Each of these embodiments is discussed in detail below.

The power pack can also be utilized for powering endoscopic linear staplers, other types of staplers as well as other surgical instruments. Examples of these instruments are also discussed below and disclosed in commonly assigned U.S. patent application Ser. No. 17/269,907, filed Feb. 19, 2021, now U.S. Pat. No. 11,564,685, the entire contents of which are incorporated herein by reference.

The present invention provides a feedback mechanism to the clinician of various parameters during the surgical procedure. The feedback can include one or more of the following a) the articulated position of the jaws; b) the position of the firing mechanism, i.e., the extent of the firing stroke; c) the force on tissue during the firing stroke; and/or d) the clamping pressure on tissue. This is all built into the program logic of the power pack (control module) software. Note the feedback mechanism includes a display for these parameters, in communication with the various sensors in the instrument or power pack, presented on a screen on the power pack. The housing can have a transparent window to enable viewing of the power pack screen when the power pack is sealingly enclosed within the housing. Alternatively, the power pack can be in communication with a screen on the housing such that the housing screen provides the display of the parameters. It should also be appreciated that these parameters can be utilized in other powered instruments other than those of the present invention. For example, in powered instruments not utilizing a replaceable power pack, such parameters can be measured and displayed to the user. This is described in more detail below.

The information during the procedure can also in some embodiments be stored for later evaluation by the clinician after the procedure. The data can be stored in the power pack and/or transferred to another storage device. It could also be stored in a central database which can provide training information to other clinicians via data collection and evaluation for future surgical procedures. This is described in more detail below.

The loadable power packs of the present disclosure are mountable into the handle housing of the surgical instrument, and are maintained in a sterile environment within the surgical instrument so they can be removed and reused. This enables the power pack to be removed from the stapler and reused in another procedure and/or instrument without the complexities, time, costs and risks of resterilization of the power pack. The sealed environment of the battery and power train within the housing also enables certain features/components to be used which might not otherwise be practical if sterilization of the internal power pack was required. Thus, by preventing contact between the power pack and the patient and/or bodily fluids and the external environment, resterilization is not required. The power pack can be used with surgical instruments discarded after use (fully disposable instruments), partially disposable surgical instruments or with fully reusable/sterilizable instruments with the advantage that the power pack need not be discarded or sterilized. Thus, the surgical stapler of the present disclosure advantageously reduces the time, resources and/or costs for preparing the surgical stapler for its next use.

The power packs are easily loadable in the surgical instrument, preferably the handle assembly or housing of the instrument, to easily and securely engage structure in the housing to effect movement of such structure in the instrument. The power packs are also easily disengageable from the structure for removal from the housing for subsequent reuse. The power packs can be configured so they can be loadable and engageable in various types of surgical instruments. The power pack is fully enclosed and sealed by the handle housing so there is no need to sterilize the power pack between uses. The power pack can in preferred embodiments include a battery that is within the housing of the power pack and thus in a sealed environment. In some embodiments, the power pack includes a replaceable battery pack so the battery can be changed during a surgical procedure. This advantageously limits the need for excess power packs for the surgical procedure.

In some embodiments the power packs include sensors, encoders or measurement devices to assess/detect certain functions of the surgical instruments. In some embodiments, automatic adjustments are made via a microprocessor in the power pack to account for such assessment and detection.

Referring now to the drawings and particular embodiments of the present disclosure, wherein like reference numerals identify similar structural features of the devices and systems disclosed herein, there are illustrated several embodiments of the surgical instruments and removable power pack of the present disclosure.

With reference to FIGS. 1-27, the power pack is used with endoscopic linear staplers which are inserted through trocars and fire linear rows of surgical staples from a cartridge through tissue into contact with an anvil which forms the individual staples. The staplers include an openable compartment in the handle housing that enables easy loading of the power pack within the stapler. The staplers also provide a tight seal to protect the power pack from contaminants so that the power pack does not need to be sterilized for multiple uses.

The power pack is engageable with a staple drive (staple firing) mechanism of the surgical stapler so that once it is loaded in the stapler, actuation of the motor within the power pack effects firing of the staples through tissue. In some embodiments, the power pack is engageable with an articulation mechanism of the stapler wherein actuation of the motor effects articulation of the stapler. The powered articulation can be in addition to the powered staple firing or alternatively the stapler could have powered articulation and manual staple firing. A specific embodiment of such powered articulation included with powered firing is shown in FIGS. 14A-27 and discussed in detail below.

The term "surgical fasteners" as used herein encompasses staples having legs which are deformed by an anvil, two part fasteners wherein a fastener or staple component with legs is received and retained in a second component (retainer), and other types of fasteners which are advanced through tissue of a patient in performing surgical procedures.

The term "proximal" as used herein denotes the region closer to the user and the term "distal" as used herein denotes the region further from the user. The terms "top" or "upper" and "bottom" or "lower" refer to the orientation of the instruments as shown in the orientation of the instrument in FIG. 2A, with the cover being on the top and the handle extending at the bottom.

Turning first to FIGS. 1-12, a first embodiment of the surgical stapler and removable power pack are illustrated. In this embodiment, the power pack, which contains a battery, motor, drive mechanism and stapler engagement structure, effects firing of the surgical fasteners (staples). In some embodiments, the power pack does not include a battery, although preferred embodiments include the battery.

Figure 1:
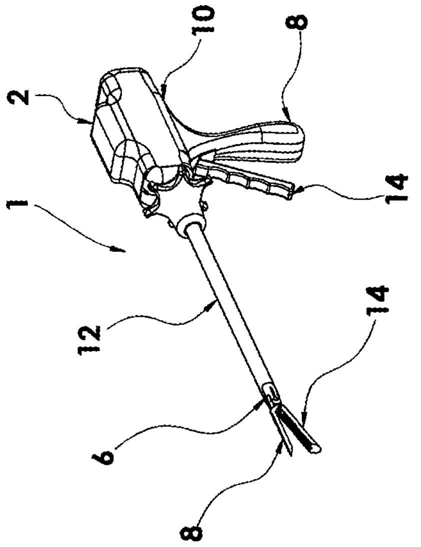
FIG. 1 is a perspective view of a first embodiment of the surgical stapler of the present disclosure having a removable power pack.
Figure 2A:
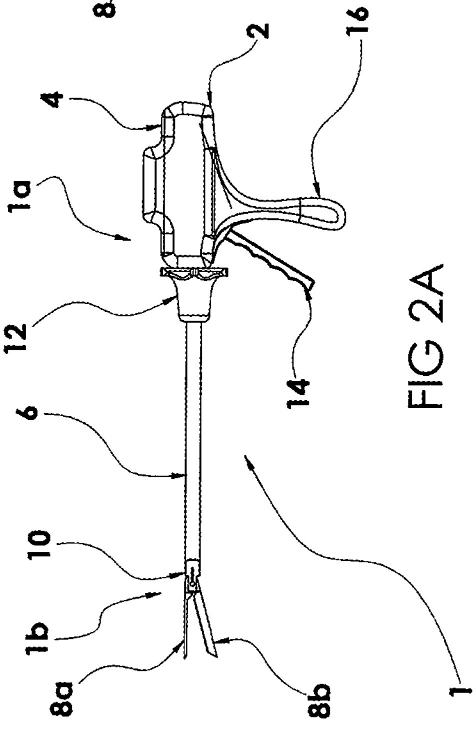
FIG. 2A is a side view of the surgical stapler of FIG. 1.
Figure 2B:
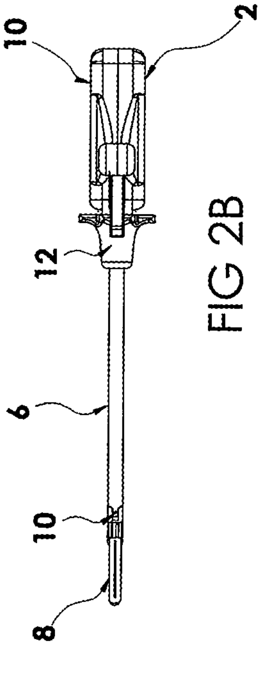
FIG. 2B is a bottom view of the surgical stapler of FIG. 1.
Figure 2C:
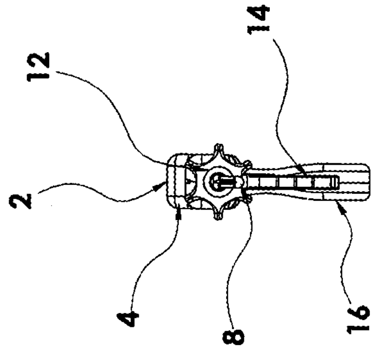
FIG. 2C is a front view of the surgical stapler of FIG. 1A.
Figure 7:
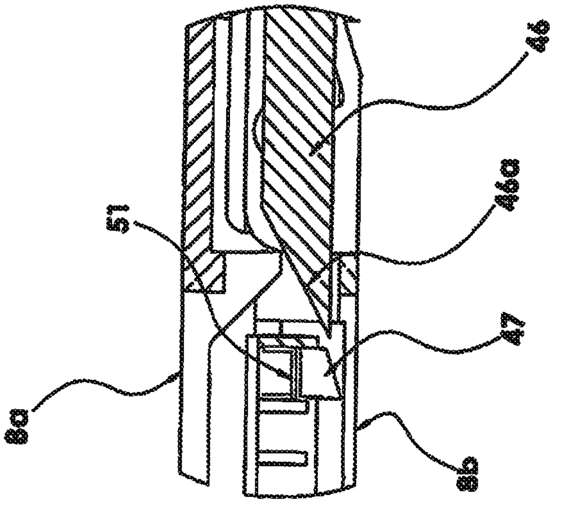
FIG. 7 is a close up view showing the firing mechanism at the distal end for firing staples.
Figure 10:
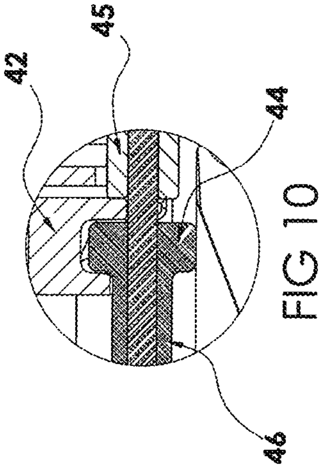
FIG. 10 is a close up view of the area of detail G of FIG. 8B.
Figure 11:
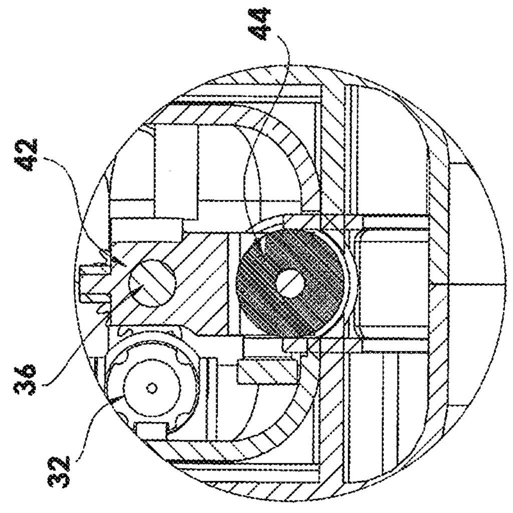
FIG. 11 is a close up view of the area of detail H of FIG. 9.
Figure 9:
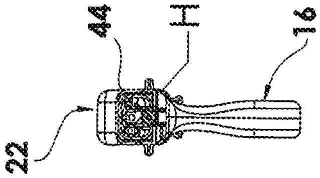
FIG. 9 is a cross-sectional view taken along line F-F of FIG. 8B.
Figure 8C:
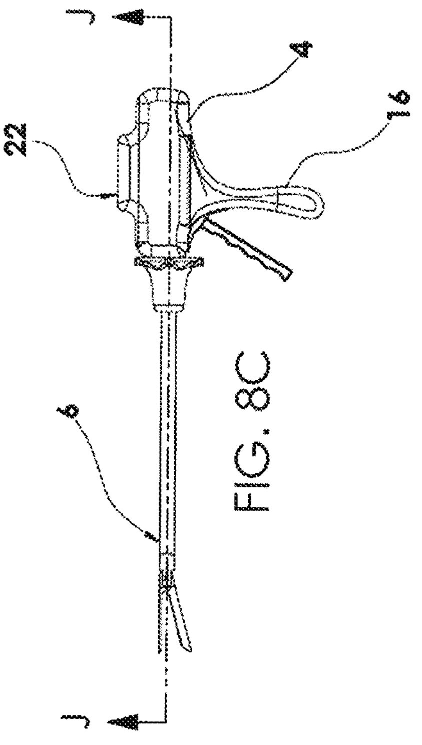
FIG. 8C is a side view of the surgical stapler of FIG. 1 showing the power pack fully inserted in the handle compartment and the compartment cover closed.
Figure 8D:
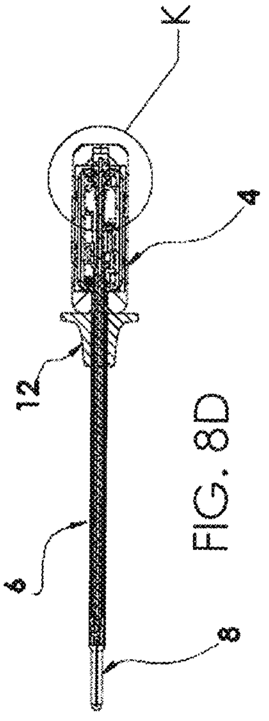
FIG. 8D is a cross-sectional view taken along line J-J of FIG. 8C.
Figure 12:
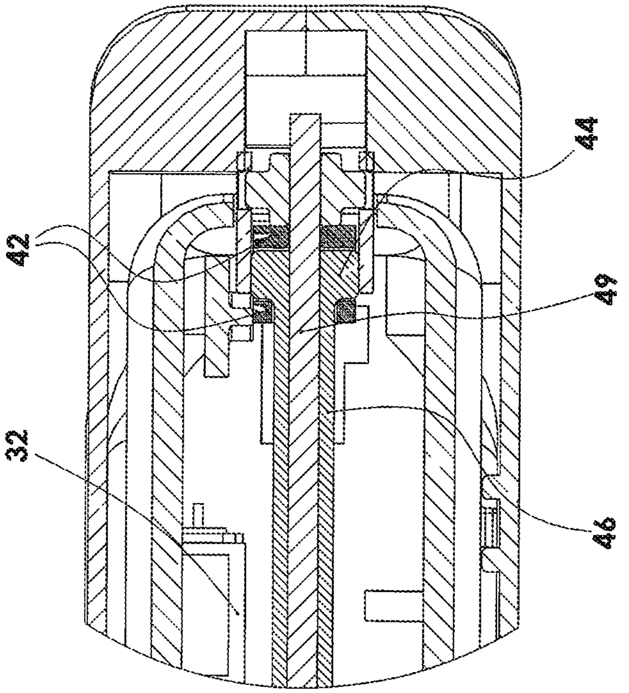
FIG. 12 is a close up view of the area of detail K of FIG. 8D.

The surgical stapler, also referred to herein as the surgical fastener applying instrument or surgical fastener applier, is designated generally by reference numeral 1 and includes a proximal portion 1*a*, a distal portion 1*b* and an elongated or endoscopic portion 6 (also referred to as an elongated tubular portion or shaft) extending between the proximal portion 1*a* and the distal portion 1*b*. A handle assembly 2 with a housing 4 (also referred to herein as a handle housing) is positioned at the proximal portion 1*a* and is configured to house and protect internal mechanisms of the stapler including the removable power pack when loaded (mounted) therein. At the distal portion 1*b* are opposing members, i.e., jaws, 8*a*, 8*b*, configured to clamp and constrain tissue during operation of the surgical stapler. At least one of the jaws is movable with respect to the other jaw from an open position to receive tissue between the jaws and a closed position to clamp tissue between the jaws. Thus, one of the jaws can be stationary and the other jaw movable with respect to the stationary jaw or alternatively both jaws can move, e.g., pivot, toward each other. In the embodiment of FIG. 1, jaw 8*b*, which contains at least one row of surgical fasteners (staples) is movable with respect to non-pivoting (stationary) jaw 8*a* which contains an anvil with staple forming pockets. In alternate embodiments, the jaw containing the anvil pivots and the jaw containing the fasteners is stationary. Jaws 8*a*, 8*b* are collectively referred to herein as jaws 8. The fasteners are fired (advanced) from jaw 8*b* by linear movement of a firing mechanism which engages staple drivers within the jaw 8*b* which move transverse to the longitudinal axis, i.e., transverse to the direction of movement of the firing mechanism, to sequentially advance (from proximal to distal) the staples in the linear rows of staples from the jaw 8*b* and through tissue to engage the anvil pockets on jaw 8*a* for formation of the staples. Such firing of the staples is illustrated in FIG. 7 and discussed below.

The elongated tubular member 6 extends distally from the housing 4 and is configured to fit through a surgical port (trocar) used for laparoscopic surgery. The endoscopic portion 6 can be of varying dimensions and in some embodiments is configured to fit through a 10 mm trocar, although other dimensions for fitting through other size trocars are also contemplated such as trocars ranging from 5 mm to 15 mm. It is advantageous to minimize the diameter of the endoscopic portion to minimize the size of the patient's incision. With the jaws 8 in the clamped position, the outer diameter of the elongated member 6 is maintained as the cross-sectional dimension of the closed jaws 8 preferably does not exceed the cross-sectional dimension (i.e., diameter) of the tubular member 6.

The surgical stapler 1 can in some embodiments include a joint 10 that provides for the articulation of the opposing members 8, i.e., pivoting of the jaw assembly (jaws 8) to angular positions with respect to the longitudinal axis of elongated member 6. Articulation can be achieved by linear motion of elongated members extending through the endoscopic portion 6 which are slidable to angle the jaw assembly. A rotational member or knob 12 is configured to rotate, with respect to the handle assembly, the elongated member 6 and connected jaws 8 about the longitudinal axis of the elongated member 6 to change the position of the jaws 8. Articulation is effected by manual manipulation of a lever adjacent the handle 2. A handle lever 14 (also referred to herein as a clamping handle), linked to an axially movable clamping bar, is pivotable from a first position to a second position closer to stationary handle 16 to effect movement of the jaw 8*b* toward the jaw 8*a* from an open (unclamped) position to a clamping position, also referred to as a closed position, of the jaws 8. Release of handle lever 14 returns the jaw 8*b* to its open position. Stationary handle 16 for grasping by the user is ergonomically designed for comfort of use. In summary, the surgical stapler operates by manual pivoting of the lever 14 toward stationary handle 16 to clamp the tissue between jaws 8, followed by powered firing of the staples from jaw 8*b*, through the clamped tissue and into contact with the staple forming pockets of the anvil of jaw 8*b*. Prior to firing, the jaws 8 can be rotated to a desired orientation by rotation of endoscopic portion 6 via knob 12 and/or articulated about joint 10, via movement of the elongated articulation members, to a desired angled position with respect to the longitudinal axis of endoscopic portion 6. In the embodiment of FIG. 1, articulation is performed by manual manipulation of a lever (not shown) which is operatively connected to an internal elongated member within tubular member 6 which extends to joint 10. A force applied to the internal elongated member pivots/articulates the jaws 8 about the joint 10. In later described embodiments (FIG. 14A), powered articulation is provided.

Figure 3:
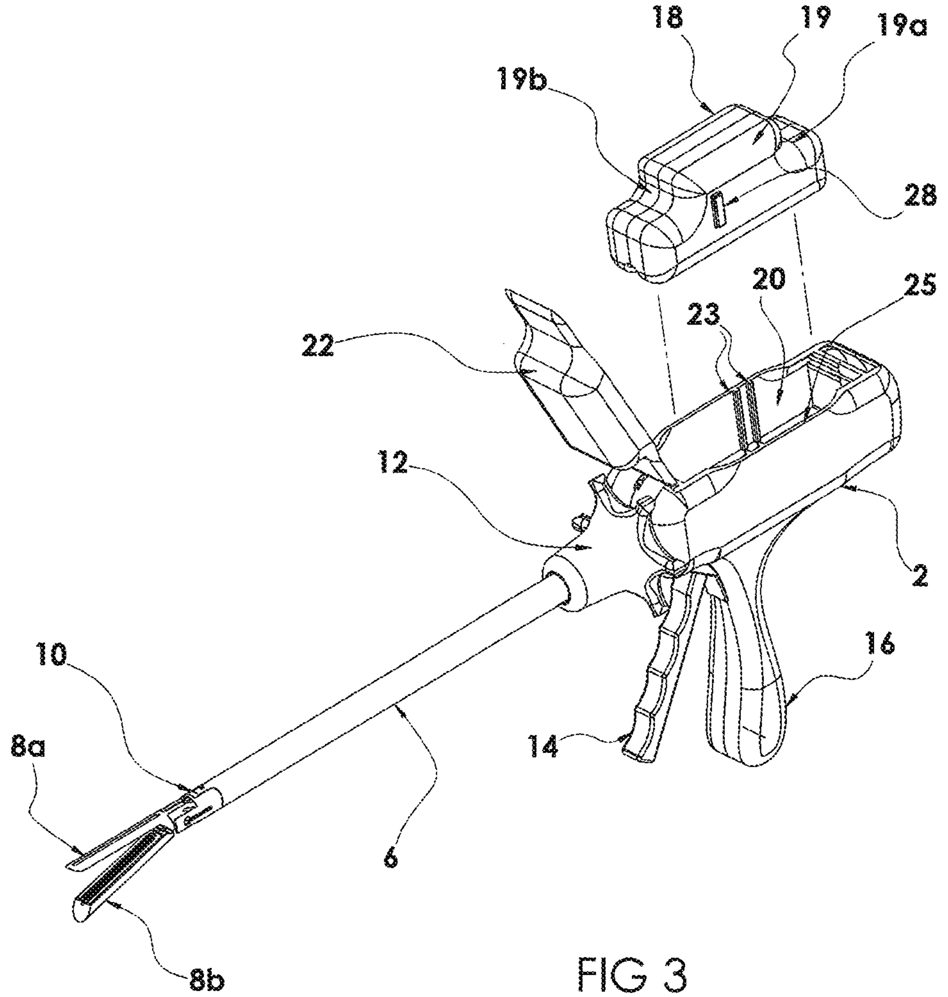
FIG. 3 is a perspective view of the surgical stapler of FIG. 1 showing the handle compartment cover in the open position and further showing the power pack prior to insertion into the handle compartment.

The housing 4 of the handle assembly 2 of the surgical stapler is configured to receive the loadable/removable power pack 18 in a receptacle (compartment) 20 as shown in FIG. 3. The receptacle includes a base 25*a* and side walls 25*b* and 25*c* having one or more guides 23 that cooperate with corresponding guiding structures 28 on the outer wall of the housing 19 of power pack 18 for proper alignment of the power pack 18 in the handle assembly 2 during insertion into the receptacle 20. In the embodiment of FIG. 3, the guides 28 on power pack housing 19 are in the form of a pair of ribs or projections 28 extending transversely to a longitudinal axis of the power pack 18 for receipt within grooves formed between guides, e.g., ribs or projections, 23 of the compartment 20, also extending transversely with respect to a longitudinal axis of the stapler 1. In the illustrated embodiment, the ribs 23 are on opposing sides of the power pack 18 and are axially offset from each other, although in alternate embodiments the ribs can be axially aligned. Additionally, a different number of ribs (axially or non-axially aligned) can be provided (with corresponding receiving structure in the compartment 20 of the housing). It should be appreciated that alternatively, the grooves could be provided on the power pack 18 and the ribs provided in the compartment 20 to provide the guiding structure for the power pack 18. The guiding structure also helps to retain power pack 18 in position within the compartment 20. The power pack 18 has front and rear concave regions 19*a*, 19*b* to reduce its overall size.

The handle assembly 2 includes a cover 22 for opening and closing the receptacle 20. The compartment cover 22 is shown as being hingedly attached to the housing 4, but may alternatively be fully removable or attached in some other manner such as a slidable connection or the like. The cover 22 is shown pivotably mounted to a top portion of the housing 4 (in the orientation of FIG. 2A) for top loading of the power pack, although alternatively, side or bottom loading can be provided. The cover 22 is shown pivotable from a closed position of FIG. 2A to an open position of FIG. 3 to enable loading of power pack into the compartment 20 of the housing 4. In some embodiments, the cover 22 is spring loaded to an open position so it remains open for loading of the power pack 18. Once loaded, the cover 22 is pivoted about hinge 22*a* to its closed position. A latch can be provided to latch the cover 22 to the housing 4 in the closed position. When the cover 22 is in an open position, e.g., as shown in FIG. 3, the power pack 18 may be removed from the receptacle 20 or inserted into the receptacle (compartment) 20.

When the cover 22 is in a closed position, the seal of the cover 22 is in contact with the rim of the housing 2 such that the receptacle 20, and the power pack 18 if inserted into the receptacle 20, is sealed from the environment exterior to the surgical stapler. The top seal 24 can be attached to the cover 22 and in some embodiments can be in the form of an elastomer that is compressed by the housing, e.g., tightly fits slightly within the housing or is pressed on the rim of the housing 2. In other embodiments, the elastomer seal 24 can be on the housing 2, i.e., extending around the perimeter of the rim of the compartment 20, and is compressed by the cover 22 to seal between the cover 22 and housing 4. Other seals can also be provided within the surgical stapler to seal/protect the power pack 18 from contaminants, e.g., body fluids. These seals are discussed in more detail below.

Turning now to the power pack of the present disclosure, and with reference to FIGS. 4A-4I, the power pack 18 includes a motor assembly, battery and electronics contained within housing 19. More specifically, as shown in FIGS. 4A-4E, the power pack 18 includes a powering assembly including a motor 32 connected to a planetary gear box 34 configured to gear down the output of the motor 32 for proper drive speeds for firing staples from jaw 8*b* through the tissue into contact with the anvil of jaw 8*a*. The planetary gear box 34 drives a lead screw 36 through one or more gears operatively connected to the motor shaft. More specifically, upon rotation of the motor shaft by motor 32 in a first direction, gear 38 is rotated in the same first direction, causing rotation of the gear 30 in a second opposite direction due to the intermeshed teeth of gears 30 and 38. Lead screw 36 is operatively connected to gear 30 so that rotation of gear 30 causes rotation of lead screw 30 in the same direction. The power pack 18 includes a battery 33 which can be rechargeable outside the stapler when the power pack 18 is removed. The power pack 18 in some embodiments can include a power switch which is activated, i.e., turned on, by the clinician to start the motor and effect staple firing. In other embodiments, the motor can automatically turn on when the power pack is fully loaded or upon actuation of another control on the stapler housing 4. In some embodiments, the motor can automatically turn off when the power pack is removed from the stapler housing.

Connected to the end of lead screw 36 (the end opposite the connection to the gear 30) is a drive mechanism 40. The drive mechanism 40 is configured to move in a linear motion (in an axial direction) along the lead screw 36 in response to rotation of the lead screw 36. For example, the drive mechanism 40 may include internal threads that engage external threads of the lead screw 36 and may include slides engaged in a track that prevent the drive mechanism 40 from rotating and therefore cause the drive mechanism 40 to move linearly (axially) in response to rotation of the lead screw 36. As depicted in FIGS. 4A-4G, the power pack 18 has a compact configuration as the lead screw 36 extends alongside, slightly spaced from, the motor 32 and gear box 34, i.e., both the motor 32/gear box 34 and lead screw 36 extending longitudinally with the lead screw 36 parallel to the motor 32. The drive mechanism 40 is connected to a proximal end of lead screw 36 and extends proximally of the proximal end of the motor 32 in the illustrated embodiment.

Figures 4A, 4B, 4C, 4D, 4E, 4F:
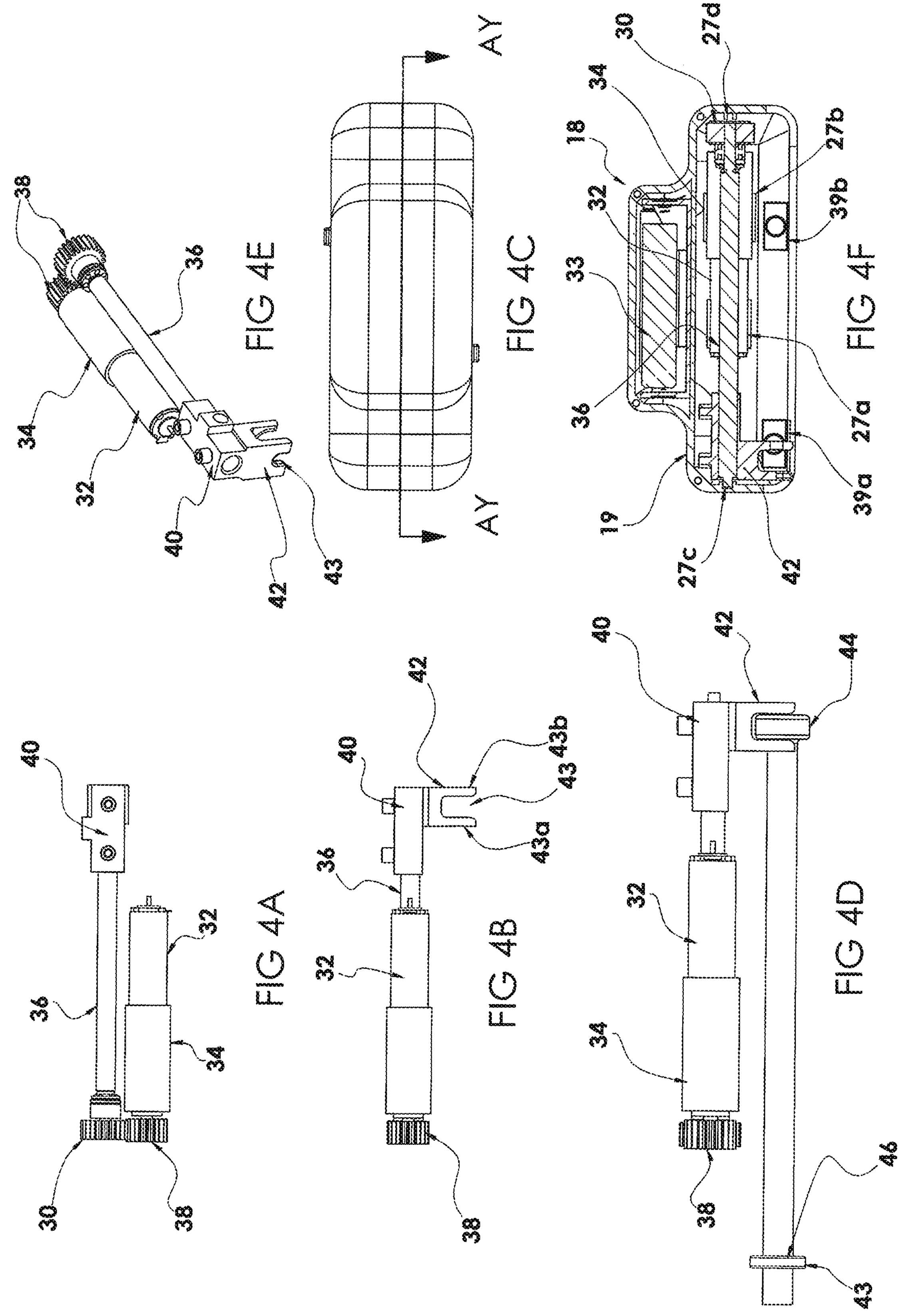
FIG. 4A is a top view of the motor and drive mechanism (assembly) of the power pack of FIG. 3.
FIG. 4B is a side view of the motor and drive mechanism of the power pack of FIG. 4A.
FIG. 4C is a top view of the power pack of FIG. 3.
FIG. 4D is a side view of the motor and drive mechanism of FIG. 4A shown engaged with the rod of the firing assembly of the surgical stapler of FIG. 1.
FIG. 4E is a perspective view of the motor and drive mechanism of the power pack of FIG. 3.
FIG. 4F is a cross-sectional view taken along line AY-AY of FIG. 4C showing the power pack engaging the firing rod of the surgical stapler of FIG. 1.
Figure 4I:
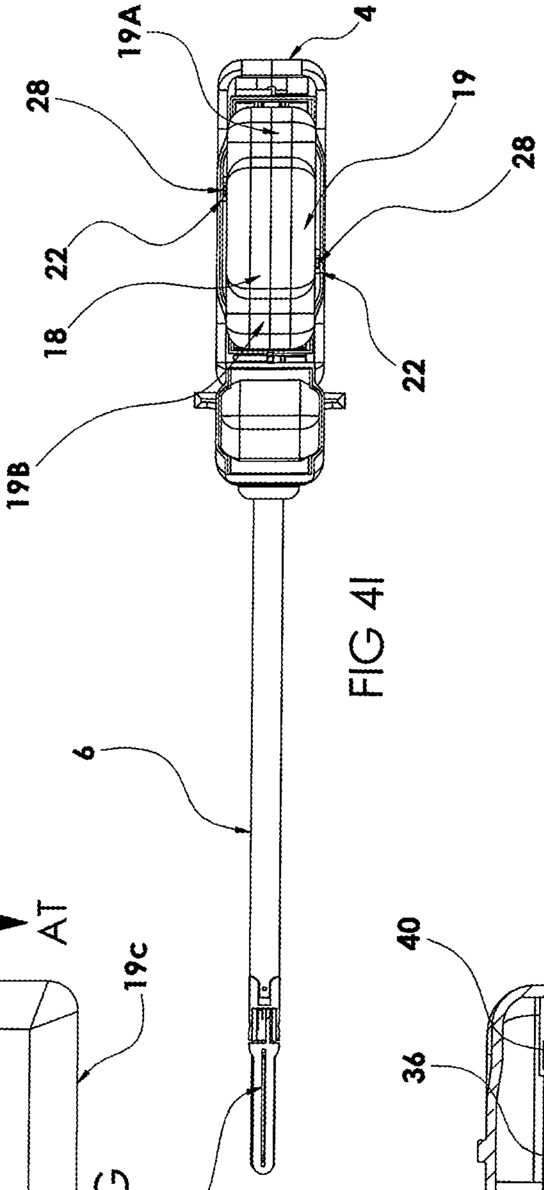
FIG. 4I is a top view of the surgical stapler of FIG. 1.

The power pack 18 can have features/structure to constrain the motor 32. In the embodiment of FIG. 4F, such feature is in the form of proximal rails 27*a* and distal rails 27*b* spaced apart axially within the housing 19. Motor 32 is seated within proximal rails 27*a* and gear box 34 is seated within rails 27*b*, the rails 27*a*, 27*b* retaining the motor and preventing axial and rotational movement within the housing 19. Bearings or bushings 27*c* and 27*d* can also be provided to constrain the lead screw 36 at opposing ends, while allowing rotation thereof, thereby also constraining the motor. Other features can additionally or alternatively be provided to restrain the motor from axial movement while allowing rotation of the lead screw.

The drive mechanism 40 includes a first output flag or yoke 42, which is discussed in more detail below, configured to engage a staple firing mechanism, e.g., firing rod 46, extending longitudinally within the handle 4. The staple firing rod 46 is operatively connected to a firing rod in the endoscopic portion 6 which is operatively engageable with a series of staple drivers in jaw 8*b* to advance the fasteners (staples) from the fastener jaw 8*b*. Alternatively, the firing rod 46 can extend through the endoscopic portion 6 and itself engage the stapler drivers as shown in FIG. 7. Thus, as the motor 32 generates rotational motion of the lead screw 36 through the planetary gear box 34 and the gears 38, 30, the drive mechanism 40 moves in linear motion along the lead screw 36. Such linear motion effects linear movement of the firing rod 46 (due to the engagement by the flag 42) which advances the staple driving mechanism to advance (fire) the staples out from jaw 8*b* through tissue and into contact with the anvil in jaw 8*a*. As noted above, the firing rod 46 can be a single element extending through the endoscopic portion 6 (see e.g., FIG. 7) and terminating adjacent jaws 8 or alternatively can be attached to one or more components intermediate the firing rod 46 and jaws 8. In FIG. 7, camming surface 46*a* of firing rod 46 engages staple drivers 47 to sequentially fire staples 51 as the firing rod 46 is advanced in a distal direction.

The power pack 18 can also include in some embodiments one or more sensors to indicate the position of the firing rod 46 to indicate to the clinician the status of staple firing. The embodiment of FIG. 4F illustrates an example of such sensors if they are provided. The power pack 18 has within the housing a proximal sensor 39*a* and a distal sensor 39*b* to sense the position of yoke 42 of the drive mechanism 40. Thus, sensor 39*a* senses the initial position of the yoke 42 (and thus the initial position of the firing rod 46) and at the end of the firing stroke, sensor 39*b* would indicate the end (final) position of the yoke 42 (and thus the final positon of the firing rod 46) which would indicate completed firing of the fasteners. The power pack 18 could also include an audible or visual indicator (viewable though the power pack housing 19 and instrument handle housing 4) actuated by the sensor to indicate to the clinician the position of the flag 42 and thus the completion or status of the firing stroke to fire the fasteners. The power pack 19 can also include sensors to detect the position of the articulation flag in the embodiments discussed below which have powered articulation. The sensor can include a potentiometer to determine the location during the firing stroke. It can also include an encoder to detect the position along the stroke. Alternatively, the stroke can also be identified by motor count.

It is also contemplated that in alternate embodiments, the sensor(s) can be carried by the handle housing rather than (or in addition to) the power pack and utilized to detect the positioning of the flag 42 and/or firing rod 46 and/or detect the position of the articulation flag and/or articulation rod in the embodiments discussed below which have powered articulation.

It is also contemplated that a sensor(s) can be provided to detect the position of the clamping rod for clamping the jaws. The sensor can be provided in (or supported by) the power pack or alternatively the sensor(s) can be carried by the handle housing rather than (or in addition to) the power pack and utilized to detect the positioning of the jaws by detecting the position of the flag or other structure engaging the jaw clamping rod and/or detecting the position of the jaw clamping rod in the embodiments which have powered clamping.

Note one or more sensors can be provided in some embodiments; in other embodiments, no sensor is provided.

The power pack in some embodiments has a battery pack that is removably mounted in or on the power pack. This is discussed in more detail in conjunction with FIGS. 35-37C.

Figures 6A, 6B, 6C, 6D:
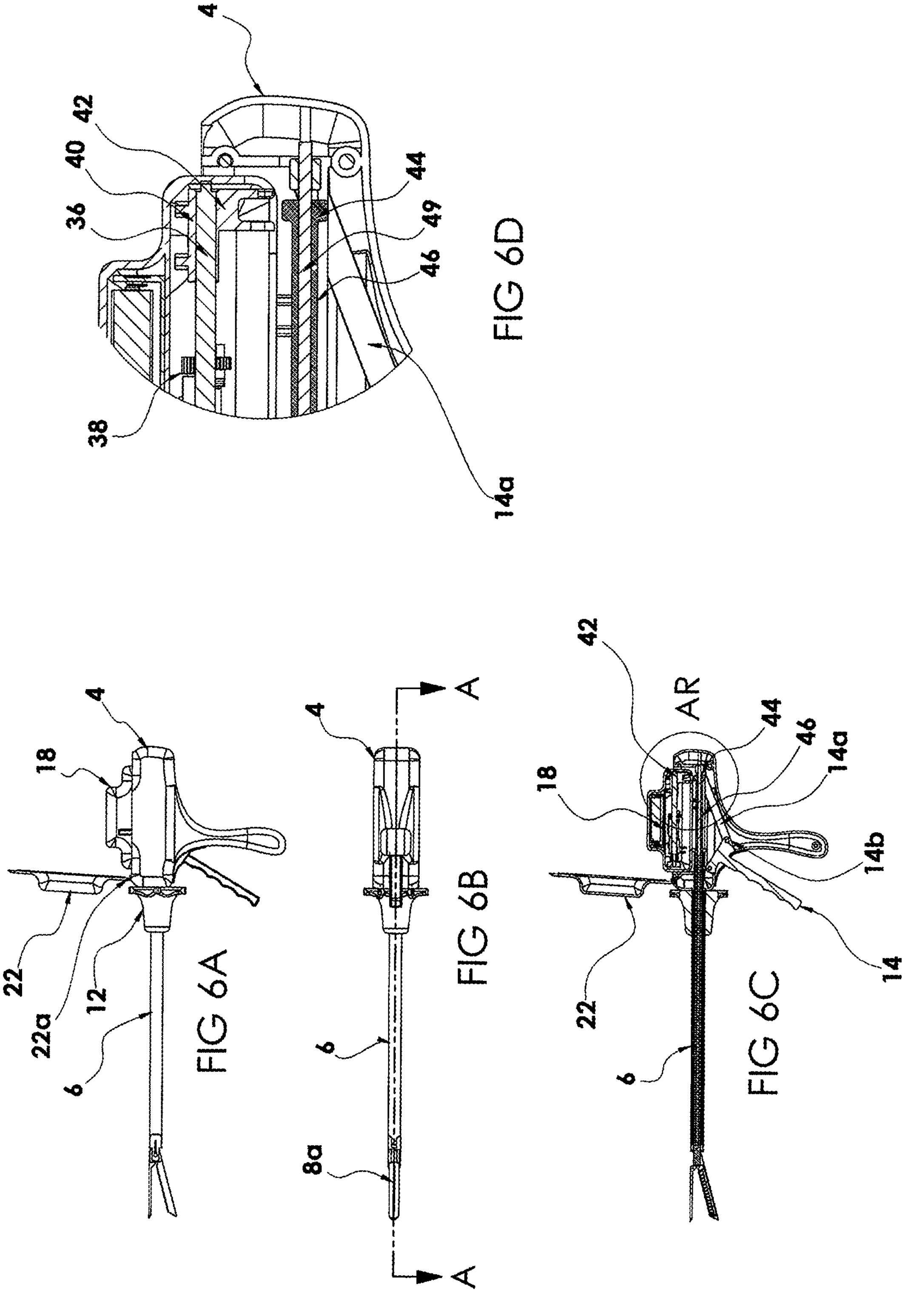
FIG. 6A is a side view of the surgical stapler of FIG. 1 showing the handle compartment cover in the open position and further showing the power pack in the process of being inserted in the compartment of the handle.
FIG. 6B is a bottom view of the surgical stapler of FIG. 6A.
FIG. 6C is a cross-sectional view taken along line A-A of FIG. 6B.
FIG. 6D is a close up view of the area of detail AR of FIG. 6C.

Turning now to the loading of the power pack 18 into the surgical stapler 1, as seen in FIGS. 6A-6D, the power pack 18 is in the process of being inserted into the receptacle 20 of housing 4. As shown, handle compartment cover 22 is open to provide access to compartment 20. The output flag 42 of the power pack 18 as noted above is driven by the motor assembly and is configured to engage and interact with structure within the handle assembly 2, e.g., firing rod 46, to control operation of the surgical stapler 1 when the power pack 18 is fully inserted into the receptacle 20. As can be appreciated in FIG. 6D, the output flag 42 is not fully engaged with the flange 44 of the firing rod 46. Also shown in FIG. 6D is the clamp bar 49 which is positioned within and concentric with firing rod 46. The clamp bar 49 is operatively connected to the pivotable handle 14 of stapler 1 via linkage 14*a* (pin 14*b* connects one end of handle 14 to the distal end of clamp bar 49). In this manner, movement of pivotable handle 14 toward stationary handle 16 causes the operatively connected jaw clamping mechanism, e.g., clamp rod 49, to be advanced distally to pivot jaw 8*b* toward jaw 8*a* to clamp tissue between the two jaws 8. Note that for clamping, clamp bar 49 slides linearly within a lumen of firing rod 46; for staple firing, firing rod 46 moves linearly over clamp bar 49. Note in an alternate embodiment, the firing rod 46 is positioned within and concentric with the clamp bar 49 and thus moves linearly (axially) in a distal and proximal direction within a lumen of the clamp bar 49 for firing and the clamp bar 49 moves linearly (axially) in proximal and distal directions over the firing rod 46 for clamping.

The output flag 42 of power pack 18 is configured to engage a bossed end 44 of the firing rod 46 when the power pack 18 is fully inserted into the receptacle 20 of the handle assembly 2. As shown, the output flag (yoke) 42 has a receiving or mounting feature or member (also referred to as the engagement feature (member) or firing rod engagement feature (member) in the form of two arms 43*a*, 43*b* and a slot 43 therebetween (see FIG. 4B), configured to frictionally (and releasably) engage the bossed end 44, the feature aligning with the bossed end 44 during insertion. (The aforedescribed guiding structure on the power pack 18 and internal wall of the compartment 20 aid such alignment).

Figure 8A:
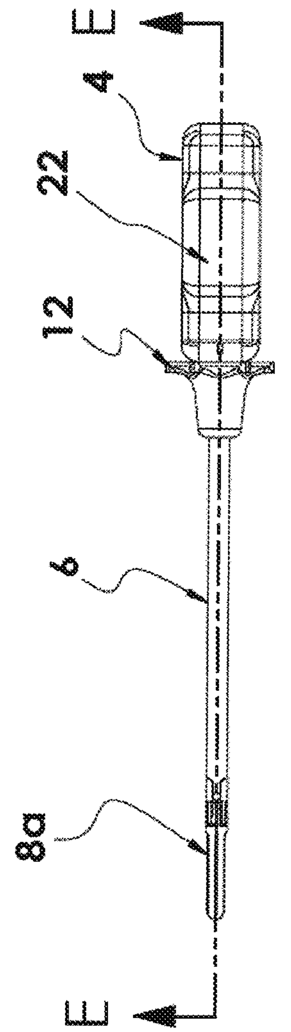
FIG. 8A is a top view of the surgical stapler of FIG. 1 showing the power pack fully inserted and the cover of the handle compartment in the closed position, the view the same as FIG. 6B but having section line E-E.
Figure 8B:
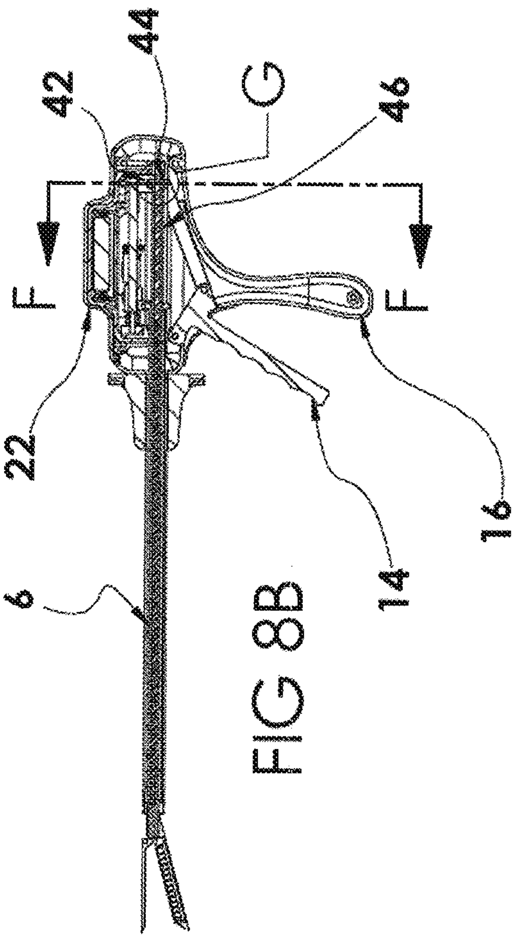
FIG. 8B is a cross-sectional view taken along line E-E of FIG. 8A.

FIGS. 8A and 8B show the power pack 18 fully inserted into the compartment 20 of stapler 1. In this position, the output flag 42 is engaged with the bossed end 44 of the firing rod 46. Note the firing rod 46 is able to rotate when the first output flag 42 of the power pack 18 is engaged with the bossed end 44. When the power pack 18 is secured to the firing rod 46 by the first output flag 42, linear motion generated at the first output flag 42 by the motor actuated drive assembly is transferred to the firing rod 46, which moves linearly to actuate the staple firing mechanism. That is, rotation of the gear 30 effects axial (linear) movement of the drive screw 36 which effects axial (linear) movement of the connected drive mechanism 40 to effect axial (linear) movement of the associated drive mechanism (rod) engaging member (i.e., flag 42). It should be appreciated that flag 42 provides one example of the releasable attachment (engagement member) of the motor assembly to the firing rod 46, it being understood that other mounting (engagement) members or features are also contemplated to engage the firing rod to advance it axially.

In use, the cover 22 of stapler 1 is opened and the power pack 18 is inserted into receptacle 20 of sterile handle assembly 2 (of sterile stapler 1), with the output flag 42 of the power pack 18 engaging a corresponding feature, e.g., boss 44 of elongated drive rod 46, in the handle assembly 2 as discussed above. Then, the cover 22 is closed to seal the power pack 18 within the receptacle 20 from the external environment and the surgical stapler 1 may be actuated, i.e., manually clamped, articulated and/or rotated if desired, and the motor actuated to effect staple firing. After applications of fasteners and release (unclamping of the jaws from tissue), the cover 22 can be opened and the power pack 18 removed and charged while the stapler and handle assembly are resterilized if the stapler is a reusable instrument or the stapler and handle assembly are disposed of if the stapler is a single use disposable instrument. The power pack 18, due to its sealed configuration discussed above, can be reused without requiring sterilization by insertion into the receptacle 20 of a resterilized handle assembly or a sterile handle assembly of an unused disposable handle assembly. Thus, as can be appreciated, the removable power pack 18 does not need to be subjected to the sterilization process and, therefore, contact between the harsh temperatures and/or chemicals of the sterilization process is advantageously avoided. Also, by being able to reuse the power pack without sterilization, significant cost savings are achieved compared to if the power pack is not resterilizable, is disposed of along with the disposable stapler.

Note that in the embodiment of FIGS. 1-12 (and FIGS. 14-27 discussed below), rotational motion caused by the motor is translated into linear motion within the power pack. This is shown schematically in FIG. 5A wherein the drive rod in the handle housing is engaged by the motor driven drive assembly of the power pack 18 (or power pack 90 which is discussed below) moves linearly (axially) to effect linear (axial) movement of the drive member in the stapler, e.g., extending through the endoscopic portion, which effects staple firing. Alternatively, or in addition, a drive assembly of the power pack engages a drive rod in the housing which moves linearly to effect linear movement of a drive rod to effect clamping of the jaws and/or a drive assembly of the power pack engages a drive rod in the housing which moves linearly to effect linear movement of a drive member to effect articulation of the jaw assembly. Alternatively, the intermediate drive member could be omitted and the drive rods engaged by the power pack directly effect respective clamping and articulation.

Figure 5A:
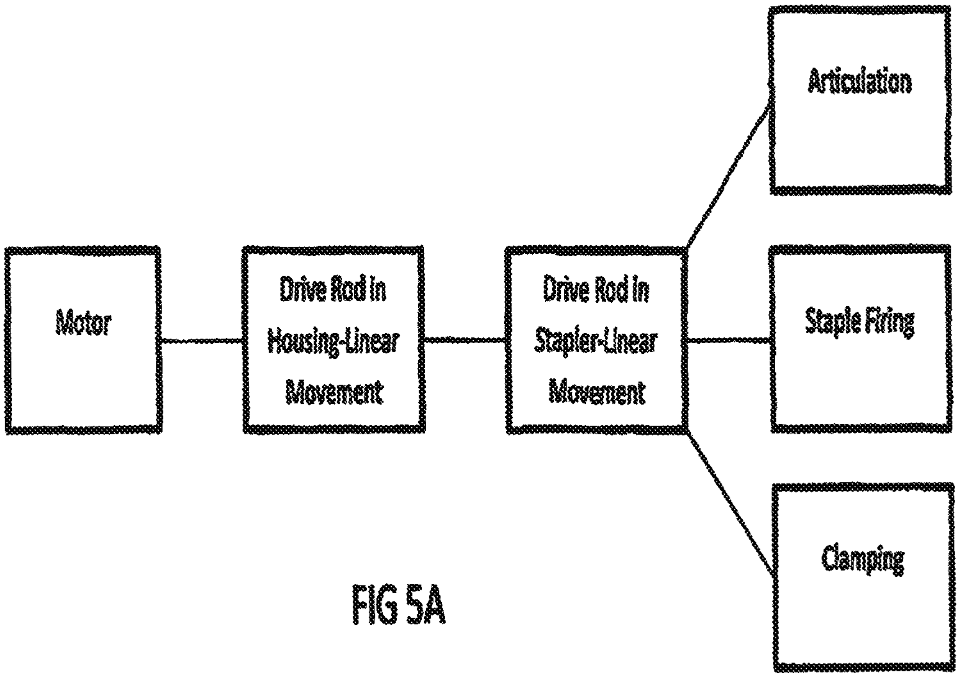
FIG. 5A is a schematic view illustrating transition from rotational movement to linear movement to effect a function of the surgical stapler.
Figure 5B:
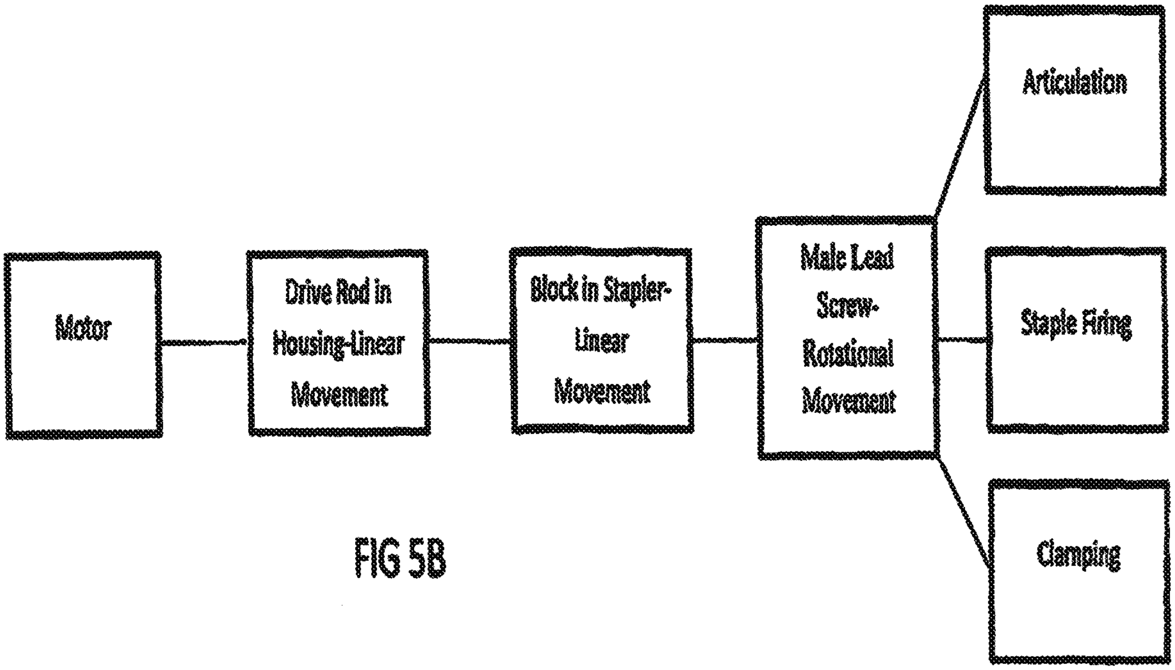
FIG. 5B is a schematic view of an alternate embodiment illustrating transition from rotational movement to linear movement to rotational movement to effect a function of the surgical stapler.

In an alternate embodiment, shown schematically in FIG. 5B, linear motion is converted back to rotational movement. That is, the handle housing has a receptacle (compartment) to receive power pack 18 (or power pack 90) which has one or more engagement features to engage or couple to a firing rod for firing staples, a clamping rod for clamping the jaws about tissue and/or an articulation rod to articulate the jaws to angular positions with respect to the longitudinal axis. The drive rod is connected at its distal end to a block in the stapler having a female thread or a slotted guide engagement to prevent rotation of the block and enable linear movement. (The drive rod could alternatively be attached to other structure). The block is connected to a male lead screw which is engaged at its proximal end via threaded engagement to the distal end of the block. The lead screw is connected at its distal end to a component that requires rotation to effect operation of the stapler, such as effecting staple firing, clamping and/or articulation. A bearing can be provided to keep the lead screw on center and control axial motion. In use, actuation of the motor advances the drive assembly of the power pack linearly which is engaged with and advances the drive rod in the handle housing linearly (axially). Linear movement of the drive rod causes linear movement of the block positioned in the endoscopic portion (or alternatively positioned in the handle housing.) Linear movement of the block causes rotation of the male lead screw to engage a staple firing component(s) to effect staple firing. Alternatively, or in addition, the drive assembly, or a separate drive assembly (assemblies), engages a drive rod in the housing which moves linearly to effect linear movement of a block to cause rotation of the lead screw to move a jaw clamping component(s) to effect clamping of the jaws and/or engages a drive rod in the housing which moves linearly to effect linear movement of a block to cause rotation of the lead screw to move an articulation component(s) to effect articulation of the jaws. Note in some embodiments such conversion from rotary to linear to rotary motion can occur within the power pack.

In the embodiment of FIGS. 1-12, the power pack 18 actuates the firing rod 46 to fire the staples while other steps are performed manually. In summary, in this embodiment, in use, the jaws 8*a*, 8*b* are moved to the closed (clamped) position manually by a hand actuated lever or control. Also, in this embodiment, the jaws 8 are articulated with respect to the longitudinal axis of the endoscopic portion manually by a hand actuated lever or control. Thus, the clinician would manually clamp the jaws, manually rotate the endoscopic portion and attached jaws 8, and manually articulate the jaws by manipulation of controls at the proximal end of the stapler 1, e.g., at the handle 4.

Figures 13A, 13B:
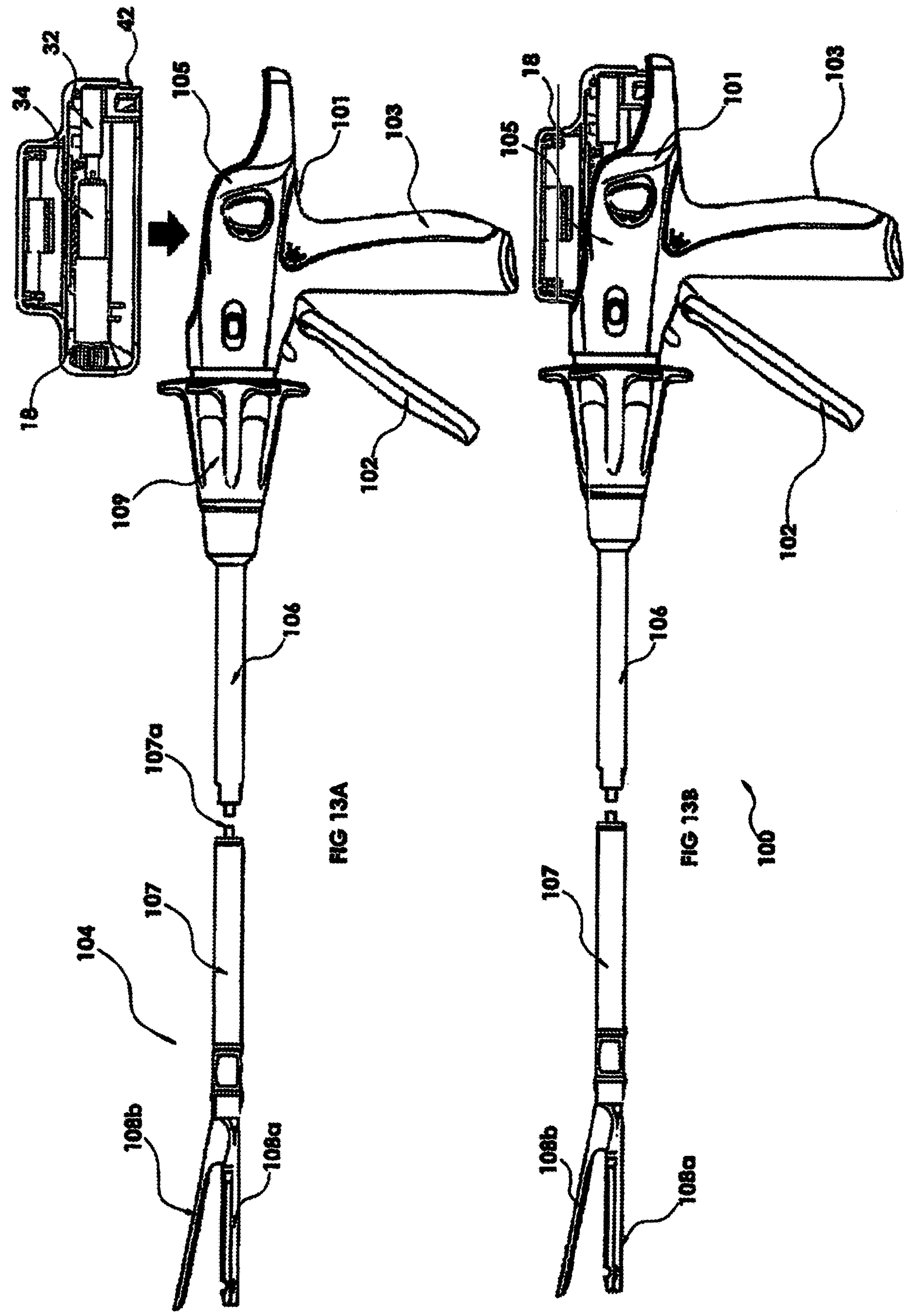
FIG. 13A is a side view of an alternate embodiment of the surgical stapler showing the power pack of FIG. 3 prior to insertion into the handle compartment.
FIG. 13B is a side view similar to FIG. 13A showing the power pack of FIG. 13A inserted into the handle compartment.
Figure 15A:
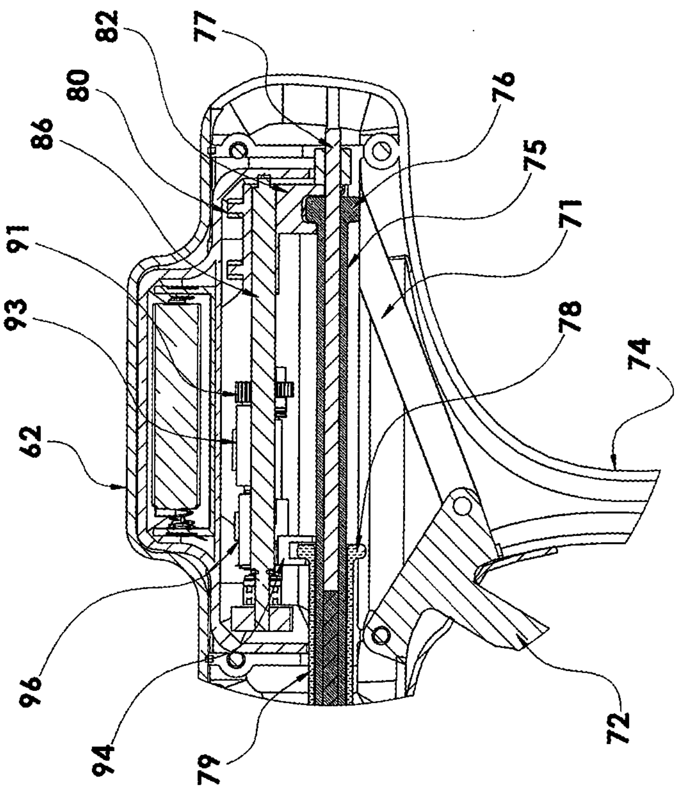
FIG. 15A is a close up view of the area of detail D of FIG. 14C.

FIGS. 1-12 show one embodiment of an endoscopic linear stapler that can be used with the power pack 19 of the present disclosure. However, the power pack 18 is not limited to such endoscopic staplers. For example, FIGS. 13A and 13B illustrate another endoscopic linear stapler, designated by reference numeral 100, that can be powered by power pack 18. Stapler 100 has a handle 102 manually pivotable towards stationary handle 103 for clamping of the jaws 108*a*, 108*b*, an endoscopic portion 106 extending from the handle housing 101, a jaw assembly 104 containing jaws 108*a*, 108*b* and connector 107*a* extending proximally from shaft or tube 107 for attachment to the endoscopic portion 106 so that the jaw assembly 104 can be replaced multiple times in a single surgical procedure to provide additional rows of staples to tissue. The stapler 100 also includes a rotation knob 109 for rotation of the endoscopic portion 106, with respect to the handle housing, to rotate the attached jaws 108*a*, 108*b*. The stapler 100 can also include an articulation knob to articulate the jaws. Power pack 18 is shown in FIG. 13A prior to loading within the handle housing 101 and shown in FIG. 13B fully loaded (inserted) within the handle housing 101. A cover (not shown) can be provided to seal the power pack 18 from the external environment. As in the embodiment of FIGS. 1-12, the flag 42 extending from lead screw 36 engages a firing rod within the handle housing 101 to effect movement of a firing rod to fire the staples when the motor of the power pack 18 is actuated. Power pack 90 having articulation described below can also be utilized with stapler 100.

Figure 34:
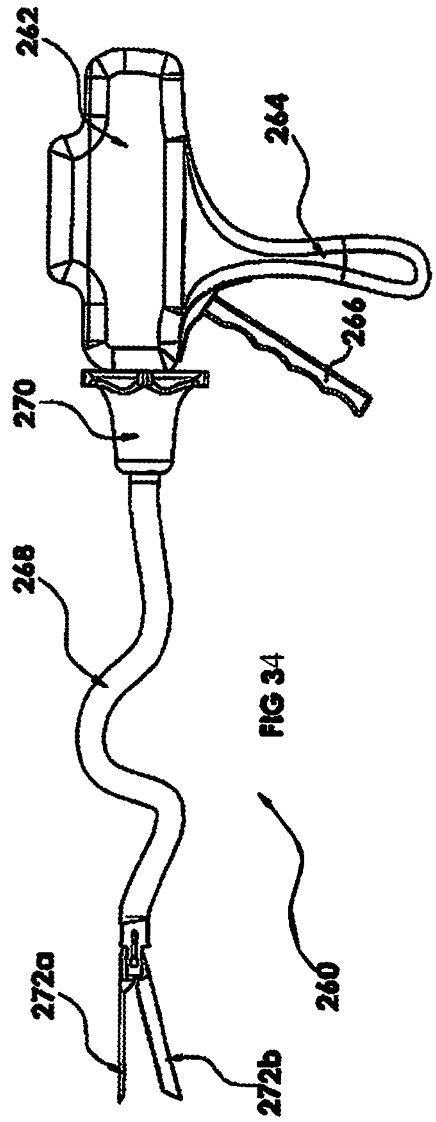
FIG. 34 is a side view of an alternate embodiment of the surgical instrument containing the power pack of FIG. 3 within the handle compartment, the surgical instrument being a flexible endoscopic linear stapler.

FIG. 34 illustrates another type of endoscopic linear stapler that can receive and be powered by the power pack 18. Stapler 260 has a handle 266 manually pivotable towards stationary handle 264 for clamping of the jaws, an endoscopic portion 268 extending from the handle housing 267, and a jaw assembly containing jaws 272*a*, 272*b*. The endoscopic portion 268 is flexible which enables use in various endoscopic procedures. The stapler 260 also includes a rotation knob 270 for rotation of the endoscopic portion 268 to rotate the jaws 272*a*, 272*b*. Power pack 18 is shown fully loaded (inserted) within the handle housing 262 and cover 263 closed to seal the power pack 18 from the external environment. As in the embodiment of FIGS. 1-12, the flag 42 extending from lead screw 36 engages a firing rod within the handle housing 262 to effect movement of a flexible firing rod extending through flexible endoscopic portion 268 to fire the staples when the motor of the power pack 18 is actuated. Power pack 90 having articulation described below can also be utilized with stapler 260.

Figure 33:
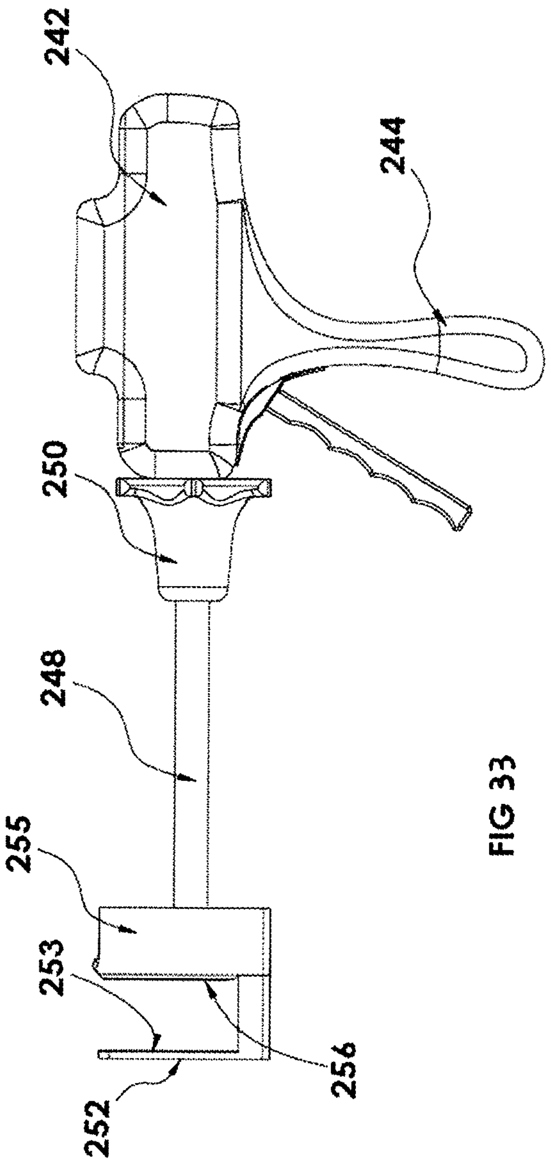
FIG. 33 is a side view of an alternate embodiment of the surgical instrument containing the power pack of FIG. 3 within the handle compartment, the surgical instrument being an open surgery linear stapler.
Figure 32:
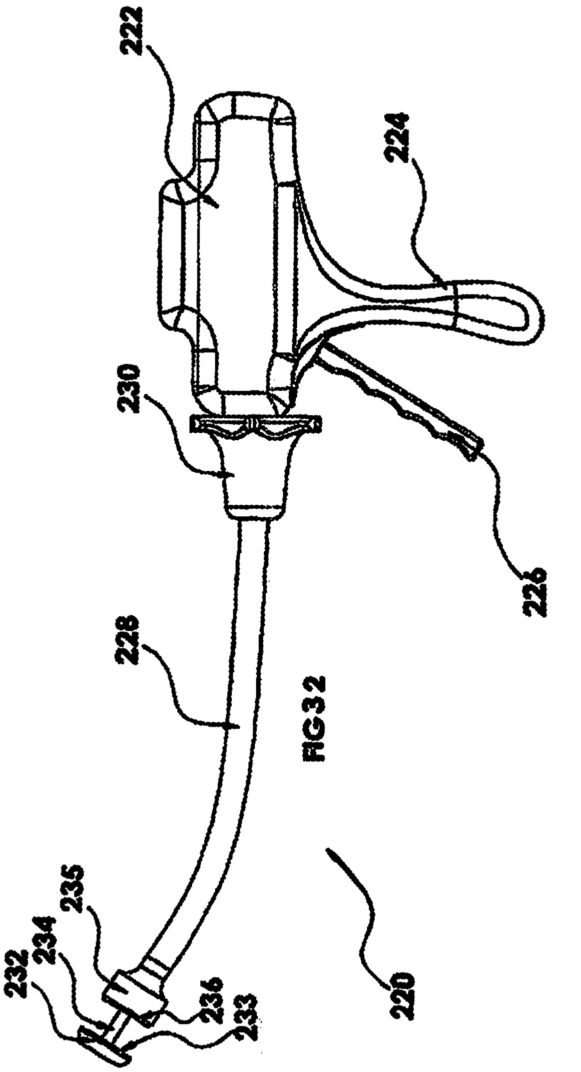
FIG. 32 is a side view of an alternate embodiment of the surgical instrument containing the power pack of FIG. 3 within the handle compartment, the surgical instrument being a circular stapler.

The power pack 18 is also not limited to use with endoscopic linear staplers, nor is it limited to use with staplers. FIGS. 32 and 33 illustrate two examples of different staplers. As in the endoscopic linear staplers discussed herein, these staplers can also have a knife bar to cut tissue between the rows of staples applied to the tissue.

By way of example, the power pack 18 can be used with a circular stapler that applies circular arrays of staples such as shown in FIG. 32. Surgical stapling instrument 220 can receive and be powered by the power pack 18 of the present disclosure. Stapler 220 has a handle 226 manually pivotable towards stationary handle 264 for clamping of the jaws, an elongated tubular portion 228 extending from the handle housing 222, and a jaw assembly having an anvil (jaw) 232 and a cartridge (jaw) 235 containing circular arrays of fasteners (staples). The anvil 232 has a proximal clamping surface 233 and is movable by anvil rod 234 toward the cartridge 235 to clamp tissue between the anvil clamping surface 233 and distal clamping surface 236 of cartridge 235 by manual movement of handle 226 toward stationary handle 224. The stapler 220 also includes a rotation knob 230 for rotation of the elongated portion (shaft) 228 to rotate the jaws 232, 235. Power pack 18 is shown fully loaded (inserted) within the handle housing 222 and cover 223 is shown closed to seal the power pack 18 from the external environment. As in the embodiment of FIGS. 1-12, the flag 42 extending from lead screw 36 engages a firing rod within the handle housing 222 to effect movement of a firing rod extending through elongated portion 228 to fire the circular arrays of staples when the motor of the power pack 18 is actuated. Power pack 90 having articulation described below can also be utilized with stapler 220.

By way of another example, the power pack can be used with a linear stapler that applies transverse rows of staples in a linear direction, i.e., parallel to the longitudinal axis of the stapler, such as shown in FIG. 33. Surgical stapling instrument 240 can receive and be powered by the power pack 18 of the present disclosure. Stapler 240 has a handle 246 manually pivotable towards stationary handle 244 for clamping of the jaws, an elongated tubular portion 248 extending from the handle housing 242, and a jaw assembly containing an anvil (jaw) 252 and a cartridge (jaw) 255 containing linear rows of fasteners (staples) arranged perpendicular to the longitudinal axis of the stapler 240. The proximal anvil clamping surface 253 of anvil 252 and distal clamping surface 256 of cartridge 255 are brought into approximation by manual movement of handle 246 toward stationary handle 244 which advances cartridge 255 toward anvil 252. (Alternatively, the anvil could be retracted toward the cartridge). The stapler 240 also includes a rotation knob 250 for rotation of the elongated portion (shaft) 248 to rotate the elongated portion 248 and jaws 252, 255. Power pack 18 is shown fully loaded (inserted) within the handle housing 242 and cover 243 is shown closed to seal the power pack 18 from the external environment. As in the embodiment of FIGS. 1-12, the flag 42 extending from lead screw 36 engages a firing rod within the handle housing 242 to effect movement of a firing rod extending through elongated portion 248 to fire the staples from cartridge 255 when the motor of the power pack 18 is actuated. Power pack 90 having articulation described below can also be utilized with stapler 240.

The power pack 18 can also be used with single firing instruments that fire a single staple, clip, tack, etc. into body tissue such as those disclosed in U.S. patent application Ser. No. 17/269,907, filed Feb. 19, 2021, now U.S. Pat. No. 11,564,685.

In the embodiments of FIGS. 1-12, a gear mechanism is driven by the motor to rotate the lead screw to advance the drive mechanism to effect firing of the staples. In the alternate embodiment of FIGS. 28-31, a belt drive mechanism is used to effect firing. The belt drive mechanism is contained in the power pack 18 in the same manner as the gear mechanism of the foregoing embodiments, and thus the power pack for the belt drive would include the housing 19 of the configuration of FIG. 1 and loaded in the stapler 1 in the same manner as power pack 18 described above. The belt drive of FIGS. 28-31 is described below for use with stapler 1 of FIG. 1A but can be used in the other surgical staplers and instruments disclosed wherein which are designed to receive power pack 18 or power pack 90 for powered actuation.

The belt drive assembly (mechanism) of the power pack includes a motor 148 connected to a planetary gear box 150 configured to gear down the output of the motor 148 for proper drive speeds for firing staples from jaw 8*a* through the tissue into contact with the anvil of jaw 8*b*. The planetary gear box 150 drives a lead screw 144 via the drive belt operatively connected to the motor shaft. More specifically, upon rotation of the motor shaft by motor 148, first rotatable disc 152 (also referred to as the first wheel or pulley) is rotated in a first direction, causing movement of belt 156 and rotation of second rotatable disc 154 (also referred to as the second wheel or pulley). Note the two discs 152, 154 are spaced apart and not in contact. Lead screw 144 is operatively connected to disc 154 so that rotation of disc 154 causes rotation of lead screw 144 in the same direction. The power pack 18 includes a battery which can be rechargeable outside the stapler when the power pack 18 is removed. The motor 148 is actuated in the various ways described above with regard to power pack 18 of FIG. 3. A tensioner can be provided such as tensioner 158, illustratively in the form of a tension disc or wheel, to apply a force against the belt 156. In the orientation of FIGS. 24C and 24D, the tensioner 158 is positioned underneath the drive belt 156 and applies an upward tensioning force against the belt 156 in a direction toward discs 152, 154. Other types of mechanisms to apply a tensioning force to the belt are also contemplated for use in the embodiment of FIGS. 28-31 if such tensioning of the drive belt 156 is desired.

Connected to the end of lead screw 144 (the end opposite of the connection to the disc 154) is a drive mechanism 142. The drive mechanism 142, like drive mechanism 40 of FIG. 4A, is configured to move in a linear motion (in an axial direction) along the lead screw 144 in response to rotation of the lead screw 144. For example, as in the drive mechanism 40, drive mechanism 142 may include internal threads that engage external threads of the lead screw 144 and may include slides engaged in a track that prevent the drive mechanism 142 from rotating and therefore cause the drive mechanism 142 to move linearly in response to rotation of the lead screw 144. As shown, the lead screw 144 extends alongside, slightly spaced from, the motor 148 and gear box 150, i.e., both the motor 148/gear box 150 and lead screw 144 extending longitudinally with the lead screw 144 parallel to the motor 148. The drive mechanism 142 extends proximally of the proximal end of the motor 148 in the illustrated embodiment.

The drive mechanism 142, like drive mechanism 140 of FIG. 4A, includes a first output flag or yoke 146 with slot 143 configured to engage a staple firing rod 46 extending longitudinally within the handle 4. The flag 146 is the same as flag 42 of FIG. 4B and engages the staple firing rod 46 in the same manner as flag 42. Therefore, for brevity, further discussion of flag 146 and its engagement with firing rod 46 is not provided as the structure and function of flag 42, and alternative firing rod engagement features, are fully applicable to flag 146 of FIGS. 28-31. In brief, as the motor 148 generates rotational motion of the lead screw 144 through the drive belt, the drive mechanism 144 moves in linear motion along the lead screw 144 to effect linear movement of the firing rod 46 which advances the staple driving mechanism to advance (fire) the staples out from jaw 8*b* through tissue and into contact with the anvil in jaw 8*a*.

Other belt drive mechanisms are also contemplated such as those disclosed in the Ser. No. 16/792,110, filed Feb. 14, 2020, now U.S. Pat. No. 11,331,099, the entire contents of which are incorporated herein by reference.

It should be appreciated that the foregoing belt drive mechanisms can be used as an alternative to the gear mechanism in power pack 18 as well as an alternative to one or both of the gear mechanisms of power pack 90 discussed below.

In the foregoing embodiments, the power pack 18 was described for powering staple firing. In an alternate embodiment, the power pack can include a drive mechanism for effecting articulation. This motor powered articulation can be in addition to the motor powered staple firing, or alternatively, the power pack can be used solely for powered articulation. The embodiment of FIGS. 14A-27 illustrate a surgical stapler and power pack which powers both staple firing and articulation. If only for articulation, the power pack described below (power pack 90) would not include the mechanism engageable with the firing rod 46 for staple firing.

Figure 14A:
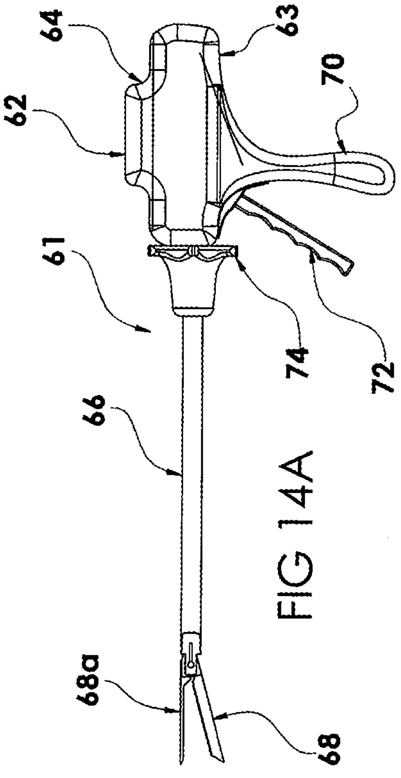
FIG. 14A is a cross-sectional view illustrating an alternate embodiment having a power pack for effecting both firing and articulation of the surgical stapler, the power pack shown fully inserted into the compartment of the handle of the surgical stapler and the compartment cover shown in the closed position.
Figure 14B:
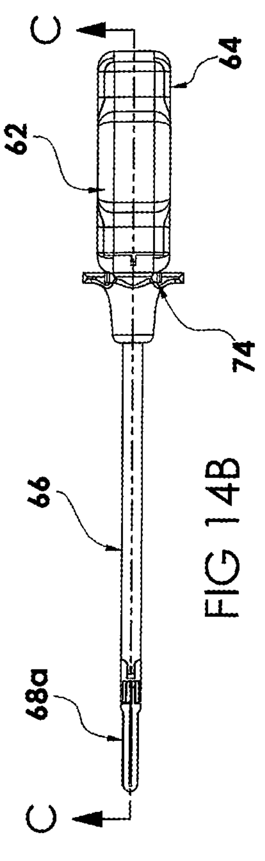
FIG. 14B is a top view of the surgical stapler of FIG. 14A.
Figure 14C:
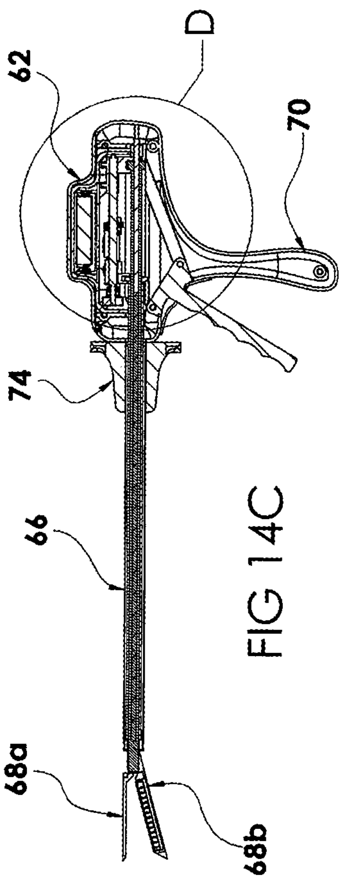
FIG. 14C is a cross-sectional view taken along line C-C FIG. 14B.
Figure 14D:
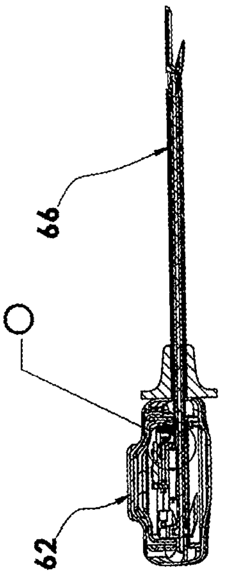
FIG. 14D is a cross-sectional view of the surgical stapler of FIG. 14B.

With initial reference to FIGS. 14A-14C, surgical stapler 61 is identical to surgical stapler 1 of FIG. 1A except for the power pack mounted in the stapler 61 and the articulation rod in the stapler 61 which is engaged by the power pack. Thus, like stapler 1, stapler 61 has a handle assembly 63, an endoscopic portion 66 extending distally therefrom and a pair of jaws 68*a*, 68*b*, (collectively "jaws 68") with at least one of the jaws movable relative to the other jaw, e.g., jaw 68*b* containing the staples (fasteners) movable toward stationary jaw 68*a* containing the anvil pockets (or alternatively jaw 68*a* movable and jaw 68*b* stationary). Handle 72 like handle 14 of stapler 1 is pivotable toward stationary handle 70 to approximate jaws 68*a*, 68*b* to clamp tissue between the closed jaws 68*a*, 68*b*. Handle assembly 63 includes a housing 64 and cover 62 which is identical to cover 22 of stapler 1, i.e., pivotably mounted to the housing 64 to move from a closed to an open position for top loading (or alternatively other directional loading) a power pack into the compartment within the housing 64. The compartment, like compartment 25 described above, sealingly retains the power pack and can include guiding structure for alignment of the power pack similar to guiding structure 28 described above to receive guides 90*a*, 90*b* of power pack 90. Stapler 61 also includes a rotation knob 74 which functions in the same manner as rotation knob 12 of stapler 1 described above to rotate tubular portion (shaft) 66. The jaw assembly, i.e., jaws 68*a*, 68*b*, articulate about joint 69 to move the jaws 68*a*, 68*b* to angular positions with respect to the longitudinal axis of stapler 61.

Figure 4G:
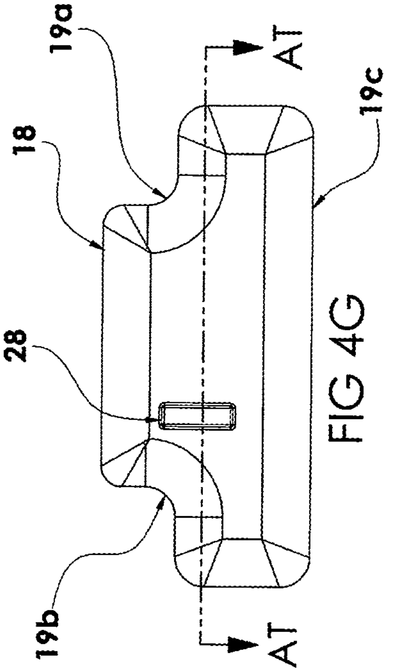
FIG. 4G is a side view of the power pack of FIG. 3.

The power pack in the embodiment of FIGS. 14A-23B is designated by reference numeral 90 and has a motor assembly and drive mechanism for firing staples which is identical to that of the power pack 18 of FIGS. 3A and 4G. However, power pack 90 differs from power pack 18 in that it additionally has a motor assembly and drive mechanism for articulating the jaws. The addition of the articulation assembly can be appreciated by a comparison of the cross-sectional view of FIG. 4H, which only effects firing of the fasteners (staplers), and the cross-sectional view of FIG. 15F which effects firing of fasteners and articulation of the jaw assembly.

Figure 4H:
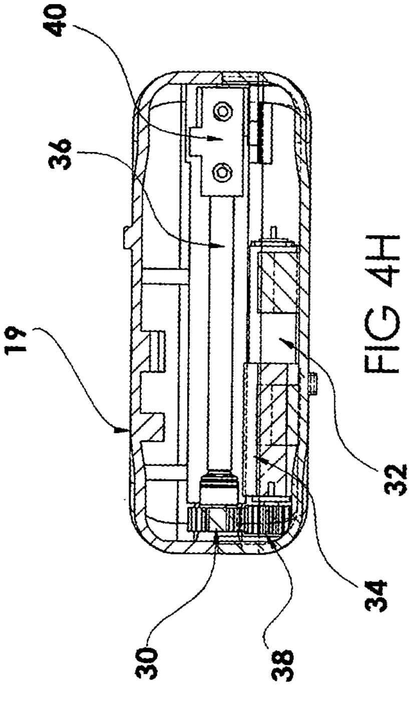
FIG. 4H is a cross-sectional view taken along line AT-AT of FIG. 4G.

More specifically, with reference to FIGS. 15A-15F and 18B, the powered staple firing assembly like the firing assembly of power pack 18 of FIG. 4H, includes a motor 83 connected to a planetary gear box 85 configured to gear down the output of the motor in the same manner as motor 32 and gear box 34 of power pack 18. The planetary gear box 85 drives a lead screw 86 through one or more gears operatively connected to the motor shaft. More specifically, upon rotation of the motor shaft by the motor 83 in a first direction, gear 81 is rotated in the same first direction, causing rotation of the gear 84 in a second opposite direction due to the intermeshed teeth of gears 81 and 84. Lead screw 86 is operatively connected to gear 84 so that rotation of gear 84 causes rotation of lead screw 86 in the same direction. The power pack 18 includes a battery 33 which can be rechargeable outside the stapler when the power pack 18 is removed. The power pack 90 in some embodiments can include a power switch which is activated, i.e., turned on, by the clinician to start the motor and effect staple firing. In other embodiments, the motor can automatically turn on when fully loaded or upon actuation of another control on the stapler housing 4.

Connected to the end of lead screw 86 (the end opposite the connection to the gear 84) is a drive mechanism 80 which is configured to move in a linear motion (in an axial direction) along the lead screw 86 in response to rotation of the lead screw 86. Drive mechanism 80 includes a flag or yoke 82 identical to yoke 42 of power pack 18 discussed above, which engages flange or boss 76 of firing rod 75 within housing 64 of stapler 61. The connection of the flag 82 to the firing rod 76, the motor and gear mechanism, and the drive mechanism 80 of power pack 90 are the same as the power pack 18 and therefore the aforedescribed functions and features/components of power pack 18 for staple firing are fully applicable to the function and features/components of power pack 90 for staple firing so for brevity are not fully repeated herein. It should also be appreciated that the alternative mechanisms for motor powered staple firing, such as the various belt drive mechanisms discussed above and/or illustrated in the Figures, can also be used in the power pack 90 as well as with other power packs described below to effect staple firing. Additionally, the various sensors discussed above with regard to sensing the firing stroke can also be provided in power pack 90 as well as with other power packs described below for the same uses.

Power pack 90 also has an articulation assembly, shown in detail in FIGS. 22-27. The articulation assembly includes a powering assembly including a motor 96 connected to a planetary gear box 93 configured to gear down the output of the motor 96. The planetary gear box 93 drives a lead screw 98 through gears 91, 92 operatively connected to the motor shaft. More specifically, upon rotation of the motor shaft by motor 96 in a first direction, gear 91 is rotated in the same first direction, causing rotation of the gear 92 in a second opposite direction due to the intermeshed teeth of gears 92 and 91. Lead screw 98 is operatively connected to gear 92 so that rotation of gear 92 causes rotation of lead screw 98 in the same direction. The power pack 90 in some embodiments can include a power switch which is activated, i.e., turned on, by the clinician to start the motor and effect articulation.

Connected to the end of lead screw 98 (the end opposite the connection to the gear 92) is a drive mechanism 95 configured to move in a linear motion (in an axial direction) along the lead screw 98 in response to rotation of the lead screw 98. For example, the drive mechanism 95, like drive mechanisms 40 and 80 described above, may include internal threads that engage external threads of the lead screw 98 and may include slides engaged in a track that prevent the drive mechanism 95 from rotating and therefore cause the drive mechanism 95 to move linearly (axially) in response to rotation of the lead screw 98. As depicted, the power pack 90 has a compact configuration as the lead screw 98 extends alongside, slightly spaced from, the motor 96 and gear box 93, i.e., both the motor 96/gear box 93 and lead screw 98 extending longitudinally with the lead screw 98 parallel to the motor 96. The drive mechanism 95 is connected to a proximal end of lead screw 98 and is moved linearly upon rotational movement of screw 98. The drive mechanism 95 has an articulation rod engagement feature in the form of a flange or yoke 94 extending therefrom having legs 99*a* and a recess 99*b* to engage an articulation rod 79 within the housing 63 to move the articulation rod linearly to articulate the jaw. In the illustrated embodiment (see e.g., FIGS. 15B and 22), the articulation rod 79 includes a flange 78 which is engageable by the flag 94 to move the rod in an axial direction as the drive mechanism moves axially (linearly). The output flag 94 can engage the bossed end 78 of the articulation tube 79 in substantially the same manner as the output flag 42 engages the bossed end 44 of the firing rod 46 as discussed above.

The articulation assembly of the power pack 90 is oriented in the opposite direction from the staple firing assembly to minimize the space required in the power pack 90, thereby providing the power pack with a compact configuration. As can be appreciated by reference to FIGS. 15A and 15F, the drive assembly 80 and associated flag 82 are at a proximal end of the assembly for firing staples with the lead screw 86 extending distally toward the gears 81, 84. The driving assembly 95 with associated flag 94 of the assembly for articulation are at a distal end with the lead screw 98 extending proximally toward gears 91, 92. Also as can be appreciated by reference to the orientation of FIGS. 15A and 15F, the articulation assembly is above (closer to the cover 22) than the firing assembly, and the articulation assembly in the illustrated embodiment is positioned axially proximal of gears 81, 84 and axially distal of drive mechanism 80, radially spaced from lead screw 86.

Figure 15B:
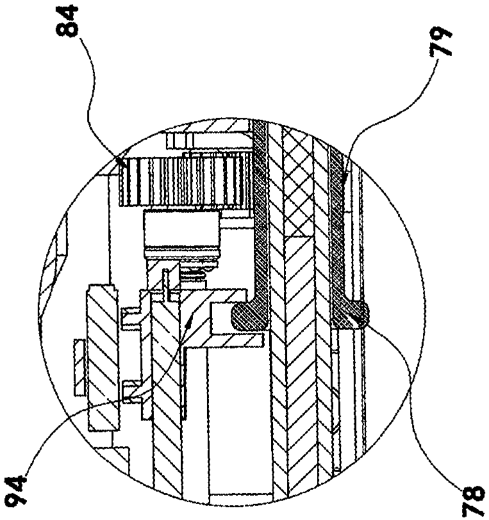
FIG. 15B is a close up view of the area of detail O of FIG. 14D.
Figure 15E:
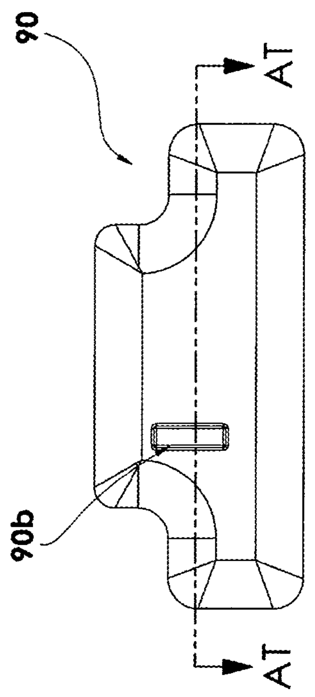
FIG. 15E is a side view of the power pack of FIG. 15C.
Figure 15F:
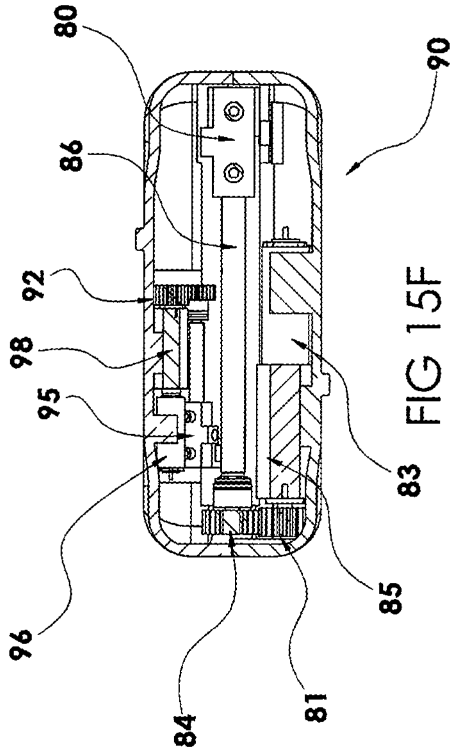
FIG. 15F is a cross-sectional view taken along line AT-AT of FIG. 15E.
Figure 15C:
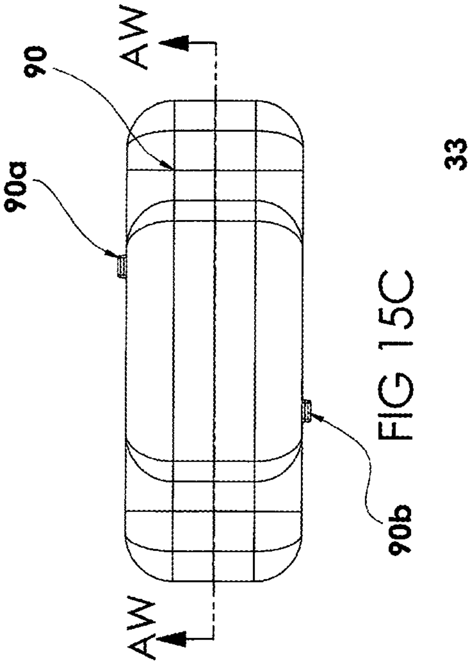
FIG. 15C is a top view of the power pack of FIG. 14A for effecting both firing and articulation of the surgical stapler.
Figure 15D:
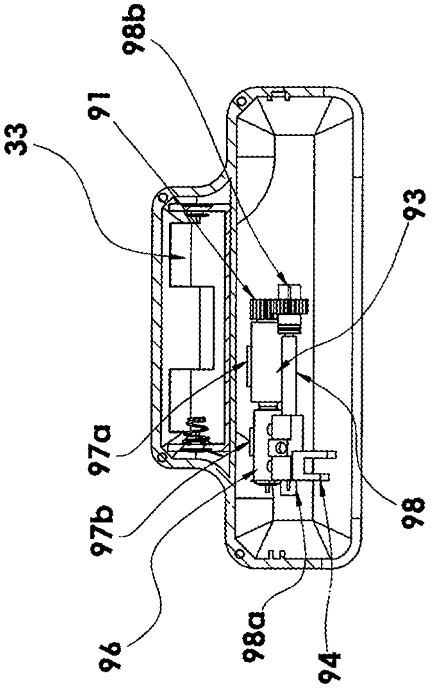
FIG. 15D is a cross-sectional view taken along line AW-AW of FIG. 15C.
Figure 16D:
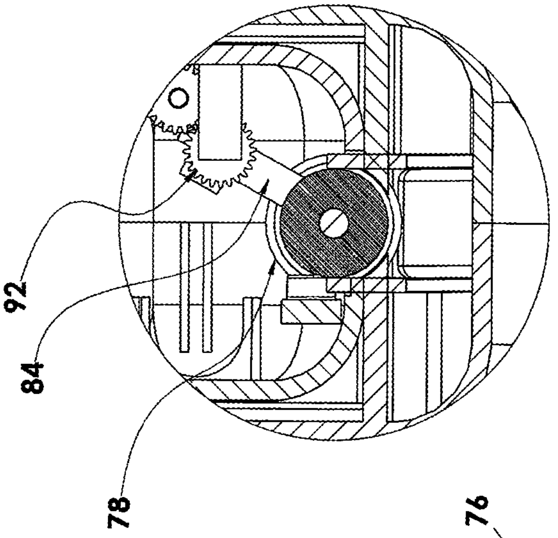
FIG. 16D is a close up view of the area of detail H of FIG. 16C.
Figure 16C:
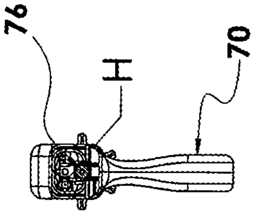
FIG. 16C is a cross-sectional view taken along line F-F of FIG. 15C.
Figure 16A:
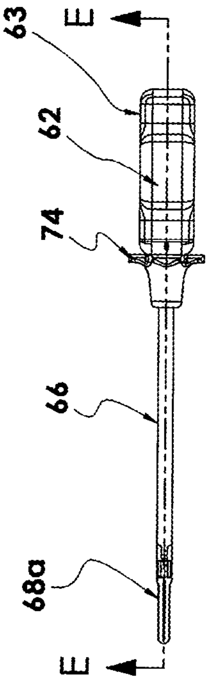
FIG. 16A is a top view of the surgical stapler of FIG. 14A, the view being the same as FIG. 14B but having section line E-E.
Figure 16B:
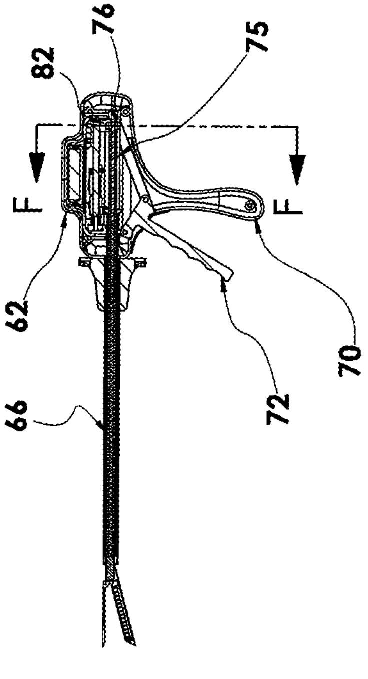
FIG. 16B is a side view of the surgical stapler of FIG. 14A, the view being the same as FIG. 14C but having section line F-F.
Figure 18B:
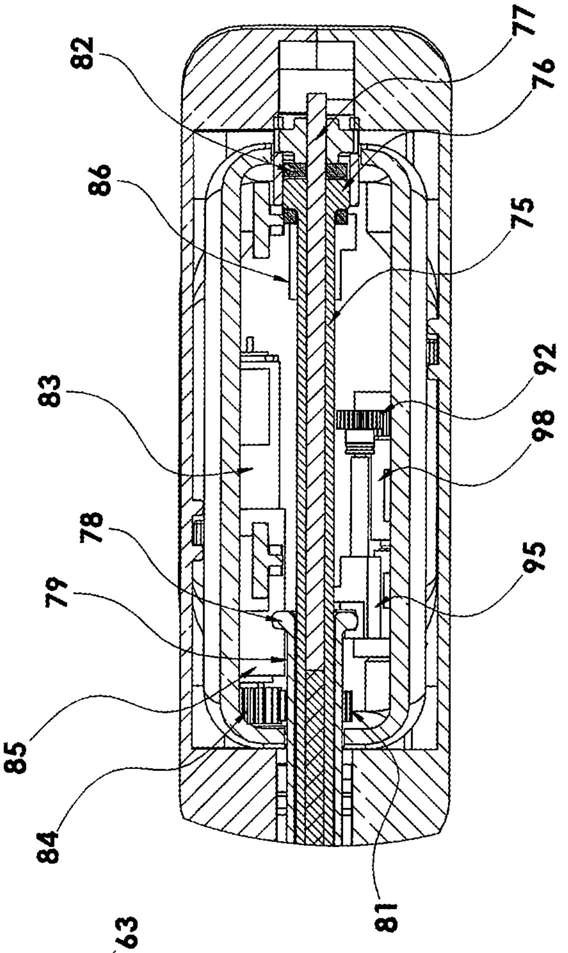
FIG. 18B is a close up view of the area of detail BA of FIG. 18A.
Figure 17:
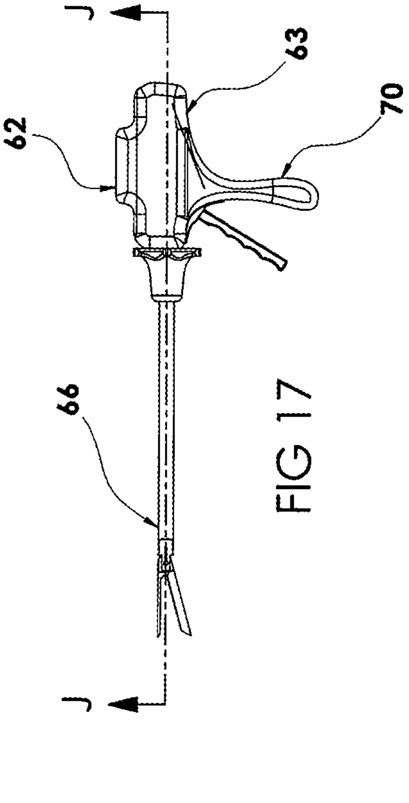
FIG. 17 is a side view of the surgical stapler of FIG. 14A, the view being the same as FIG. 14A but having section line J-J.
Figure 18A:
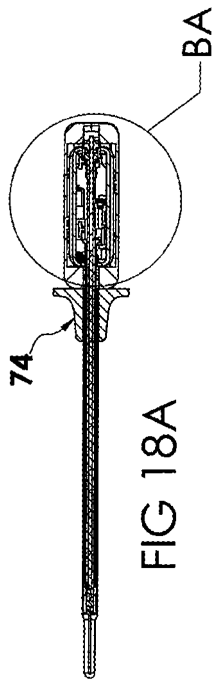
FIG. 18A is a cross-sectional view taken along line J-J of FIG. 17.
Figure 19C:
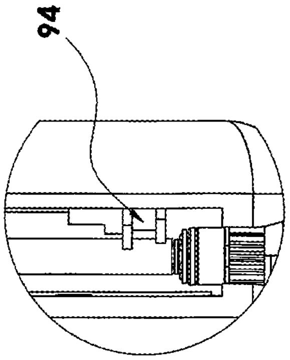
FIG. 19C is an enlarged view of the area of detail AL of FIG. 19A.
Figure 19B:
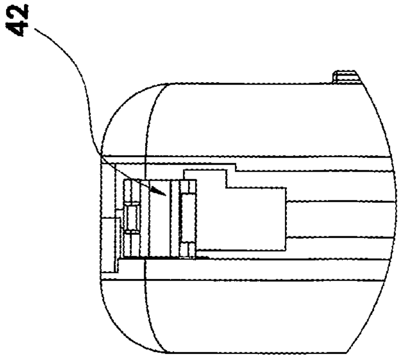
FIG. 19B is an enlarged view of the area of detail AK of FIG. 19A.
Figure 19A:
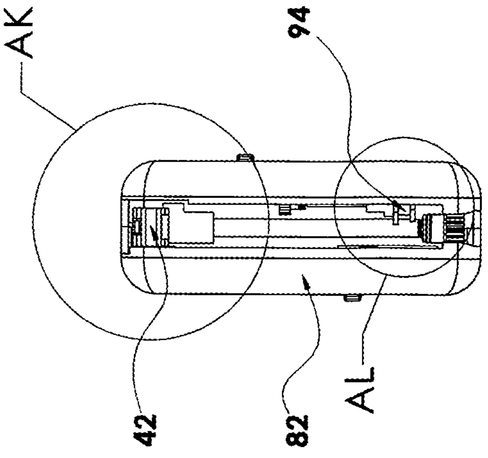
FIG. 19A is a top cutaway view of the power pack of FIG. 14A.

The power pack 90, like power pack 18 can have features/structure to constrain the motors 84 and 96. In the embodiment of FIG. 15D, such feature is in the form of proximal rails 97*a* and distal rails 97*b* spaced apart axially within the housing of the power pack 90. Gear box 93 is seated within proximal rails 97*a* and motor 96 is seated within distal rails 97*b*, the rails 97*a*, 97*b* retaining the motor and preventing axial and rotational movement within the housing of power pack 90. Bearing or bushings 98*a*, 98*b* can also be provided to constrain the lead screw 98 at opposing ends, while allowing rotation thereof, thereby also constraining the motor. Other features can additionally or alternatively be provided to restrain the motor from axial movement while allowing rotation of the lead screw.

The power pack 90 can include guides, e.g., projections 90*a*, 90*b*, either axially aligned or axially offset, similar to guides 28 of power pack 18 for alignment with guiding structure in the compartment of stapler 61. This can prevent misloading of the power pack.

In use, with the cover 62 of stapler 61 in the open position, power pack 90 is loaded into the compartment of the handle housing 63. The cover 62 is closed to seal the power pack 90 from contaminants in same manner as cover 22 of stapler 1. Upon loading of the power pack 90, flag 82 of the drive mechanism 80 of the staple firing assembly engages flange 76 of firing rod 75 and flag 94 of drive mechanism 95 of the articulation assembly engages flange or bossed end 78 of articulation rod 79. Actuation of the motor 96 rotates the lead screw to effect linear motion of the flag 94 which moves the articulation rod 79 linearly (axially). The articulation rod 79 is either directly coupled to the joint 69, or coupled to another member or multiple members which are coupled to the joint 69. When moved linearly, the articulation rod 79 effects movement of the jaws 68A, 68*b* of the stapler 61 to angular positions with respect to the longitudinal axis of the stapler 61. Note the articulation drive assembly operates in a similar manner as the firing drive assembly of power pack 18 in that when the power pack 90 is secured to the tube 79 by the second output flag 94, linear motion generated at the second output flag 94 is transferred to linear motion of the tube 79.

Actuation of the motor 83 effects linear motion of the flag 82 which moves the firing rod 75 linearly (axially). The firing rod 75 either extends through the elongated portion 66 for engagement of the firing mechanism in the jaw 68*b* or is coupled to another elongated component(s) extending through the endoscopic portion 66 to engage the firing mechanism in the jaw 68*b*. Note that the articulation rod or tube 79 can be configured to receive the firing rod 75 so that the firing rod 75 can move within the tube 79 to effect firing and the articulation rod 79 can slide linearly over the firing rod to effect articulation or alternatively articulation rod tube 79 can be configured to slide linearly within the firing rod 75.

After use, the cover 62 can be opened and the power pack 90 removed and charged while the handle assembly 63 (and stapler 61) is sterilized or disposed of if the stapler is a disposable instrument. The power pack 90, like power pack 18 described above, may be reused without requiring sterilization by being inserted into the receptacle of the now-sterilized handle assembly 63 or a different sterile handle assembly. Thus, the removable power pack 90, like power pack 18, does not need to be subjected to the sterilization process and, therefore, contact between the harsh temperatures and/or chemicals of the sterilization process is advantageously avoided.

Figure 21B:
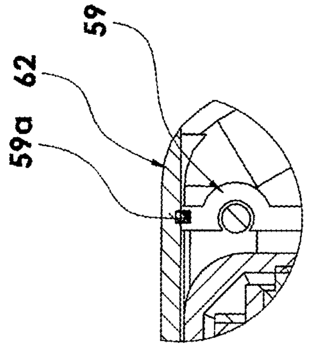
FIG. 21B is an enlarged view of the area of detail R of FIG. 19A.
Figure 21A:
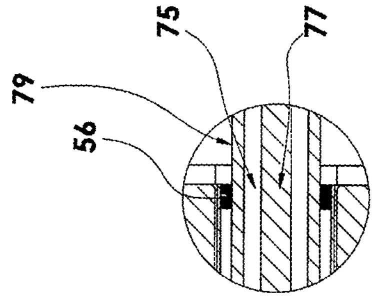
FIG. 21A is an enlarged view of the area of detail Q of FIG. 20.
Figure 21C:
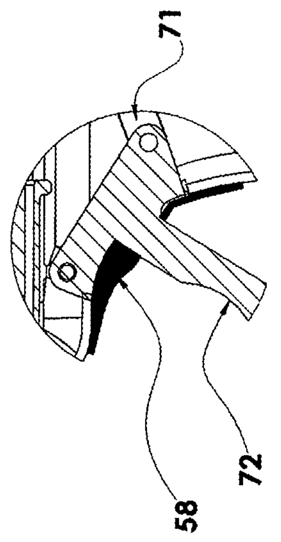
FIG. 21C is an enlarged view of the area of detail S of FIG. 19A.

One or more seals are utilized for sealing power pack 18 and power pack 90 within the handle assembly 2 or 63 (or within the other handle assembles disclosed herein) so that the power pack remains sterile and is not exposed to bodily fluids during surgical procedures. For example, as discussed above, in the stapler 1 of FIG. 1, the top seal 24 is positioned at the interface between the cover 22 and the housing 4 of the handle assembly 2 where the cover 22 closes for sealing the opening into the receptacle 20 and, therefore, power pack 18 from the environment when positioned therein. Similarly, in the stapler 61 of FIG. 14A, the top seal is positioned at the interface between the cover 62 and the housing 64 of the handle assembly 63 wherein the cover 62 closes for sealing the opening into the receptacle and, therefore, power pack 90 from the environment when positioned therein. As shown in FIGS. 21A-21C, further seals can be provided to further seal the receptacle and thus the power pack. An O-ring 56 is placed around the articulation rod 79 to seal the space around the rod 79. A flexible trigger seal 58 surrounds the lever 72 for sealing the internal components of the handle assembly 63 throughout the range of positions of the movable lever 72. Thus, all of the openings into the receptacle of the handle assembly 63 are sealed from the external environment. The O-ring seal 56 and trigger seal 58 can also be used in stapler 1 so the openings into the receptacle 20 of handle assembly 2 are sealed from the external environment. Elastomeric seal 59*a* seals cover 62 from U-channel 59 within the handle which supports the power pack 90. Additional seals can be provided to prevent flow of body fluid through the endoscopic portion 66 (and endoscopic portion 6). Other types of seals and seals in different locations are also contemplated. Such seals can be used with the other embodiments of the surgical instruments disclosed herein.

FIGS. 35-38B illustrate alternate embodiments of the power pack having a removable battery pack. Each of the power packs (power trains) 406, 420 and 430 in the embodiments of FIGS. 35-37C can have a motor assembly and drive mechanism for firing staples which is identical to that of the power pack 18 of FIGS. 3 and 4G or alternatively can have a motor assembly and drive mechanism for firing staples and additionally a motor assembly and drive mechanism for articulating the jaws as in power pack 90 of FIG. 14A described above. The surgical staplers for receiving power packs 406, 420 or 430 are the same as the surgical stapler 1 (except for the compartment and cover) so that it has been labeled with like reference numerals. The power packs 406, 420 and 430 with removable/interchangeable battery pack could also be used with the other surgical staplers described herein or with other surgical instruments such as those described herein. Therefore, further discussion of the surgical staplers is not provided herein as the description of the stapler 1 components (e.g., shaft 6, jaws 8*a*, 8*b*, handle 12, etc.) and its functions, as well the description of other staplers, are fully applicable to the stapler receiving power packs 406, 420 or 430.

Figure 35:
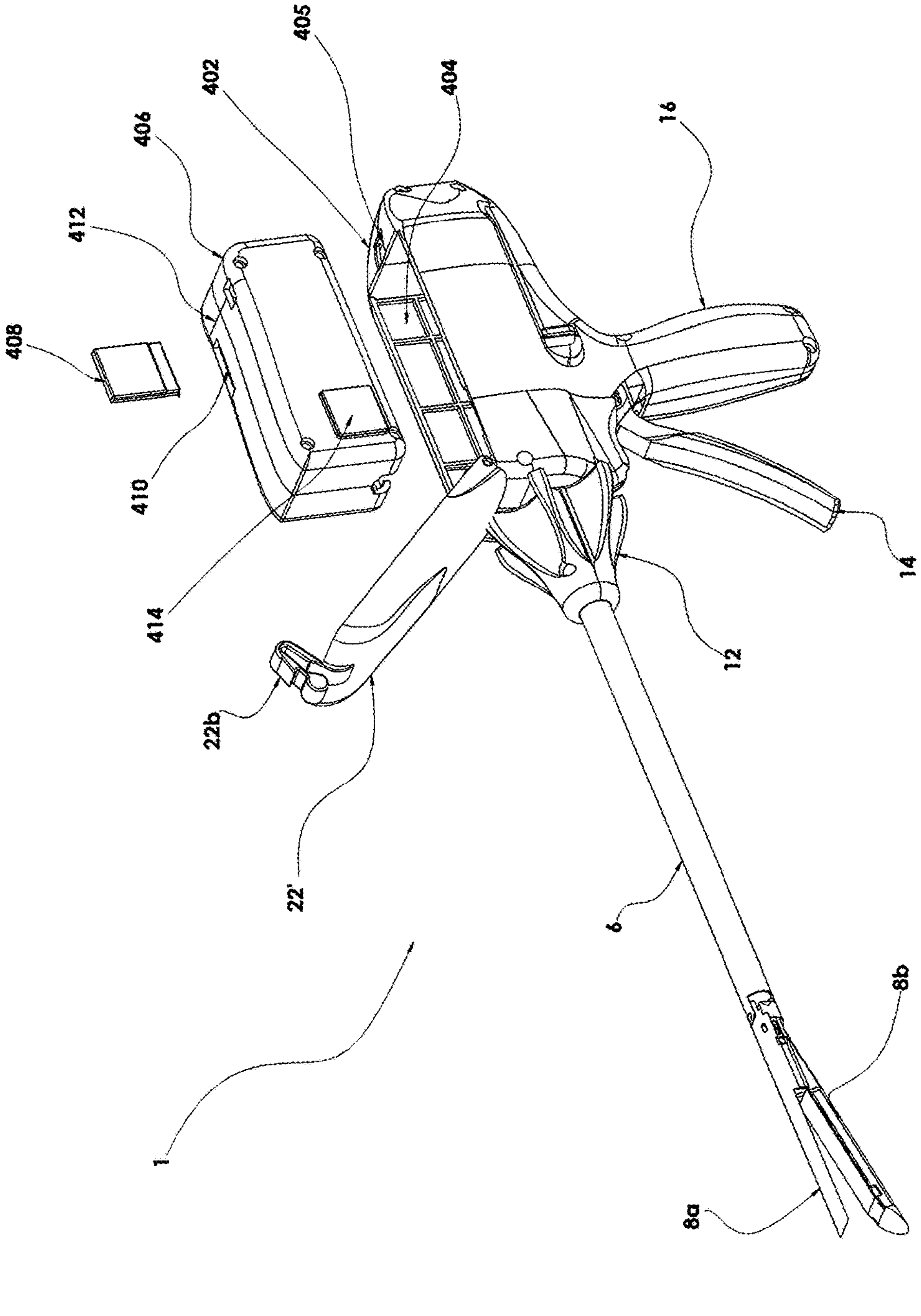
FIG. 35 is a perspective view of an alternate embodiment of the power pack of the present invention having a replaceable battery pack, the power pack shown prior to loading in the instrument compartment.

Turning first to the embodiment of FIG. 35, the power pack 406 has an upper surface 412 having a cavity 410 to slidably receive card-like battery pack 408. Battery pack 408 is slid into the cavity and engages a contact within the housing to enable actuation of the motor to power the drive mechanism within the power pack 406 to effect staple firing and/or jaw articulation in the same manner as described above (via engagement by the flag or yoke). Power pack 406 is placed into the cavity 404 of housing 402 in a similar manner as described above, e.g., top loaded into the compartment, and the hinged cover 22' is closed to seal the power pack 406 from the external environment. Cover 22' differs from cover 22 in that it includes a spring loaded latch 22*b* received in latch cavity 405 of housing 402 to retain the cover 22' in the closed position. The latch 22*b* is released by pressing latch 22*b* to disengage the latch so the cover 22' can be opened to access the power pack 406. Raised surface (tab) 414 on one or both sides of the power pack 406 aligns with a recess in the compartment 404 for alignment of the power pack 406 during insertion.

In use, the battery pack 408 can be aseptically preloaded in the power pack 406, either by a user or packaged with the battery pack 408 preloaded, and the power pack 406 is aseptically preloaded into the surgical instrument. During a surgical procedure, in the event of a battery failure, the cover 407 can be opened and the power pack 406 can be removed intraoperatively from compartment 404, the battery pack 408 removed from cavity 410, a new (second) charged battery (battery pack) aseptically placed in cavity 410 and the power pack 406 with the replacement battery pack reloaded into compartment 404. In an alternative use, during a surgical procedure, in the event of a battery failure, the cover 407 can be opened and with the power pack 406 remaining in compartment 404, the battery pack 408 is removed from cavity 410 of the power pack 406 and a new (second) charged replacement battery (battery pack) aseptically placed in cavity 408 while the power pack 406 remains loaded (positioned) within the compartment 404 of the surgical instrument. In either case, the replaceable battery, in this and other embodiments, limits the number of extra more expensive power packs which otherwise would need to be stocked in the OR for backup.

Figure 36:
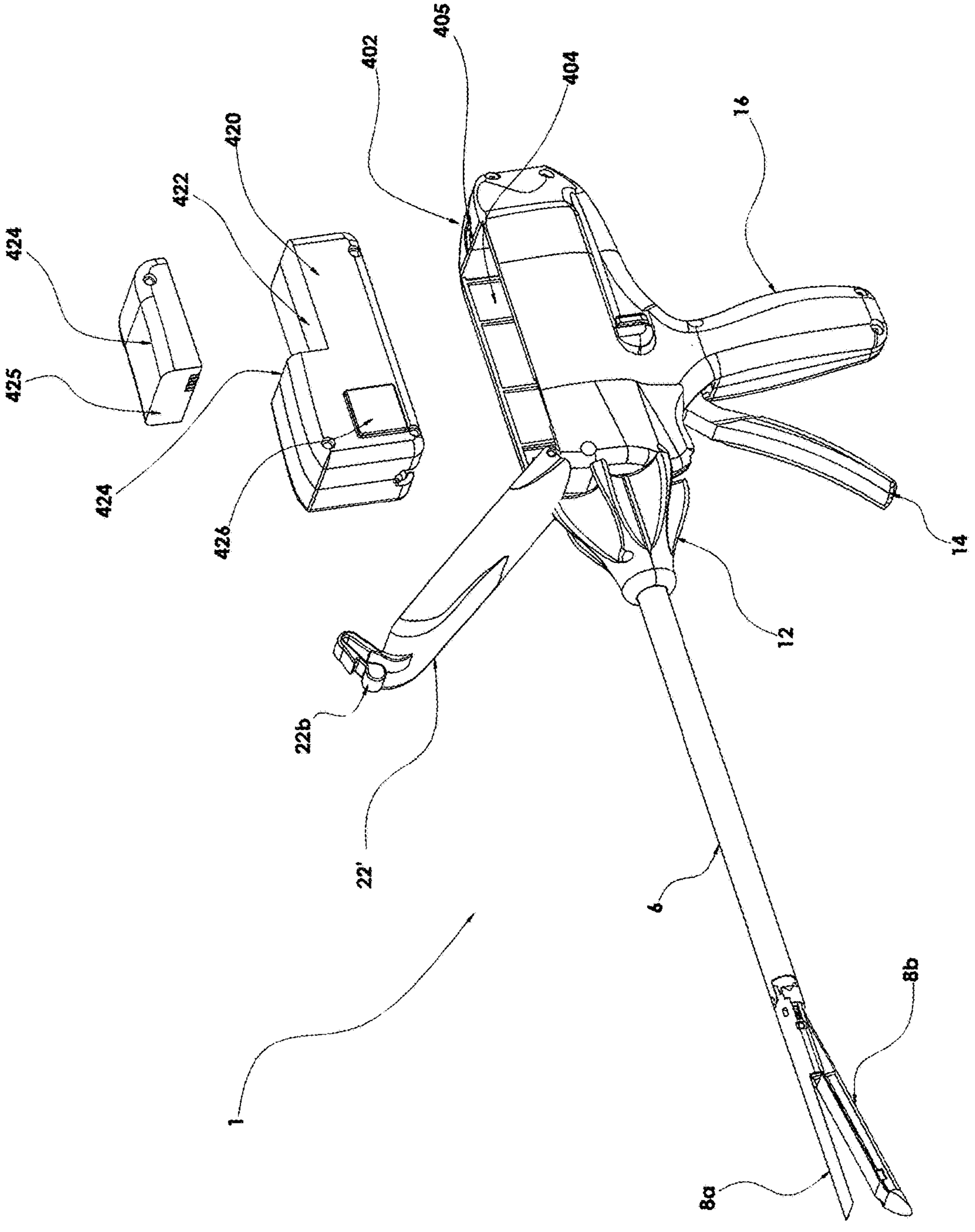
FIG. 36 is a perspective view of another alternate embodiment of the power pack of the present invention having a replaceable battery pack, the power pack shown prior to loading in the instrument compartment.

In the alternate embodiment of FIG. 36, the stapler 1 is the same as in FIG. 35, the difference being the power pack and battery pack. More specifically, power pack 420 has an outer upper surface 422 extending proximally from wall 428, on which the battery pack 424 is mounted. Wall 425 of battery pack 424 can be placed in abutment with wall 428, and the power pack 420 and battery pack 424 can be dimensioned so that the battery pack 424 becomes part of the outer contour of the power pack 420, e.g., the upper surface 427 of the power pack can be substantially flush with the upper surface 429 of the power pack 420, although in alternate embodiments the upper surface can be below or above the upper surface 429. Power pack 422 can have an alignment tab 426 on one or both sides to aid insertion/alignment. The battery pack 424 can include an engagement feature 420 interacting with the power pack/to secure the battery pack 424 on the power pack 420.

In use, as with power pack 406 described above, the battery pack 424 can be preloaded, i.e., pre-mounted, onto the power pack 420 (by the user or prepackaged) and can be removed and replaced with another (second) charged battery (battery pack) during a surgical procedure by first removing the power pack 420 from the compartment 404 of stapler 1 or alternatively the battery pack 424 can be removed from the power pack 420 and replaced by another charged battery pack while the power pack 420 remains in the compartment 404.

Figure 37:
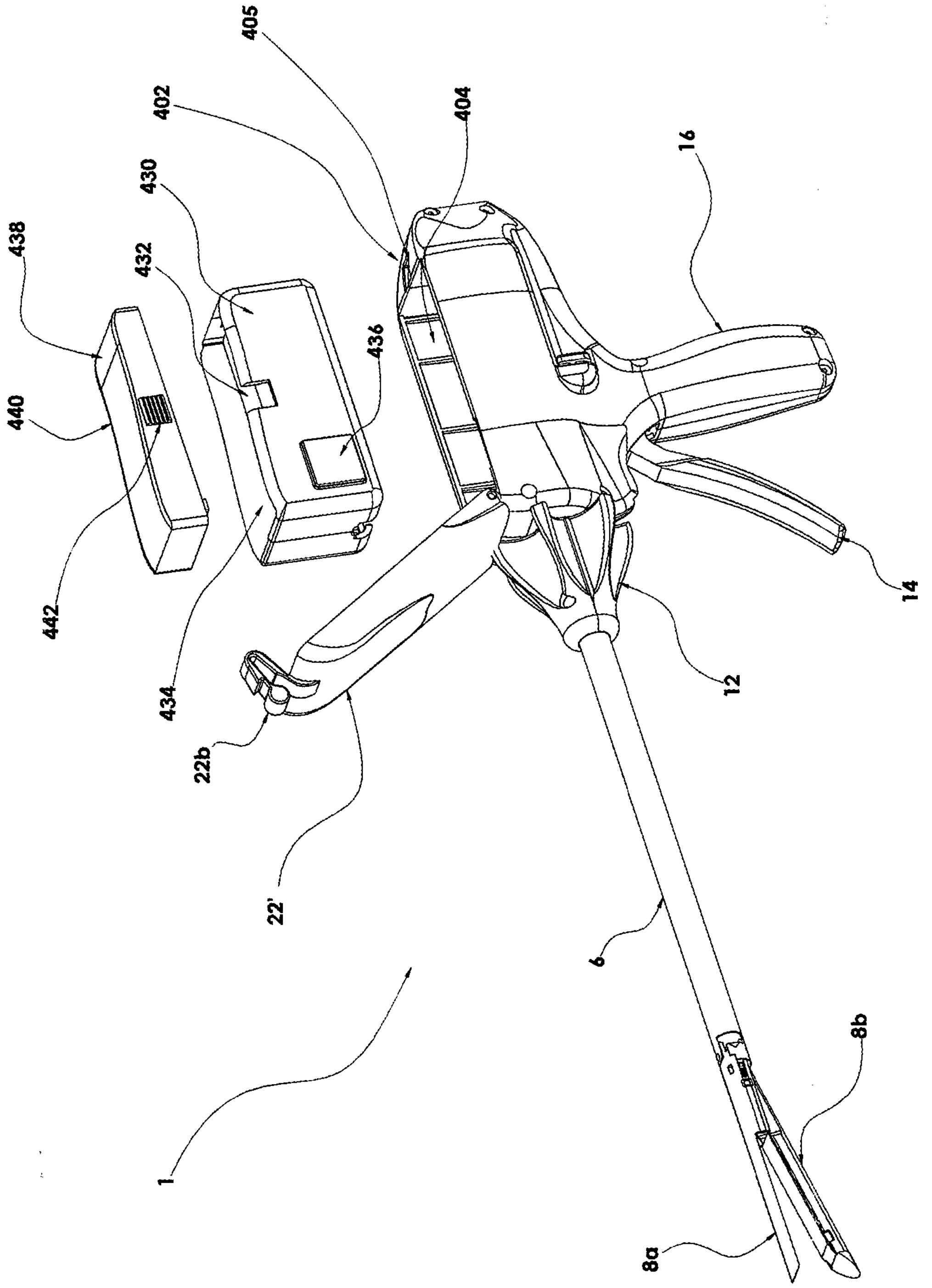
FIG. 37 is a perspective view of another alternate embodiment of the power pack of the present invention having a replaceable battery pack, the power pack shown prior to loading in the instrument compartment.
Figure 38A:
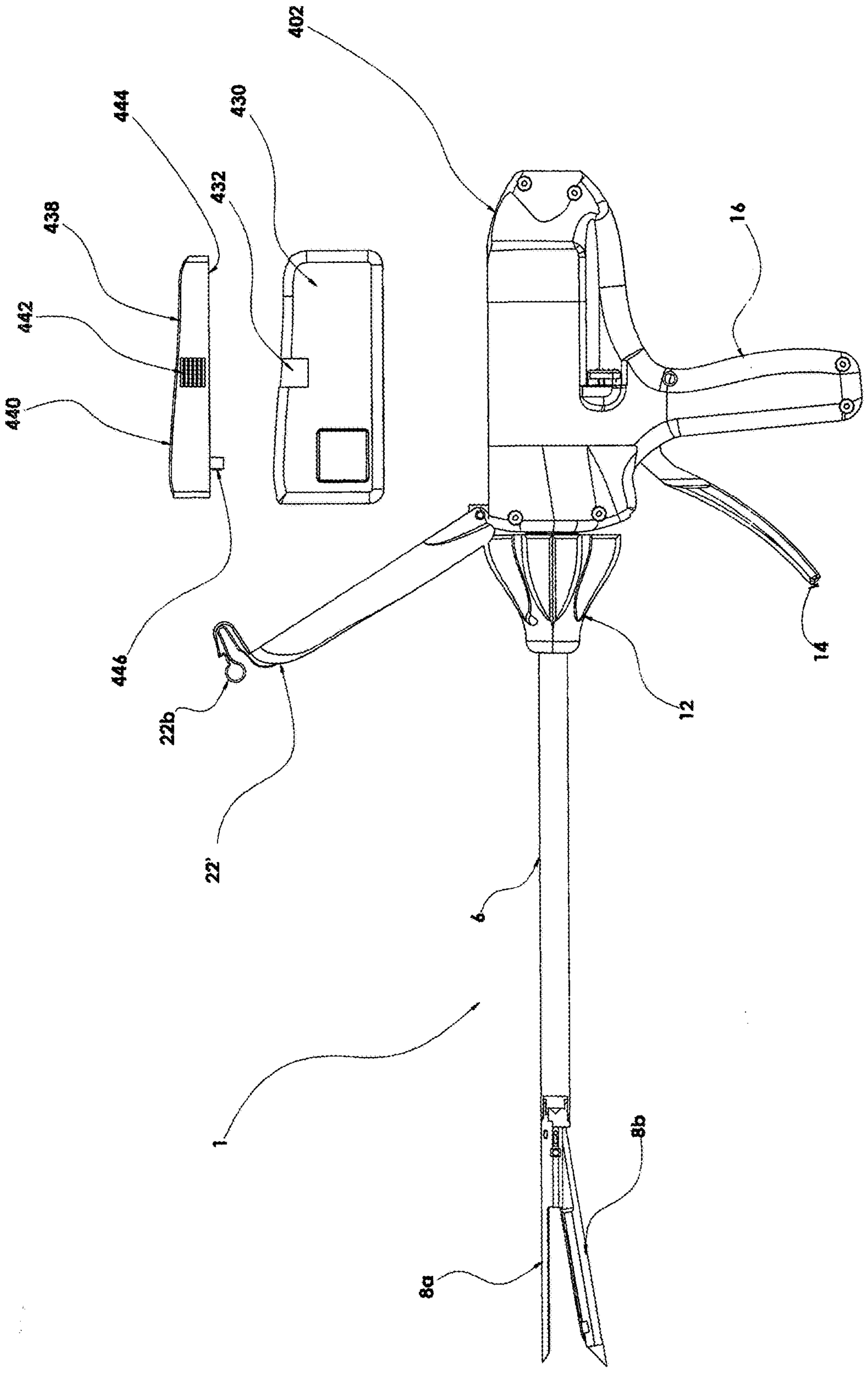
FIG. 38A is a side view of the surgical instrument and power pack of FIG. 37A.
Figure 38B:
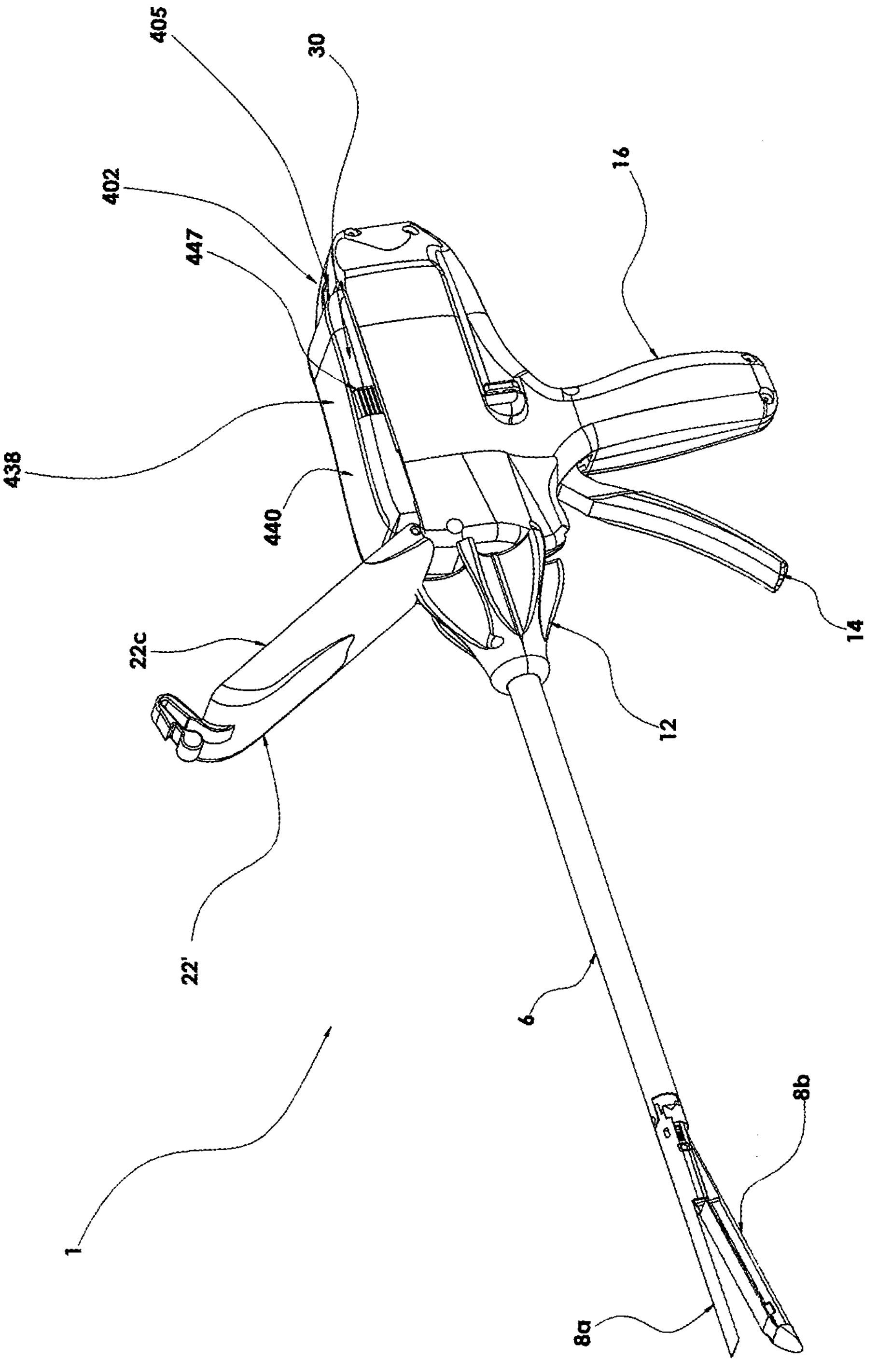
FIG. 38B is a perspective view of the surgical instrument of FIG. 37A showing the power pack and battery pack within the compartment of the surgical instrument.
Figure 38C:
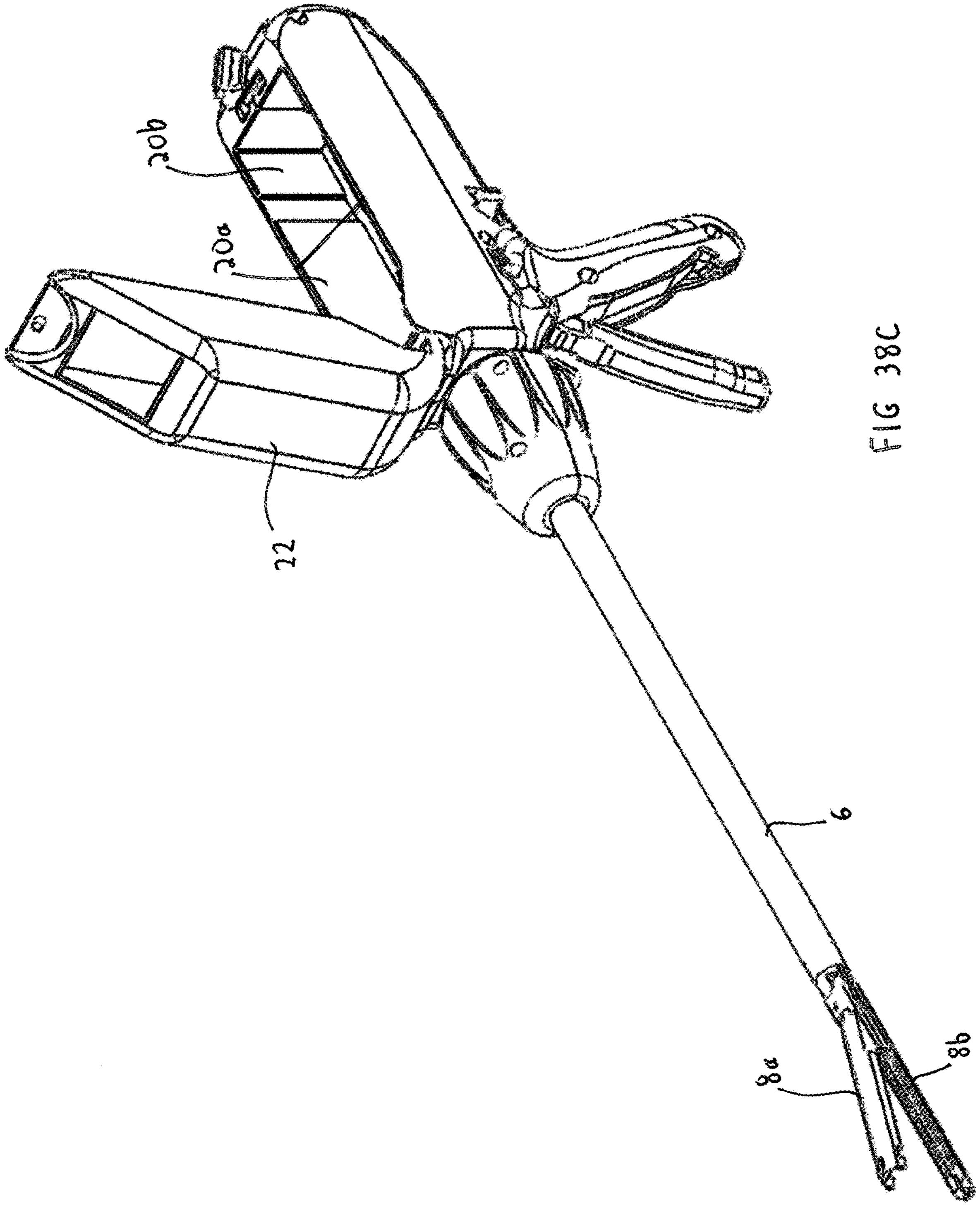
FIG. 38C is a perspective view of an alternate embodiment of the surgical instrument of the present invention having two compartments for receiving two power packs.

In the alternate embodiment of FIGS. 37-38B, the battery pack 440 is mounted into a cavity (receptacle) in the power pack 430. Note the stapler 1 of FIGS. 37-38B is the same as in FIG. 35, the difference being the power pack and battery pack. Power pack 430 has a cavity 434 extending along its length dimensioned to receive battery pack 440. The power pack 430 and battery pack 440 can be dimensioned so that the battery pack 440 becomes part of the outer contour of the power pack 430. Irregular gripping surface or tab 442 on side wall 443 of battery pack 440 is received in cutout 432 on the side wall of power pack 430. The gripping surface can be grasped by the user to facilitate removal as the battery pack 440 is removed from the power pack 430. In some embodiments, a gripping surface or tab like surface 442 can also be provided on the opposing side wall (received in another cavity like cavity 432 positioned on the opposing side) for facilitating grasping both sides of the battery pack 440 for removal from the power pack.

In the loaded position, the battery pack can protrude slightly above the plane of the top edges 404*a* of the compartment 402 as shown in FIG. 38B or alternatively can be flush or below the plane of the compartment edges 404*a*. In any case, the power pack and mounted battery pack 440 are placed sufficiently within the compartment 402 so that the cover 22' can be completely closed to seal the power pack 430 and battery pack 440 from the external environment.

In use, the battery pack 440 can be preloaded in the power pack 430, either by a user or packaged with the battery pack 440 preloaded. During a surgical procedure, in the event of a battery failure, the cover 22' can be opened, power pack 430 removed from compartment 404, the battery pack 440 removed from cavity 434, a new (second) charged battery (battery pack) aseptically placed in cavity 434 and the power pack 440 with a replacement battery pack reloaded into compartment 404. In an alternative use, during a surgical procedure, in the event of a battery failure, the cover 22' can be opened and with the power pack 430 remaining in compartment 404, the battery pack 440 is removed from cavity 434 of the power pack 440 and a new (second) charged battery (battery pack) aseptically placed in cavity 434 while the power pack 430 remains loaded (positioned) within the compartment 404.

Note the battery packs disclosed herein can include custom cells or alternatively off the shelf batteries. The use of the term battery pack as used herein encompasses different types of batteries and different housings for the batteries which are mounted on or inserted either fully or partially into the power pack housing (which contains the powertrain therein) to operatively connect with the motor in the power pack.

The battery packs can be retained, e.g., locked, in or on the power pack housing in various ways such as a latch, spring loaded engagement, frictional engagement, interlocking tabs, etc., and such mountings can also include a release button for disengaging/removing the battery pack from the power pack.

As noted above, the power pack 90 can be used with the other staplers disclosed herein, e.g., circular staplers, linear staplers, as well as other instruments wherein two powered functions are desired. The first motor assembly can effect linear motion of a first elongated member to effect a first function of the stapler, e.g., clamping, articulation, firing, and the second motor assembly can effect linear motion of a second elongated member to effect a second different function of the stapler, e.g., clamping, articulation, firing. In the embodiment of FIG. 14A, one function is articulation and another function is staple firing. Note the power pack 90 can also be used with surgical instruments other than surgical staplers such as those illustrated in U.S. Pat. No. 11,564,685 e.g., surgical graspers or scissors.

Figure 39:
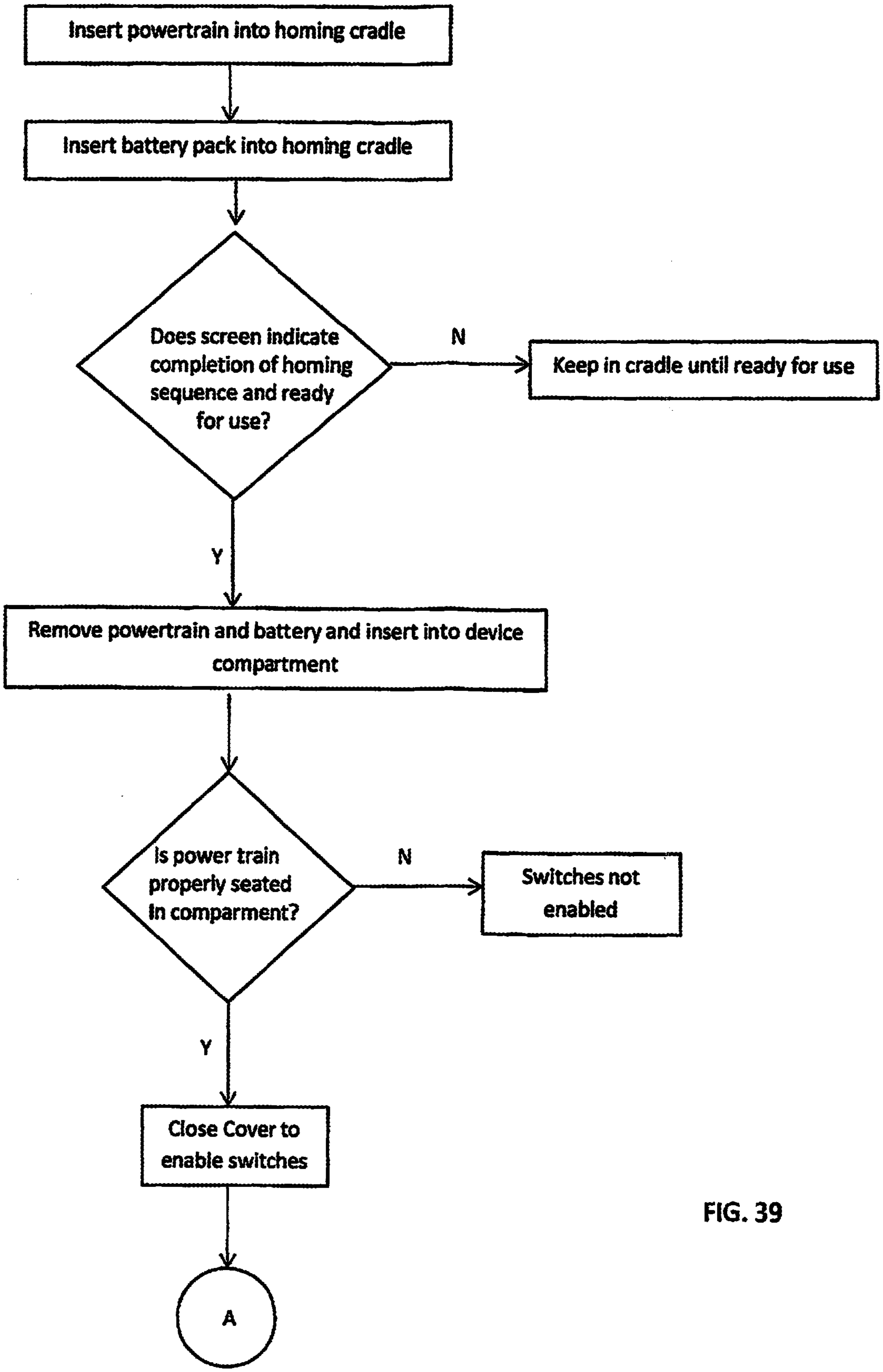
FIGS. 39, 40 and 41 show steps of use of the instrument in accordance with some embodiments of the present invention.
Figure 40:
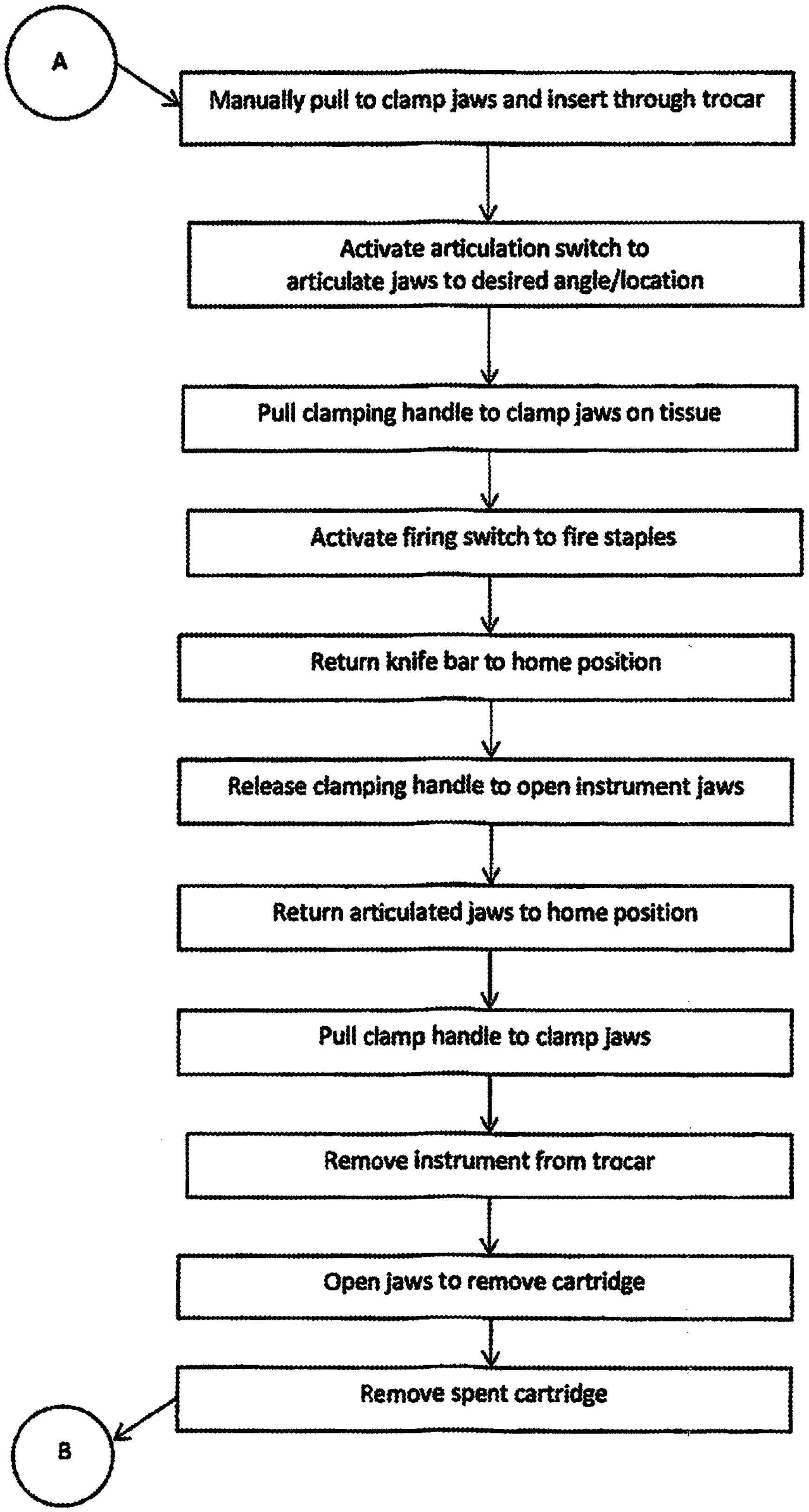

An encoder with switching devices to effect articulation and firing can be provided as described in the concept diagrams of FIGS. 38-40 of U.S. Pat. No. 11,564,685, the entire contents of which are incorporated herein by reference.

Figure 41:
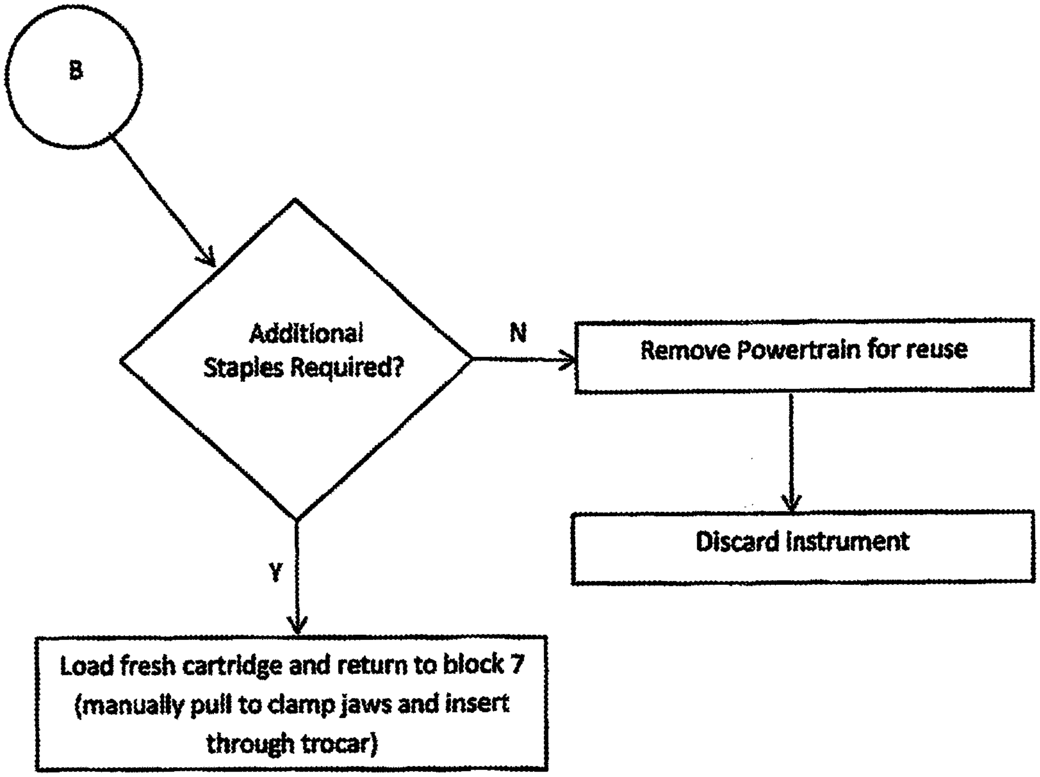

The steps for loading the powertrain and using the instrument in accordance with some embodiments will now be described in conjunction with the flow chart of FIGS. 39-41. The powertrain is inserted into the homing cradle followed by insertion of the battery into the homing cradle. This moves the articulation and firing motors into the home position. If the screen indicates completion of the homing sequence, i.e., ready for use, the powertrain and charged battery are removed from the cradle and placed into the compartment of the instrument housing as described above with respect to the other staplers. Once the powertrain is properly seated in the compartment, the compartment cover can be closed which then enables subsequent actuation of the switches. If not properly seated, the switches are not enabled. In some embodiments, as described below, closing of the cover automatically activates an enable switch.

Note a latch release can be provided as shown in FIG. 81H. The latch release 680 is rotatable to release the cover 663 so it can be opened to access the compartment. In some embodiments, rotation of the latch release 680 automatically causes the cover 663 to spring open; in other embodiments rotation of the latch release 680 released the cover lock/latch and the clinician manually opens the cover 663. In the alternate embodiment of FIGS. 81I and 81J, the latch release 690 is in the form of a press button that slides/translates axially. An upper surface of the release button 690, when pressed inwardly, engages a lower surface of latch hook 692 to cam it upwardly out of engagement with the openings 693 in the housing to release the cover 663. The press button can be biased proximally to a cover latch position by spring 694. In this embodiment, the latch can be configured so once released the cover springs open, however, alternatively, manual opening of the cover is also contemplated. Other forms of latches and latch releases are also contemplated that require interaction by the user and can spring open, or alternatively, not spring open.

To use the stapler, the clamping handle is closed to move the jaws to the closed position for insertion through the trocar. Once inserted, if articulation is desired, the handle is unclamped to move the jaws to the open position and the articulation switch, e.g., a rocker switch or other switches preferably accessible on either side of the instrument, is activated, e.g., pivoted, to move the jaws from the 0 position to the left or right. The encoder via a motor count detects the articulated position of the jaws which in some embodiments can be visually displayed on the instrument or power pack screen. After reaching the articulated position of the jaws, tracked via the motor count, the articulation switch is released to maintain the jaws in this position. In some embodiments a double pump articulation switch can be utilized to bring articulation back to zero automatically.

Next, the jaws are clamped via the manually actuated handle, which enables activation of the firing mode. With the jaws closed, the firing switch is actuated, to advance the firing rod and knife bar to apply staples and cut tissue. A motor count tracks the position of the firing rod. That is, the motor encoder detects motor location within a full stroke, i.e., informs what portion of the cycle (revolutions) of the complete cycle the firing mechanism is in along the firing stroke. The count correlates to the amount (number) of spins of the driveshaft, effectively controlling the distance of the drive mechanism, e.g., collar. The number of revolutions is tied into a predetermined (selected) speed and a predetermined time. The motor speed can be automatically adjusted during use. Note as the motor operates, if there is a spike in amperage, the central processing unit will slow down the motor rpm, and the time cycle will be adjusted accordingly, along with the encoder detection of the full stroke.

In some embodiments, to effect firing, the firing trigger needs to be pressed a first time as a pre-actuation mode and then pressed a second time to advance the firing rod and knife bar. In some embodiments, the firing button/trigger needs to be held during the firing strike, and once released, the motor automatically stops. Thus, in these embodiments, the circuit is complete to effect firing only during the time the trigger/button is held in the activated/engaged position. In some embodiments, the articulation button/trigger needs to be held during articulation and once released the motor automatically stops. Thus, in these embodiments, the circuit is complete to effect articulation only during the time the articulation button is held in the activated/engaged position.

After application of staples, the firing rod and knife bar are retracted to the home position. The jaws are opened and the articulation switch is then actuated to return the articulation motor and thus the jaws to the home position. The jaws are closed by the clamping handle and the instrument is removed from the patient's body through the trocar. Note an abort switch can be provided to reverse motor rotation to retract the firing mechanism and knife bar during the procedure.

FIG. 81H shows an example of an abort switch. If the user desires to reverse motor rotation to retract the firing member and cutting knife, the user holds the button 681 located on the rear of the housing. The motor reversal continues until the button 681 is released by the clinician. Note the button 681 is shown in the rear of the housing, below the latch release 680, but alternatively can be located in other regions of the housing. Note in this embodiment (and the embodiment of FIG. 81J), the user holds the button, however, in alternate embodiments, the button can be provided so it needs to be actuated/activated but not held to cause reverse motor rotation. FIG. 81J illustrates a button 695 for reversing the motor. When button 695 is pressed inwardly (distally), contact 696 engages contact/switch 699 which is connected to the flex cable (described below) which is in communication with the microprocessor in the power pack to actuate motor reversal. In the illustrated embodiment, button 695 is biased proximally to a non-actuated position by spring 698. Note other form of buttons or mechanisms/actuators for causing reverse motor rotation are also contemplated.

In some embodiments, the button can have a through hole which is plugged. The hole is aligned with the ball screw of the motor/firing assembly and provides access to the screw (e.g., screw 36, 710 or any other screws disclosed herein) to provide a manually operated reverse of the motor in the case of a motor malfunction which does not reverse spin the motor to reverse the firing member and knife to move these components proximally. In such case, the individual can remove the plug and insert a T-handle wrench into the back of the screw and manually rotate the wrench to manually rotate the ball to move the firing member and knife bar proximally.

After removal of the instrument, the jaws are open and the spent cartridge is removed. If additional staples are required, a fresh cartridge is loaded into the cartridge receiving jaws and the instrument jaws are closed and the instrument is inserted through the trocar (returning to block 7 of the diagram of FIG. 40—"manually pull handle to clamp jaws and insert through trocar.")

In some embodiments, a switch is located on the power pack which is actuated by the instrument cover when the cover is closed. This is shown in FIGS. 77 and 78. Instrument 900, like instrument 61 of FIG. 14A described above, has an elongated member 902, a pair of jaws 907, 905 at a distal portion and rotation knob 914. Pivotable handle 924 is movable toward stationary handle 922 to close the jaws for clamping onto tissue. A clamp release button 926 releases the clamp lever to open (unclamp) the jaws. Pivotable cover 912 has a projection or boss 934 extending at a proximal region which engages activation (power enable) switch 932 on the power module (power pack) 950 when the cover 912 is moved from its open position of FIG. 77 to the closed position. The power module 950 can be the same as power pack 700 discussed below or any of the other power packs disclosed herein. In this manner, the motors within the power pack cannot be activated unless the cover 912 is in the closed position. Power pack 950 includes a screen 952 like screen 704 disclosed herein. A pair of articulation buttons/switches 930, symmetrical about the axis, are disposed on each side of the instrument housing 920 to articulate the jaws 905, 907 in either direction, e.g., button 930 articulates the jaws to the left and the button on the opposing side (not shown) articulates the jaws to the right. In alternate embodiments, the opposite buttons can articulate the jaws to the left and right. Once the cover 912 is closed and boss 934 engages the power enable switch 932, the firing mechanism can be activated via switch 928 which in communication with the motor operatively connected to the drive mechanism within the power pack. The electromechanical switch is mounted to a PCB board which is fixed within the power pack which communicates with the CPU within the power pack.

The cover can have a seal about its periphery and/or a seal around the periphery of the opening to the compartment can be provided, as discussed above, to seal the power pack within the compartment to prevent entry of contaminants.

Below is a chart summarizing the safety mechanisms of the surgical instrument in accordance with some embodiments:

| | |
|---|---|
| Pre-loading of power train into instrument | Can't activate switch when powertrain in cradle |
| | Thermosensor in battery pack monitored by electronics in charger to shut down charger if overheating |
| | Viewable screen indicates ready/not ready condition of powertrain |
| | Can't activate switch if powertrain not properly loaded and instrument compartment cover not fully closed |
| | Loading into instrument prevented if firing and articulation not in home position |
| Once powertrain loaded | Opening of jaws breaks circuit to disable firing mode |
| | Closing of jaws disables articulation mode |
| | Cant actuate firing switch if articulation switch activated |
| | Can't actuate articulation switch if firing button activated |
| | Encoder following error if resistance in firing |
| | Encoder detects proper functioning of motor |
| | Encoder detects position and completion of firing stroke via motor count |
| | Encoder detects articulated jaw position via motor count |
| | Fire button needs to be depressed first as initial step before firing |
| | Copycat position so can resume where left off if power pack replaced |
| | Firing abort button to cease advancement of firing rod and retract to home position |
| Removal of Powertrain | Can't remove powertrain if articulation driver not in home position |
| | Can't remove powertrain if staple driver not in home position |

FIGS. 68-76C illustrate two embodiments utilizing an encoder to measure either rotational movement of the ball screw (FIGS. 68-73) or linear movement of the collar/drive mechanism (FIGS. 74-76B). This provides a failsafe if the motor loses communication with the CPU.

Figure 68:
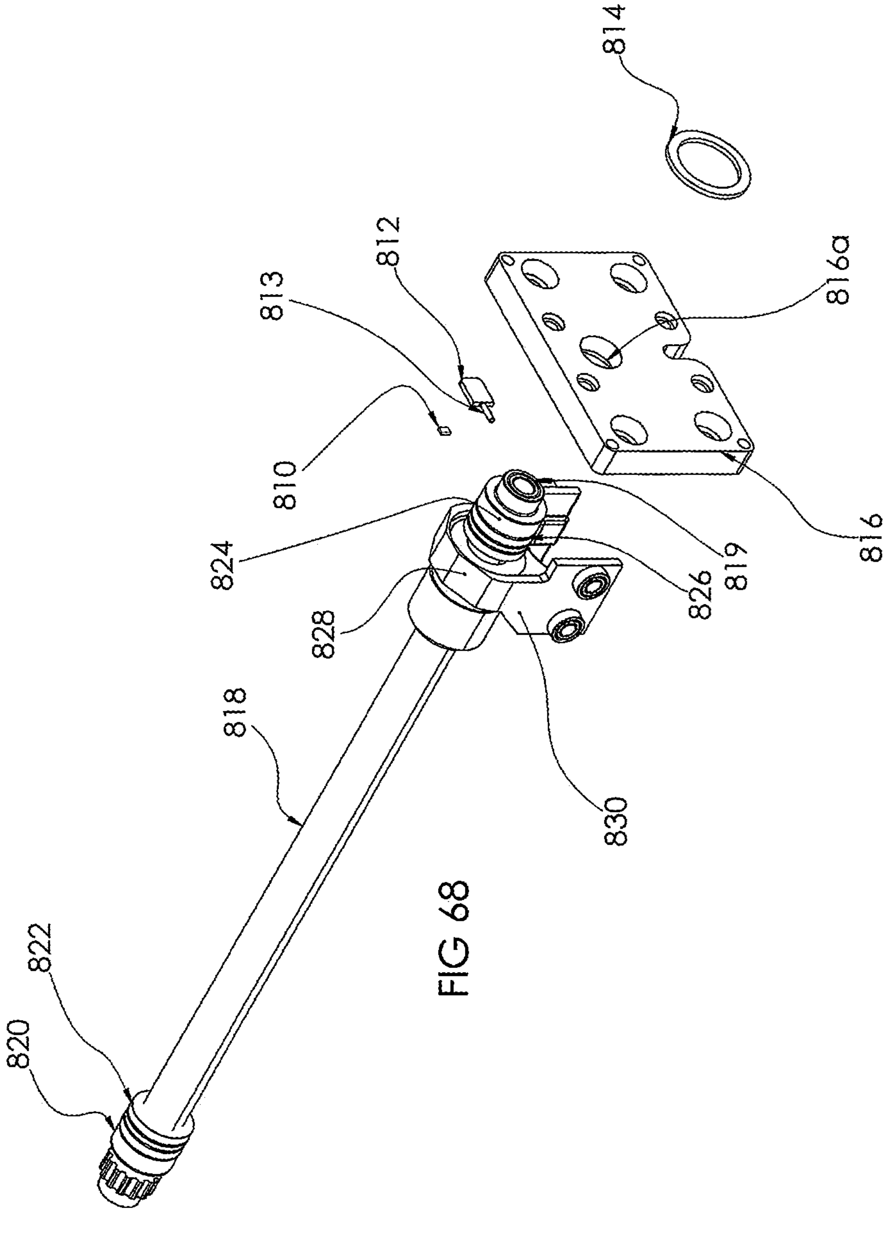

Turning first to FIG. 68, the deployment screw 818 has a collar 830 extending therefrom which functions like collar 94 of the deployment screw of FIGS. 22-25 in that it forms an engagement member for engaging and advancing the firing rod (firing mechanism) in the housing of the surgical stapler. This collar configuration is similar to that of collar 756 of FIG. 59A of application Ser. No. 16/792,110, filed Feb. 14, 2020, now U.S. Pat. No. 11,331,099, the entire contents of which are incorporated herein by reference.

Deployment screw 818 differs from these deployment screws in that it supports an electromechanical encoder 810. More particularly, the encoder 810 is mounted to encoder holder 812 which has a post 813 inserted into opening 826 at a proximal (back) end of screw 818. Other ways to mount the encoder to the screw are also contemplated. Code wheel 814 is mounted in opening 816*a* of proximal chassis 816. When the motor is actuated to rotate the deployment screw 818 as described herein to advance the collar 756 and firing mechanism, the static (fixed) code wheel 814 reads the discrete positions of the encoder and sends a signal to the CPU within the power pack indicative of such reading/position. Such rotation count determines the location of the firing mechanism and thus the location of the I-beam firing the staples from the cartridge. Note the number of discrete positions can vary and in some embodiments there are 64 discrete positions. In an alternate embodiment, the encoder is attached to the chassis and is thus stationary, while the code wheel is mounted to the screw. The discrete positions, i.e., axial positions, are detected/read and sent to the PCB within the power pack for determining the location (axial position) of the firing mechanism.

In the alternate embodiment of FIGS. 74-76B, encoder 846 is fixably attached to collar 846 of deployment screw 848. (Deployment screw 848 and collar 846 are otherwise the same as screw 818 and collar 830). As the collar 846 moves axially distally when the deployment screw is actuated by the motor as described in the embodiments above, the positon of the collar 846 is detected by scale 850. Scale 850 is attached to the chassis 856 of the power pack housing, and runs along the length of the stroke. The detected axial position of the encoder is sent to the PCB within the power pack for determination of firing mechanism location. Note in this embodiment, the encoder 846 is positioned in an indentation at a proximal end of the collar 852 adjacent nut 854, but can alternatively be mounted to the collar in other ways/locations.

In an alternate embodiment, the encoder is attached to the chassis and is thus stationary, while the scale is attached to the collar. The discrete positions are detected/read and sent to the PCB within the power pack for determining the location (axial position) of the firing mechanism.

Note an encoder similar to that of FIG. 68-73 or 74-76B (or the alternatives discussed above) can also be utilized with the articulation screw to determine the positions of the articulation mechanism and thus the articulation angle of the jaws. The encoder could be mounted for example to the articulation screw or collar.

Figure 55:
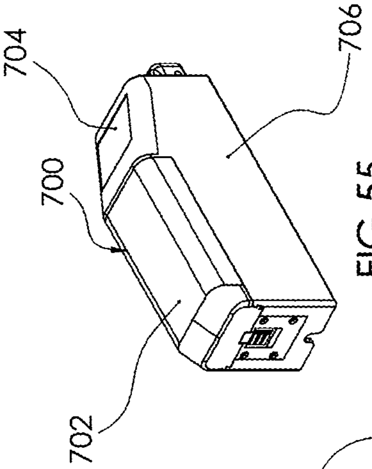
FIG. 55 is a perspective view of an alternate embodiment of the power pack of the present invention.
Figure 57B:
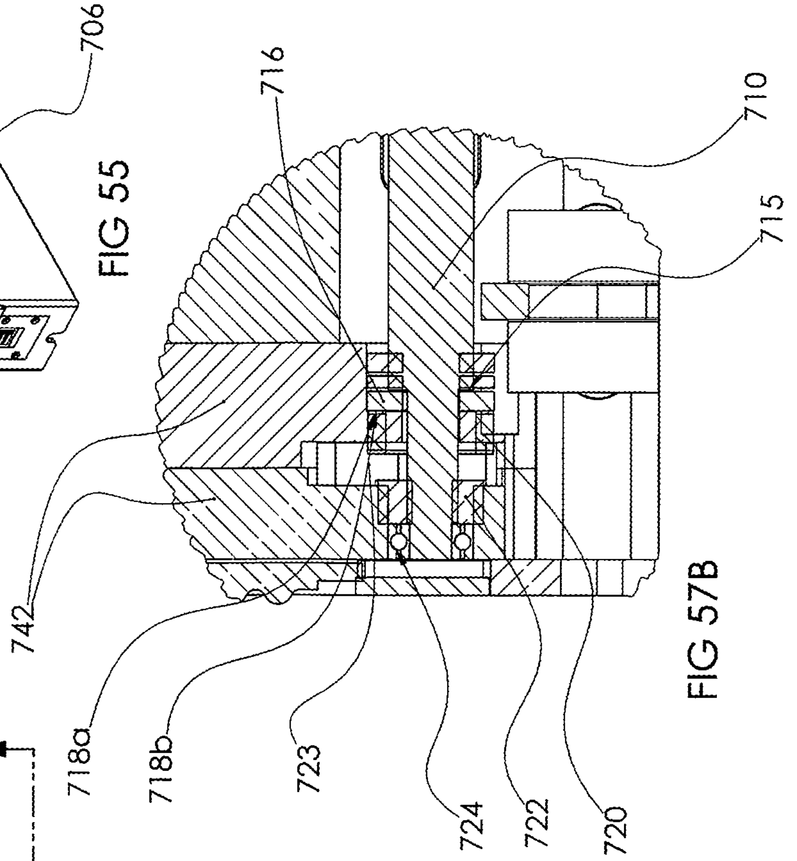
FIG. 57B is an enlarged view of the area of detail B of FIG. 57A.
Figure 56:
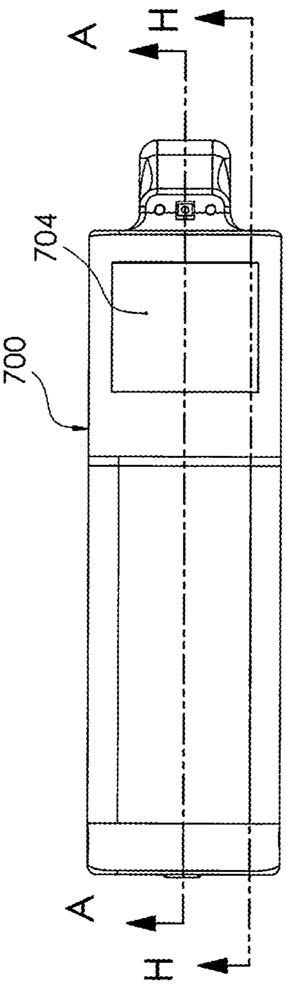
FIG. 56 is a top view of the power pack of FIG. 55.
Figure 57A:
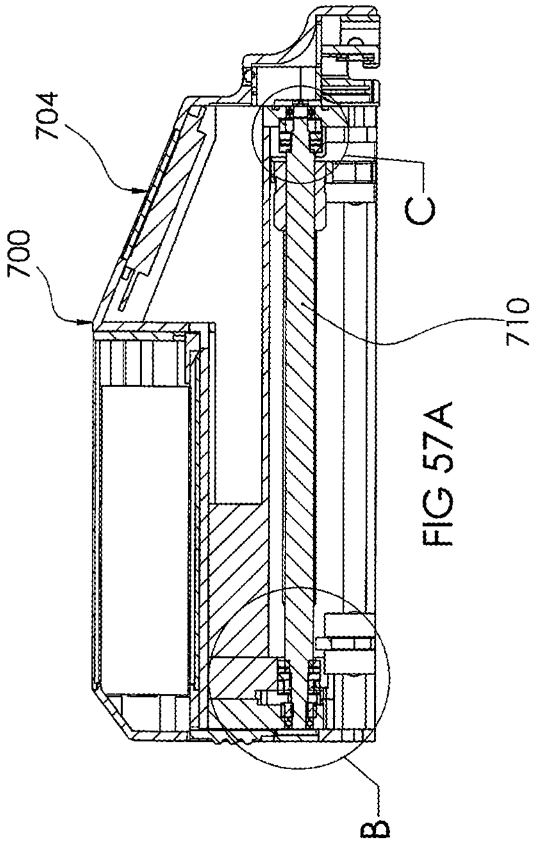
FIG. 57A is a cross-sectional view taken along line A-A of FIG. 56.

A screen/display can be provided on the top of the powertrain to indicate the firing, clamping and/or articulation modes/positions. The screen can be visible through a clear window in the housing of the instrument. An example of the screen is shown in FIGS. 55 and 57A wherein screen 704 is on a proximal portion of the housing 706 of power pack 700. The screen in this embodiment angles toward the user. It is covered when instrument compartment cover 702 is closed, and cover 702 has a transparent portion or window (such as window 913 of cover 912 of FIG. 77 or window 660 of cover 663 of FIG. 81H) so that the screen 704 is visible when the cover 702 is closed. As can be appreciated, the screen can be provided in other positions and portions of the power pack 700. The screen 704 can show various features and parameters via numeric designations light or other indicators. For example, the screen can show one or more of firing position, articulation position (degree of articulation), the type (staple size and length) of cartridge selected, battery life, clamping position, tissue range, confirmation of home positon of articulation mechanism and/or firing mechanism when loaded and/or when ready for removal from the instrument compartment, confirmation that the cover is in the fully closed position, and/or other conditions of the motor or other components of power pack or instrument. Thus, the power pack microprocessor communicates the measured/detected/evaluated parameter to the display screen, i.e., the graphical user interface.

In alternate embodiments, the screen/display is contained on the housing and the power pack during use communicates the measured/detected parameters to the housing screen/user interface for display. The housing would also contain the display in embodiments of the surgical instruments which are motor powered but do not have a removable/replaceable power pack but still advantageously provide measurements and readouts for feedback to the clinician of tissue and instrument conditions. The display screens can automatically change based on the status of the instrument or alternatively the user can control the display, e.g., by toggling through the screens. The articulation button in some embodiments can provide the toggling mechanism but other locations/mechanisms are also contemplated.

With reference to FIGS. 87A-88B, one embodiment of a display/graphical user interface for depicting articulation of the instrument jaws is shown. The display is provided on the screen of the power pack, such as screen 704 on power pack 700 of FIG. 55. The articulation range can be viewed in reference to a half-moon or semi-circular shape as shown, although other shapes are also contemplated. The display 1100 provides a visual indication of the right and left articulation angle of the jaws as sensed by the various articulation sensors disclosed herein. As shown, the screen depicts articulation angle of 55 degrees to the right and left, which in this embodiment is the maximum articulation angle. Other maximum articulation angles are also contemplated. The display also provides numeric demarcations of a 20 degree right and left angle. Additional or different demarcated angles could also be provided. Along with the numeric indication, a darkened or color coded geometric shape, e.g., triangular or pie-shaped, is also displayed to enhance the angle indication to the clinician. In this manner, the screen shows the exact angle corresponding to the infinite number of positions between the non-articulated 0 degree angle and the maximum articulation angle.

Figure 88B:
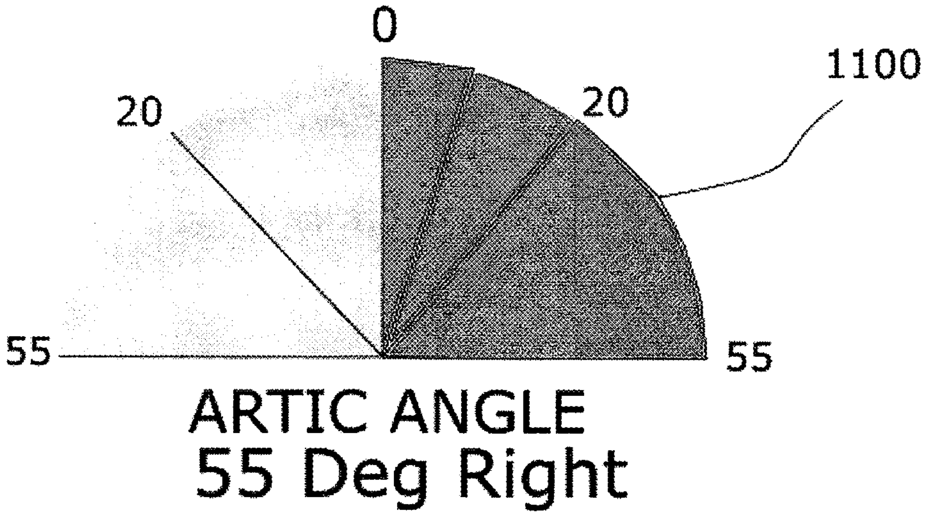

In FIG. 87A, none of the regions of the semi-circle are darkened or colored, thereby indicating the jaws are not articulated and are aligned with the longitudinal axis of the instrument shaft. FIGS. 87B-88B provide examples of indication of specific angles, with FIG. 87B showing a region darkened or colored to indicate jaw articulation to a 10 degree angle to the left, FIG. 87C showing a region darkened or colored to indicate jaw articulation to a 45 degree angle to the left, FIG. 87D showing a region darkened or colored to indicate jaw articulation to a 55 degree angle to the left; FIG. 88A showing a region darkened or colored to indicate jaw articulation to a 10 degree angle to the right and FIG. 88B showing a region darkened or colored to indicate jaw articulation to a 55 degree angle to the right. Note these Figures provide examples of how articulation is displayed on the screen, it being understood the jaws can be articulated to any angle within the range from 0 to its full articulation, such as 55 degrees in some embodiments, and the screen displays the corresponding angle to indicate to the clinician the jaw position.

Note the angle in some embodiments is detected by a sensor detecting the position of the articulation rod. In other embodiments, it is detected by a motor count of the articulation motor as described herein. In other embodiments, a sensor can be placed at the articulation joint, or at another articulating region to detect the position and communicate to the display, e.g.; communicate to a microprocessor in the power pack which processes the sensed data and communicates with the monitor/display screen. Other sensor locations are also contemplated.

The articulation switch (as well as the clamping and tissue force sensors or other sensors) can be connected, e.g., wired, e.g., via a flex cable, to a communication bus in the housing of the instrument which communicates with the microprocessor in the power pack when the power pack is loaded into the compartment and placed in contact with the bus. The microprocessor communicates with the screen to display the data.

Note the display could include the wording of the angle, e.g., 10 degrees left or just a number, e.g., 10. Alternatively, the wording is not provided and only the darkened regions and numeric values along the geometric shape are displayed. Other arrangements, numerical and/or geometric, are also contemplated to provide a display of particular articulation angle of the jaws.

The power pack communicates with the instrument in the manner described below.

FIGS. 89A-89C illustrate a display/graphical user interface for indicating to the user the force during deployment (firing of the staples). The force can be measured by using the sensors disclosed herein which can communicated with the microprocessor in the power pack which transmits the data for display. In the graph, the x axis provides the distance in the firing stroke (in mm) and the y axis provides the force reaction from tissue during firing. As the staples (fasteners) are fired from the cartridge, they advance through the tissue and contact the anvil on the opposing jaw where they are deformed. The tissue applies a force to the staple during firing. The force can be measured for example by motor current, by a sensor at a distal region of the instrument, e.g., in the fastener cartridge, by a sensor at a proximal portion, e.g., in the housing by measuring a load or force on the firing mechanism (e.g., load cells to measure the load on the firing bar) etc. to communicate to the power pack (e.g., to the microprocessor in the power pack via the communication bus in the housing to which the sensors are electrically connected, e.g., wired or alternatively a wireless connection), or by utilizing other sensors or by measuring other motor parameters which can be determinative of tissue force. As discussed herein, the microprocessor communicates with the screen to display the data.

The surgical instruments are configured to accommodate staples of different sizes. An array of surgical staples is positioned in a staple cartridge which is mounted in the cartridge jaw of the instrument (see e.g., cartridge jaw 607 of FIG. 51). There are various staple cartridges which contain different sized staples and these various cartridges can be loaded into the surgical instrument. Thus, the term staple cartridge size denotes the size of the staples held within the cartridge. The clinician, after assessing tissue thickness, selects the cartridge size based on such assessment. During a surgical procedure, multiple cartridges are fired and during such procedure staples of the same size or of different sizes might need to be deployed since tissue thickness can vary along the line of staple firing and/or vary on different anatomy, e.g., stomach vs. intestine. The current challenge for the clinician is selecting the appropriate size cartridge during the multiple firings required in the procedure.

The present invention provides a system for tracking the tissue force required to form staples during firing of the staples and an easy to read graphical representations of force for the clinician. In this manner, the clinician can be informed throughout the procedure if the selected cartridge/staple size is best suited for the intended staple formation in the particular tissue. By continuously monitoring the force during the entire procedure, the user can be informed whether in the next staple firing, a different or same size cartridge/staples should be selected. Thus, the feedback provided by the present invention improves staple size selection.

In the present invention, such indication/feedback is provided in an easy to discern manner as the display shows whether the force is in the desired range. One way to achieve this is with the graph shown in FIGS. 89A-89C. The graph appears on the staple screen of the power pack. The graph/chart 1110 is divided into three horizontal blocks, with the lower block 1112 indicating the staples are overformed, usually due to thin tissue, the middle block 1114 indicating the preferred (optimal) or desired/intended (optimal) range, where the staples are properly formed, and the upper block 1116 indicating a spike in force or staple underformed typically due to thick tissue (e.g., stapling at a current higher than the desired/optimal range). In this manner, the user can match the target tissue with the best sized (optimal) cartridge/staples. Additional zones could be provided, e.g., each zone could be subdivided.

For example, if too small staples are used on too thick tissue, the staples would not be fully formed and leakage or bleeding could occur and the inadequate tissue compression could fail to properly promote healing. On the other hand, if too large staples are formed on too thin tissue, the staples could be overformed which could cause oozing, bleeding, unwanted tissue necrosis and/or tissue damage from over compressing tissue, as well as not completely seal the thinner tissue. The sensors and graphical display of the present invention provides a solution to the clinician trial and error and avoids the "after the fact" assessment of staple formation correlation to tissue thickness.

It also aids in cartridge selection during the procedure as the clinician by observing the data from the previous firing can decide for the next firing if larger staples (thicker tissue), smaller staples (thinner tissue) or the same size staples should be used, and thereby select a staple cartridge accordingly. It will also aid consistency in surgical procedures.

Thus, for example, during a surgical procedure, the clinician can see via the graphical display the force applied to tissue in the current firing. This enables the clinician to select the appropriate cartridge.

The graphical presentation can also be used to educate and train clinicians as to what cartridge sizes to select via real time feedback of force reaction during application of staples to tissue. The data from each firing can be stored and later analyzed for clinician education/training. That is, the clinician can review staple size/pressure history of all the firings in the surgical procedure for self-education for subsequent surgical procedures. Furthermore, the data can be collected from a collection of procedures and analyzed for informing clinicians to improve clinical outcomes in future procedures. This objective data can be utilized to reduce the subjectivity of cartridge size/staple size selection.

FIGS. 89A, 89B and 89C provide three examples of graph plots during a firing to illustrate how the data is displayed for clinician interpretation. The graphs, as noted above, show the advancement (distal of travel) of the firing mechanism or rod (the firing stroke) on the X-axis in millimeters, and motor current reflective of resultant force or force reaction from tissue during firing) on the y-axis. Thus, the graphs display deployment force simultaneous with stroke distance. (As noted above the y-axis can alternatively display pressure or other readings if for example pressure sensors/load cells are utilized to thereby show the correlation of deployment force and stroke distance). The pressure can have numeric designations along the Y-axis such as pounds/force (correlate current in motor (amperage) to pounds/force) or alternatively in mmHg (since it correlates to blood flow). The graph is divided into three zones—zone B being the targeted or recommended pressure zone, zone A being below the targeted or recommended pressure and zone C being above the targeted or recommended pressure. Stated another way, zone B represents the optimal range. The graph also shows the firing profile during the entire stroke. In FIG. 89A, deployment mechanism or staple formation force is in the optimal range once past the 10 mm mark, with no spikes in pressure; in FIG. 89B the force is below the optimal range for about the first 30 mm of stroke, and spiking a bit after 50 mm, but still within the optimal range. In FIG. 89C, the pressure has a series of spikes, with a number of spikes above the optimal range (in Zone C). Thus, as can be appreciated, indications of outside the optimal range are continuously depicted. Thus, if the force is outside the intended range, the user can be notified via the graphical representation. In some embodiments, the lines themselves of the plotted graph could also change color depending on which zone/range they are in. It should be appreciated that these three graphs are provided herein to show firing profiles by way of example; the profiles will depend on tissue thickness and staple size selection. With tracking of staple size selection and correlating it with the graphical representation of pressure for each cartridge firing, the clinician can better understand the staple application, better ensure the staples are properly formed, have better information for selection of the next cartridge, and have a data base for analysis for future surgical procedures by the user as well as other clinicians.

Note in some embodiments, if there is a spike in pressure, which can be caused if the tissue is too thick for the staples, or other anomalies, the motor will automatically slow down or will stop. The system can include a wait time wherein after a predetermined amount of time, the motor will restart or return to the home position. In other embodiments, the user alternatively or in lieu of the automatically slowing or stopping can intervene to adjust, slow and/or stop the system.

Note a spike could also provide an indication of where staples were not fully formed because of the thick tissue so the clinician can revisit the site, e.g., add sutures.

Note the screen can in certain instances enable clinicians to obtain the same results as if using a buttress. If for example the staple is too large for the tissue, e.g., there is medium tissue and a large staple (which can cause bleeding), a buttress, which is interposed between the cartridge and anvil, can be used to take up the thickness. Thus, the addition of the buttress "thickens" the tissue. However, with knowledge of the firing profiles of the present invention, the clinician can select a smaller staple size for the next firing which avoids the need for a buttress.

The screen can also in some embodiments provide a firing count to indicate the number of cartridges fired during a surgical procedure. This data can also be stored for later analysis for use as described above. In some embodiments, the firing is disabled after a predetermined number of cartridges are fired, e.g., 12.

Note the pressure in some embodiments is detected by a sensor detecting the position of the firing rod. In other embodiments, it is detected by a motor count or motor current of the firing motor as described herein. In other embodiments, a sensor can be placed in at the cartridge, e.g., at the firing mechanism within the cartridge. Other sensor locations are also contemplated. The sensors communicate with the bus in the instrument housing (preferably via cables but alternatively wireless), which communicate with the microprocessor in the loaded power pack in contact with the bus which transmits the data to the display/screen.

FIGS. 90A-90D illustrate a display/graphical user interface for indicating to the user the clamping force on tissue prior to actuation of the firing (deployment) of the staples. As described above, prior to firing, the tissue is placed between the staple cartridge and the anvil and the cartridge is pivoted toward the anvil to clamp the tissue (or in other instruments, the anvil is pivoted toward the cartridge, or both the anvil and cartridge can be pivoted). The compressive force needs to be in a range that is not too low so the tissue is not sufficiently compressed, but not too high so the tissue is crushed. The graphs of the present invention provide continuous real time feedback, i.e., the progress of clamping is depicted and indicated if it's in the desired or optimal range, or below or above the optimal range. As shown in the Figures, the display shows a sensor in the shape of semi-circle (although other shapes are contemplated) divided into zones, which can be color coded or shaded, with the optimal (desired/preferred) range in the middle and the low and high range to the left and right, respectively. As can be appreciated, the semi-circle is over formed shown by way of example as other geometric shapes can be utilized.

Clamping pressure in the illustrated embodiment is in a pie graph format and includes both a shading corresponding to the clamping pressure and a numeric readout of the exact clamping pressure (displayed in mm Hg). It further includes zones correlating to the indicated range for the staple size wherein for example zone X is the indicated (optimal/desired) range for the staple size selected, zone Y is under the indicated range and zone Z is over the indicated range. The zones can be color coded so that each zone is a different color. The area of the zone can fill in as that zone is reached.

FIGS. 90A-90D each show an example of how clamping pressure is depicted. FIG. 90A depicts on the screen 1120 the initial pre-clamping phase of the instrument wherein there is no clamping pressure on tissue. In FIG. 90B, clamping pressure is in the low zone at 45 mm Hg; in FIG. 90C clamping pressure in within the range, but at the lower end of the range, with pressure at 76 mm Hg; in FIG. 90D clamping pressure is still within the target/desired range, at a higher end of the range at 102 mm HG; and in FIG. 90E clamping pressure is outside the target range and in the high zone at 153 mm Hg. It should be appreciated that in alternate embodiments, the numeric readouts can be displayed in other locations relative to the graph. In other embodiments, the numeric display is not provided and the clinician relies only on the shading of the zone. Other geometric shapes for the graph and other types of graphs/charts are also contemplated to provide the clinician with the continuous tissue compressive force feedback during clamping.

FIG. 91 illustrates a graphical display in the form of dial used to measure clamping force prior to firing via a dummy cartridge or a spent cartridge as described herein.

Figure 20:
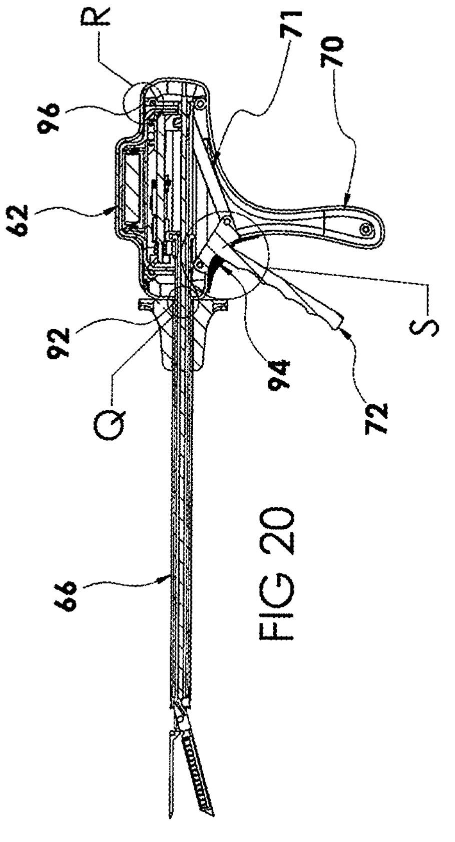
FIG. 20 is a cross-sectional side view of the surgical stapler of FIG. 14A, the view being the same as FIG. 14C but having identified areas of detail Q, R and S.
Figure 25:
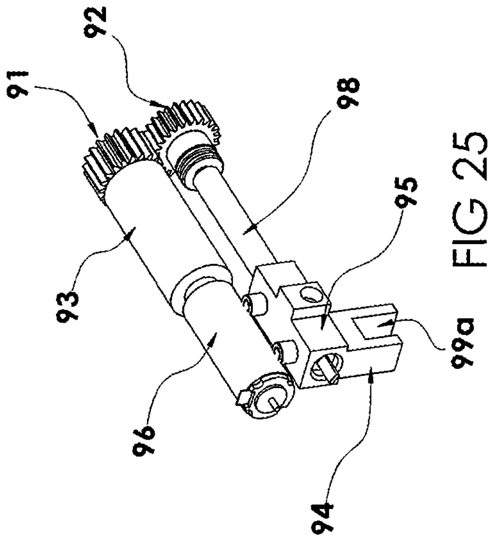
FIG. 25 is a perspective view of the motor and drive mechanism (assembly) of the power pack of FIG. 14A.
Figure 24:
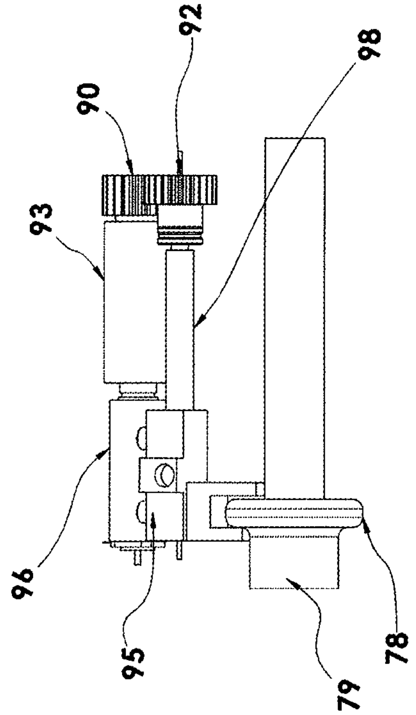
FIG. 24 is a side view of the motor and drive mechanism of FIG. 14A shown engaged with the articulation rod of the articulation assembly of the surgical stapler of FIG. 14A.
Figure 23:
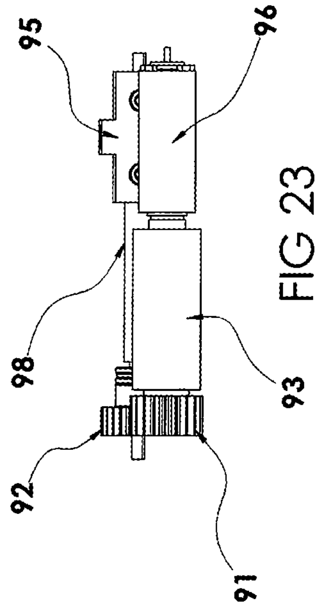
FIG. 23 is a side view of the motor and drive mechanism of the power pack of FIG. 14A.
Figure 22:
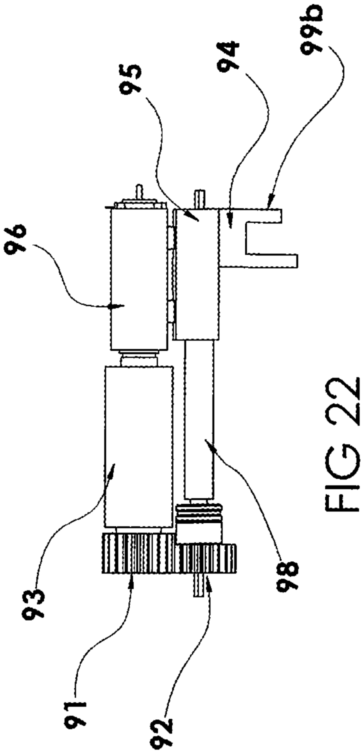
FIG. 22 is a top view of the motor and drive mechanism (assembly) of the power pack of FIG. 14A for effecting staple firing and articulation.
Figure 27:
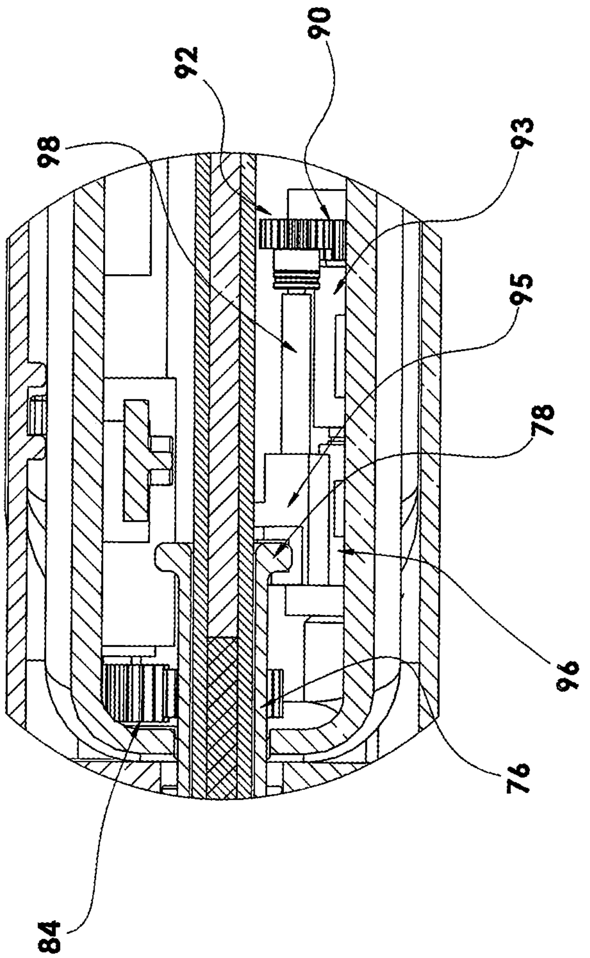
FIG. 27 is an enlarged view of the area of detail AU of FIG. 26.
Figure 26:
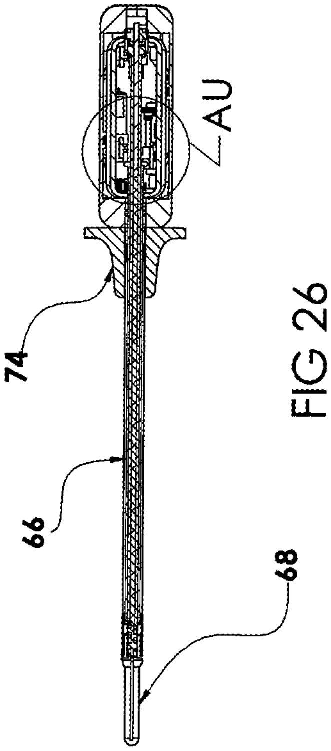
FIG. 26 is a cross-sectional side view of the surgical stapler of FIG. 14A, the view being the same as FIG. 18A but having an identified area of detail AU.
Figure 30:
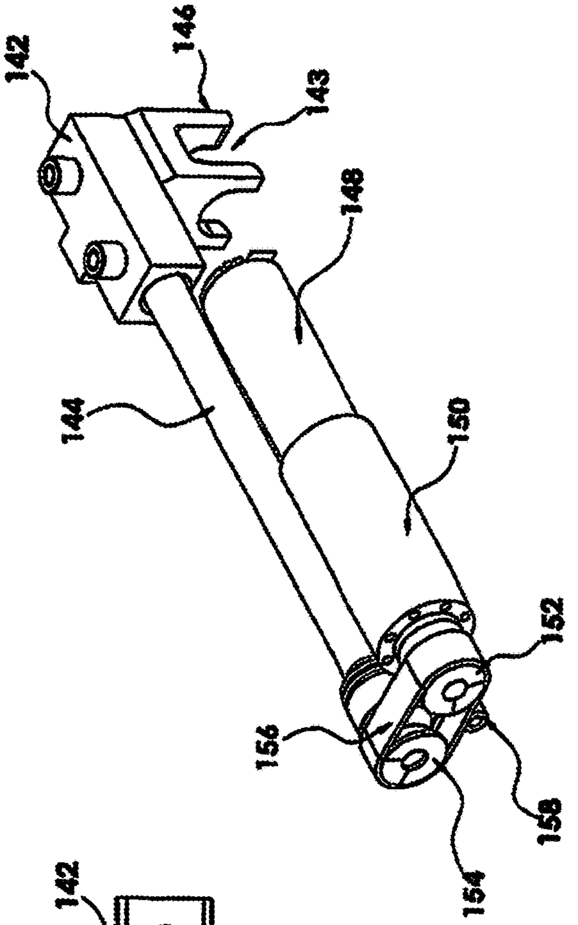
FIG. 30 is a perspective view of the motor and drive mechanism of FIG. 28.
Figure 31:
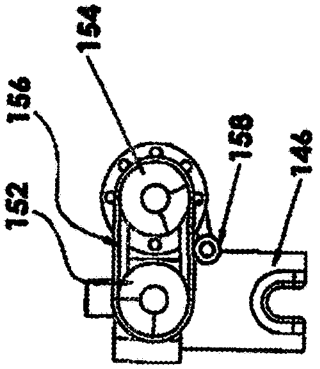
FIG. 31 is a front view of the motor and drive mechanism of FIG. 28.
Figure 28:
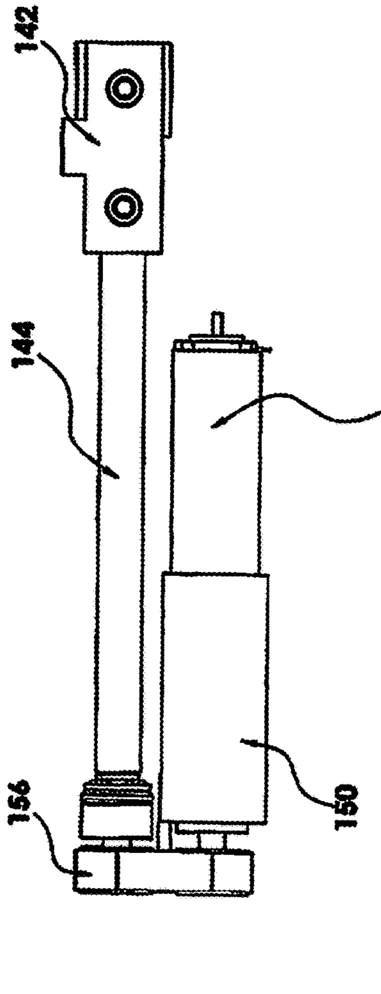
FIG. 28 is a top view of the motor and drive mechanism (assembly) of the power pack of an alternate embodiment having a belt drive.
Figure 29:
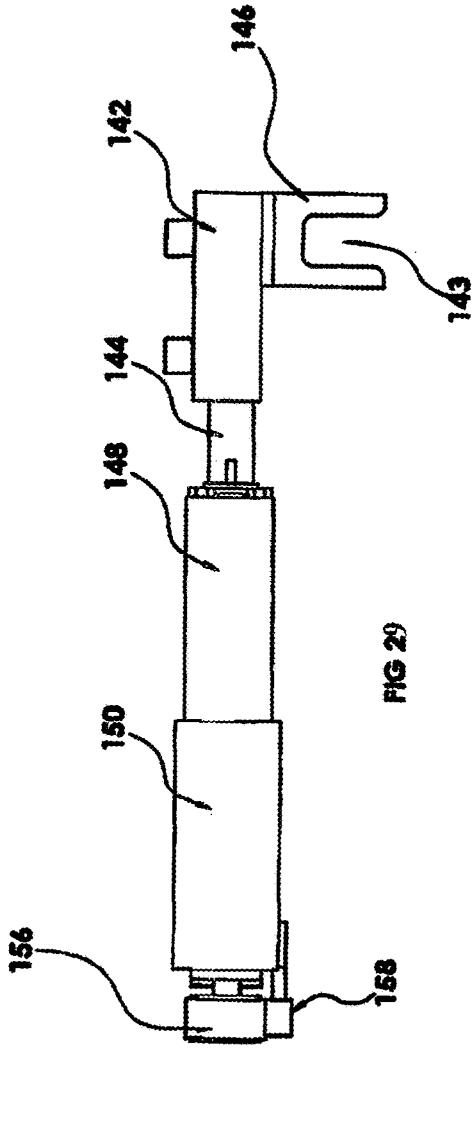
FIG. 29 is a side view of the motor and drive mechanism of FIG. 28.

Note in preferred embodiments, the tissue clamping is effected manually by for example handle 14 of FIG. 1 or handle 72 of FIG. 20 or handle 667 of FIG. 79A. Due to the manual clamping, the clamping pressure can be assessed and adjusted independent of the firing. That is, in certain prior art instruments, clamping of the jaws is provided by a linearly translatable I-beam which closes the jaws to clamp on tissue during the firing stroke, immediately preceding the staple firing which trails the clamping in the linear translation. In the independent clamping of the present invention, the clamping pressure can be analyzed and adjusted by the user prior to initiating the firing stroke.

The graphs of the present invention enable real time feedback to the clinician with progress tracking during the entire clamping stroke to communicate progress of clamping as well as the final clamping force on tissue between the jaws.

The graphical presentation can also be used to educate and train clinicians as to optimized clamping pressure which can be correlated with tissue pressure during staple firing. The data from the clamping measurement for each firing can be stored and later analyzed for clinician education/training. That is, the clinician can review clamping pressure along with staple size/pressure history of all the firings in the surgical procedure for self-education for subsequent surgical procedures. Furthermore, the data can be collected from a collection of procedures and analyzed for informing clinicians to improve clinical outcomes in future procedures.

Clamping pressure can be provided via a sensor located at various locations. For example, it can be provided at the linkage of the clamping mechanism. The clamp sensor can in some embodiments be provided on the cartridge to measure compression force on tissue. It could also be provided at the pivots for the cartridge or linkage or handle. It could also be provided in line with the clamping rod (see FIG. 79E). The sensor provides force measurement during the entirety of the clamping stroke. When fully clamped, the sensor can provide the final clamping force and also detect if this force changes during firing as noted above. As an alternative to pressure, resultant force on the load sensor can be measured.

In some embodiments, the clamping pressure can be correlated to the later measured tissue pressure during firing of the staples.

The program logic of the power pack software can in some embodiments include an evaluation of wait time as a function of clamp pressure. That is, this wait time can be tied into readouts of clamping pressure. In use, as the tissue is clamped between the jaws, the clamp pressure drops as fluid is squeezed out of the tissue, then stabilizes and sits for a given amount of time when sufficient fluid has egressed. By providing a viewing screen on the power pack (or instrument) with a graph plotting a) the clamping pressure (x-axis) and b) time, e.g., in seconds, (y-axis), the clinician can readily discern when the tissue has been sufficiently compressed (sufficient fluid has been squeezed out) so there is the optimal distance between the jaws. At this time, the staples can be deployed via initiation of the firing stroke. This reduces the chance that the clinician will initiate staple firing prematurely. By way of example, if initial clamping force is at x lbs., and drops to y-lbs. over "a" seconds, this indicates that the fluid is egressing from tissue. After "b" seconds, if the clamping force drops a much smaller amount, the clinician can see that most of the fluid has egressed. When the force stays at substantially the same amount for a period of time, then staple firing can commence. Stated another way, the graph in a typical clinical application will initially have a steep slope, followed by a flatter slope and eventually a substantially zero slope (flattens out), at which point, with clamping pressure constant over a period of time, the clinician knows firing can be initiated. Thus, there are two ways such pressure can be discerned: a) if a sufficient drop in pressure is displayed; and/or b) if a plateau is displayed (indicating the value is static). Note this also can provide an indication of the density of the clamped tissue since density changes as fluid egresses from the tissue.

In some embodiments, the rate of change of pressure over time can provide a safety. That is, if the rate of change exceeds a predetermined percentage, then the firing can be locked out. That is, an automated system can be provided which prevents firing if clamping pressure drops a preset percentage over a given amount of time since such rapid pressure drop indicates that more fluid still needs to be expelled from the tissue in the clamping stroke and the pressure stabilized.

As can be appreciated, with the foregoing screen/graph, safety of firing staples can be provided after clamping as function of time, pressure or percent reduction, either each independent or in conjunction.

In some embodiments, a memory chip (EPROM) in the disposable instrument can continuously communicate with the power pack (control module) when loaded therein. Once loaded, it can write to the memory chip so the instrument cannot be used again. Additionally, once the power pack is loaded, the number of firings, firing forces, clamping pressure, tissue pressure, etc. can be recorded and transmitted to the power pack, creating a data file of all information/stats. The data can then be retrieved from the power pack for storage and evaluation. Since the power pack can be used in multiple instruments, a new file can be created each time the power pack is loaded into the instrument. Note the instrument memory can store the information/data and transmit it to the power pack memory during and/or after the procedure. For example, if there is manual clamping of the jaws of the instrument, clamping pressure is sensed outside the power pack and would subsequently be transmitted to the power pack while firing of the fasteners is motor driven so force on tissue during firing can be sensed at the jaws which would then require signal transmission to the power pack or alternatively can be sensed at the power pack. Thus, the instrument could provide redundant data storage to the power pack (control module) or the data stored only in the instrument itself. Conversely, the power pack (control module) could provide redundant data storage to the instrument. Alternatively, the data can be stored only in the power pack itself with measurements transmitted to the power pack and not stored in the instrument. In an alternate embodiment, data can be stored in the homing cradle (docking station) in lieu of or in addition to storage in the power pack and/or storage in the instrument. That is, after the procedure, the power pack removed from the instrument compartment can be placed in the homing cradle and the data retrieved from the power pack and transferred to the homing cradle memory. If stored in the homing cradle rather than the power pack, this can reduce the size of the local storage capacity of the power pack as the hardware can be moved to the homing cradle. This reduces the complexity and size of the power pack.

An error screen can also be provided in some embodiments. The error screen can provide feedback display to the clinician of various aspects/parameters such as a) abnormality as a % of a normal firing profile (e.g., if x amp motor current is desired and the firing stroke indicates only y % or lower, of x); b) amperage above or below a predetermined parameter (e.g., if above a preset parameter, a warning signal is provided and if a higher than the preset parameter by a predetermined amount, the motor automatically shuts down); c) comparative analysis of motor current vs motor count to detect abnormality; and/or d) a following error matching actual motor count to intended count (e.g., if motor is intended to spin y times for z mm of stroke but spins less than y times) or actual firing rod or drive mechanism position with intended position. Other errors can also be indicated on the display of the error screen. Note in some embodiments, upon detection of certain errors, the system can automatically make adjustments (e.g., slow down, reverse the firing mechanism, etc.) or stop; in other embodiments, the user alternatively or in lieu of the automatically adjusting or stopping can intervene to adjust or stop the system.

In alternate embodiments of the present invention, the surgical instruments have features to aid staple size selection. These instruments can also provide motor speed adjustments to accommodate different tissue thicknesses.

Features include a measurement device such as a force gauge, load sensor, a strain gauge pressure sensor or other gauges/sensors to measure one or more of i) the clamping force on tissue clamped between the instrument jaws; ii) the clamping pressure on the tissue clamped between the jaws and/or iii) tissue density within the jaws of the instrument. The gauges/sensors can be placed on various locations of the instrument, including proximal and distal portions. Alternatively, the sensors/gauges can be placed on the loadable power pack. These variations are discussed in detail below with reference to FIGS. 42A-45F. Note that the instruments of FIGS. 42A-44C show several gauges/sensors within the instrument to illustrate examples of possible locations for the gauges/sensors. It is not intended that all of the depicted gauges/sensors need to be in a single instrument as it is contemplated for example that only one of the gauges/sensors is in the instrument. However, it is also contemplated that more than one gauge/sensor can be provided in the instrument.

In some embodiments a screen is located in the handle housing or on the power module to provide a visual indicator to the clinician of the measured parameter(s). For example, clamping forces, tissue or clamping pressures, and/or tissue densities measured or calculated by the sensors/gauges as disclosed herein can be displayed on the power module TTF, LCD or Human Machine Interface screen to give real-time feedback to the surgeon. This real-time feedback can be used along with tactile manual clamping. This can induce faster learning for the surgeon on acceptable tissue being clamped. Other tissue parameters, as well as firing and articulation parameters, such as discussed herein, can also be displayed on the screen.

Turning first to FIGS. 42A-43C, several different possible locations for the force measurement device are provided. For brevity of the drawings, as noted above, FIG. 43A shows in a single drawing multiple possible locations for the gauges/sensors. Note only one of these locations can be utilized or alternatively, gauges/sensors can be placed on more than one of the identified locations, as well as in other locations. These locations can be on a movable part related to clamping of the jaws or on a joint where there is a transfer of force. As used herein, the term measurement device will be used to denote gauges or sensors or other devices to measure one or more of clamping force, clamping pressure, tissue density and/or other parameters. Other tissue parameters, as well as firing an articulation parameter such as discussed herein can also be displayed on the screen.

The instrument 600 of FIGS. 42A-43C is identical to the instrument of FIG. 14A described above except for the measurement features and the cam pin/slot arrangement for opening and closing the jaws.

Figure 42B:
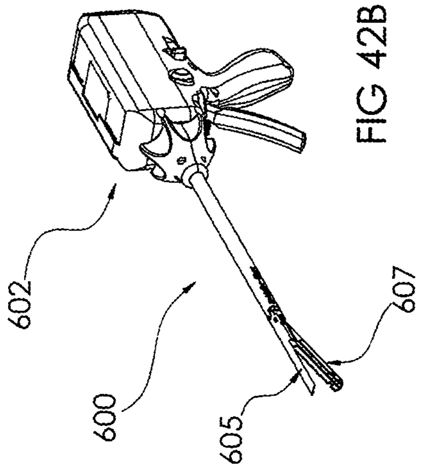
FIG. 42B is a perspective view of the surgical instrument.
Figure 42A:
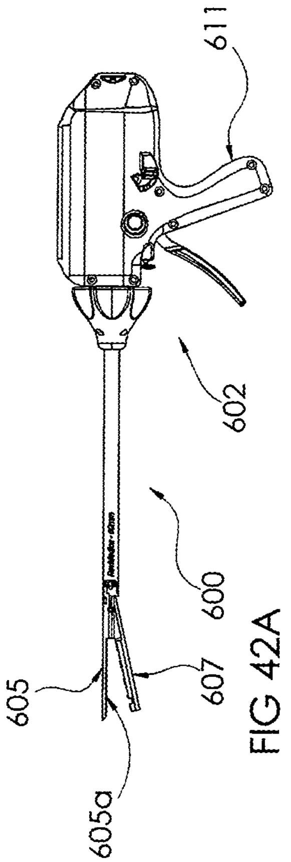
Figure 42C:
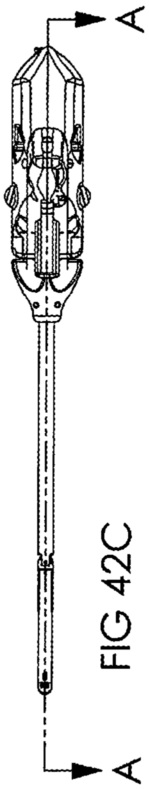
FIG. 42C is a top view of the surgical instrument.
Figure 43B:
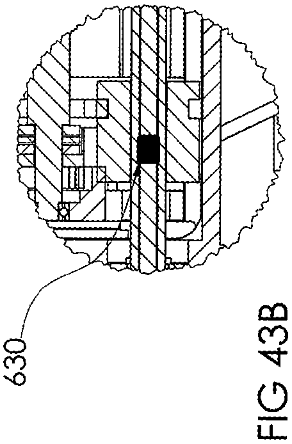
FIG. 43B is an enlarged view of the area of detail E of FIG. 43A.
Figure 43C:
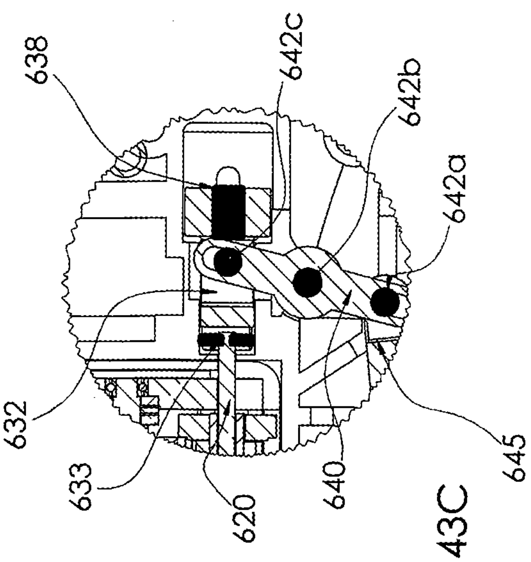
Figure 43A:
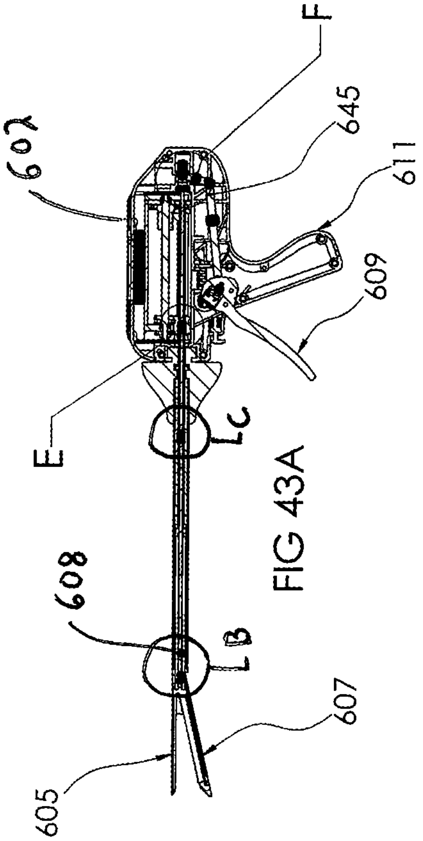
FIG. 43A is a cross-sectional view taken along line A-A of FIG. 42C.

The cartridge jaw 607 is shown in the open position in FIGS. 42A, 42B and 43A, spaced from anvil (or anvil jaw) 605, i.e., the cartridge received in cartridge receiving channel of cartridge jaw 607 is spaced from anvil forming surface 605*a* of anvil 605. The anvil forming surface 605*a* deforms the staples fired from the cartridge jaw 607. In the open (unclamped) position, the clamp pin 604 is at a distal end of clamp pin slot 603 (see FIG. 51). In this position, the clamp rod (clamp shaft) 620 and the clamp laminates 616 are in the distal position. (This jaw arrangement is also shown in the exploded view of FIG. 83E discussed below in conjunction with the embodiment of FIG. 79A wherein the cartridge jaw pivots about pin 624. Pin 604 extends through distal openings 616*a* in clamp laminates 616 and pins 617 connect clamp laminates 616 at a proximal end to the distal end of clamp rod 672 via openings 616*b* and 672*b*.) Clamp laminates 616 connect clamp rod 620 to the distal clamp adapter 610 via hook engagement of hook 616*a* at the distal end of clamp laminates 616 (See FIGS. 42A-42F and 43A-45C of the Ser. No. 17/269,907 application and of PCT/US22/16892, filed Feb. 18, 2022, the entire contents of which is incorporated herein by reference) and a hook at the proximal end of the clamp adapter 622. The clamp laminates 616 and adapter 610 can be attached via a through pin rather than the hook engagement. The adapter includes a web and hold the laminates 616 in place during assembly and ensures the laminates do not flex during use. Other ways to connect the adapter 610 and clamp laminates 616 are also contemplated. In another alternate embodiment, there is a direction connection of the clamp laminates and an adapter is not provided such as in the embodiment of FIG. 83E.

The clamp laminates 616 can be fixedly attached to the clamp rod 620 and clamp adapter 610 or alternatively floatably attached to these components. The flexibility of the clamp laminates 616 allows for articulation of the jaws 605, 607. The knife laminates are designated by reference numeral 618.

Figure 49:
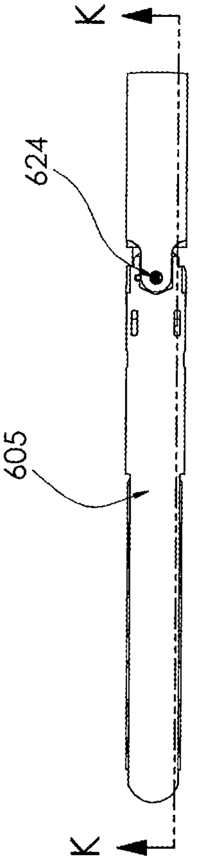
FIG. 49 is top view of the jaw assembly having a cam slot arrangement for closing the jaws of the instrument.
Figure 50:
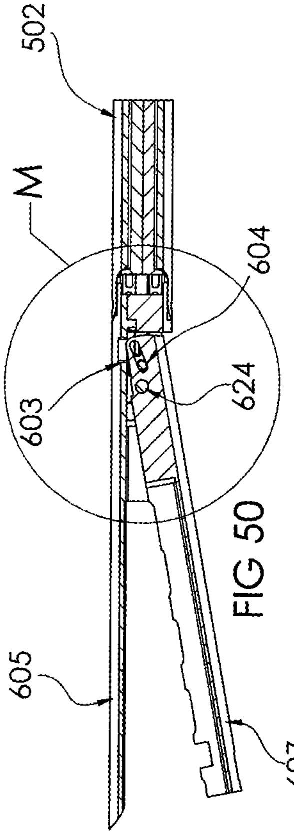
FIG. 50 is a cross-sectional view taken along line K-K of FIG. 49 showing the cartridge jaw in the open unclamped position.
Figure 51:
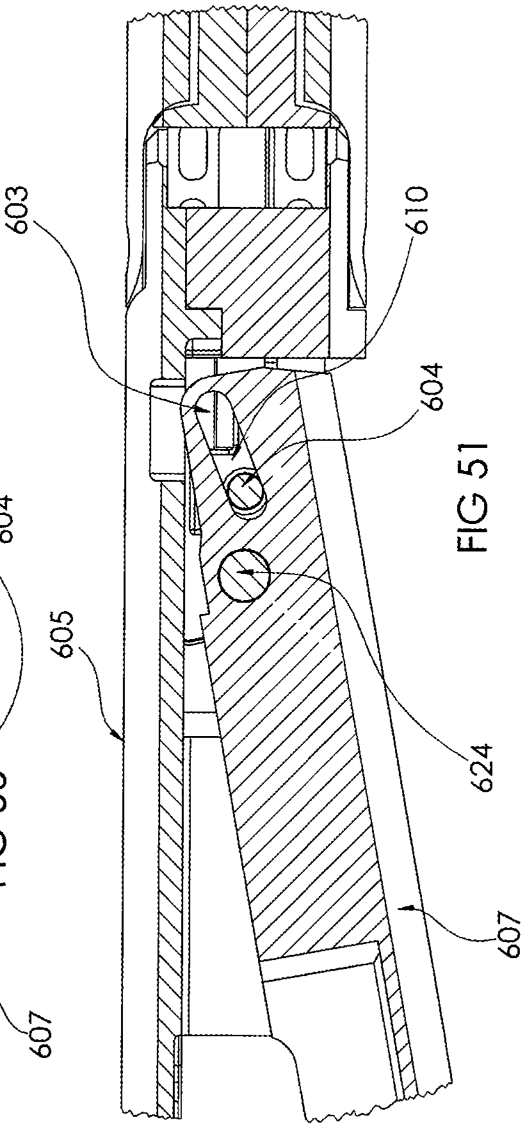
FIG. 51 is an enlarged view of the area of detail M identified in FIG. 50.

Upon manual clamping of the handle 609, i.e., movement toward stationary handle 611, to effect closure of the cartridge jaw 607, the clamp rod 620, which is operatively connected to the clamping handle 609, is pulled proximally, thereby pulling the attached clamp adapter 622 proximally. This moves the through pin 604 which is attached to clamp adapter 610, proximally within the cam slot 603 to move the cartridge jaw 607 toward the anvil jaw 605 to a clamped (closed) position as the cartridge jaw 607 pivots about pivot pin 624. The clamp pin 604 translates in the slot 603 relative to the location of the clamp rod position. The cartridge jaw 607 rotates around the pivot pin 624 relative to the location of the clamp pin 604 in the cam slot. The pin/slot arrangement is shown in FIGS. 49-51. Further details of the clamp pin/slot structure for closing and opening the jaws are described in application Ser. No. 16/792,110, now U.S. Pat. No. 11,331,099, and provisional application Ser. No. 62/900,146, filed Sep. 13, 2019, the entire contents of which are incorporated herein by reference.

Figure 43D:
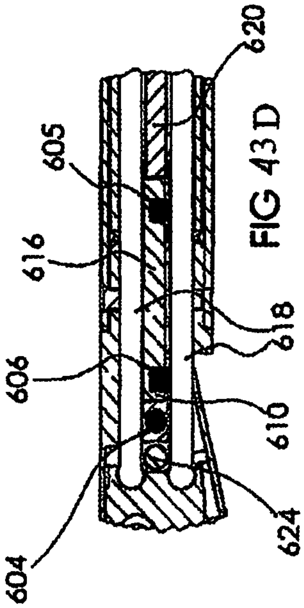
FIG. 43D is an enlarged view of the area of detail B of FIG. 43A.
Figure 43E:
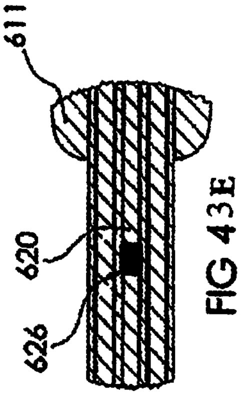
FIG. 43E is an enlarged view of the area of detail C of FIG. 43A

In the embodiment of FIGS. 43A and 43D, the measuring device is placed distal of the handle housing 602. More specifically, the load pin (clamp pin) 604, which is movable within the cam slot 603 as described above based on the axial movement of the clamp rod 620 (see FIG. 51), measures force as the cartridge jaw 607 is moved to the closed position.

In an alternate embodiment, the load cell 606 is located in the distal clamp adapter 610. The load cells herein can form transducers for converting force into a measurable electrical signal. The distal clamp adapter 610 is actuated, i.e., moved axially, by the clamp laminates 616 which are connected to the clamp rod 620 which is movable to close and open the cartridge jaw 607. Note the laminates have slots which interact with the wall of the clamp rod 620 to move with the clamp rod, thus they are floatably connected to the clamp rod. The load cell 606 is shown located at a proximal portion of the clamp adapter 610 where it is hooked to the clamp laminates 616, however it could be located at other regions of the clamp adapter 610. Axial movement of the clamp rod 620 moves the clamp adapter 610 to measure force as the cartridge jaw 607 is moved to the closed position. The load cell 606, being fixed to adapter 610, translates with adapter 610.

In an alternate embodiment, the load cell 608 is located at a distal end of the clamp rod 620 (FIG. 43A). It is shown at the distalmost end of the clamp rod 620, where the clamp rod 620 is hooked to the clamp laminates 616, but alternately can be located at other regions of the clamp rod 620. Axial movement of the clamp rod 620 measures force as the cartridge jaw 607 is moved to the closed position. The load cell 608, being fixed to clamp rod 620, translates with adapter 610.

Note these load cells 604, 606 and 608 are positioned at the distal region of the instrument adjacent and proximal of the instrument jaws 605, 607 and proximal of the jaw pivot pin 624. Note load cell 604 provides an example of the measurement device on a pin of the instrument; load cells 606, 608 provide an example of the measurement device on an axially movable part tied into jaw movement placed under load during clamping of the jaws on tissue. In this manner, clamping pressure or clamping force can be measured. Tissue density can also be measured.

Note the clamp laminates 616 in some embodiments interact with the load cells at opposing proximal and distal ends. Note the load can be translated down the shaft at any connection point.

The measurement device can alternatively be positioned further proximally of the jaws 605, 607 as shown for example in FIG. 79G. As shown, strain gauge 626 is located in the clamp shaft (clamp rod) 620 distal of the handle seal. That is, it is adjacent the handle 602 and distal thereof (and distal of the rotation knob 615). The clamp shaft 620 is movable axially to effect jaw opening and closing and thereby enabling gauge 626 to measure the force. Alternatively, the strain gauge can be located in a proximal region of the clamp shaft 620 proximal of the handle seal as shown for example in FIG. 43B discussed below.

In the foregoing embodiments, the measurement devices are positioned distal of the handle housing 602. In the alternate embodiments of FIGS. 43A-44C, the measurement devices are positioned in the handle portion with FIG. 43B illustrating the measurement device within the handle housing 602 and located in/on the axially movable clamp rod 620 and FIGS. 43C, 44B and 44C illustrating the measurement device on the manually actuated clamping handle or linkage.

Figure 48:
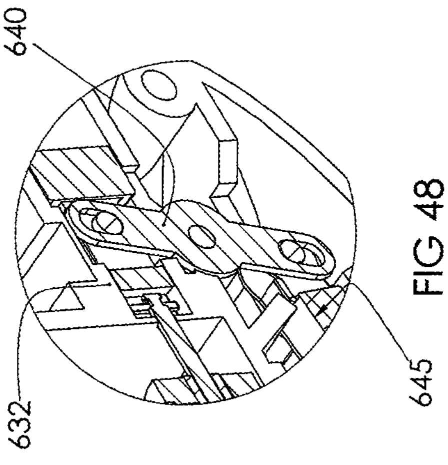
FIG. 48 is a sectional view of the components of FIG. 46 (with the handle housing removed)
Figure 47:
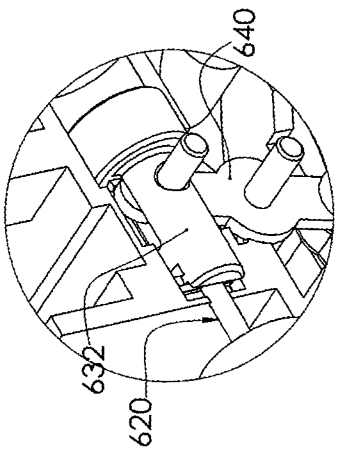
FIG. 47 is a perspective view of the components of FIG. 46 (with the handle housing removed)
Figure 46:
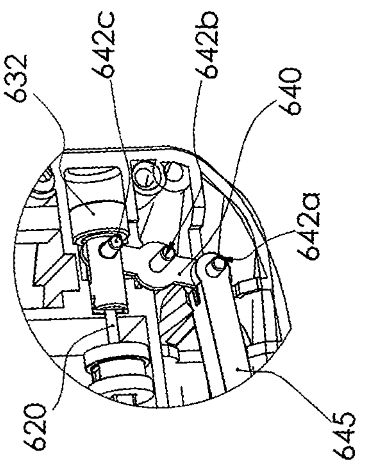
FIG. 46 is a perspective view of components within the handle assembly in accordance with an alternate embodiment.

More specifically, FIG. 43B illustrates strain gauge 630 positioned in the proximal region of the axially movable clamp rod 620 within the handle housing 602. Thus, the gauge 630 is positioned proximal of the handle seal. FIG. 43C illustrates a) strain gauge 638 located, e.g., attached, at the proximal end of the proximal clamp adapter 632; and b) strain gauge 633 located, e.g., attached, at the distal end of the clamp adapter 632. Alternatively, strain gauge 633 can be attached to a proximal end of clamp rod 620. Proximal clamp adapter 632 is actuated/moved by the clamp pivot plate 640. Strain gauge 633 is actuated by the proximal lip of the clamp rod 620 which is attached to proximal clamp adapter 632. The clamp adapter 632, clamp rod 620 and clamp pivot plate 640 are shown in the enlarged view of FIGS. 46-48.

In alternate embodiments, the load pin can be located at one or more of the pin locations on the clamp pivot plate 640. The pivot plate 640 pivots about pin 642*b* (FIG. 46) and is connected at one end to link or clamp yoke 645 via pin 642*a* and at the other end to clamp adapter 632 via pin 642*c*. Link 645 is connected to clamping handle 609 at the opposing end. Pin 642*b*, positioned between pins 642*a* and 642*c* connects to the adapter 632. Pins 642*a*, 642*b*, 642*c* form load pins for force measurement based on movement of the pivot plate during clamping of the jaws 607, 605 initiated by manual movement of handle 603. It should be appreciated that only one, only two or all three load pins 642*a*, 642*b* and 642*c* could be used in a single instrument. When clamping handle 609 is moved toward stationary handle 611, it causes movement of yoke 645 which pivots the plate 640 clockwise about pivot pin 642*b* to move the proximal clamp adapter 632 proximally to effect proximal movement of the clamp rod 620 which moves the cam pin 604 (FIG. 51) proximally within cam slot 603 to move cartridge jaw 607 toward anvil jaw 605 to clamp the jaws.

Figure 44B:
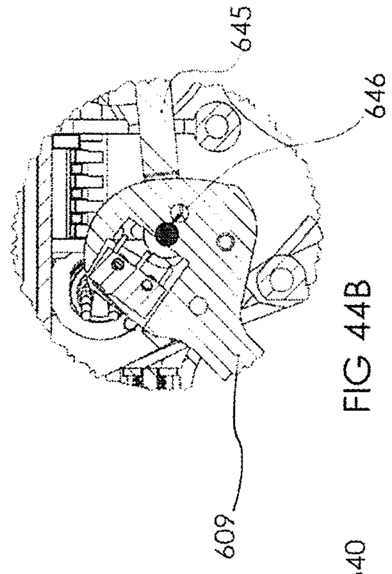
FIG. 44B is an enlarged view of the area of detail I of FIG. 44A.
Figure 44C:
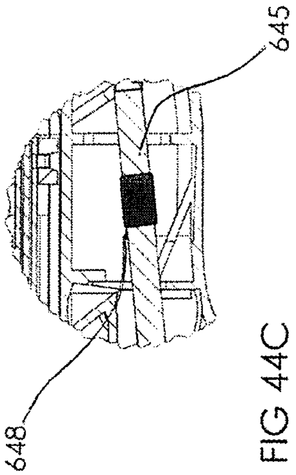
FIG. 44C is an enlarged view of the area of detail H of FIG. 44A.
Figure 44A:
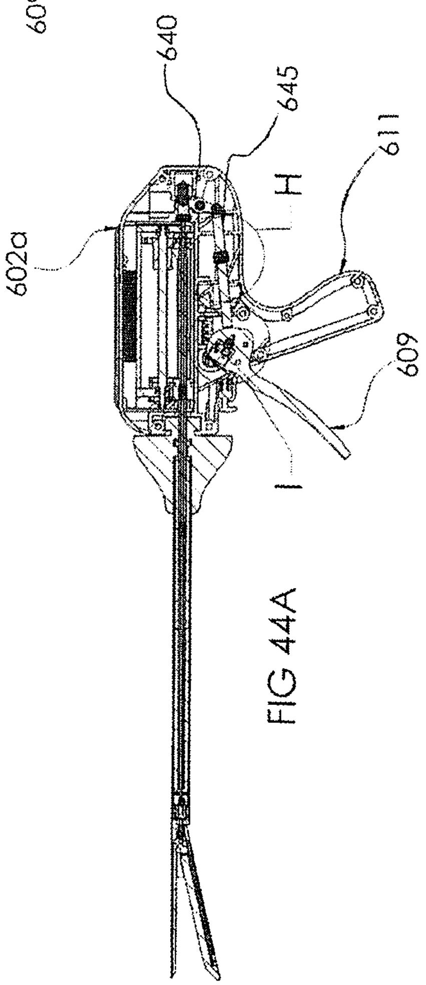
FIG. 44A is a cross-sectional view identical to the cross-sectional view of FIG. 43A illustrated to identify the areas of detail H and I.
Figures 45A, 45B, 45C, 45D, 45E, 45F:
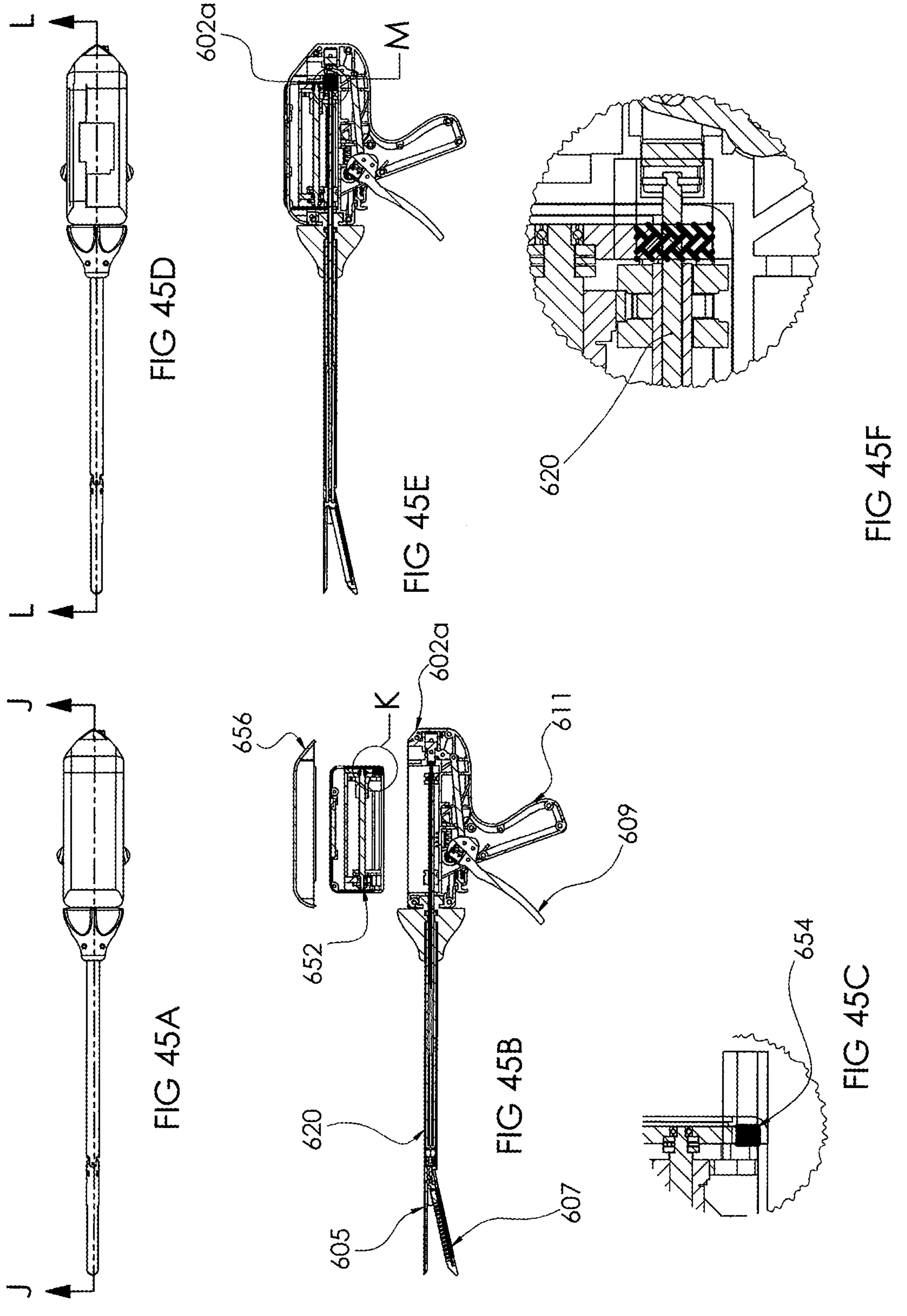

In the embodiment of FIG. 44B, the load pin 646 is located at the clamp pivot location, i.e., it connects handle 603 with the clamp yoke (link) 645. Movement of handle 609 effects movement of clamp yoke 645 as described above. In FIG. 44C, the load cell 648 is located in or on the clamp yoke 645 which can be in the form of a split yoke or complete yoke. It is outside the sterile portion of the handle housing 602*a* and is positioned on yoke 645 between the handle 609 and the pivot plate 640. The load cell can alternatively be positioned in other regions of the link 645.

As in the embodiments above, when provided on the instrument, the measurement device, e.g., the force gauge/strain gauge can be in line with the clamp linkage of the disposable instrument and/or in line with the clamp rod. It can be in the front of the clamp stroke, in the middle or in the back at or near the proximal clamp adapter. It can be inside or outside the handle housing. It can also be offset from the clamp rod such as below or side by side with the clamp bar. It could also be in line in the tube, distal of the handle so it does not need to rotate. It can also be inside the distal jaws of the instrument.

As noted above, the load cell can in alternative embodiments be located in the removable power pack as shown in FIGS. 45A-45F. The force gauge/strain gauge 654 is inside the reusable power module 652 and connected to the clamp linkage of the disposable instrument either through a split clamp linkage or at end of the clamp linkage stroke supported with a spring. As described above, the power module 652 is loaded into the compartment of the handle housing 602*a* and cover 656 seals the compartment. The measurement device e.g., load cell 654, within power module 652 measures clamp linkage linear movement/distance to determine the theoretical gap between the jaws for force measurement. That is, the load cell 654 mates with the clamp rod 620 as it drops into the linkage and translates with the clamp rod 620 during axial movement of the clamp rod 620 to measure clamp force. This can be used together with strain gauge/force gauge reading to calculate tissue density through the entire clamp stroke.

The force gauge is powered from power module and communicates with the power module microprocessor.

The instrument 660 of FIGS. 79A-83A is identical to the instrument of FIG. 14A described above except for the measurement features, jaw clamping mechanism and the cam pin/slot arrangement for opening and closing the jaws. Instrument 660 has a similar cam/pin slot arrangement as instrument 660 wherein proximal movement of the clamp rod closes the jaws, and although has some commonalities with the manual jaw clamping mechanism of instrument 660 of FIGS. 46-48, has some differences.

The instrument 660, like instrument 600 of FIG. 42B has an anvil jaw 605 and a movable (pivotable) cartridge jaw 607. Pin 604 rides with cam slot 603 in the same manner as shown in FIG. 51.

Instrument 660 has a compartment with a cover 663 openable in the same manner as described above to removably receive a power pack. The power pack is the same as in the aforedescribed embodiments to power firing and articulation, and engages the firing rod and articulation rod in the same manner as described above. Therefore, for brevity, the powered features for firing and articulation and power pack for brevity are not repeated herein, it being understood that the description above of these components/features, and their alternatives, are fully applicable to instrument 660.

Instrument 660, as shown in FIGS. 79 and 82, has a trigger 669 to actuate the firing motor for firing the fasteners and a push button 664 on opposing sides of the instrument to actuate the articulation motor to effect articulation in left and right directions with respect to the longitudinal axis of the shaft 661. Proximal movement of the trigger 669 brings the proximal end of 669*e* of post 669, which is attached to trigger 669 via pin 669*b*, into contact with an electrical switch to complete the electrical circuit to actuate the firing motor. Inward movement of the actuation button 664 via pressing button 666 brings it into contact with an electrical contact, e.g., a switch, to complete the electrical circuit to actuate the articulation motor. This is described in detail below. The clamping mechanism is configured to enable switch activation or completion of the circuit by the firing trigger and the articulation button based on positions of the clamping handle 667 (and thus the position of the jaws 605, 607).

Instrument 660 has a handle 667 movable (pivotable) with respect to stationary handle 665. Such movement of handle 667 toward stationary handle 665 applies a proximal force to clamp rod 672 (see e.g., FIG. 79E), operatively connected thereto via linkages, to effect movement of cartridge jaw 607 toward anvil jaw 605 to clamp tissue between the two jaws. It should be appreciated that in alternate embodiments, the anvil jaw 605 can be movable in addition to the cartridge jaw or in lieu of the cartridge, i.e., the cartridge jaw remains stationary as the anvil jaw moves. A pivotable locking member 678 (FIG. 79G) engages a component of the clamping mechanism in the handle portion to lock the handle 667 in the clamped position as described below. The locking member 678 includes a thumb release 678*d* (FIG. 82) to release the locking member as also described below.

Instrument 660 also includes a load sensor 676 (see e.g., FIG. 79E) at a proximal end of the housing which measures clamping force in response to a force applied by the clamping mechanism. The sensor 676 is in line with the elongated clamping member 672 (also referred to herein as the clamping rod) of the clamping mechanism which is achievable due to the proximal movement of the clamp rod 672 to clamp tissue. Thus, the load sensor is in compression opposing the jaw mechanism. The adapter 675, connected to clamp rod 672, keeps the components in alignment to minimize or eliminate sliding to improve the accuracy of the pressure measurements.

Turning now in more detail to the components of the clamping mechanism, and with initial reference to FIGS. 79C, 79E and 79G (which show the clamping handle 667 in the open position) and FIG. 82 (exploded view), the clamping mechanism includes link 668 (also referred to herein as the yoke) which is connected at a distal end to clamping handle 667 via pin 668*f* extend through an upper opening in the handle 667 and connected at a proximal end to pivot plate 670 via pin 668*a*. Pin 668*a* rides within lower slot 670*b* of pivot plate 670 as the handle 667 is clamped. Lower slot 670*c* also has a dwell slot region 670*d* for clamp handle release as described below. (An enlarged view of the pivot plate 670 is shown in FIG. 83B). Handle 667 pivots about pin 667*a* which connects handle 667 to the housing. Pivot plate 670 also has an upper slot 670*c* to receive pin 675*b*. Pivot plate 670 pivots about pin 670*a*. As shown in FIG. 83A, there are two identical pivot plates 670, one attached on each side of yoke 668, only one of which is shown in the sectional view of FIG. 79E. Pivot plates 670 are operatively connected to clamp bar 672 so that pivotal movement of pivot plates 670 moves the clamping bar 672 linearly (axially) between distal (unclamping) and proximal (clamping) positions.

Clamp bar 672 is attached at a proximal end 672*a* to adapter 674 via an enlarged proximal end received in a slot in adapter 674, the slot having a narrowed region to prevent detachment of the clamp bar 672. Proximal of adapter 674, and in abutment with adapter 674, is force member 675, also referred to herein as puck 675, which is in abutment with load sensor 676 Load sensor can be in the form of piezoelectric sensor wherein when force is applied it changes material composition which drops resistance and allows more voltage, although other types/forms of sensors are also contemplated. Transversely extending force pin 675*b* extends through adapter 674 and is seated within slot/recess 675*a* of puck 675. Pin 675*b* also extends through the upper slots 670*c* of pivot plates 670. When the clamp rod 672 is pulled proximally by the clamping handle 667 (which is operably connected to the clamp rod 672 via yoke 668 and pivot plates 670 connected to adapter 674), it applies a proximal force to the puck 675 which is in contact with sensor 676. In this manner, sensor 676 can measure the clamping force of the jaws 605, 607 on tissue. This clamping force/clamping pressure is transmitted via wires, e.g., a flex cable(s), to a communications bus 699 in the power pack receiving compartment of the instrument housing, best seen in FIGS. 84A and 84B. Bus 699 is shown on the bottom wall surface of the housing compartment but could alternatively be placed in other locations, e.g., a side wall. With the power pack (control module) loaded in the compartment of the housing in the loading manners discussed herein with regard to the other embodiments, the communication bus transmits the data to the power pack for displaying the information on the viewing screen, i.e., the viewing screen displays described herein. It should be appreciated that although in preferred embodiments, wires connect the sensor to the bus, it is also contemplated that wireless communication could be utilized.

A pivotable locking member 678, pivotable about pin 678*c*, moves into engagement with the yoke 668 when the clamping handle 667 is in the fully clamped position to lock the clamping handle 667 and the clamping bar 672 in the clamping position so the jaws remain in their clamped (closed) position. More specifically, in the unclamped (open) position, engagement edge 678*a* of locking member 678, as shown in FIG. 79G, is out of engagement with the upper indentation/recessed surface 668*c* of yoke 668. In this position, movement of yoke 668 is unrestricted so that movement of clamping handle 667 to close the jaws 605, 607 is unrestricted. In the locking position of locking member 678 as shown in FIG. 81G, edge 678*b* of locking member 678 is in engagement with shoulder 668*e* at the distal end of indentation 668*c*. In this position, proximal movement of yoke 668 is blocked so that movement of clamping handle 667 is restricted so it cannot be pulled further, i.e., cannot be pivoted further proximally toward stationary handle 665 nor can it move away from the stationary handle to unclamp the jaws 605, 607. This locking position, also referred to as a blocking position, corresponds to the fully clamped position of handle 667 and fully clamped position of the jaws 605, 607 on tissue. Thus, the jaws 605, 607 are retained in their fully clamped position and cannot open during firing of the fasteners.

A manual release 678*d*, which can be actuated by the user's thumb, is provided to unlock the handle 667. Manual release 678*d* extends outwardly on both sides of the locking member 678 to protrude on both sides of the instrument housing so it can be actuated from either side. A force applied to the manual release 678*b* by the user pivots the locking member 678 about pivot pin 678*c* out of engagement with shoulder 678*b* of yoke 668 for movement so that handle 667 can be squeezed further proximally so that yoke 668 can bypass the locking member 678 (as shoulder 668*e* is no longer engaging locking edge 678*a*) and handle 667 can return to the unclamped position of FIG. 79A to open the jaws to the position of FIG. 79C.

The position of the clamping handle 667 also effects the enabling/disabling of the firing motor and the articulation motor to ensure that the instrument can only be articulated with the jaws 605, 607 in the open position and that firing can only occur only when the jaws 605, 607 are in the closed position. In the position of the clamping handle 667 of FIG. 79A, the contact on an inner D-shaped surface 666*a* of the articulation button 666 is aligned with the electrical switch 699 in the housing as shown in FIG. 83C so articulation can be activated; when the clamping handle 667 is moved from the open position, the contact of the inner surface 666*a* articulation button 666 is no longer aligned with the electrical switch 699 as shown in FIG. 83D so articulation cannot be activated. In the position of the clamping handle 667 of FIGS. 79A (open) and 80A (partially clamped), proximally facing surface 669*c* of post 669*d* of trigger 669 is out of reach with the electrical switch 692 on a forward (distally) facing surface of the clamping handle as shown in FIG. 79G so firing cannot be activated; when the clamping handle 667 is moved to the fully closed position of FIG. 81A, when the trigger is actuated, i.e., pivoted about pivot pin 669*a*, post 669*d* is able to come into contact with electrical switch 692 as shown in FIG. 81G so firing can be activated as it compresses switch 692 to activate it. It should be appreciated that alternatively the trigger and clamping handle electrical contacts and the articulation button and housing electrical contacts can be configured so their contact completes the electrical circuit to activate firing and articulation.

The use of the instrument 660 will now be described. In the initial unclamped position of FIGS. 79A-79G, the handle 667, which corresponds to the unclamped position of the jaws, is in a distal position with respect to the stationary handle 665. In this position, yoke pin 668*a* is in an upper portion of lower slot 670*b* of pivot plate 670 and pin 675*b* is in an upper portion of upper slot 670*c*. Clamp rod 672 is in a distal position with pin 604 within slot 603 of the jaw pivot mechanism (see also FIG. 51). In this distal position of clamp rod 672, no force (or minimal force) is applied to puck 675 by adapter 674 so the sensor reads a zero clamping force. Note in this initial position, puck 675 can be in abutment or slightly spaced from sensor 676. The sensor 676 is affixed to the clamp adapter 674. In this unclamped position, pivotable locking member 678 is in an unlocking (unblocking) position wherein surface 678*a* is spaced from shoulder (surface) 668*e* of yoke 668 to allow free movement of the yoke 668 to pivot plates 670 about pivot pin 670*a* to effect proximal linear movement of the clamping rod 672.

Further, in this unclamped position, articulation button 665 can be pressed inwardly so the electrical contact on the inner D-shaped surface 665*a* can make contact with the switch 698 in the housing (FIGS. 79I, 83CS) to complete the circuit (or activate the switch via compression of the switch) since the contact of surface 665*a* is aligned with switch 698. Completion of the circuit enables the motor to move the articulation rod in the manner described above. However, in this unclamped position, the contact 669*a* on a rearwardly facing surface 669*e* of the trigger assembly is spaced a distance from switch 692 on the distally facing surface of clamping handle 667 (FIG. 79G) so it is out of reach. That is, even if the trigger 667 is squeezed in this position, due to the open position of the clamping handle 667, the post 669*d* of the firing trigger mechanism would not make contact with the switch 692 so it cannot activate the switch so the firing motor cannot be actuated (or cannot complete the circuit in alternate embodiments). Thus, in this initial unclamped position, motor powered articulation of the jaws 605, 607 can be effected while motor powered firing of the jaws cannot be effected. Thus, articulation occurs in the open position of the jaws 605, 607.

To clamp the jaws 605, 607 on tissue, handle 667 is squeezed toward handle 665. Note spring 690 biases handle 667 to the open (unclamped) position. FIGS. 80A-80I illustrate the instrument in the partially clamped position. In this position, handle 667 has pivoted about pivot pin 667*a* and moved further toward the stationary handle 665. Locking member 678 still remains out of engagement of the indentation 668*c* of yoke 668 as although yoke 668 has moved closer to locking member 678, locking edge 678*a* remains out of engagement with shoulder 668*e* of yoke 668 as it rests on a surface of yoke 668 outside the indentation 668*c*. In this position, post 669*a* of trigger 669 is still out of reach of contact 692 positioned on upper surface of clamping handle 667 so that even if the firing trigger 669 is fully squeezed, surface 669*e* would not come into contact with switch 692 to compress it so the firing motor cannot be activated. In this partially clamped position, the contact on the surface 666*a* of articulation button 664 is no longer aligned with the switch 698 on the instrument housing so even if the articulation button 666 is pressed inwardly, the contact surface 666*a* will not make contact with the switch 698 (due to the non-alignment) and the circuit cannot be completed (or switch activated via compression of the switch) so that the articulation motor cannot be actuated.

In this intermediate clamping position, clamp rod 672 is pulled proximally so that jaw pin 604 rides within the slot 603 to move cartridge jaw 607 toward anvil jaw 605. Note the clamp rod 672 slides within a lumen of the firing rod 671 as its movement is independent of the firing rod. Also note that the clamp rod 672 is rotatable within the firing rod and can be rotatable 360 degrees and utilized to rotate the jaws. Proximal movement of clamp rod 672 moves adapter 675 proximally which applies a force against puck 675, aided by transverse force pin 675*b* within slot 675*a* of puck 675, which applies a force to sensor 676. The force measurements are communicated to the power pack microprocessor via communication bus 699 for providing clamping pressure readouts as described herein. Note as clamping rod 672 is pulled proximally during the clamping stroke, a force is continued to be applied to the load sensor 676 (via the adapter 674 and puck 675) so force can be measured during the entire clamping stroke and transmitted to the power pack and displayed on the power pack screen to provide continuous feedback to the user.

To fully clamp the jaws 605, 607, handle 667 is squeezed further toward stationary handle 665 to pull clamp rod 672 further proximally so that jaw pin 603 rides within the slot 604 to move cartridge jaw 607 toward anvil jaw 605. This proximal movement of clamp rod 672 continues to adapter 675 to apply a force against puck 675 to apply a force to sensor 676. The force measurements are communicated to the power pack via communication bus 669.

In the fully clamped position shown in FIGS. 81A-81G, the locking member 678 engages the yoke 668 such that locking edge 678*a* is engaged with shoulder 668*e* of yoke 668 to block movement of the yoke 668 and thus block movement of the clamping handle 667 which prevents further movement of the clamping rod 672 and thus further clamping of the jaws 605, 607. In this position, post 669*d* of trigger 669 is now within reach of contact 692 positioned on upper surface of clamping handle 667 so that when the firing trigger 669 is fully squeezed, post 669*d* comes into contact with switch 692 to activate the switch so the firing motor can be activated to advance the firing mechanism to fire the fasteners in the manner described above. Note trigger 669 (with attached post 669*d*) is biased distally by spring 669. In this partially clamped position, the contact on the surface 666*a* of articulation button 664 remains non-aligned with the switch 698 on the housing so if the articulation button 666 is pressed inwardly, the contact surface 666*a* will not make contact with the contact or switch (due to the non-alignment) and the circuit cannot be completed so that the articulation motor cannot be actuated. Note alternatively, the switch can be on the trigger and the contact on the clamping handle to activate motor power firing and/or the switch can be on the actuation button and the contact on the housing to activate motor powered articulation.

As noted above, in some embodiments, only when the firing trigger 669 is held in its squeezed/activated position is the firing motor actuated. Once the user releases the firing trigger 669, the motor actuation ceases and firing member axial movement ceases. Such holding of the firing trigger to effect axial movement of the firing member can be utilized for distal movement for fastener firing, and/or for proximal movement of the firing member after one or both of completion of the firing stroke or aborting/ceasing movement during the firing stroke.

To release the clamping handle 667 from the closed/locked position, the user applies a force to release 678*d* to pivot locking member 678 clockwise and pulls handle 667 further proximally toward stationary handle 665. Note that during this movement, pin 668*a* rides in the dwell region 670*d* (FIG. 83B) of slot 670*b* of pivot plate 670 so that although the yoke 668 is moving under the force of handle 667, there is no further clamping of the jaws since the pivot plate 670 is not being rotated. Pivoting of locking member 678 by release 678*d* enables yoke indentation 668*c* to separate from locking member 678 so the clamping handle 667 can then be released to return to its normally biased open (unclamped) position of FIG. 79A due to the force of biasing spring 690.

FIGS. 56-66B illustrate another alternate embodiment wherein the load cell is positioned in the power pack. In this embodiment, the deployment screw 710 and articulation screw 750 are supported by axial bearings and thrust bearings.

Thrust (axial) bearings and radial bearings on opposing ends of the screw 710 provide centering and axial alignment of the screw 710 during use. These thrust and radial bearings function in the same manner as thrust bearings 768, 780 and radial bearings 757, 782 of screw 754 of the embodiment of FIG. 59B of co-pending application Ser. No. 16/792,110, filed May 15, 2020, now U.S. Pat. No. 11,331,099, the entire contents of which are incorporated by reference as noted above. As shown, thrust bearing 716 is mounted at the distal end of screw 710 and thrust bearing 736 is mounted at the proximal end of the screw 710, proximal of collar 712, to resist any axial force applied to the rotating screw 710 and maintain its axial position. Radial bearings 724, 734 are provided to resist radial loads (forces that are perpendicular to the direction of the screw) and are located on the respective distal and proximal ends of the screw 710 with radial bearing 724 distal of thrust bearing 716 and radial bearing 734 proximal of thrust bearing 736. The thrust bearings 716, 736 are slip fit over the outer diameter of the deployment screw 710 (FIG. 59), at distal and proximal ends, respectively, and thus float relative to the screw 710. They are sandwiched together with the chassis. The radial bearings are press fit into openings in distal plate 744 and proximal plates as in application Ser. No. 16/792,110, now U.S. Pat. No. 11,331,099. The deployment screw 710 has a reduced diameter portion at the proximal end (FIG. 57C) and distal end (FIG. 57B) to form a shoulder 713 and 715, respectively, at the larger diameter portions which abut, i.e., contact, thrust bearings 736, 716, respectively. Thus, the thrust bearings 716, 736 can rotate freely within the housing, but are constrained by the steps (shoulders) of the ball screw 710 so they cannot move along the axis of the screw. The belt 723 and pulley 722 of the deployment (firing) mechanism are shown in FIG. 57B and are the same as in the foregoing embodiments.

Collar 712 has mounted thereto a pair of left and right track bearings 714 (FIG. 58), which function in the same manner as left track bearings 779 and right track bearings 778, e.g., traveling along tracks in the 760, 762, described in detail in the Ser. No. 16/792,110 application, now U.S. Pat. No. 11,331,099, thereby preventing rotation out of the track as forces are translated linearly along shaft as the nut translates forward and backward. The tracks can be attached to or integrated (monolithic) with the chassis. The collar 712, like collar 756 of FIG. 59A of the Ser. No. 16/792,110 application, now U.S. Pat. No. 11,331,099, includes a blade/tab extending inwardly from the wall which engages a circumferential recess (groove) in the deployment disk of the stapler which is attached to (or extends from) the firing rod of the stapler. In this manner, axial movement of collar

712 (via ball screw 710 when actuated by the motor) moves the deployment disk axially, the collar traveling along the respective left and right tracks (runners) via respective left and right bearings 714.

Figure 57C:
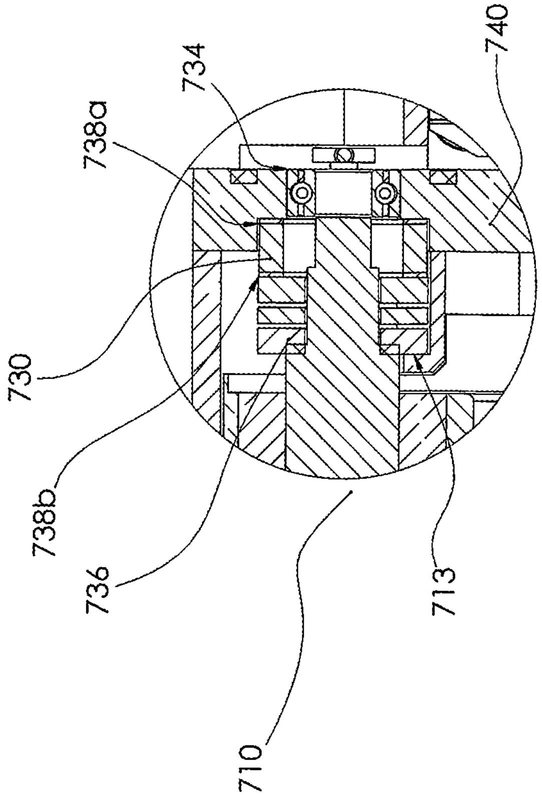
FIG. 57C is an enlarged view of the area of detail C of FIG. 57A.

The deployment screw 710 includes a load cell or strain gauge 730 at the proximal end which is sandwiched between distal and proximal plates 738*b*, 738*a* (FIG. 57C). The deployment screw 710 further includes a load cell or strain gauge 720 at the distal end which is sandwiched between distal and proximal plates 718*b*, 718*a* (FIG. 57B). These load cells behind the thrust bearings measure force during firing. This can prevent the motor from being faulted. If the load cell detects an energy spike, a signal is sent to the microprocessor within the power pack 700 to slow down the motor.

Figures 58, 59, 60A, 60B:
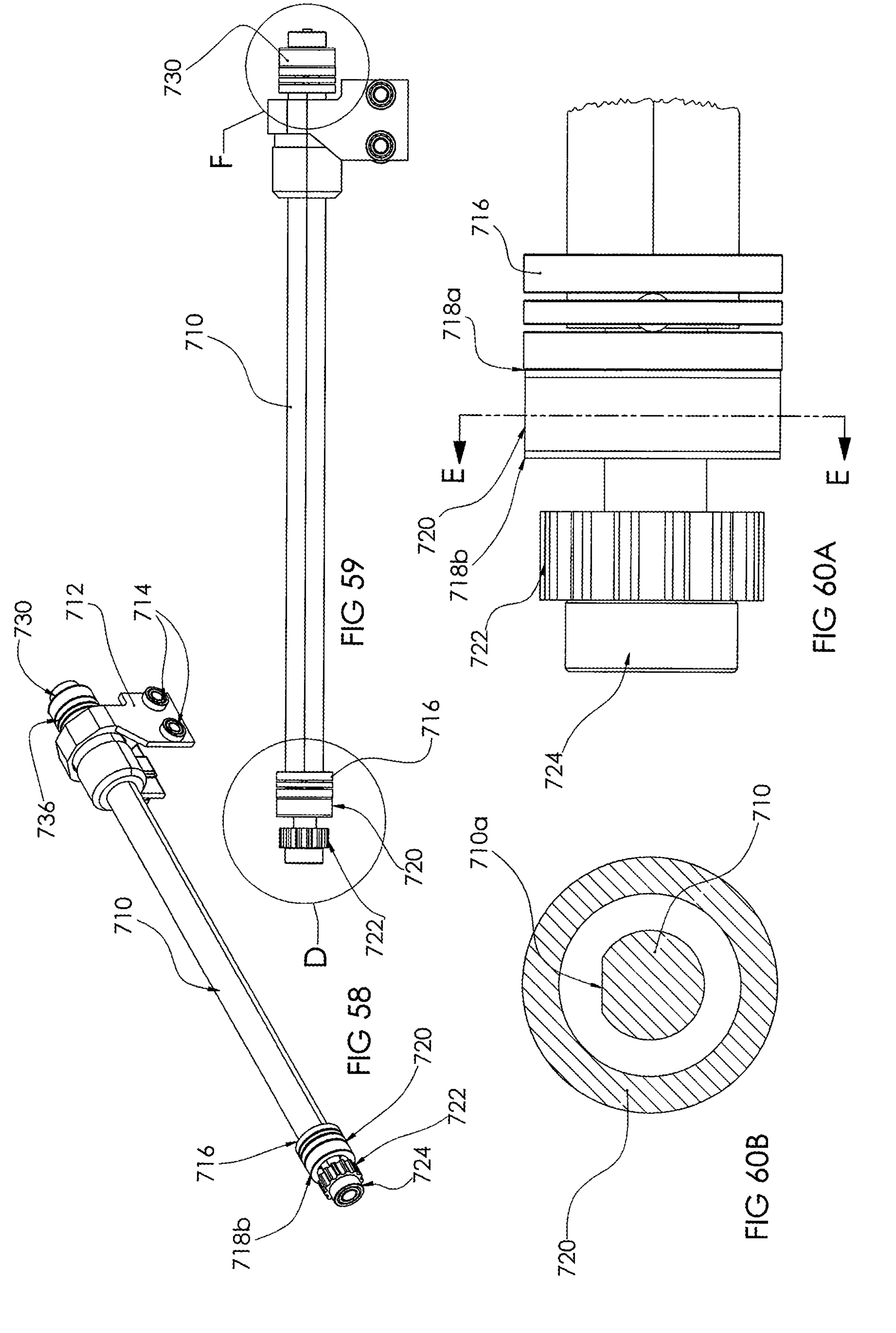
FIG. 58 is a perspective of the deployment (firing) screw assembly of the power pack of FIG. 55.
FIG. 59 is a side view of the assembly of FIG. 58.
FIG. 60A is an enlarged view of the area of detail D of FIG. 59.
FIG. 60B is a cross-sectional view taken along line E-E of FIG. 60A.
Figure 61A:
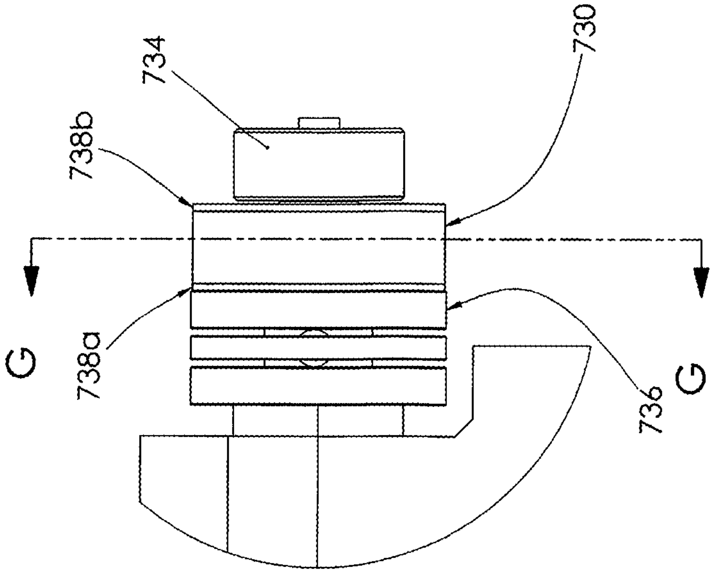
FIG. 61A is an enlarged view of the area of detail F of FIG. 59.
Figure 61B:
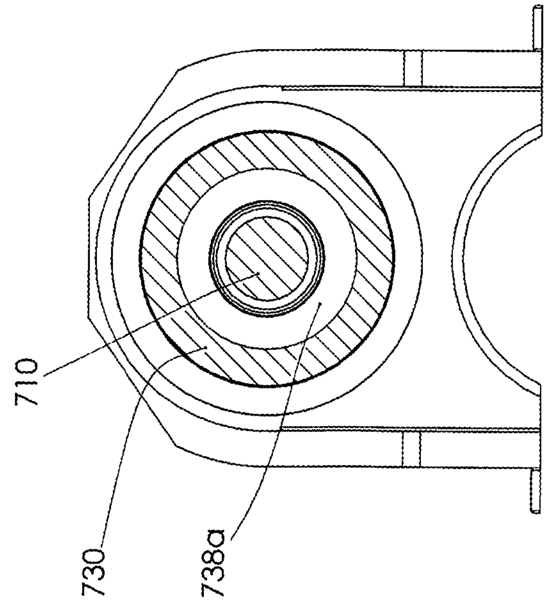
FIG. 61B is a cross-sectional view taken along line G-G of FIG. 61A.
Figure 62B:
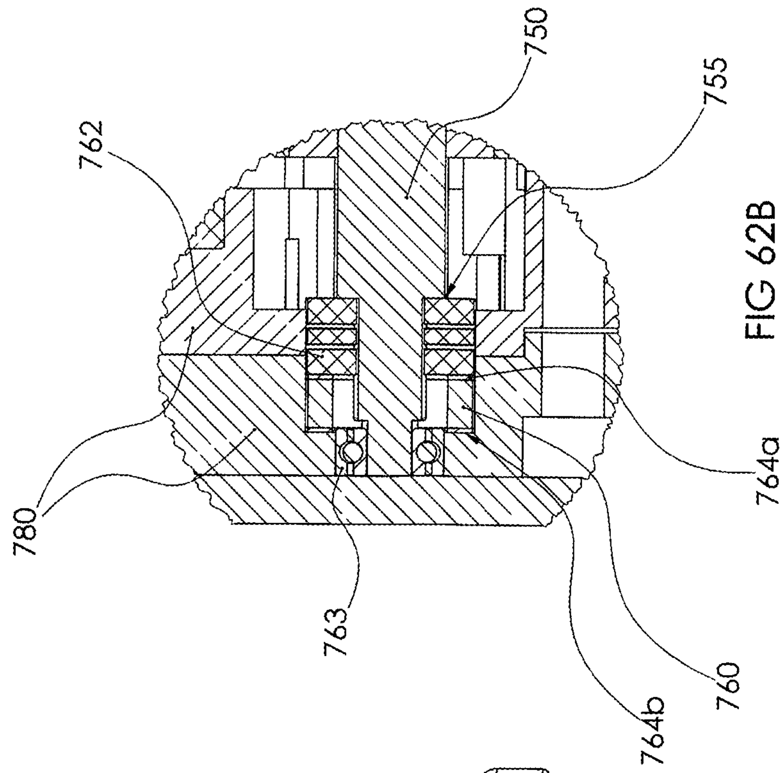
FIG. 62B is an enlarged view of the area of detail I of FIG. 62A.
Figure 62A:
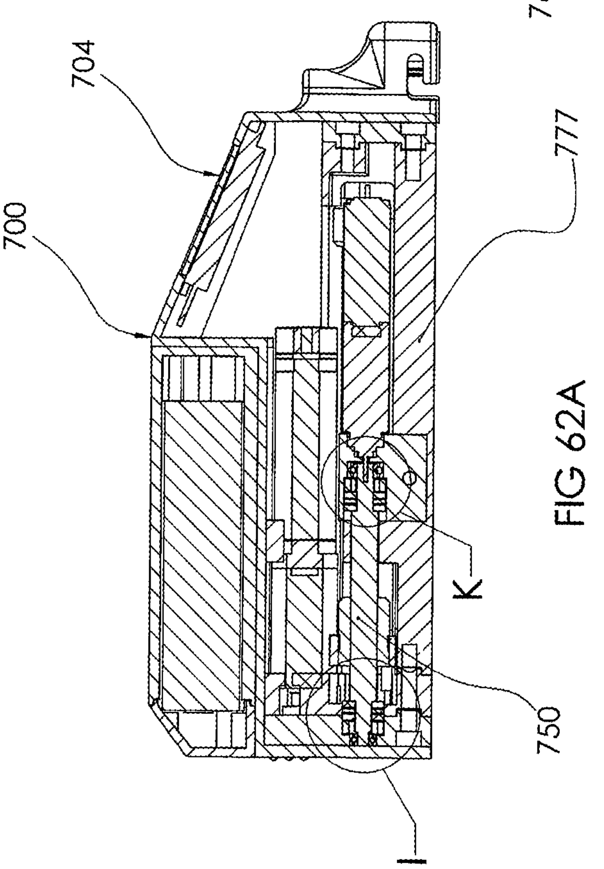
FIG. 62A is a cross-sectional view taken along line H-H of FIG. 56.
Figure 62C:
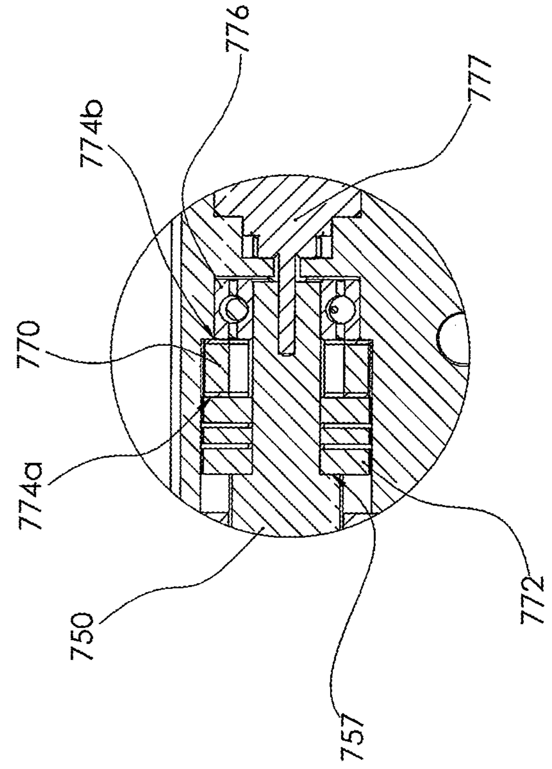
FIG. 62C is an enlarged view of the area of detail K of FIG. 62A.
Figure 64:
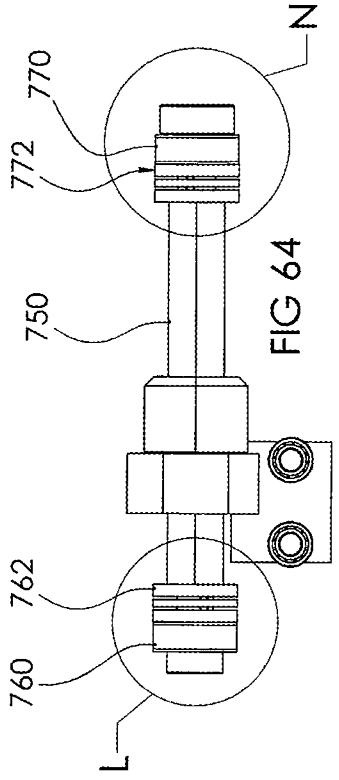
Figure 65A:
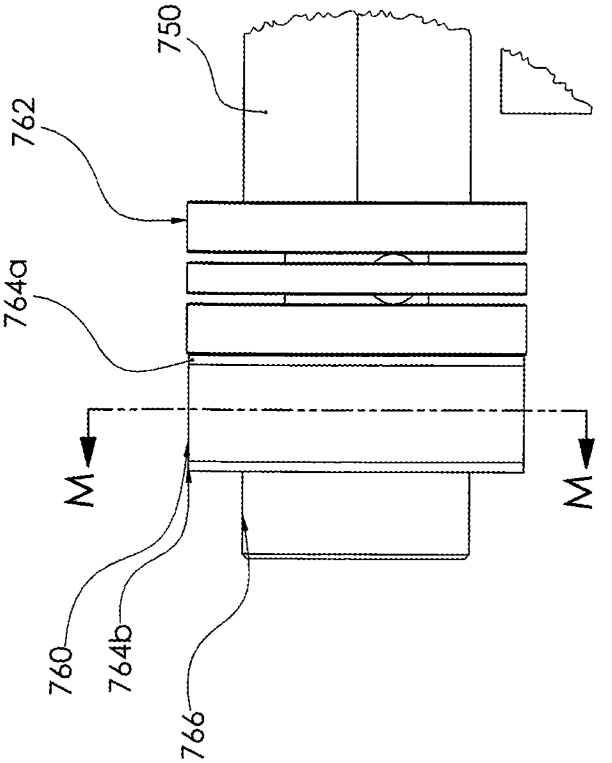
Figure 63:
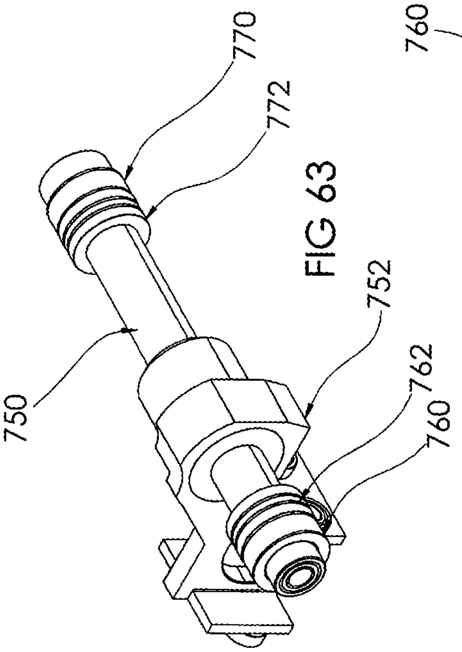
Figure 65B:
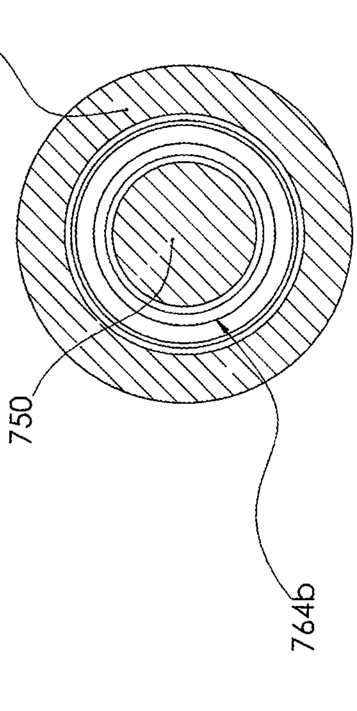
Figure 66A:
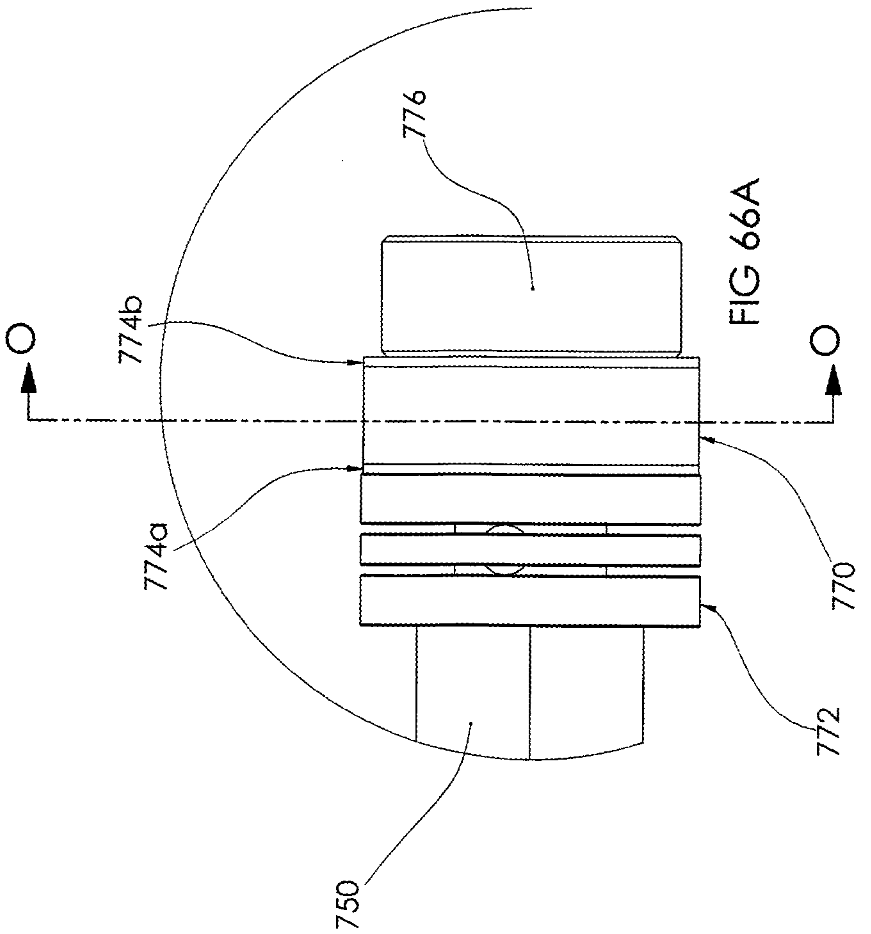
Figure 66B:
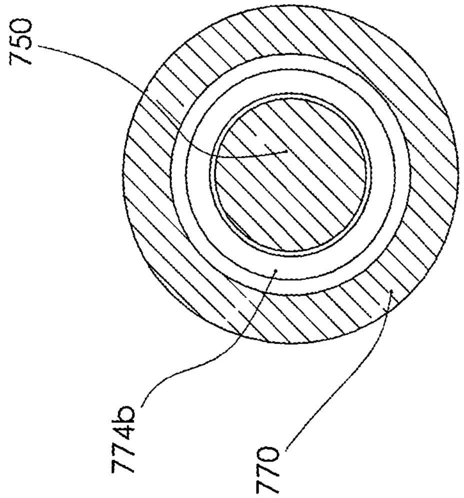

The articulation screw 750 has distal thrust and axial bearings 762,763 (FIG. 62B) and proximal thrust and axial bearings 772,776 (FIG. 62C), similar to the thrust and axial bearings of the articulation screw 752 of FIG. 60A of the Ser. No. 16/792,110 application, now U.S. Pat. No. 11,331,099. Articulation screw 752 has a load cell or strain gauge 760 (FIG. 62B) at the distal end which is sandwiched between distal and proximal plates 764*b*, 764*a*. The articulation screw 750 further includes a load cell or strain gauge 770 at the proximal end which is sandwiched between distal and proximal plates 774*a*, 774*b* (FIG. 62C). These load cells behind the thrust bearings measure articulation force. This can prevent the motor from being faulted. If the load cell detects an energy spike, a signal is sent to the microprocessor within the power pack 700 to slow down the motor.

Figure 52:
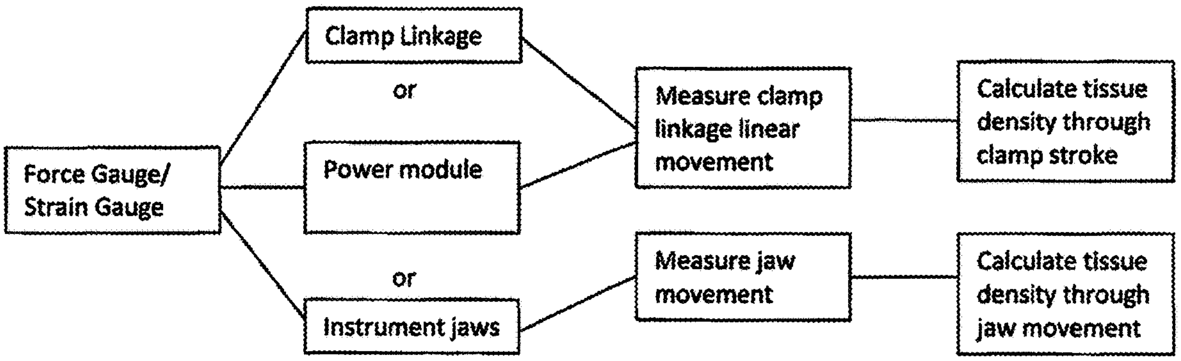
FIG. 52 is a block diagram depicting various measurement devices.

The present invention can also provide a system that indicates to the user acceptable ranges for fastener application. Forces, tissue or clamping pressures, and/or tissue densities measured or calculated by the sensors/gauges as disclosed herein can be displayed on the power module TTF, LCD or Human Machine Interface screen on the instrument housing to give real-time feedback to the surgeon. Based on forces, measured pressure and densities pre-calculated from tissue testing which provide a baseline and maximum and interim values, the Human Machine Interface (HMI) screen will indicate if the measurement is within an optimal range for acceptable staple line outcome. This can be understood with reference to the diagram of FIG. 52. FIG. 52 shows the gauges can be provided a) in the clamp linkage (which includes components effecting mechanical clamping of the jaws (e.g., the manual clamp handle, cam pivot plate, adapter, clamp rod etc.) and/or b) in the power module, e.g., the component(s) therein tied into clamp rod movement; and/or c) in the instrument jaws. For (a) and (b) the clamp linkage movement, e.g., linear or pivotal movement is measured; for (c) the jaw movement toward the opposing jaw is measured. This can provide sufficient information for force determination. However, the information can also be used to determine tissue density as depicted in the optional last boxes of the diagram of FIG. 52.

Figure 54:
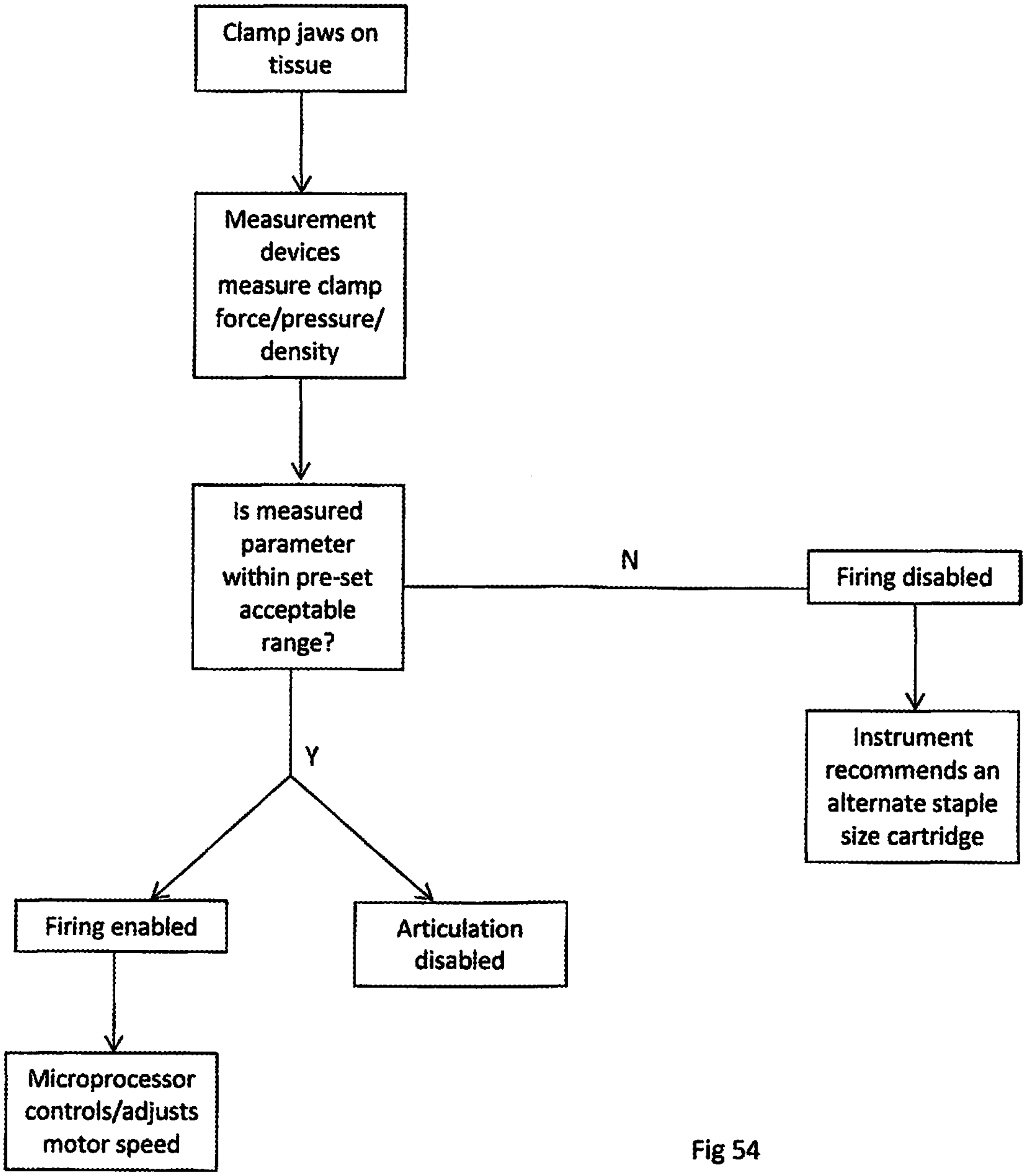
FIG. 54 is a flow chart depicting motor speed adjustment based on measurements.

FIG. 54 provides a flow chart depicting one embodiment of a system where the instrument determines if the staple size is appropriate based on the preset ranges where the values are pre-calculated/predetermined. More particularly, the jaws are clamped on tissue in the manners discussed herein and a parameter, e.g., clamping force, pressure and/or tissue density is measured utilizing one or more of the measurement devices disclosed herein. The measured parameter is compared by the microprocessor (e.g., a microprocessor in the power module) to the pre-set range. If the measured parameter is within the acceptable range, then firing is enabled and articulation is disabled. The microprocessor, based on the measured parameter, will then account for motor speed accordingly. That is, the microprocessor will control and adjust the motor speed, i.e., the microprocessor using AI will control or change the firing speed of the deployment motor based on the range detected whereas thin tissue will fire at faster speeds, medium tissue at nominal speeds and thick tissue will fire at slower speeds to enable tissue fluid to egress and reduce the forces on the stapler system.

If the measured parameter is outside the acceptable range, then firing is disabled and the instrument recommends, e.g., via a screen or other indicator on the instrument or power module, alternative size staple load either smaller or larger in size.

Note the Human Machine Interface screen will indicate whether it is in the acceptable range (thin/less dense/low pressure or medium/average density/nominal pressure or thick/more dense/high pressure). It is contemplated that in some systems, the optimal force/pressure/density of tissue would be staple load size agnostic and the same ranges would apply to all load sizes. In other systems, a staple size selector switch on the power module is provided so the forces/pressure/density would be staple load size specific and in certain applications provide more precise indications/motor controls.

In some embodiments, if a strain gauge or other sensor reading records a force/pressure or tissue density within a predetermined range so the stapling function is indicated, i) the power module microprocessor will enable the firing sequence of the device to deploy staples and ii) the power module microprocessor will disable the articulation functionality of the device. On the other hand, if a strain gauge or other sensor reading records a force/pressure or tissue density outside a predetermined range so the stapling function is not indicated, the power module microprocessor will disable the firing sequence of the device putting it in a lockout condition not allowing staple firing.

In some embodiments, the surgeon will be provided the option to override the device.

Figure 53A:
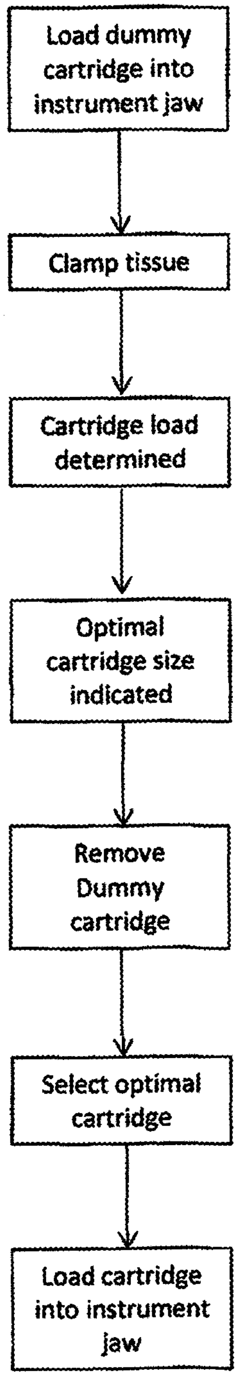
FIG. 53A is a flow chart depicting utilization of a dummy cartridge for measurement.

A gauge in the form of a cartridge can be provided in some embodiments so the surgeon can load and clamp on tissue prior to selecting a cartridge load size. This cartridge load gauge enables the surgeon to select a proper cartridge size without potentially wasting the wrong size cartridge. The gauge (dummy cartridge) can come preloaded in the instrument or alternatively the surgeon can load the gauge (dummy cartridge) into the instrument. Then the surgeon palpates tissue with the jaws to determine staple height size and the device will indicate an optimal cartridge size such as via an output on the screen. The surgeon then removes the dummy cartridge and inserts the indicated staple cartridge in the cartridge jaw. These steps are shown in the flow chart of FIG. 53A.

Figure 53B:
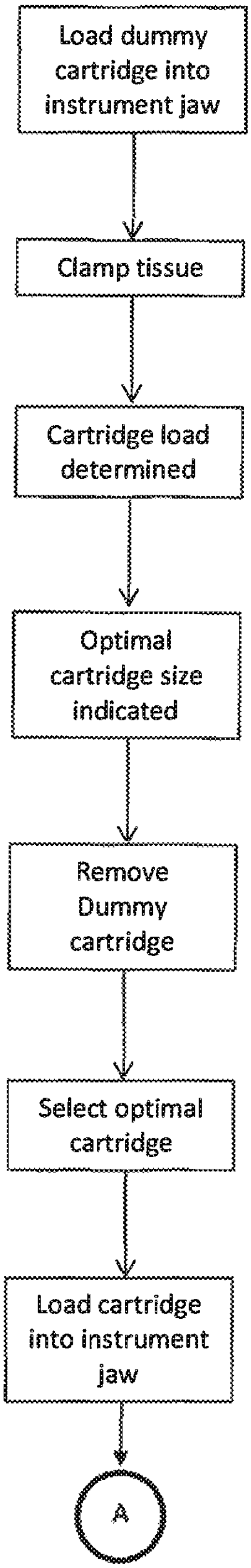
FIGs. 53B and 53C show a flow chart depicting utilization of a dummy cartridge for measurement in accordance with an alternate embodiment of the present invention.
Figure 53C:
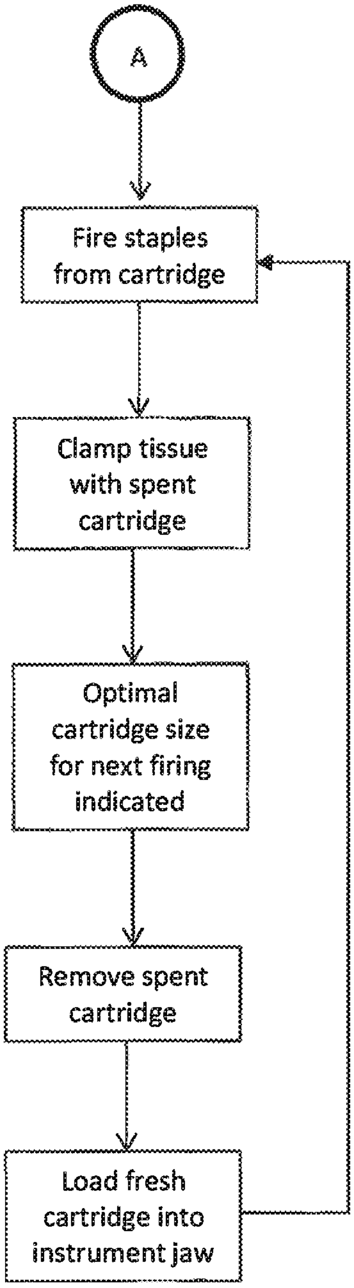
Figure 53D:
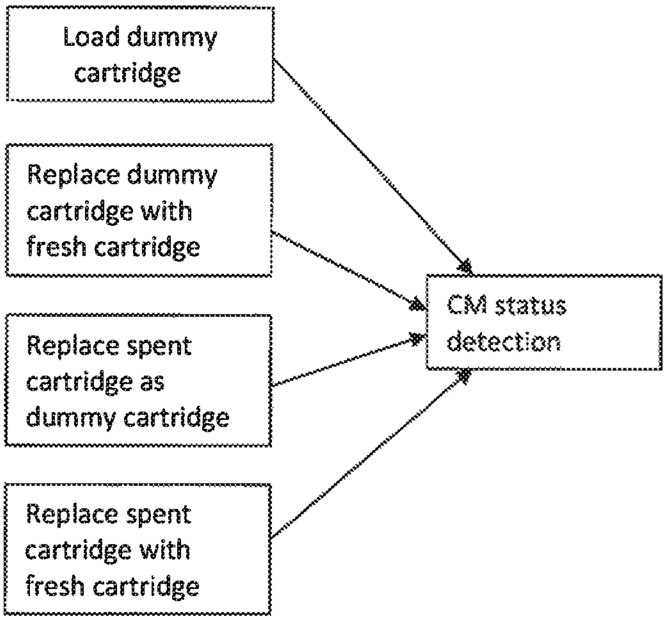
FIG. 53D is a diagram showing the power pack (control module) status detection of the dummy cartridge utilized in the method of FIGS. 53B and 53C.

FIGS. 53B and 53C depict an alternate embodiment wherein the spent cartridge can function as the dummy cartridge. In this method, as in the method of FIG. 53A, the surgeon will load the dummy cartridge into the instrument, palpate the tissue with the jaws to determine staple height size and remove the dummy cartridge and insert based on the screen output the indicated staple cartridge in the cartridge jaw. However, the method of FIGS. 53B, 53C and 53D also enables the clinician to continuously gauge the staple size selection during the procedure. After the indicated staple cartridge is loaded in the instrument and its size detected by the instrument and the fasteners fired, the spent cartridge is then used as the dummy cartridge. The spent cartridge is clamped onto tissue and a readout will indicate to the surgeon the next cartridge size to be utilized for the next firing. The spent cartridge is removed, and a fresh cartridge is loaded into the instrument, and its size is detected by the instrument. After firing, the spent cartridge is used as a dummy cartridge to gauge tissue thickness for staple height selection of the next cartridge. This can continue for all staple firings. Thus, the instrument identifies the cartridge and after firing can provide a readout for the next cartridge size utilizing the spent cartridge as the dummy cartridge. Note the dummy cartridge size and volume of tissue it can accommodate is necessary to the force readings and for providing a recommended staple (cartridge) size. FIG. 91 illustrates one type of a display in the form of a dial showing cartridge size indicated by the dummy cartridge tissue gauge. The cartridge sizes are indicated around the dial, displayed clockwise in progressively increasing cartridge size, i.e., progressively increasing staple size. The color corresponds to staple sizes conventional in the industry. Thus, with the dummy cartridge loaded and the jaws manually clamped, the sensor measures the clamping force on tissue as described herein, communicates the data to the microprocessor via the communication bus and the microprocessor communicates with the screen to display it on the display screen dial along the arc. The user can easily select the cartridge correlated to the range indicator. Note the dial can also be used when the spent cartridge is used as a tissue gauge like the dummy cartridge after the fasteners have been fired to enable selection of next cartridge. Note FIG. 91 shows that a gold cartridge has been selected by way of example as it is shown in the center. In preferred embodiments, initially the screen would not show any cartridge in the center but just identify which cartridge to select along the arc/dial. Once the cartridge is selected, e.g., identified by the instrument pre-loading or loaded, the selected cartridge, identified by cartridge color, is displayed on the screen as in FIG. 91.

In some embodiments, once the dummy cartridge indicates the proper staple size, the clinician then loads the indicated cartridge and utilizing a button or toggle scrolls through the viewing window to match the loaded cartridge, or first toggles to the indicated cartridge size and then loads the proper sized cartridge. FIG. 81H illustrates an example of a button 681 at the back of the housing that can be used to toggle to the selected cartridge size as indicated on the viewing screen. In alternate embodiments, rather than the user scrolling to the indicated cartridge size, once the dummy cartridge indicates the staple size, the system automatically moves to the indicated cartridge size which is indicated on the screen. This eliminates the need for user selection/scrolling. Once the cartridge is selected in the measurement mode, the system can then transition to the firing mode. In some embodiments, this automatic indication can be overridden by the clinician.

It should be appreciated that it is also envisioned that in some embodiments the instrument can be used without the initial tissue gauging before cartridge selection, e.g., without use of the dummy cartridge.

A clamp indicator in the window/can be provided to show where in the range the tissue falls based on the cartridge selected. The firing speed via AI (machine inference) can be controlled based on the cartridge selected and/or clamp indication measurements.

In some embodiments, the power pack can have a reader, such as an RFID reader, for detecting a type of staple cartridge prior to loading the staple cartridge in the instrument. The staple cartridge can have a code or tag, such as an RFID tag, and would be held adjacent the loaded power pack for detection of the type of cartridge, i.e., the size of the staples in the cartridge and/or the length of the arrays of staples within the cartridge. When detected, a signal is sent to the control module within the power pack to indicate which cartridge size is selected so the clamp force can be adjusted accordingly, and in some embodiments, indicated in the window/screen of the power module. The microprocessor can also preset the motor to correspond to the type of cartridge selected. The control module can be configured so that if a cartridge is loaded without its chip being read by the RFID reader, then the instrument cannot be actuated, e.g., cannot be fired. It can also be configured so that the reader will detect if the cartridge has been fired (spent), i.e., devoid of staples, and if spent, the instrument cannot be actuated e.g., cannot be fired. The RFID tag can be on the plastic cartridge cover to minimize interference or assembled into the cartridge. Note alternatives to RFID readers to identify cartridge type, e.g., size, are also contemplated, with such identifiers communicating with the microprocessor in the power pack to adjust the clamping and/or firing parameters. In other embodiments, the user can manually select the cartridge size through a switch that communicates with a microprocessor. In other embodiments, once clamped, the screen automatically changes to the indicated cartridge size, which in some embodiments, can be manually overridden.

The logic circuit in some embodiments could be as follows: 1) load the power pack (in the home position) into the instrument compartment (the instrument cannot be actuated unless a power pack is loaded); 2) close the cover to enable the switch for articulation and the switch for firing (an enable mode); 3) select a cartridge and hold it adjacent the power pack to calibrate/set the cartridge (staple) size to the device and activate the load cells and to send a signal to the microprocessor confirming the cartridge has not been previously fired and to set the firing speed and adjust for other parameters, e.g., staple line length and firing stroke; 4) once all is active, place the cartridge in the instrument jaw; 5) the articulation switch and firing switch can be activated for performing the surgical procedure.

In some embodiments, the logic circuit can provide for firing of less than the entire staple firing line. An indicated length of staple line can be user selected, e.g., firing 50% of the staples along the axial line, in certain procedures and then the system will provide for motor actuation and advancement of the firing rod a distance corresponding to the desired length of staple line. Once the desired distance (% of complete staple line/complete firing stroke) is achieved, the motor will pause and then can either automatically or via user control, return to the home/initial position to retract the firing rod.

In some embodiments, a supercapacitor on the PCB can be provided to store enough energy to maintain microprocessor memory if the battery is exchanged or if the wrong size cartridge is utilized (wasted).

The load cell can be utilized in some embodiments for data acquisition to provide post procedure evaluation. In the manual option, the sales/OR staff will download case data from the power module via data transfer interface (e.g., USB). Data will be sent to HQ for trending and optimization for future cases. The feedback can be used to provide surgeons with ideal load/cartridge selection. Note this would require staff present to input outcomes. In an alternative automatic option, the sales/OR staff will connect to the device via Bluetooth/wireless on their iPad or other mobile device and the data will be sent from the sales staff iPad (or other device) for trending and optimization for future cases. Other data collected and stored for such uses can further include biometrics, number of devices fired by the power pack, the length of the surgical procedures, forces generated, tissue information, operation of the stapling components and power pack components and other parameters of the tissue, surgical procedure, stapling instruments and/or power pack.

The foregoing measurement devices were discussed for use in surgical staplers. They can be used in open and endoscopic and laparoscopic staplers. However, they can also be used to measure pressure, force and/or tissue density in other instruments with clampable jaws such as graspers, energy devices, shears, clip appliers (where the measurement would prompt the surgeon to check clip closure based on force feedback of clip deployment).

Note the output can be digital. The output can be serial. It can be measured by voltage output.

A firing profile graph can be shown through HMI on the power module, visible through an instrument screen. High/low lines as with a statistical process control chart (SPC) will allow the surgeon to maintain a "safe" firing speed. That is, the graph will provide an indication to the surgeons where they are during the stroke. For example, if force is too high, they may want to take action to reduce the force or pause firing. An example of a chart is provided in FIG. 86. In the chart, line A represents motor speed, line C represents the measured force and line B represents the optimal force. As shown, for example, if the force spikes, the motor speed is slowed accordingly.

In some embodiments, relative change in amperage/current during fastener firing is detected and abnormalities flagged. For example, if a spike exceeds a first threshold (a first predetermined amount), but less than a second threshold (a second predetermined amount) which can be measured via a quantitative value compared to the indicated/desired value or alternatively via a relative (%) increase from the indicated/desired value, then a warning can be indicated in the view screen for observation by the clinician. If the spike exceeds the second threshold, then the motor will automatically shut down. By way of example, assuming 1 amp is indicated for firing force, if it increases to 2 amps, the motor won't shut down, but a warning will be indicated on the screen, but if it increases to 3 amps, the motor will automatically shut down. By way of another example, assuming 1 amp is indicated for firing force, if it increases by 100% but less than 200%, the motor won't shut down, but a warning will be indicated on the screen, but if it increases by 200%, the motor will automatically shut down. It should be appreciated that these values (amps and percentages) are given solely by way of example as other values are also contemplated as initial values as well as threshold values.

In the foregoing embodiments, use of the power pack of the present disclosure to fire staples such as in endoscopic linear staplers, open surgery linear staplers, circular staplers, as well as firing single clips or tacks were disclosed as examples. It should be appreciated that the power packs of the present disclosure can also be used to power functions of other surgical instruments such as endoscopic scissors and graspers as disclosed in the Ser. No. 16/792,110 application, now U.S. Pat. No. 11,331,099.

The power packs 18 and 90, as well as other power packs disclosed herein, can be used in surgery where the clinician manually clamps the jaws and actuates the motor or motors to provide powered staple firing and/or powered jaw articulation. It is also contemplated that the power packs 18 and 90 can be used with robotic driven surgical staplers wherein clamping, motor actuation and any other functions of the instrument are performed robotically, including remote robotic control.

The power pack can also be used in robotics systems as described in the commonly assigned PCT application PCT/US2022/16892, filed Feb. 18, 2022, the entire contents of which are incorporated herein by reference. In the embodiment of FIG. 85, the robotically assisted system 1000 includes a robot arm 1002 connected via a connection, e.g., cable 1005, to the surgeon interface console 1004. The surgeon console 1004 includes an input device, also referred to as master device, that allows the surgeon to manipulate the robot arm 1002 to various positions from the surgeon's remote location. The robot arm 1002 has multiple joints and multiple degrees of freedom to provide for a wide range of maneuverability and positioning of the surgical instrument held by the robot arm 1002. The robot arm 1002 secures the instrument in position with the distal end portion of the instrument at the target site for the surgical procedure. In the system of FIG. 85, a seven-axis robotic arm is illustrated by way of example, although other robot arms are also contemplated.

The instrument 1006, also referred to herein as an end effector, performs one or more surgical functions and can be for example in the form of a surgical stapler, surgical clip applier, grasper, scissors, or any other instrument described herein or in the form of other surgical instruments for performing surgical functions. A mechanical connection 1007 of instrument 1006, preferably a universal connector to fit a variety of end effectors, is connected to the robot arm 1002 for connecting the instrument 1006 to the robot arm 1002 for securement thereto so robot arm 1002 can move the instrument 1006 to a variety of positions, and retain it in a desired position, e.g., retain it in position extending through a trocar or port to minimally invasively reach the target tissue site. The connector can be in various forms such as a snap on connector. By providing a universal mechanical end effector connector, different instruments (end effectors) can be exchanged and mounted to the robot arm 1002.

The instrument 1006 receives a power pack 1008 (also referred to herein as the control module). Power pack 1008 can be of the form of the power packs described herein and contains one or more motors to effect one or more functions of the surgical instrument 1006. In this manner, the power pack 1008, and thus the instrument functions and movements (e.g., jaw clamping, jaw articulation, fastener firing, etc.) operate independently of the robot arm 1004 so there is no interface between the robot arm 1002 and instrument/end effector 1006 other than the mechanical fixation. Stated another way, in such embodiments, there is no communication between the power pack and the input, i.e., master, that controls the robot arm 1002. Instead, a separate communication is provided, either through cable 1009, or alternatively a wireless connection, that controls the power pack 1008 at the surgeon console 1004. In this embodiment, the surgeon input at the console 1004 remotely selectively actuates the motors contained in the power pack 1008. The motors in the power pack 1008 initiate movement of engagement members (engagers) within the power pack 1008 which in turn effect movement of movable members (actuators) within the surgical instrument 1006 to which the power pack engagement members/engagers are operatively connected. Thus, the power pack 1008 can be considered a "second robot" (the first robot being the robot arm) which via remote initial actuation effects a variety of movements and functions of the surgical instruments held by the robot arm 1002. The functions and movements can be in the form for example of firing fasteners into tissue, clamping tissue, cutting tissue, articulating the arms or jaws of the instrument, bending the arms in multiple planes, etc. As used herein, instrument functions can also encompass instrument portion movements. Note the movements of portions of the instrument are controlled by the power pack; the movement for placement of the instrument itself is controlled by the robot arm 1002.

The drive mechanisms in the power pack 1008 in some embodiments include engagement members as in the power packs described herein which can include a flag or yoke which engages a movable member of the instrument. In such embodiments, rotational motion of the motor and ball screw convert rotational motion to linear motion within the power pack as motor shaft rotation causes the engagement member to move linearly to thereby move the movable member of the instrument linearly to effect a surgical function such as firing, clamping articulation, etc. Other structure to convert rotational motion to linear motion is also contemplated. In alternate embodiments, instead of a linear drive, a rotational drive can be provided to transmit rotational movement through the end effector for various functions. Thus, in such embodiments, there would be no conversion to linear motion, just direct rotation, as the in line motion just causes rotation (spinning) to engage.

Other features of the power packs described above, including for example sensors, load cells, etc., can also be utilized in the power packs loaded into the instrument of the robotic systems disclosed herein.

In an alternate embodiment, a cable/pulley system is provided to effect an end effector articulation function such as disclosed in FIG. 89 of the PCT application PCT/US20220/16892. Thrust bearings and load sensors as shown in FIGS. 90 and 91 of the PCT/US2020/16892 application can also be used in the robotic systems.

Turning back to the interaction/connection of the end effector to the robot arm, in some embodiments, a sterile drape can be placed over the robot arm and the end effector can be attached over this creating a sandwich so that the drape is sandwiched between the robot arm and end effector. The control module would be placed distally of the drape in an aseptic compartment of the instrument.

As can be appreciated, multiple robot arms can be provided, one for holding and manipulating each surgical instrument, or fewer robot arms could be provided, with the robot arms having one or more branches for manipulating the respective surgical instruments. The multiple robot arms, end effectors and control modules could in some embodiments be used/operated simultaneously. In some embodiments, the multiple robot arms can communicate with each other. Communication between robot arms can be wired or wireless. Such communication can allow the robot arms and instruments to work together ("talk to each other") during the surgical procedure.

In some embodiments, the robot arm activation adjusts the instrument position by controlling the joints of the robot arm; the control module activation powers the instrument functions by actuating the various motors contained within the control module 1008. The control module power and communications are provided through a separate cable, that is directly plugged into the control module (power pack). In an alternate embodiment, the power and communications are provided through a separate cable that is directly plugged into the end effector which transfers both power and communications to the control module. Note alternatively, a wireless connection can be utilized.

The end effectors (instruments) can include energy, visualization, RF, fiber optics, ultrasound, etc. which can be directly plugged in from the robot console, e.g., to the robot arm, to communicate with the end effector through the robot arm, or, alternatively, can be directly plugged into the control module for communication with the end effector through the control module or alternatively, a separate cable can be provided to directly plug into the end effector. Aspiration can be achieved through a vacuum line connected to the control module, end effector, or partially through the robot arm.

Note the various cables and communication lines can in some embodiments route through a balloon portion of the robot arm to communicate with the control module.

The control module is inserted into the instrument compartment via an aseptic transfer. The loading of the control module can take place either before the instrument is mounted to the robot arm or after mounting of the instrument to the robot arm. In alternate embodiments, the instruments are provided with the control module pre-loaded. The control modules in preferred embodiments are removably loaded into the instrument compartment so they can be removed and replaced with another control module if desired.

In some embodiments, multiple end effectors (instruments) can be pre-loaded with control modules and arranged in a gang/group for automatic robot loading to the arm. The robot arm in these embodiments removes the selected pre-loaded end effector from the rack. In this manner, the robot arm could exchange end effectors, by releasing one end effector and engaging another end effector. This is enabled since the robot arm in these embodiments serves for instrument positioning and not for instrument functioning.

A proximity identification, RFID, or other reader/identifier (either electrical or mechanical or a combination thereof) can be provided to identify to the user at the console the type of end effector which is supported in each robot arm. An initialization can occur automatically when the end effector is loaded onto the robot arm, or alternatively, a pre-initialization can occur before loading. The identification can be electrical or mechanical, e.g., a mechanical actuator can achieve part detection and recognition.

A single motor can effect movement of more than one engager (and thus activator) so that a single motor can power multiple instrument functions or alternatively separate motors can power separate functions.

In some embodiments, the main robot CPU for the user console controls in concert the movement of the robot arm and end effector functions. Thus, it speaks to the control module via the communications interface. That is, robot control of the front end of the end effector (the instrument functions) can occur at the same time as the positioning, e.g., angular positioning, back and forth positioning, etc. of the end effector by the robot arm.

In the embodiment of FIG. 85, the surgical instrument (end effector) is mounted to the robot arm and the control module/power pack is inserted into the compartment of the surgical instrument to engage the actuators within the surgical instrument. The connector for the robot arm is therefore located on the surgical instrument. The control module can be loaded into the surgical instrument compartment after the instrument is mounted to the robot arm, or, alternatively, the control module can be preloaded into the instrument prior to connection of the instrument to the robot arm. Note the compartment of the instrument to receive the power pack can be similar to the compartments described above, e.g., have a closable sealable cover to protect the control module from external contaminants. The control module can have an internal power source such as a battery which in some embodiments can be removed from the power pack and replaced, as described above or, alternatively, be connected via a cable or wire to an external power source (e.g., AC outlet or DC outlet), the cable preferably being different than the communications cable extending between the control module and the CPU.

In an alternate embodiment, the control module, rather than the instrument is connected to the robot arm. The control module contains several motors and engagers (engagement members) operably connected to the motors for movement upon activation of the motor. In this embodiment, the control module is connected to the robot arm 1002 via a connector on the control module. The control module can include a sterile plate that forms a support base that snaps into or onto the robot arm 1002 and then snaps onto the end effector/instrument. The sterile plate can form the top cover of the instrument. After connection to the robot arm 1002, the instrument is positioned over the control module, so the control module is captured within the compartment of the instrument, or otherwise connected thereto, and the engagers of the control module connect to the respective activators of the instrument. After such loading, the motors are remotely actuated to effect surgical functions as described above. It should be appreciated, that the control module can be the same as control module 1008, or other control modules described herein, for connection to movable members within the instrument to effect instrument movements and functions, e.g., articulation, clamping, fastener firing etc. These power pack controlled movements and functions can be independent of the robot arm control as described above.

In an alternate embodiment of the present invention, the robotically assisted system utilizes the control module (power pack) to control activation of the robot arm as well as to power the instrument. The CPU at the surgeon console remotely activates the control module which is the master input for robot arm control (manipulation) as well as for instrument movements and functions. Thus, the control module CPU would be the primary and drive robot arm function also. Stated another way, the control module would control manipulation of the robot to adjust the instrument position and the same control module would control the instrument movements and functions. A communications connector would extend between the control module and CPU.

In an alternate embodiment, a handheld remote control, e.g., a joystick, or multiple remote control can be connected directly to the end effector or control module for bedside operation. A wireless remote or a corded hand held remote, like a video game remote, could be provided. A soft touch robot arm can be utilized where there is no control console. The user places the robot arm in the desired position by manual manipulation via a soft touch and the remote user control is utilized solely for instrument actuation not robot arm control.

In alternate embodiments, the motor drivers of power packs described herein can instead of being internal to the control module, reside with the main CPU. This would place the hardware for the motors in the CPU, simplifying the control module so the module would have purely mechanical features.

In some embodiments, the control modules can include a generator(s) or energy delivery mechanism.

Surgical methods for utilizing the control modules disclosed herein are also provided by the present invention.

The encoders and sensors described herein can also be utilized with the power packs for the robotic systems disclosed herein.

It should be appreciated that the various power packs disclosed herein and their alternative configurations and features, can be utilized with the robotic systems.

In alternate embodiments, two separate compartments in the housing can be provided—one for loading a power pack for powered firing of fasteners and one for powered articulation of the end effector. This is shown for example in FIG. 38C which illustrates a first compartment 20*a* to receive the power pack for motor driven articulation and second compartment 20*b* to receive the power pack for motor driven fastener firing. Note it is also contemplated that alternatively the articulation power pack can be loaded into compartment 20*b* and the firing power pack loaded into compartment 20*a*. Each of the power packs can contain the motor, drive screw, etc. as described above for the firing and articulation, with the engagement member of the articulation power pack engaging the articulation rod in the instrument housing in the same manner as for example in FIGS. 15F and 24 and the engagement member of the fastener firing power pack engaging the firing rod in the instrument housing in the same manner as for example in FIG. 4D.

In another alternative embodiment, two separate power packs are utilized, one for firing and one for articulation, but both are loaded in a single compartment of the instrument housing.

In another alternate embodiment, one of the compartments 20*a* or 20*b* is configured to receive a separate battery/battery pack and the other compartment 20*a* or 20*b* is configured to receive a power pack for motorized firing and/or articulation.

The staplers disclosed herein, or certain components thereof, can be made of environmentally friendly biodegradable materials. For example, the handle can be made of biodegradable material. Such material can include for example corn based lactic acid. The packaging for the surgical staplers and/or the packaging for the power packs and/or the battery packs can also be composed of biodegradable materials to minimize the carbon footprint.

Although the apparatus and methods of the subject disclosure have been described with respect to preferred embodiments, those skilled in the art will readily appreciate that changes and modifications may be made thereto without departing from the spirit and scope of the present disclosure as defined by the appended claims.

Additionally, persons skilled in the art will understand that the elements and features shown or described in connection with one embodiment may be combined with those of another embodiment without departing from the scope of the present invention and will appreciate further features and advantages of the presently disclosed subject matter based on the description provided.

Throughout the present invention, terms such as "approximately," "generally," "substantially," and the like should be understood to allow for variations in any numerical range or concept with which they are associated. For example, it is intended that the use of terms such as "approximately" and "generally" should be understood to encompass variations on the order of 25%, or to allow for manufacturing tolerances and/or deviations in design.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present disclosure.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A power pack loadable into a surgical fastener applier for use in a surgical procedure comprising a first motor, a first movable member and a first engagement member, wherein actuation of the first motor effects movement of the first movable member and first engagement member which effects movement of a firing mechanism in the surgical fastener applier from a first position to a second position to fire a plurality of fasteners, the first engagement member having an initial position and a second position;

wherein the power pack has a data storage device to store data relating to the surgical procedure;

wherein the power pack is configured for loading into a housing of the surgical fastener applier which has the firing mechanism movable between the first position and the second position to fire the plurality of fasteners into tissue clamped between first and second jaws of the surgical fastener applier which are at a distal portion of an elongated member of the surgical fastener applier.

2. The power pack of claim 1, wherein the power pack is initially placeable in a homing cradle to ensure loading of the power pack into the housing with the first engagement member in the home position.

3. The power pack of claim 1, wherein the power pack is placeable in a homing cradle after the surgical procedure and the data is transferable from the power pack to a memory device in the homing cradle for storage therein.

4. The power pack of claim 2, wherein data is transferable from the power pack to a memory device in the homing cradle for storage therein.

5. The power pack of claim 1, wherein the power pack can be loaded into the housing of the surgical fastener applier only if the first engagement member is in the home position.

6. The power pack of claim 1, wherein the data includes a firing force during firing of the plurality of fasteners.

7. The power pack of claim 1, wherein the data includes a clamping force of the first and second jaws on tissue.

8. The power pack of claim 1, wherein the data is transferred from the power pack to another memory device and a new file is created each time the power pack is loaded into a surgical fastener applier.

9. The power pack of claim 1, wherein clamping pressure is sensed outside the power pack and subsequently transmitted to the power pack.

10. The power pack of claim 1, wherein clamping measurement for each firing of multiple firings of the surgical fastener applier is stored for review by a clinician of all the firings in the surgical procedure.

11. The power pack of claim 9, wherein a clamping force is measured by a sensor positioned in the surgical fastener applier.

12. The power pack of claim 1, wherein the data is transferable from the power pack to a memory device in the surgical fastener applier.

13. The power pack of claim 1, further comprising a second motor and a second engagement member removably engageable with an articulating mechanism in the housing of the surgical fastener applier to effect movement of an articulation mechanism to effect articulation of the first and second jaws from a linear position to a position angled with respect to a longitudinal axis of the elongated member, the second engagement member having a home position and an advanced position, and the power pack cannot be loaded into the compartment if the articulation mechanism is not in the home position.

14. The power pack of claim 1 in combination with a homing cradle, wherein the power pack is placeable in the homing cradle after a surgical procedure and the data is transferable from the power pack to a memory device in the homing cradle for storage therein.

15. A power pack removably loadable into a compartment of a surgical fastener applier, the power pack having a housing having a) a first motor; b) a first drive mechanism having a first engagement member, the first drive mechanism operably connected to the first motor and the first engagement member removably engageable with a firing mechanism of the surgical fastener applier when the power pack is loaded into the compartment to effect movement of the firing mechanism from a first position to a second position; c) a movable member movable by the motor to effect linear movement of the first engagement member; and d) a stationary encoder positioned within the housing of the power pack to detect movement of the movable member to determine a firing position of the firing mechanism.

16. The power pack of claim 15, wherein the encoder is attached to the housing and a scale is movable with respect to the encoder.

17. The power pack of claim 15, wherein the encoder is attached to the housing and a code wheel is movable with respect to the encoder.

18. The power pack of claim 15, wherein discrete axial positions of the firing mechanism are detected and readings of the discrete axial positions are sent to a central processing unit within the power pack.

19. The power pack of claim 15, further comprising a second motor, a rotatable member operatively connected to and rotatable by the second motor and a second drive mechanism operatively connected to the second rotatable member and having a second engagement member removably engageable with an articulating mechanism of the surgical fastener applier to effect movement of the articulation mechanism to effect articulation of first and second jaws of the surgical stapler from a linear position to an angled position, and a second encoder positioned within the power pack to detect movement of the rotatable member to determine an articulation position of the articulation mechanism.

* * * * *